US012018051B2

United States Patent
Collins et al.

(10) Patent No.: US 12,018,051 B2
(45) Date of Patent: *Jun. 25, 2024

(54) RECOMBINANT HUMAN PARAINFLUENZA VIRUS TYPE 1 EXPRESSING A CHIMERIC RSV/HPIV1 F PROTEIN AND USES THEREOF

(71) Applicant: The United States of America, as represented by the Secretary, Department of Health and Human Services, Bethesda, MD (US)

(72) Inventors: Peter Collins, Silver Spring, MD (US); Bo Liang, Boyds, MD (US); Shirin Munir, Potomac, MD (US); Anne Schaap Nutt, Austin, TX (US); Ursula Buchholz, Silver Spring, MD (US); Natalie Mackow, East Setauket, NY (US); Peter Kwong, Washington, DC (US); Barney Graham, Smyrna, GA (US); Jason McLellan, Austin, TX (US)

(73) Assignee: The U.S.A., as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/162,530

(22) Filed: Jan. 31, 2023

(65) Prior Publication Data

US 2023/0287055 A1    Sep. 14, 2023

Related U.S. Application Data

(63) Continuation of application No. 16/877,319, filed on May 18, 2020, now Pat. No. 11,591,372, which is a continuation of application No. 15/545,218, filed as application No. PCT/US2016/014154 on Jan. 20, 2016, now Pat. No. 10,654,898.

(60) Provisional application No. 62/105,667, filed on Jan. 20, 2015.

(51) Int. Cl.
| | | |
|---|---|---|
| C07K 14/005 | (2006.01) | |
| A61K 39/12 | (2006.01) | |
| A61K 39/155 | (2006.01) | |
| A61P 31/14 | (2006.01) | |
| A61K 39/00 | (2006.01) | |

(52) U.S. Cl.
CPC .......... *C07K 14/005* (2013.01); *A61K 39/12* (2013.01); *A61K 39/155* (2013.01); *A61P 31/14* (2018.01); *A61K 2039/5254* (2013.01); *A61K 2039/5256* (2013.01); *A61K 2039/575* (2013.01); *A61K 2039/70* (2013.01); *C07K 2319/03* (2013.01); *C07K 2319/033* (2013.01); *C12N 2760/00022* (2013.01); *C12N 2760/18534* (2013.01); *C12N 2760/18571* (2013.01); *C12N 2760/18622* (2013.01); *C12N 2760/18634* (2013.01); *C12N 2760/18641* (2013.01); *C12N 2760/18643* (2013.01); *C12N 2760/18671* (2013.01); *C12N 2760/18722* (2013.01); *C12N 2760/18734* (2013.01); *C12N 2760/18741* (2013.01); *C12N 2760/18743* (2013.01); *C12N 2760/18771* (2013.01)

(58) Field of Classification Search
None
See application file for complete search history.

(56) References Cited

U.S. PATENT DOCUMENTS

| | | | |
|---|---|---|---|
| 5,993,824 A | 11/1999 | Murphy et al. | |
| 6,410,023 B1 | 6/2002 | Durbin et al. | |
| 7,192,593 B2 | 3/2007 | Murphy et al. | |
| 7,201,907 B1 | 4/2007 | Schmidt et al. | |
| 7,208,161 B1 | 4/2007 | Murphy et al. | |
| 7,250,171 B1 | 7/2007 | Tao et al. | |
| 7,314,631 B1 | 1/2008 | Murphy et al. | |
| 7,425,618 B2 | 9/2008 | Oliver | |
| 7,465,574 B2 | 12/2008 | Jin et al. | |
| 7,622,123 B2 | 11/2009 | Skiadopoulos et al. | |
| 7,632,508 B2 | 12/2009 | Schmidt et al. | |
| 7,704,509 B2 | 4/2010 | Murphy et al. | |
| 7,820,182 B2 | 10/2010 | Buchholz et al. | |

(Continued)

FOREIGN PATENT DOCUMENTS

| | | |
|---|---|---|
| WO | WO 2004/027037 | 1/2004 |
| WO | WO 2010/039224 | 4/2010 |
| WO | WO 2014/160463 | 10/2014 |

OTHER PUBLICATIONS

SEQ 1 alignment with PIR_80 db access B28929 Johnson et al. 1988.*
SEQ 31 alignment with Geneseq db access No. ADJ97205 Young et al. 2003.*
SEQ 135 alignment with Geneseq db access BBN47168 Nov. 2014.*
Bailly et al., "Sequence Determination and Molecular Analysis of Two Strains of Bovine Parainfluenza Virus Type 3 that are Attenuated for Primates," *Virus Genes* 20.2: 173-182, 2000.
Bailly et al. Alignment of Seq Id 43. Geneseq, db acc No. Q9J7E1_PI3B, Oct. 2000.

(Continued)

*Primary Examiner* — Shanon A. Foley
(74) *Attorney, Agent, or Firm* — Klarquist Sparkman, LLP

(57) ABSTRACT

Recombinant paramyxoviruses including a viral genome encoding a heterologous gene are provided. In several embodiments, the recombinant paramyxovirus is a recombinant parainfluenza virus, such as a recombinant PIV3 including a viral genome encoding a heterologous respiratory syncytial virus F ectodomain linked to the transmembrane domain and the cytoplasmic tail of the F protein from the PIV3. Nucleic acid molecules including the genome of a recombinant paramyxoviruses are also provided. The recombinant viruses may advantageously be used in vaccine formulations, such as for vaccines against parainfluenza virus and respiratory syncytial virus.

20 Claims, 62 Drawing Sheets

Specification includes a Sequence Listing.

(56) References Cited

U.S. PATENT DOCUMENTS

| | | | |
|---|---|---|---|
| 7,842,798 | B2 | 11/2010 | Buchholz et al. |
| 7,846,455 | B2 | 12/2010 | Collins et al. |
| 7,951,383 | B2 | 5/2011 | Murphy et al. |
| 8,084,037 | B2 | 12/2011 | Haller et al. |
| 8,367,074 | B1 | 2/2013 | Skiadopoulos et al. |
| 8,372,963 | B2 | 2/2013 | Grunwald et al. |
| 11,591,372 | B2 * | 2/2023 | Collins ............... A61P 31/14 |
| 2006/0099226 | A1 | 5/2006 | Schmidt et al. |
| 2009/0017517 | A1 | 1/2009 | Schickli et al. |
| 2009/0263883 | A1 | 10/2009 | Haller et al. |
| 2011/0081708 | A1 | 4/2011 | Liu et al. |
| 2012/0045471 | A1 | 2/2012 | Haller et al. |
| 2012/0064112 | A1 | 3/2012 | Samal et al. |
| 2013/0052718 | A1 | 2/2013 | Skiadopoulos et al. |
| 2014/0186397 | A1 | 7/2014 | Hurwitz et al. |
| 2014/0248314 | A1 | 9/2014 | Swanson et al. |
| 2014/0271699 | A1 | 9/2014 | Kwong et al. |
| 2016/0046675 | A1 | 2/2016 | Kwong et al. |
| 2018/0312544 | A1 | 11/2018 | Collins et al. |

OTHER PUBLICATIONS

Bailly et al. Alignment of Seq Id 48. UniProt, db acc No. Q9J7E0_PI3B, Oct. 2000.

Bailly et al. Alignment of Seq Id 49. UniProt, db acc No. Q9J7D9_PI3B, Oct. 2000.

Bailly et al. Alignment of Seq Id 53. UniProt, db acc No. Q9J7D8_PI3B, Oct. 2000.

Bartlett et al., "Attenuation and Efficacy of Human Parainfluenza Virus Type 1 (HPIV1) Vaccine Candidates Containing Stabilized Mutations in the P/C and L Genes," *Virol J.* 4: 67 (13 pages).

Basavarajappa et al., "A Recombinant Newcastle Disease Virus (NDV) Expressing Infectious Laryngotracheitis Virus (ILTV) Surface Glycoprotein D Protects Against Highly Virulent ILTV and NDV Challenges in Chickens," *Vaccine* 32.28: 3555-3563, Jun. 2014.

Bernstein et al., "Phase 1 Study of the Safety and Immunogenicity of a Live, Attenuated Respiratory Syncytial Virus and Parainfluenza Virus Type 3 Vaccine in Seronegative Children," *Pediatr Infect Dis J.* 31.2: 109-114, Feb. 2012.

Clements et al., "Evaluation of Bovine, Cold-Adapted Human, and Wild-Type Human Parainfluenza Type 3 Viruses in Adult Volunteers and in Chimpanzees," *J Clin Microbiol.* 29.6: 1175-1182, Jun. 1991.

Connors et al., "A Cold-Passaged, Attenuated Strain of Human Respiratory Syncytial Virus Contains Mutations in the F and L Genes," *Virology* 208.2: 478-484, Apr. 1995.

Collins et al. Alignment of Seq Id 52. Geneseq, db acc No. ADV68236, Jun. 2007.

Cullen et al., "Cotton Rat Immune Responses to Virus-Like Particles Containing the Pre-Fusion Form of Respiratory Syncytial Virus Fusion Protein," *J Transl Med.* 13: 350, Nov. 2015 (13 pages).

Durbin et al., "Mutations in the C, D, and V Open Reading Frames of Human Parainfluenza Virus Type 3 Attenuate Replication in Rodents and Primates," *Virology* 261.2: 319-330, Sep. 1999.

Fath et al., "Multiparameter RNA and Codon Optimization: A Standardized Tool to Assess and Enhance Autologous Mammalian Gene Expression," *PLoS One* 6.3: e17596, Mar. 2011 (14 pages).

Fu et al., "Intranasal Immunization with a Helper-Dependent Adenoviral Vector Expressing the Codon-Optimized Fusion Glycoprotein of Human Respiratory Syncytial Virus Elicits Protective Immunity in BALB/c Mice," *Virol J.* 10: 183, Jun. 2013 (8 pages).

Graham et al., "Challenges and Opportunities for Respiratory Syncytial Virus Vaccines," *Challenges and Opportunities for Respiratory Syncytial Virus Vaccines.* Springer Berlin Heidelberg: 391-404, 2013.

Graham et al., "Novel Antigens for RSV Vaccines," *Current Opinion in Immunology* 35: 30-38, Aug. 2015.

International Search Report and Written Opinion for International Application No. PCT/US2016/014154, mailed by the European Patent Office acting as International Searching Authority on Apr. 26, 2016.

Jones et al., "Sendai Virus-Based RSV Vaccine Protects African Green Monkeys from RSV Infection," *Vaccine* 30.5: 959-968, Jan. 2012.

Joyce et al., "Iterative Structure-Based Improvement of a Fusion-Glycoprotein Vaccine Against RSV," *Nat Struct Mol Biol.* 23.9: 811-820, Sep. 2016.

Karron et al., "Evaluation of Two Chimeric Bovine-Human Parainfluenza Virus Type 3 Vaccines in Infants and Young Children," *Vaccine* 30.26: 3975-3981, Jun. 2012.

Kohlmann et al.,. "Protective efficacy and immunogenicity of an adenoviral vector vaccine encoding the codon-optimized F protein of respiratory syncytial virus." *Journal of Virology* 83.23: 12601-12610, 2009.

Kwon et al. Alignment of Seq Id 21. Geneseq, db acc No. BBN47168, Nov. 2014.

Lamb et al., "Paramyxoviridae," *Fields Virology*, $6^{th}$ Edition, eds D.M. Knipe and P.M. Howley (Philadelphia, PA: Lippincott, Williams & Wilkins), 957-995, 2013.

Lawlor et al., "A Single Amino Acid in the F2 Subunit of Respiratory Syncytial Virus Fusion Protein Alters Growth and Fusogenicity," *J Gen Virol.* 94.Pt 12: 2627-2635, Dec. 2013.

Liang et al., "Chimeric Bovine/Human Parainfluenza Virus Type 3 Expressing Respiratory Syncytial Virus (RSV) F Glycoprotein: Effect of Insert Position on Expression, Replication, Immunogenicity, Stability, and Protection Against RSV Infection," *J Virol.* 88.8: 4237-4250, Apr. 2014.

Liang et al., "Enhanced Neutralizing Antibody Response Induced by Respiratory Syncytial Virus Prefusion F Protein Expressed by a Vaccine Candidate," *J Virol.* 89.18: 9499-9510, Sep. 2015.

Liang et al., "Packaging and Prefusion Stabilization Separately and Additively Increase the Quantity and Quality of Respiratory Syncytial Virus (RSV)—Neutralizing Antibodies Induced by an RSV Fusion Protein Expressed by a Parainfluenza Virus Vector," *J Virol.* 90.21: 10022-10038, Oct. 2016.

Maykowski et al., "Seasonality and Clinical Impact of Human Parainfluenza Viruses," *Influenza and Other Respir Viruses* 12.6: 706-716, Nov. 2018.

McAuliffe et al., "Codon Substitution Mutations at Two Positions in the L Polymerase Protein of Human Parainfluenza Virus Type 1 Yield Viruses with a Spectrum of Attenuation In Vivo and Increased Phenotypic Stability In Vitro," *J Virol* 78.4: 2029-2036, Feb. 2004.

McGinnes et al., "Assembly and Immunological Properties of Newcastle Disease Virus-Like Particles Containing the Respiratory Syncytial Virus F and G Proteins," *J Virol.* 85.1: 366-377, Jan. 2011.

McLellan et al., "Structure of RSV Fusion Glycoprotein Trimer Bound to a Prefusion-Specific Neutralizing Antibody," *Science*, 340.6136: 1113-1117, May 2013.

McLellan et al., "Structure-Based Design of a Fusion Glycoprotein Vaccine for Respiratory Syncytial Virus," *Science* 342.6158: 592-598, Nov. 2013, including supplementary information.

Nelson et al., "Genetic Stability of RSV-F Expression and the Restricted Growth Phenotype of a Live Attenuated PIV3 Vectored RSV Vaccine Candidate (MEDI-534) Following Restrictive Growth in Human Lung Cells," *Vaccine* 31.36: 3756-3762, Aug. 2013.

Newman et al., "Generation of Recombinant Human Parainfluenza Virus Type 1 Vaccine Candidates by Importation of Temperature-Sensitive and Attenuating Mutations from Heterologous Paramyxoviruses," *J Virol.* 78.4: 2017-2028, Feb. 2004.

Newman et al., "Sequence Analysis of the Washington/1964 Strain of Human Parainfluenza Virus Type 1 (HPIV1) and Recovery and Characterization of Wild-Type Recombinant HPIV1 Produced by Reverse Genetics," *Virus Genes* 24.1: 77-92, 2002.

Park et al., "Engineered Viral Vaccine Constructs with Dual Specificity: Avian Influenza and Newcastle Disease," *Proc Natl Acad Sci U.S.A.* 103.21: 8203-8208, May 2006.

Quiñones-Kochs et al., "Mechanisms of Loss of Foreign Gene Expression in Recombinant Vesicular Stomatitis Viruses," *Virology* 287.2: 427-435, Sep. 2001.

Ray et al. Alignment of Seq Id 101. Geneseq, db acc No. AAB08627, Dec. 2000.

Schmidt et al., "Bovine Parainfluenza Virus Type 3 (BPIV3) Fusion and Hemagglutinin-Neuraminidase Glycoproteins make an Impor-

(56) References Cited

OTHER PUBLICATIONS tant Contribution to the Restricted Replication of BPIV3 in Primates," *J Virol.* 74.19: 8922-8929, Oct. 2000.
Schmidt et al., "Long-Term and Memory Immune Responses in Mice Against Newcastle Disease Virus-Like Particles Containing Respiratory Syncytial Virus Glycoprotein Ectodomains," *J Virol.* 86.21: 11654-11662, Nov. 2012.
Schmidt et al., "Modification of the Respiratory Syncytial Virus F Protein in Virus-Like Particles Impacts Generation of B Cell Memory," *J Virol.* 88.17: 10165-10176, Sep. 2014.
Schmidt et al., "Mucosal Immunization of Rhesus Monkeys against Respiratory Syncytial Virus Subgroups A and B and Human Parainfluenza Virus Type 3 by using a Live cDNA-Derived Vaccine Based on a Host Range-Attenuated Bovine Parainfluenza Virus Type 3 Vector Backbone," *J Virol.* 76.3: 1089-1099, Feb. 2002.
Schmidt et al., "Progress in the Development of Human Parainfluenza Virus Vaccines," *Expert Rev Respir Med.* 5.4: 515-526, Aug. 2011.
Schmidt et al., "Recombinant Bovine/Human Parainfluenza Virus Type 3 (B/HPIV3) Expressing the Respiratory Syncytial Virus (RSV) G and F Proteins can be used to Achieve Simultaneous Mucosal Immunization against RSV and HPIV3," *J Virol.* 75.10: 4594-4603, May 2001.
Seq. alignment of Geneseq db access No. ADJ97204 in WO2004010935, 2007, with instant Seq Id No. 24.
Seq. alignment of Geneseq db access No. ADJ97205 in WO2004010935 with instant Seq Id 31, 2004.
Seq. alignment of Genesq db access No. BBN47168 in USPgPub 2014271699 with instant Seq Id 135, Nov. 2014.
Skiadopoulos et al., "Determinants of the Host Range Restriction of Replication of Bovine Parainfluenza Virus Type 3 in Rhesus Monkeys are Polygenic," *J Virol.* 77.2: 1141-1148, Jan. 2003.
Skiadopoulos et al., "Evaluation of the Replication and Immunogenicity of Recombinant Human Parainfluenza Virus Type 3 Vectors Expressing Up to Three Foreign Glycoproteins," *Virology* 297.1: 136-152, May 2002.
Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine," *J Virol.* 73.2: 1374-1381, Feb. 1999.
Tang et al., "Effects of Human Metapneumovirus and Respiratory Syncytial Virus Antigen Insertion in Two 3' Proximal Genome Positions of Bovine/Human Parainfluenza Virus Type 3 on Virus Replication and Immunogenicity," *J Virol.* 77.20: 10819-10828, Oct. 2003.
Tang et al., "Parainfluenza Virus Type 3 Expressing the Native or Soluble Fusion (F) Protein of Respiratory Syncytial Virus (RSV) Confers Protection from RSV Infection in African Green Monkeys," J Virol. 78.20: 11198-11207, Oct. 2004.
Tang et al. Alignment of Seq Id 43. Geneseq, db acc No. AZY46953, Sep. 2012.
Ternette et al., "Immunogenicity and Efficacy of Codon Optimized DNA Vaccines Encoding the F-Protein of Respiratory Syncytial Virus," *Vaccine* 25.41: 7271-7279, Oct. 2007.
Whitehead et al., "Addition of a Missense Mutation Present in the L Gene of Respiratory Syncytial Virus (RSV) *cpts*530/1030 to RSV Vaccine Candidate *cpts*248/404 Increases Its Attenuation and Temperature Sensitivity," *J Virol.* 73.2: 871-877, Feb. 1999.
Whitehead et al., "Recombinant Respiratory Syncytial Virus (RSV) Bearing a Set of Mutations from Cold-Passaged RSV is Attenuated in Chimpanzees," *J Virol.* 72.5: 4467-4471, 1998.
Yang et al., "Implication of Respiratory Syncytial Virus (RSV) F Transgene Sequence Heterogeneity Observed in Phase 1 Evaluation of MEDI-534, a Live Attenuated Parainfluenza Type 3 Vectored RSV Vaccine," *Vaccine* 31.26: 2822-2827, 2013.
Zimmer et al., "A Chimeric Respiratory Syncytial Virus Fusion Protein Functionally Replaces the F and HN Glycoproteins in Recombinant Sendai Virus," *J Virol.* 79.16: 10467-10477, 2005.

\* cited by examiner

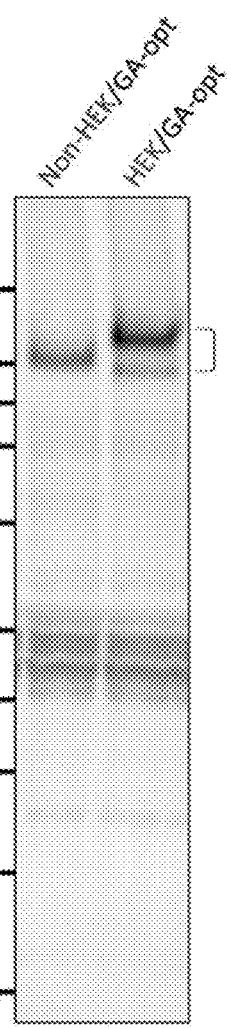
FIG. 2A Reducing Boiled
FIG. 2B Non-reducing Not boiled

HEK/GA-opt

Non-HEK/GA-opt

Outlined syncytium

Non-HEK/non-opt
HEK/GA-opt
HEK/D2-opt
HEK/GS-opt

B/HPIV3
(B/H3)

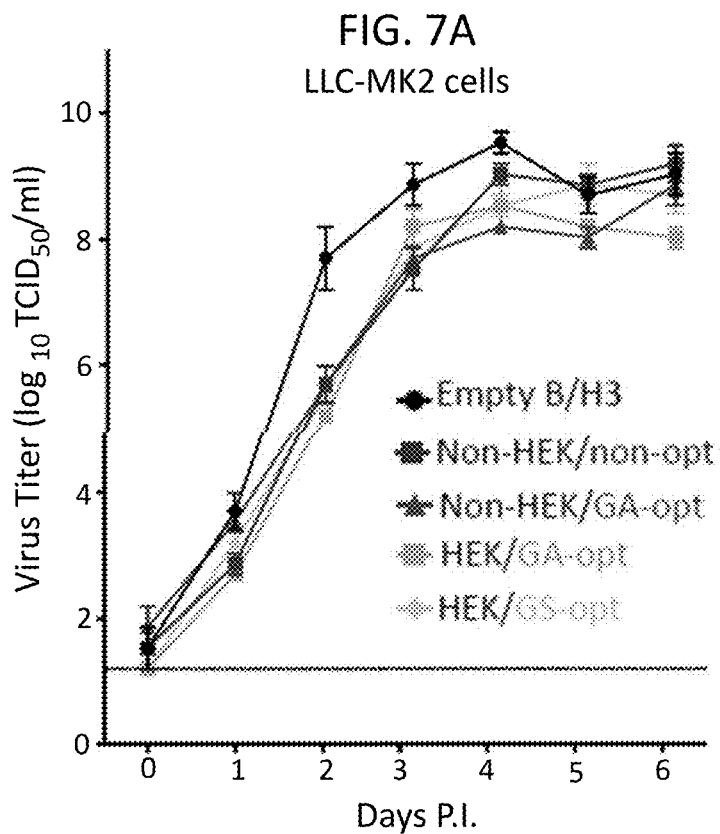
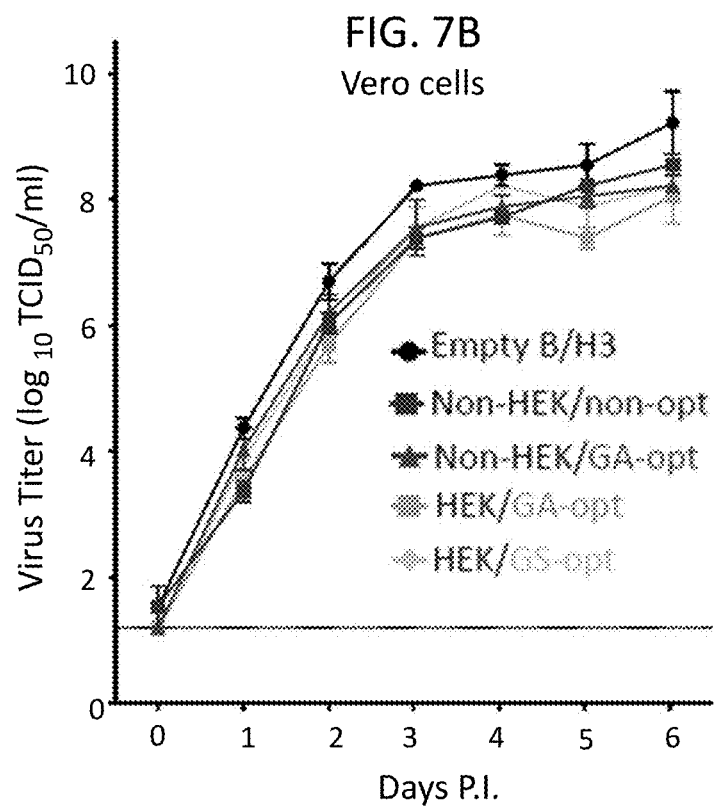

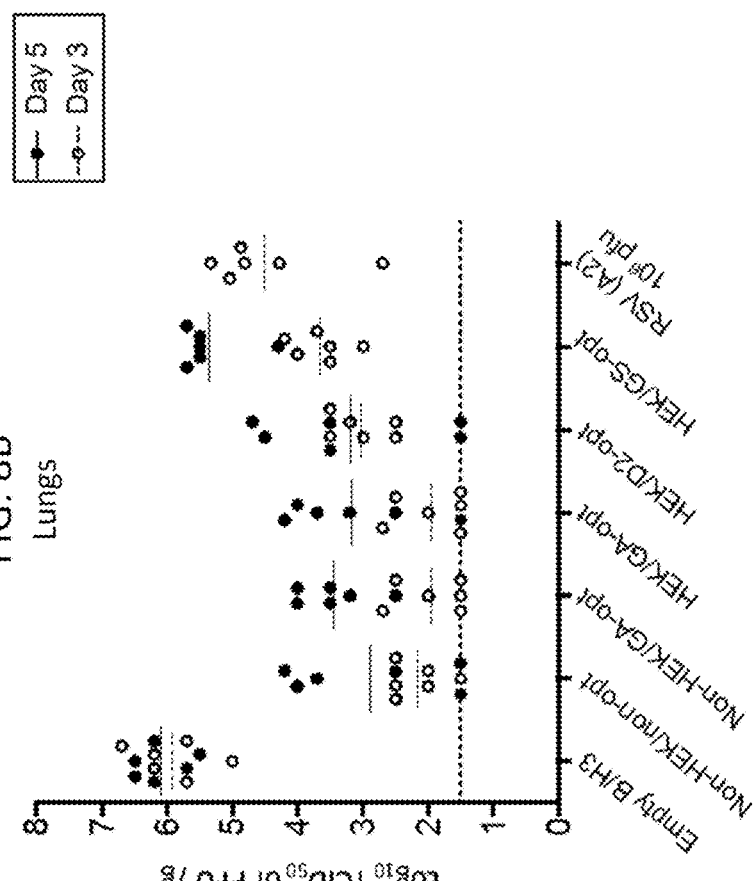
FIG. 8A Nasal turbinates
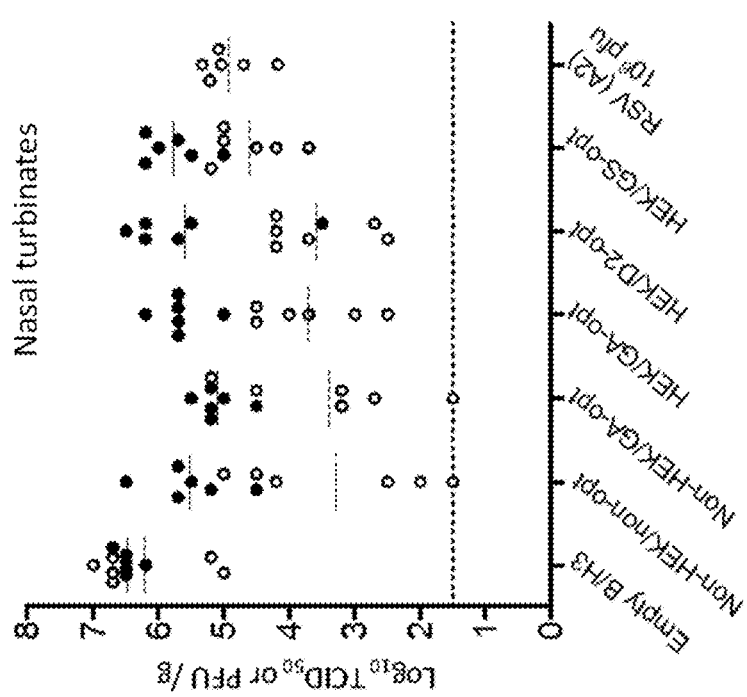
FIG. 8B Lungs

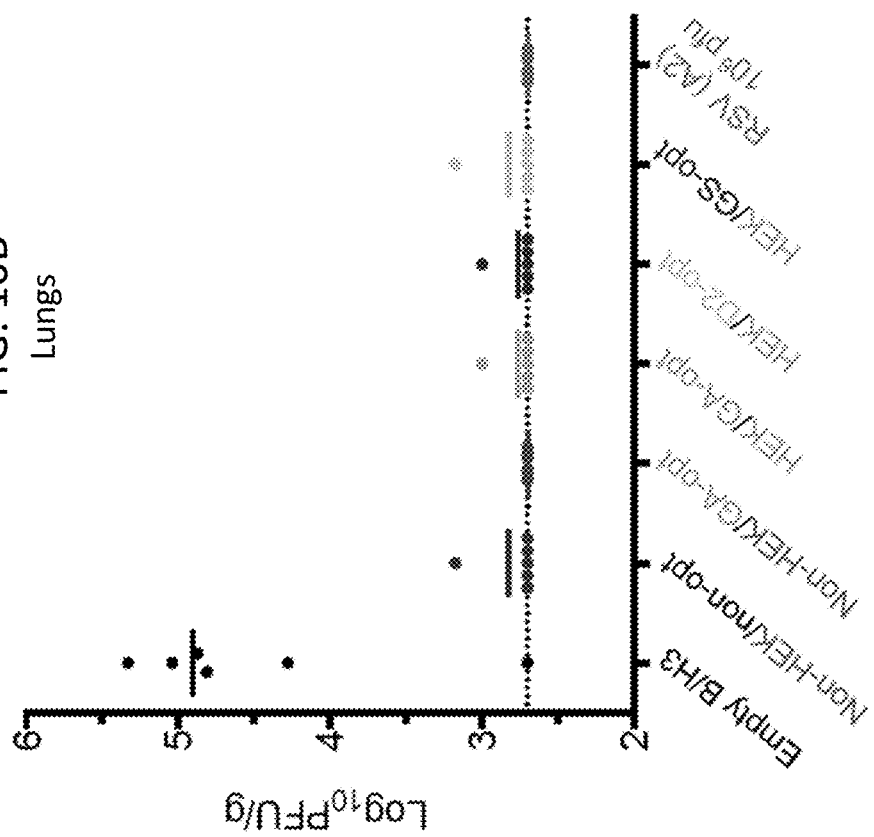
FIG. 10A Nasal turbinates
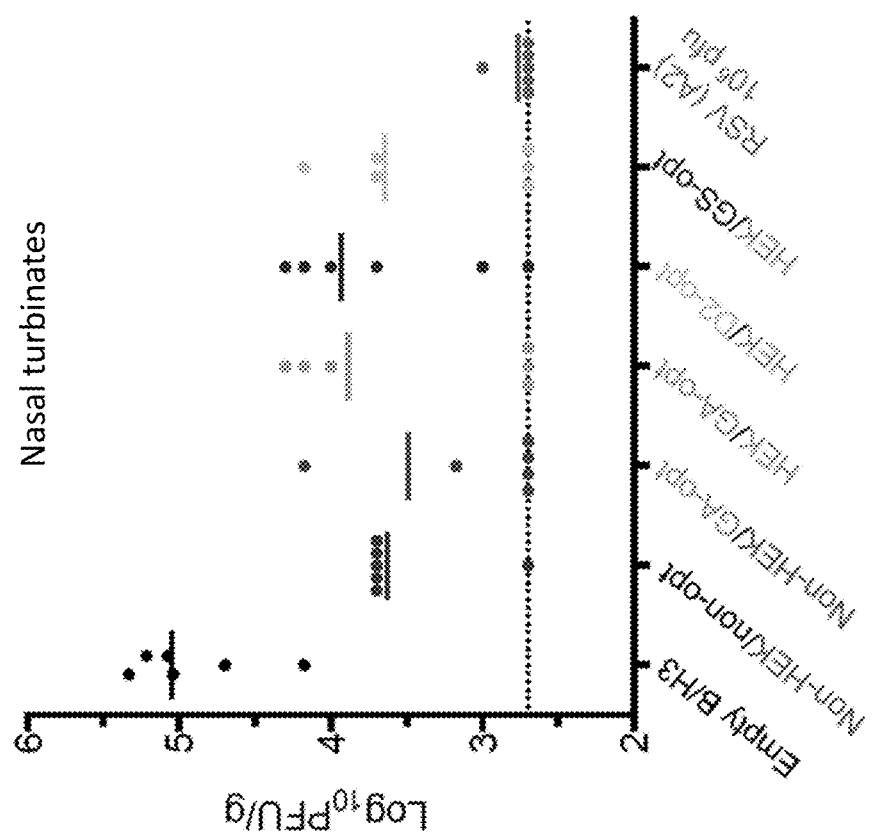
FIG. 10B Lungs

Pre-fusion form of RSV F
37°C

Post-fusion form of RSV F
32°C

* HEK and GA codon-optimized

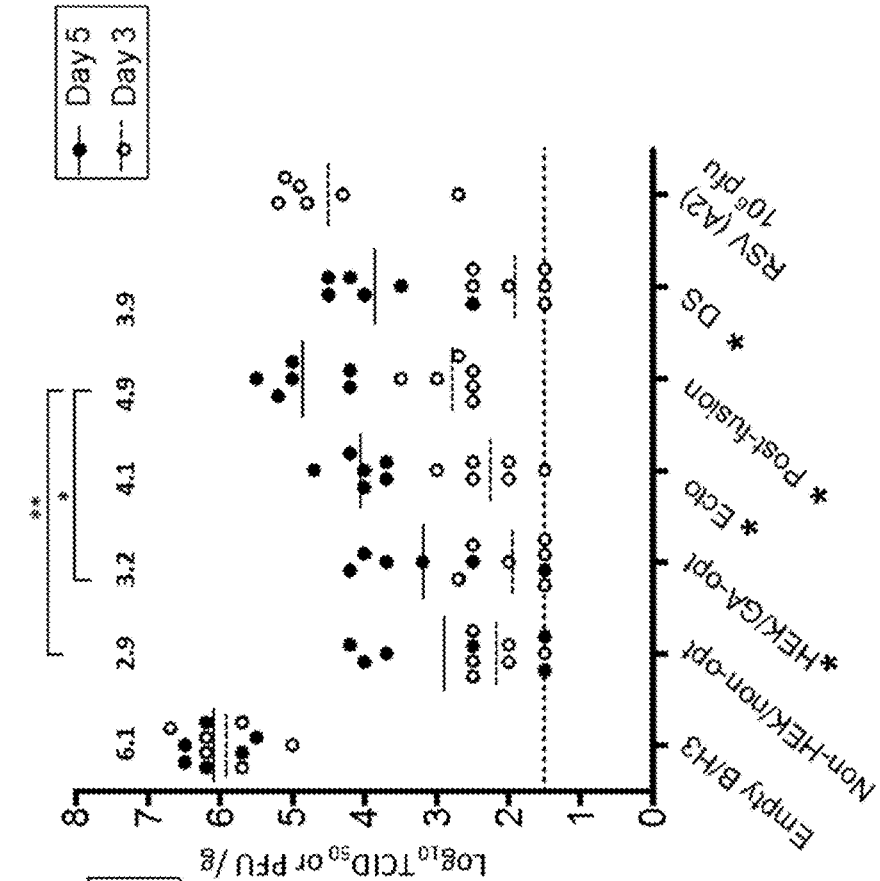
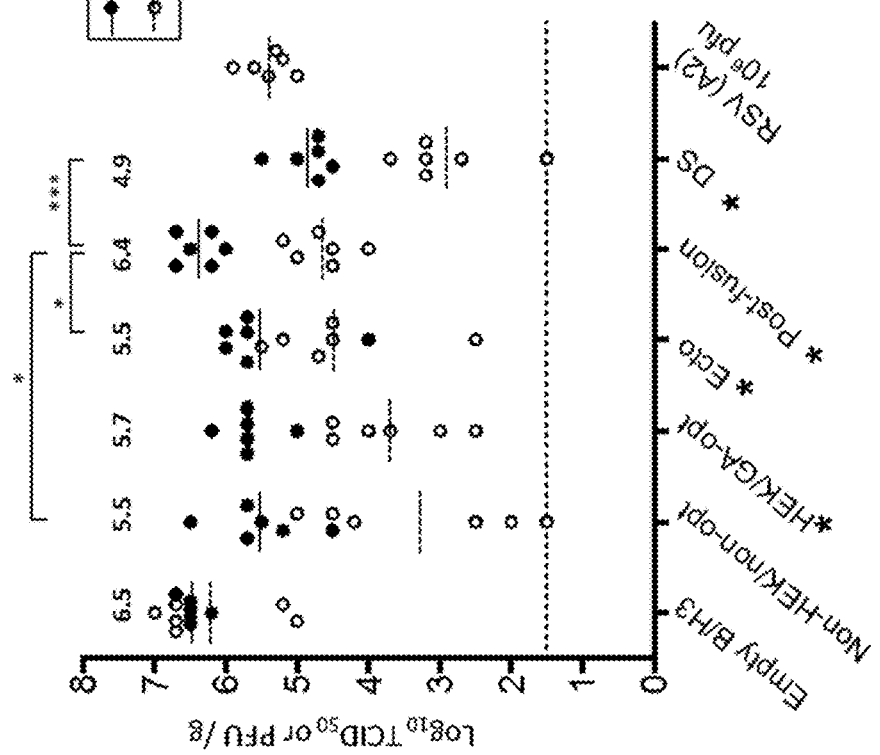
FIG. 14A
FIG. 14B

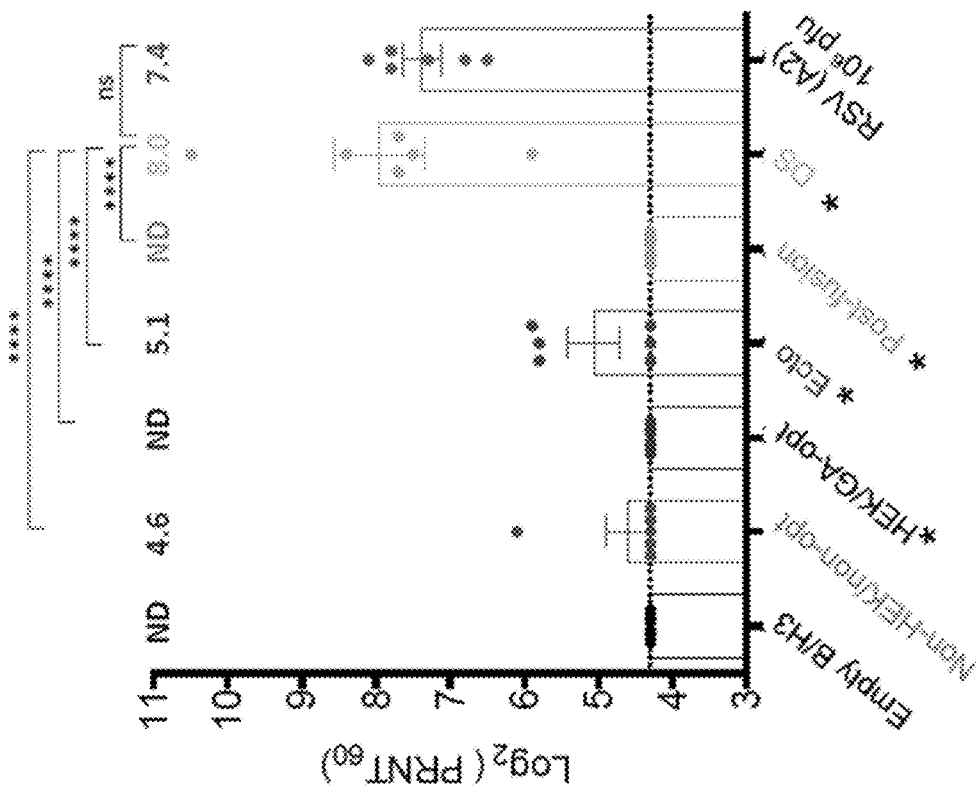
FIG. 15B w/o complement
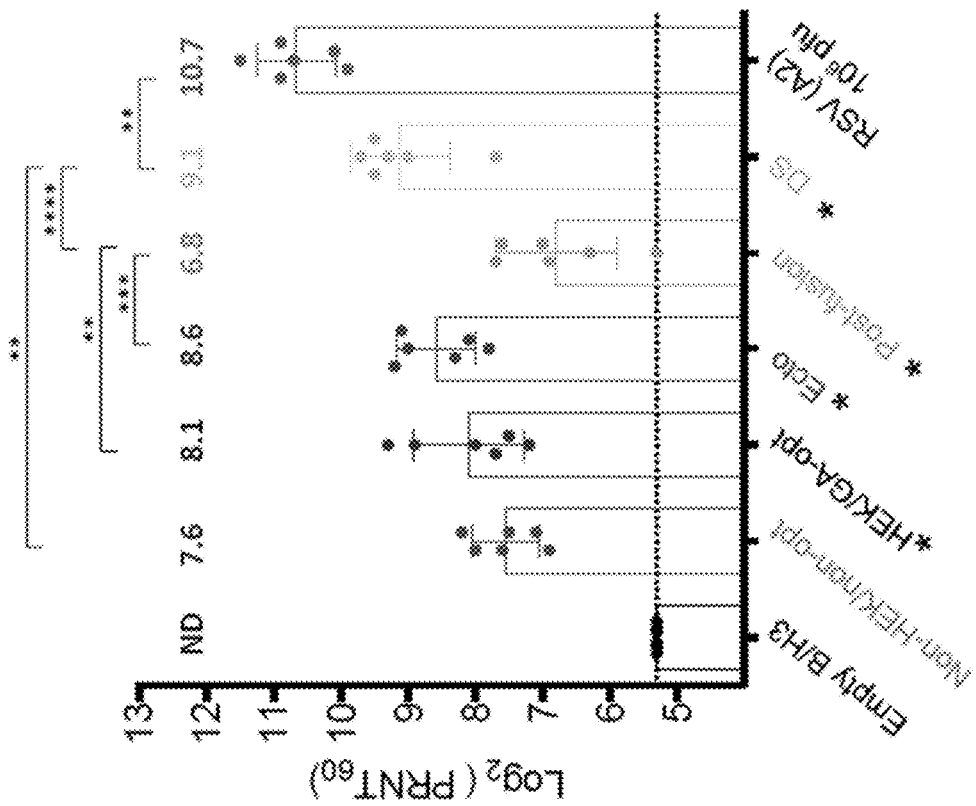
FIG. 15A with complement

FIG. 17B

| | Ectodomain | | TM | | CT | |
|---|---|---|---|---|---|---|
| RSV(A2)F | 510 DELLHNVNAGKSTTNIMITT | 530 | IIIVIIVILLSLIAVGLLLYC | 551 | KARSTPVTLSKDQLSGINNIAFSN | 574 |
| BPIV3 F | 478 NQKLDSVGSWYQSSAT | 494 | ITIIIVMIIILVIINITIIVV | 515 | IIKFHRIQGKDQNDKNSEPYILTNRQ | 540 |
| B3CT | 510 DELLHNVNAGKSTTNIMITT | 530 | IIIVIIVILLSLIAVGLLLYC | 551 | IIKFHRIQGKDQNDKNSEPYILTNRQ | 576 |
| B3TMCT | 510 DELLHNVNAGKSTTNIMITT | 530 | ITIIIVMIIILVIINITIIVV | 551 | IIKFHRIQGKDQNDKNSEPYILTNRQ | 576 |

FIG. 18A

~ 0.5ug of sucrose purified viruses were loaded each lane

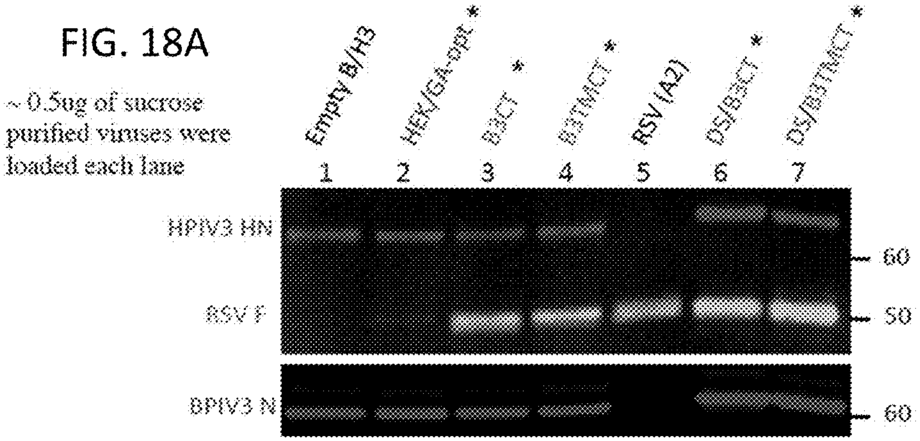

➢ B3CT, B3TMCT packaging efficiency similar to RSV

FIG. 18B

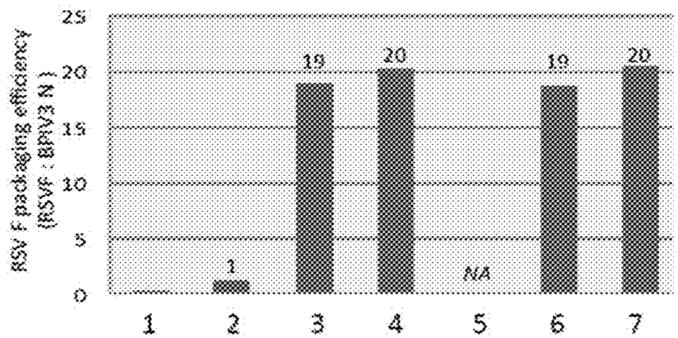

* HEK and GA codon-optimized

FIG. 19A
➢ Observed surface labeling
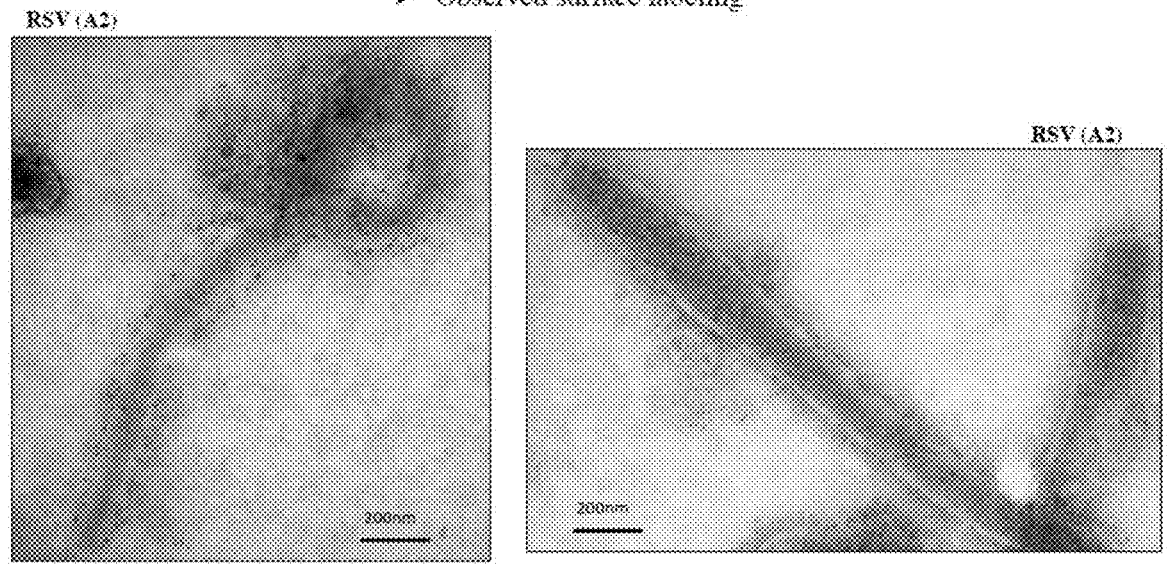
FIG. 19B
➢ No surface labeling
FIG. 19C
➢ Very little surface labeling
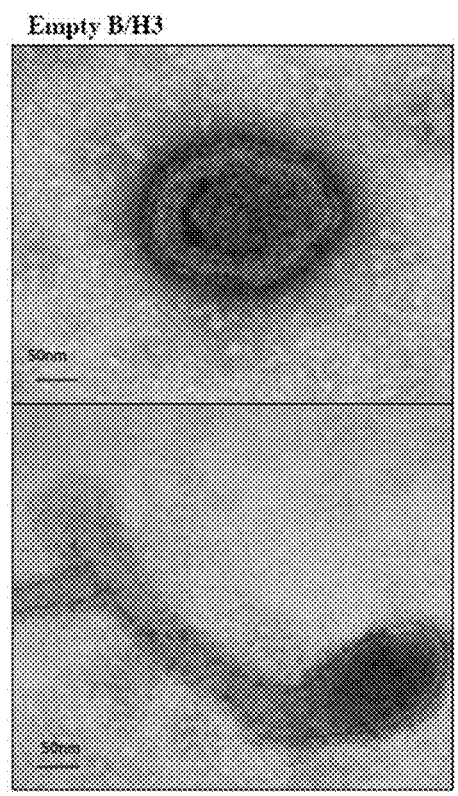
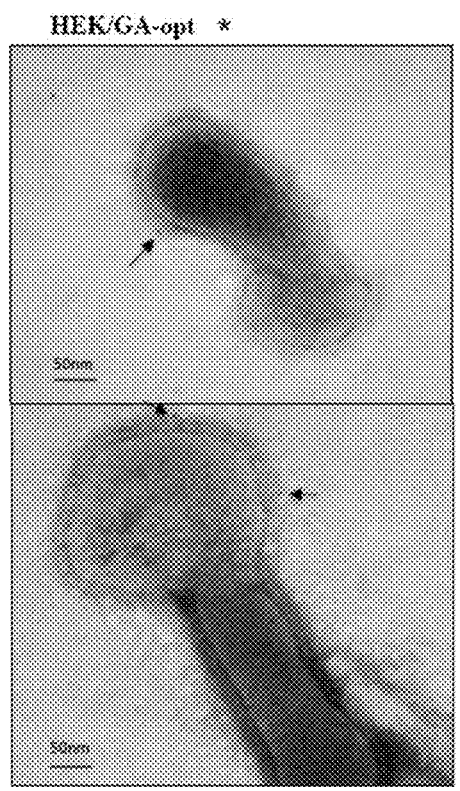
\* HEK and GA codon-optimized

B3CT*     B3TMCT*     DS/B3TMCT*

* HEK and GA codon-optimized

FIG. 20A
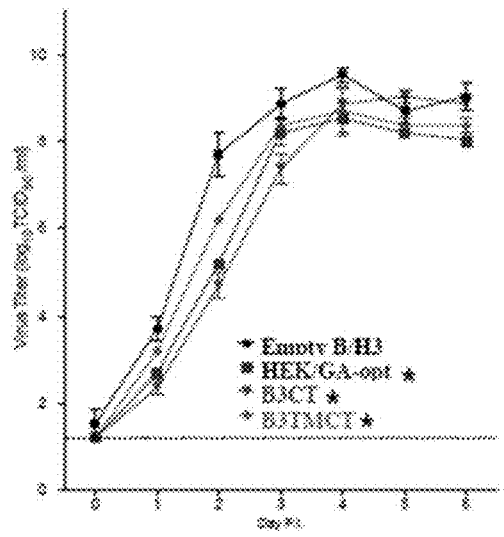
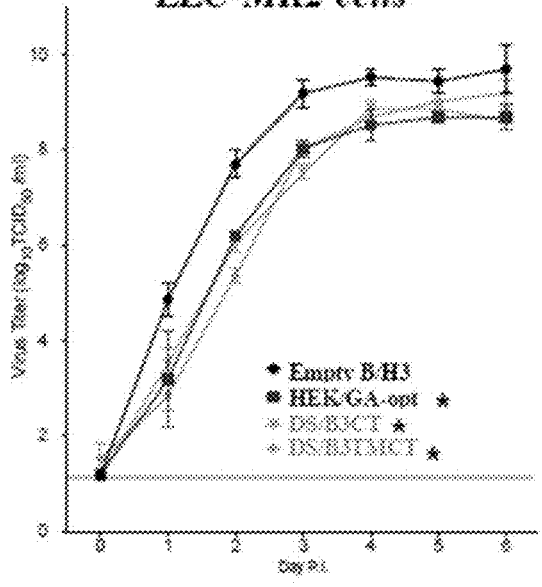
FIG. 20B
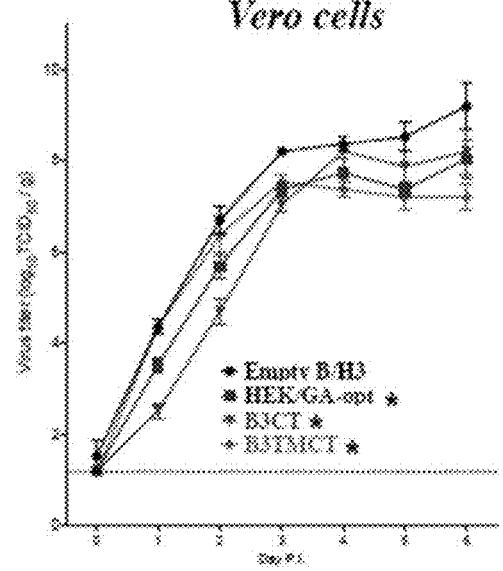
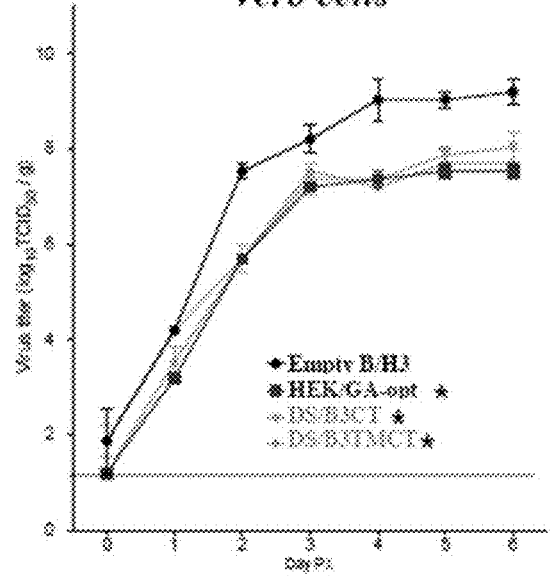

FIG. 26

| Group # | Viruses | Hamster ID | Day 3 | | Hamster ID | Day 5 | |
|---|---|---|---|---|---|---|---|
| | | | NT | Lung | | NT | Lung |
| 1 | Empty 8/83 | 463 | 0 | 0 | 379 | 0 | 0 |
| | | 464 | 0 | 0 | 380 | 0 | 0 |
| | | 465 | 0 | 0 | 381 | 0 | 0 |
| | | 466 | 0 | 0 | 382 | 0 | 0 |
| | | 467 | 0 | 0 | 383 | 0 | 0 |
| | | 468 | 0 | 0 | 384 | 0 | 0 |
| 2 | Non-HEK/non-opt | 469 | NA | NA | 385 | 100 | 100 (p=1) |
| | | 470 | 100 | 100 (p=1) | 386 | 100 | 100 (p=5) |
| | | 471 | 100 | 100 (p=1) | 387 | 99 | 100 |
| | | 472 | 100 (p=1) | 100 (p=1) | 388 | 97 | 100 |
| | | 473 | NA | 100 (p=1) | 389 | 100 | 100 (p=1) |
| | | 474 | 100 | 100 (p=1) | 390 | 100 | NA |
| 3 | Non-HEK/GA-opt | 475 | 100 | NA | 391 | 100 | 100 (p=2) |
| | | 476 | 100 (p=5) | 100 (p=3) | 392 | 100 | 100 (p=2) |
| | | 477 | 100 (p=5) | NA | 393 | 100 | 100 |
| | | 478 | 98 | NA | 394 | 98 | 100 |
| | | 479 | 100 (p=5) | NA | 395 | 97 | 100 |
| | | 480 | 100 (p=5) | NA | 396 | 100 | 100 |
| 4 | HEK/GA-opt | 481 | 100 | NA | 397 | 100 | NA |
| | | 482 | 100 (p=5) | NA | 398 | 100 | NA |
| | | 483 | 100 | NA | 399 | 100 | 100 |
| | | 484 | 100 | NA | 400 | 100 | 100 (p=4) |
| | | 485 | 100 (p=2) | 100 (p=1) | 401 | 100 | 100 |
| | | 486 | 100 (p=7) | 100 (p=3) | 402 | 100 | 100 |
| 5 | HEK/D2-opt | 487 | 100 | 100 (p=1) | 403 | 100 | 92 |
| | | 488 | 100 (p=5) | 100 (p=4) | 404 | 100 (p=1) | NA |
| | | 489 | 100 (p=1) | 100 (p=8) | 405 | 100 | 100 |
| | | 490 | 100 (p=5) | 100 (p=4) | 406 | 100 | NA |
| | | 491 | NA | 100 (p=2) | 407 | 100 | 100 (p=2) |
| | | 492 | NA | NA | 408 | 100 | 100 |
| 6 | HEK/G5-opt | 493 | 100 | 100 | 409 | 100 | 100 |
| | | 494 | 100 | 100 (p=6) | 410 | 100 | 100 |
| | | 495 | 100 | 100 | 411 | 100 | 100 |
| | | 496 | 100 | 100 | 412 | 100 | 100 |
| | | 497 | 100 | 100 (p=2) | 413 | 100 | 100 |
| | | 498 | 100 | 100 (p=4) | 414 | 100 | 100 |
| 7 | HEK/GA-opt/83CT | 499 | 100 (p=1) | NA | 415 | 100 (p=5) | 100 (p=1) |
| | | 500 | NA | NA | 416 | 100 (p=8) | NA |
| | | 501 | NA | NA | 417 | NA | NA |
| | | 502 | NA | NA | 418 | 100 (p=1) | 100 (p=1) |
| | | 503 | NA | NA | 419 | 100 (p=3) | NA |
| | | 504 | NA | NA | 420 | NA | 100 (p=1) |
| 8 | HEK/GA-opt/83TMCT | 505 | 100 (p=3) | NA | 421 | 100 (p=9) | NA |
| | | 506 | NA | NA | 422 | 100 (p=3) | NA |
| | | 507 | 100 (p=8) | NA | 423 | 100 (p=1) | NA |
| | | 508 | 100 (p=1) | NA | 424 | 100 (p=4) | NA |
| | | 509 | 100 (p=1) | NA | 425 | 100 (p=8) | NA |
| | | 510 | 100 (p=3) | NA | 426 | 100 | 100 (p=1) |
| 9 | HEK/GA-opt/Ecto | 511 | 100 | 100 (p=4) | 427 | 100 (p=4) | 100 (p=8) |
| | | 512 | 100 | NA | 428 | 100 | 92 |
| | | 513 | 100 | NA | 429 | 100 | 100 |
| | | 514 | 100 | 100 (p=1) | 430 | 100 | 100 |
| | | 515 | 100 (p=3) | NA | 431 | 98 | 100 |
| | | 516 | 100 | 100 (p=5) | 432 | 98 | 100 |
| 10 | HEK/GA-opt/post-fusion | 517 | 100 | NA | 433 | 100 | 100 |
| | | 518 | 100 | 100 (p=8) | 434 | 100 | 100 |
| | | 519 | 100 (p=6) | 100 (p=6) | 435 | 100 | 100 |
| | | 520 | 100 | 100 (p=3) | 436 | 100 | 100 |
| | | 521 | 98 | 100 (p=8) | 437 | 100 | 100 |
| | | 522 | 100 | 100 | 438 | 100 | 100 |
| 11 | HEK/GA-opt/DS | 523 | NA | 100 (p=1) | 439 | 98 | NA |
| | | 524 | 100 | NA | 440 | 100 | 100 |
| | | 525 | 100 (p=2) | 100 (p=1) | 441 | 100 | 100 |
| | | 526 | 100 | NA | 442 | 100 | 100 (p=1) |
| | | 527 | 100 | NA | 443 | 100 | 100 |
| | | 528 | 100 (p=1) | NA | 444 | 95 | 100 (p=3) |
| 12 | HEK/GA-opt/DS/83CT | 529 | 100 | 100 (p=2) | 445 | 100 | 100 |
| | | 530 | 100 (p=5) | NA | 446 | 99 | 100 |
| | | 531 | 100 (p=7) | 100 (p=1) | 447 | 100 | 88 |
| | | 532 | NA | NA | 448 | 100 | 92 |
| | | 533 | 100 | 100 (p=1) | 449 | 98 | 100 (p=2) |
| | | 534 | 100 (p=3) | NA | 450 | 100 | 100 |
| 13 | HEK/GA-opt/DS/83TMCT | 535 | 100 (p=2) | NA | 451 | 100 (p=5) | 100 (p=1) |
| | | 536 | NA | NA | 452 | 100 | NA |
| | | 537 | 100 (p=3) | NA | 453 | 100 | 100 (p=1) |
| | | 538 | NA | NA | 454 | 95 | NA |
| | | 539 | 100 (p=3) | NA | 455 | 100 (p=6) | 100 (p=1) |
| | | 540 | 100 (p=2) | NA | 456 | 100 | 100 (p=2) |

FIG. 27

| Group # | Viruses | Virus titer at permissive temp of 32°C (log10 pfu/ml) | Virus titer (log₁₀ PFU/ml) at increasing temperature | | | | | |
|---|---|---|---|---|---|---|---|---|
| | | | 35°C | 36°C | 37°C | 38°C | 39°C | 40°C |
| 1 | Empty B/H3 | 6.3 | 6.4 | 6.3 | 6 | 5.7 | 5.4 | 2.2 |
| 2 | Non-HEK/non-opt | 7.7 | 7 | 7.2 | 6.4 | 4.3 | 3.6 | <1.7 |
| 3 | Non-HEK/GA-opt | 7.2 | 6.5 | 6 | 5.3 | 4.3 | <1.7 | <1.7 |
| 4 | HEK/GA-opt | 6.9 | 6.5 | 6 | 5.4 | 4.9 | 3.3 | <1.7 |
| 5 | HEK/D2-opt | 7.4 | 7 | 6.6 | 6.5 | 5.7 | <1.7 | <1.7 |
| 6 | HEK/Ds-opt | 7.8 | 7.6 | 7.2 | 6.8 | 5.7 | 3.3 | <1.7 |
| 7 | HEK/GA-opt/B3CT | 7.3 | 6.7 | 5.8 | 4.9 | <1.7 | <1.7 | <1.7 |
| 8 | HEK/GA-opt/B3TMCT | 7.7 | 6.8 | 6.1 | 5.2 | <1.7 | <1.7 | <1.7 |
| 9 | HEK/GA-opt/Ecto | 7.3 | 6.8 | 6.6 | 5.9 | 4.7 | <1.7 | <1.7 |
| 10 | HEK/GA-opt/post-fusion | 7.6 | 6.9 | 6.8 | 5.9 | 5.3 | <1.7 | <1.7 |
| 11 | HEK/GA-opt/DS | 7.2 | 6.8 | 6.3 | 5.9 | 4.7 | <1.7 | <1.7 |
| 12 | HEK/GA-opt/DS/B3CT | 6.8 | 6.6 | 5.9 | 5.3 | 2.9 | <1.7 | <1.7 |
| 13 | HEK/GA-opt/DS/B3TMCT | 6.5 | 5.9 | 5.3 | 5 | | | |

FIG. 28

Non-HEK/non-opt (n = 5)

HEK/GA-opt/DS (n = 5) — S155C, S290C

HEK/GA-opt/DS/B3TMCT (n = 4) — (66E, 101P), S155C, S290C (All above versions of RSV F are HEK, GA codon-optimized)

B/HPIV3

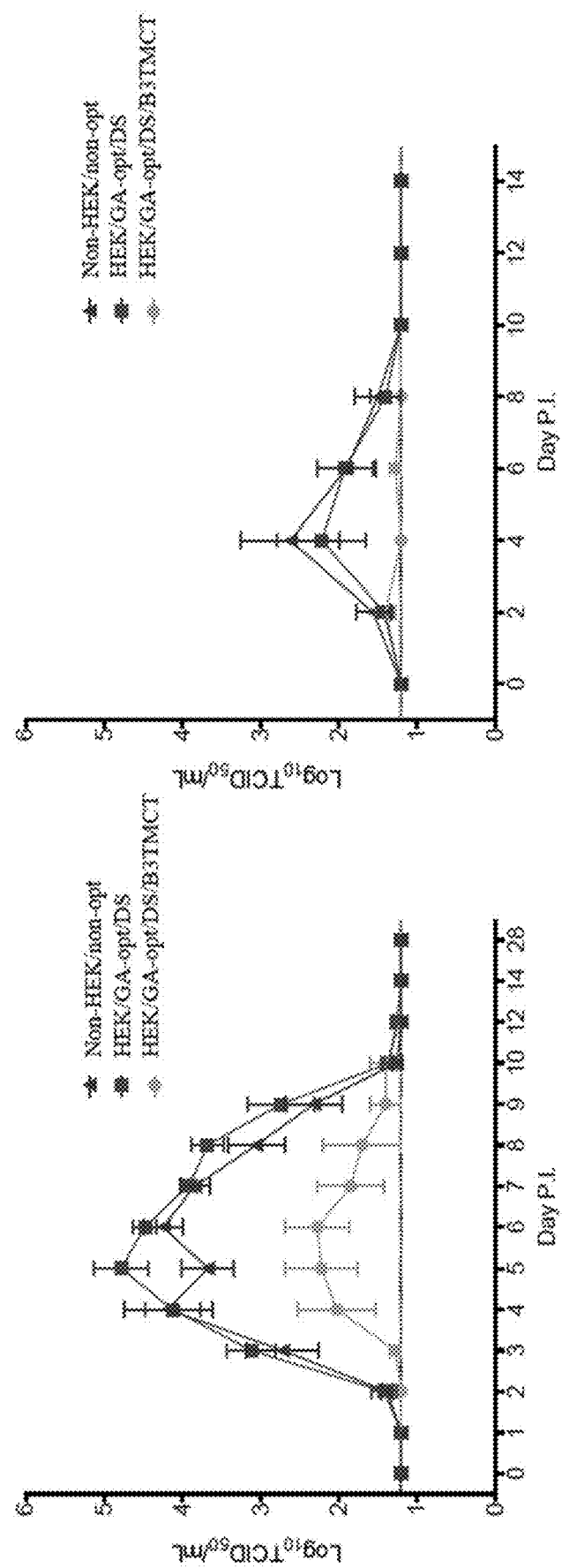
FIG. 29A Nasopharyngeal swab
FIG. 29B Tracheal lavage

FIG. 33

| Viruses | Monkey ID | % of viruses in NP swab expressing RSVF | | |
|---|---|---|---|---|
| | | Day 4 | Day 5 | Day 6 |
| Non-HEK/non-opt | RH37033 | 100 | ≥97 | ≥98 |
| | RH37051 | 91 | 93 | 93 |
| | RH37057 | 97 | ≥99 | ≥98 |
| | RH37063 | ≥99 | 92 | ≥98 |
| | RH37380 | ≥98 | ≥98 | ≥99 |
| HEK/GA-opt/DS | RH37034 | ≥98 | 94 | 100 |
| | RH37073 | ≥99 | ≥99 | 100 |
| | RH37078 | 93 | ≥98 | 96 |
| | RH37103 | ≥98 | ≥98 | ≥98 |
| | RH37760 | ≥99 | 95 | 96 |
| HEK/GA-opt/DS/B3TMCT | RH38487 | NA | NA | NA |
| | RH37324 | ≥98 | ≥99 | 100 |
| | RH37140 | 100 | 93 | 100 |
| | RH37360 | 100 | ≥98 | ≥99 |

Indicates 100% viruses in this sample expressed RSV F
Indicates 90-99% viruses in this sample expressed RSV F Samples with ≥98 or ≥99 % of viruses expressing RSV F indicates that only 1-2 out of more than 50 overlapping plaques did not have RSV F expression (an example shown in Figure 33 D-F).

"NA" means no plaque was developed with that sample.

Examples of plaque images were shown with arrows pointing to corresponding tissue specimens. All plaques were derived directly from tissue without further passaging.

FIG. 35

| | Viruses | 1st hamster study | 1st NHP study (14RSV02) | 2nd hamster study | 2nd NHP study (15PIV06) |
|---|---|---|---|---|---|
| 1 | Non-HEK/non-opt | X | X | X | |
| 2 | Non-HEK/GA-opt | | | | |
| 3 | HEK/GA-opt | X | | | |
| 4 | HEK/DNA2.0-opt | | | | |
| 5 | HEK/GS-opt | X | | X | |
| 6 | HEK/GA-opt/B3CT | X | | | |
| 7 | HEK/GA-opt/B3TMCT | X | | X | |
| 8 | HEK/GA-opt/Ecto | X | | | |
| 9 | HEK/GA-opt/Postfusion | X | | | |
| 10 | HEK/GA-opt/DS | X | X | X | X |
| 11 | HEK/GA-opt/DS/B3CT | X | | | |
| 12 | HEK/GA-opt/DS/B3TMCT | X | X | X | |
| 13 | HEK/GA-opt/DS-Cav1 | | | X | |
| 14 | HEK/GA-opt/DS-Cav1/B3CT | | | | |
| 15 | HEK/GA-opt/DS-Cav1/B3TMCT | | | X | X |
| 16 | HEK/GS-opt/DS-Cav1 | | | X | |
| 17 | HEK/GS-opt/DS-Cav1/B3CT | | | | |
| 18 | HEK/GS-opt/DS-Cav1/B3TMCT | | | X | X |
| 19 | HEK/GS-opt/DS-Cav1/(1-513) Foldon | | | X | |

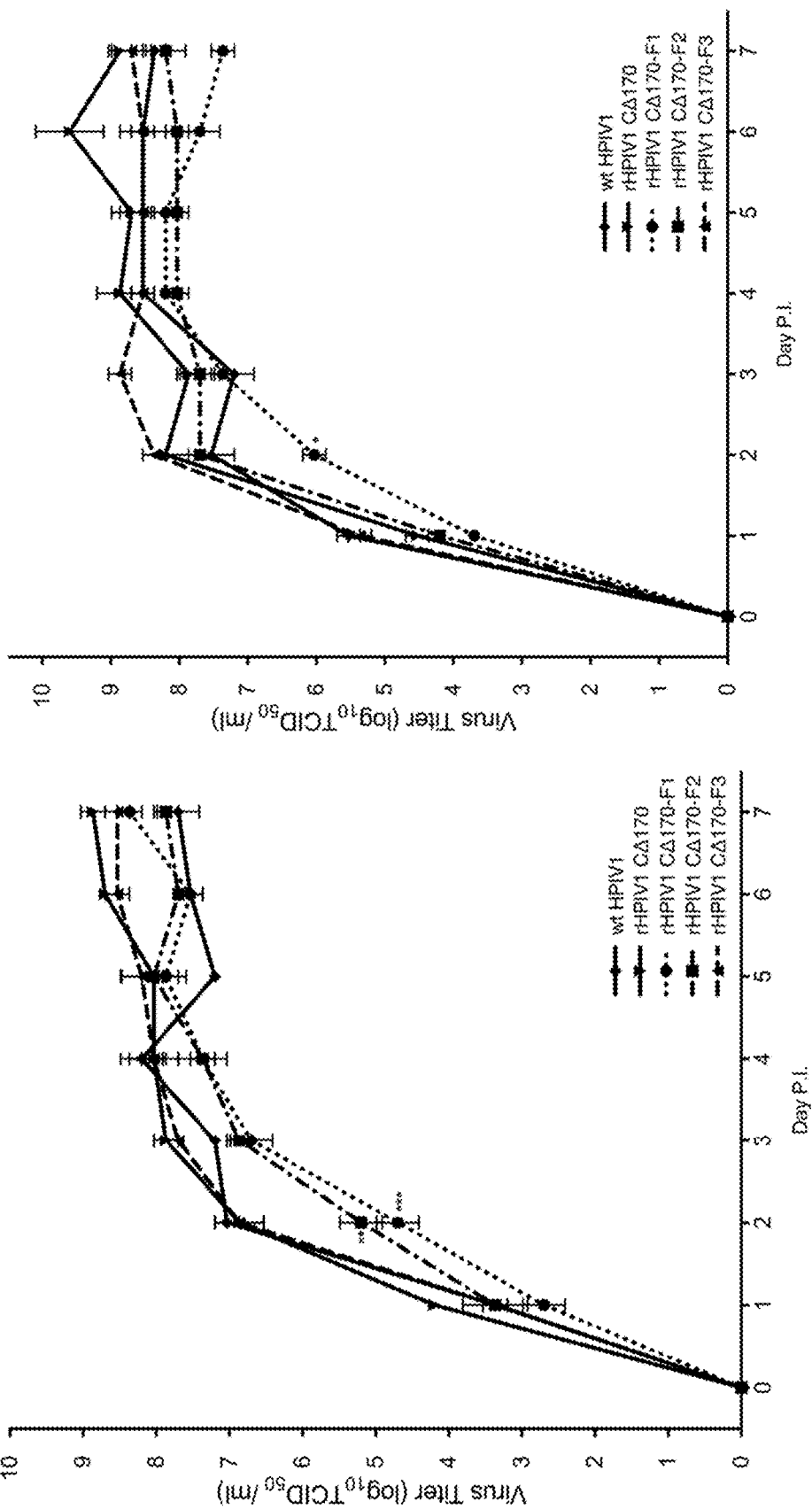

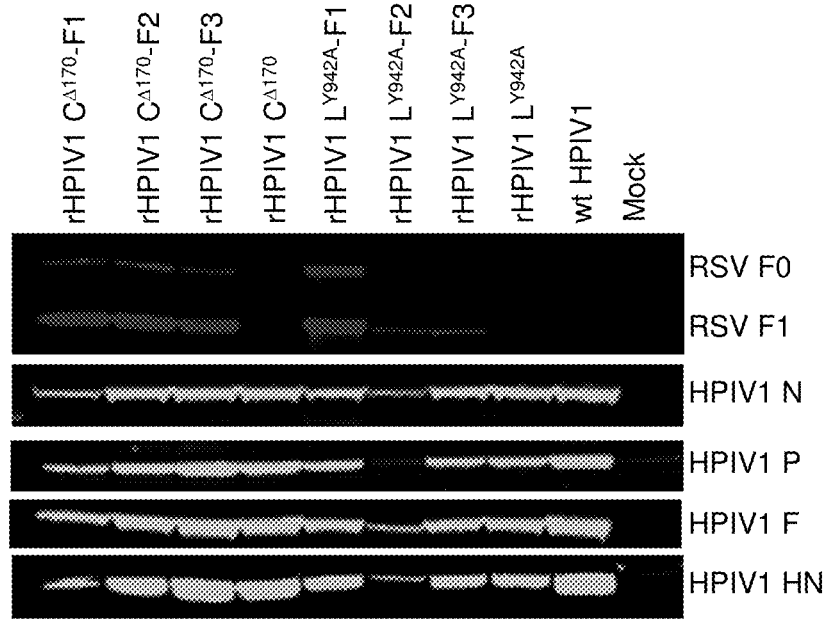

FIG. 39A
rHPIV1 C$^{\Delta170}$-F1

FIG. 39B
rHPIV1 C$^{\Delta170}$-F2

FIG. 39C
rHPIV1 C$^{\Delta170}$-F3

FIG. 39D
rHPIV1 C$^{\Delta170}$

FIG. 39E
rHPIV1 L$^{Y942A}$-F1

FIG. 39F
rHPIV1 L$^{Y942A}$-F2

FIG. 39G
rHPIV1 L$^{Y942A}$-F3

FIG. 39H
rHPIV1 L$^{Y942A}$

FIG. 39I
wt HPIV1

FIG. 42

Attenuating mutations introduced in the HPIV1 backbone in the P/C or the L ORF

| Gene | Mutation | ORF | Nucleotide changes → mutant | Type of mutation | Codon position | Amino acid change | # of nucleotide changes needed for reversion to wt |
|---|---|---|---|---|---|---|---|
| P/C | Δ170 | C | AGG GAT TTC → AGC | deletion | 168-170 | RDF → S (D Deletion; 3 nt deletions in the flanking R-F codons resulting in an S substitution) | 6 (insertions) |
| L | Y942A | L | TAT → GCG | Substitution | 942 | Y → A | 3 |

FIG. 43

Temperature sensitivity of recombinant viruses on LLC-MK2 cell monolayers

| Virus | Virus Titer ($\log_{10}$ TCID$_{50}$/ml) at | | | | | | |
|---|---|---|---|---|---|---|---|
|  | 32°C | 35°C | 36°C | 37°C | 38°C | 39°C | 40°C |
| wt rHPIV1 | 7.7 | 8.5 | 7.5 | 7.5 | 8.0 | 7.2 | 6.2 |
| rHPIV1 C$^{\Delta170}$ | 7.0 | 7.0 | 6.5 | 6.2 | 6.7 | 6.5 | 3.2 |
| rHPIV1 L$^{Y942A}$ | 8.0 | 7.2 | 5.2 | 4.5 | 2.2 | ≤1.2 | ≤1.2 |
| rHPIV1 C$^{\Delta170}$-F1 | 7.0 | 6.7 | 7.0 | 6.2 | 6.2 | 3.2 | 1.5 |
| rHPIV1 C$^{\Delta170}$-F2 | 8.2 | 6.5 | 7.7 | 7.0 | 7.7 | 6.5 | 2.2 |
| rHPIV1 C$^{\Delta170}$-F3 | 8.0 | 8.0 | 7.5 | 8.0 | 7.7 | 6.7 | 2.0 |
| rHPIV1 L$^{Y942A}$-F1 | 7.0 | 4.7 | 4.7 | 1.5 | 1.5 | ≤1.2 | ≤1.2 |
| rHPIV1 L$^{Y942A}$-F2 | 5.5 | 3.2 | ≤1.2 | ≤1.2 | ≤1.2 | ≤1.2 | ≤1.2 |
| rHPIV1 L$^{Y942A}$-F3 | 8.2 | 7.2 | 5.5 | 4.2 | ≤1.2 | ≤1.2 | ≤1.2 |

FIG. 44

Percentage of virus population expressing RSV F after *in vivo* replication

| | % PFU expressing RSV F | |
|---|---|---|
| | Day 3 | Day 5 |
| Virus | Nasal Turbinate | Nasal Turbinate |
| rHPIV1 $C^{\Delta 170}$-F1 | 100 (6/6) | 100 (5/6) <br> 98 (1/6) |
| rHPIV1 $C^{\Delta 170}$-F2 | 100 (6/6) | ND |
| rHPIV1 $C^{\Delta 170}$-F3 | 100 (6/6) | 100 (6/6) |

FIG. 45

Immunization of hamsters with rHPIV1 expressing RSV F induces serum neutralizing antibodies against RSV

| | Neutralizing serum antibody response (mean reciprocal $\log_2 \pm$ SE) to: | | | |
|---|---|---|---|---|
| | RSV | | HPIV1 | |
| Immunizing Virus | Pre | Day 28 | Pre | Day 28 |
| rHPIV1 $C^{\Delta 170}$ | ≤ 3.3 | ≤ 3.3 (A) | ≤ 1 | 3.9 ± 0.3 (A) |
| rHPIV1 $L^{Y942A}$ | ≤ 3.3 | ≤ 3.3 (A) | ≤ 1 | ≤ 1 (B) |
| rHPIV1 $C^{\Delta 170}$-F1 | ≤ 3.3 | 7.3 ± 0.3 (B, C) | ≤ 1 | 2.8 ± 0.5 (A) |
| rHPIV1 $C^{\Delta 170}$-F2 | ≤ 3.3 | 4.7 ± 0.7 (C) | ≤ 1 | ≤ 1 (B) |
| rHPIV1 $C^{\Delta 170}$-F3 | ≤ 3.3 | 6.7 ± 0.8 (C, B) | ≤ 1 | ≤ 1 (B) |
| rHPIV1 $L^{Y942A}$-F1 | ≤ 3.3 | ≤ 3.3 (A) | ≤ 1 | ≤ 1 (B) |
| rHPIV1 $L^{Y942A}$-F2 | ≤ 3.3 | ≤ 3.3 (A) | ≤ 1 | ≤ 1 (B) |
| rHPIV1 $L^{Y942A}$-F3 | ≤ 3.3 | ≤ 3.3 (A) | ≤ 1 | ≤ 1 (B) |
| rB/HPIV3-F2 | ≤ 3.3 | 9.7 ± 0.4 (D) | ≤ 1 | ≤ 1 (B) |
| wt RSV | ≤ 3.3 | 11.3 ± 0.4 (D) | ≤ 1 | ≤ 1 (B) |

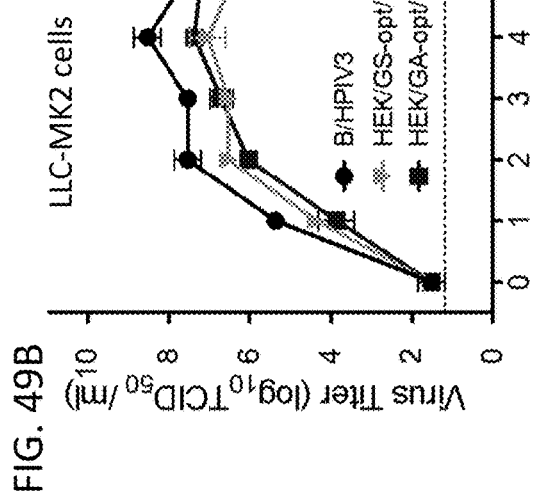
FIG. 49A
FIG. 49B
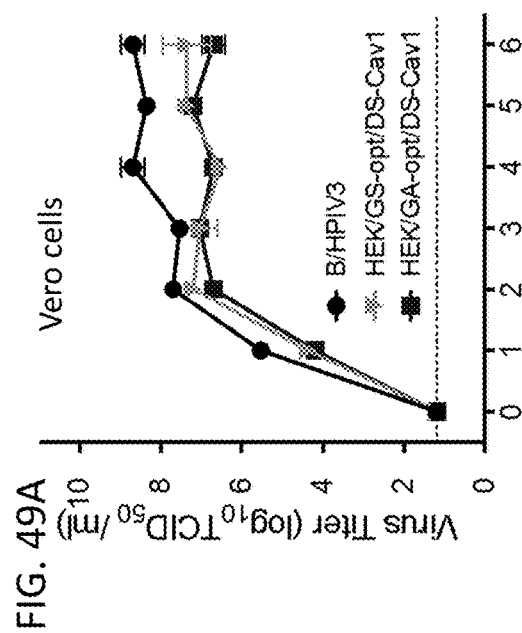
FIG. 49C
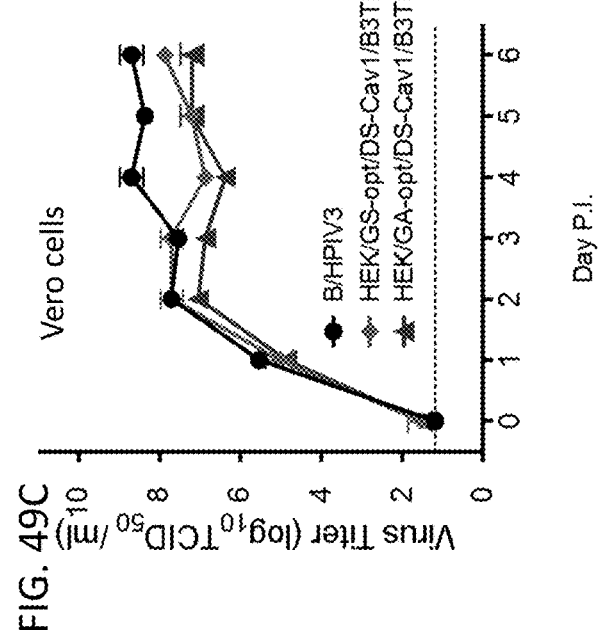
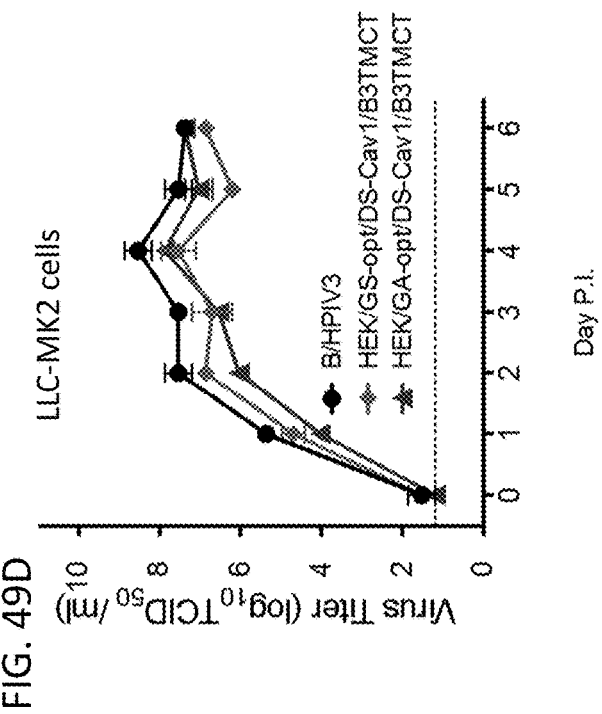
FIG. 49D

FIG. 50A

Lanes (1-8):
1. Empty B/H3
2. HEK/GA-opt
3. HEK/GS-opt
4. HEK/GS-opt/DS-Cav1
5. HEK/GS-opt/DS-Cav1/B3TMCT
6. wtRSV
7. Mock
8. HEK/GS-opt/DS-Cav1/(1-513)Foldon RSV $F_0$
RSV $F_1$
GAPDH
BPIV3 N
secreted RSV F ($F_1$)

Vero
32C, 48h p.i

FIG. 50B

RSV $F_0$
RSV $F_1$
GAPDH
BPIV3 N

LLC-MK2
32C, 48h p.i

FIG. 50C

RSV $F_0$
RSV $F_1$
GAPDH
BPIV3 N

LLC-MK2
37C, 48h p.i

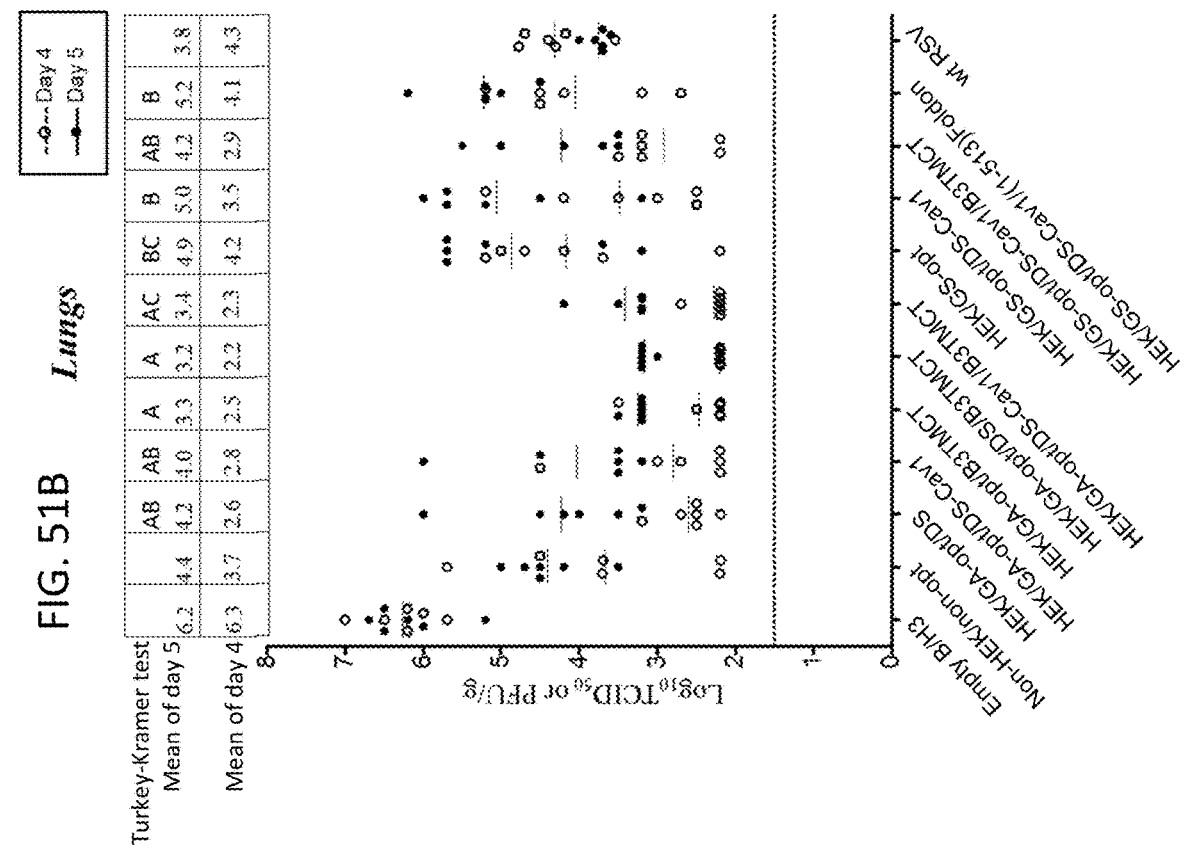
FIG. 51B *Lungs*
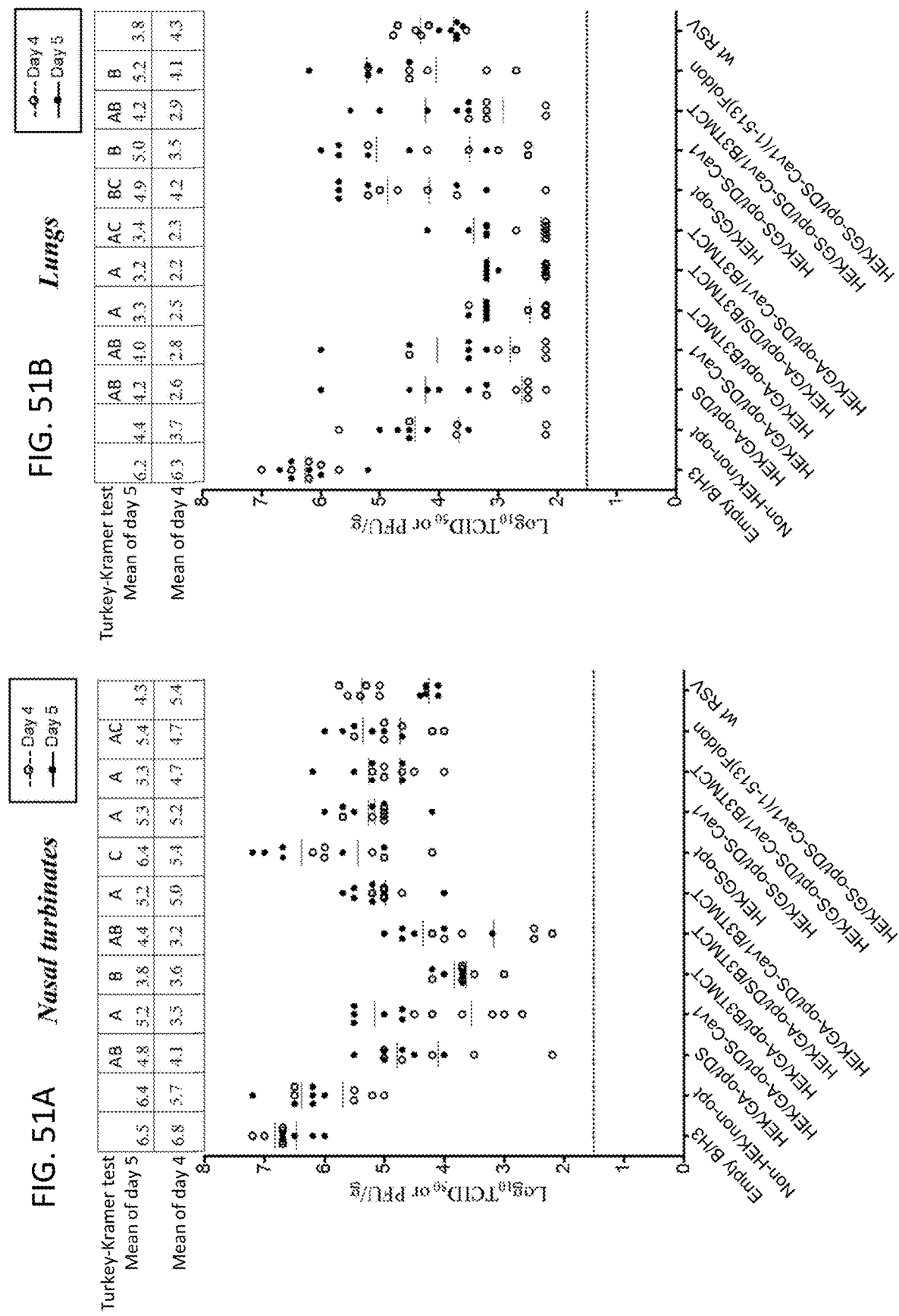
FIG. 51A *Nasal turbinates*

*Tracheal lavages*

*Nasopharyngeal swabs*

FIG. 58A  B/HPIV3-wtHN-RSVF (HEK/GS-opt/DS-Cav1/B3TMCT/pre-N)

HEK/GS-opt/DS-Cav1/B3TMCT 0  22     109 136    S155C S190F V207L    S290C                    530 551 576
                                                                    B3  B3
                                                                    TM  CT rB/HPIV3-wtHN
(B/H3)

N   P   M   F   HN   L
         I263T  T370P
              TM

FIG. 58B  Correction of HN assignments (aa 263 and 370) to wt HPIV3 HN in B/HPIV3

Mutant HN*
            7593
             |
7589-- AAT ATA GAT
       N   I   D
      262 263 264 wt HN
7589-- AAT ACA GAT
       N   T   D
      262 263 264

Mutant HN*
            7913 7915
             |   |
7910-- AGT ACT TGG
       S   T   W
      369 370 371 wt HN
7910-- AGT CCA TGG
       S   P   W
      369 370 371

*"mutant HN" = the assignments in the original recombinant HPIV3 (Durbin et al Virology 235:323-332 1997)

FIG. 59A

[Western blot labels — Vero cells]
RSV F0 Fragment
RSV F1 Fragment
B/HPIV3 P Protein
B/HPIV3 N Protein
GAPDH Lanes:
1. empty B/H3
2. wt RSV
3. DS-Cav1/HEK/GS-opt/pre-N
4. CL20a (wtHHN/HEK/GS-opt/pre-N)
5. CL24a (wtHN/B3TMCT/pre-N)
6. DS-Cav1/B3TMCT/pre-N
7. HEK/GS-opt/non-opt/pre-N / Mock

FIG. 59B

LLC-MK2

RSV F0 Fragment
RSV F1 Fragment
B/HPIV3 P Protein
B/HPIV3 N Protein
GAPDH

FIG. 60   TM and CT Domains of RSV F protein and HPIV1 F protein

|  | Ectodomain |  | TM |  | CT |  |
|---|---|---|---|---|---|---|
| RSV A2 F | 510 | DELLHNVNAGKSTTNIMITT | 530 | IIIVIIVILLLSLIAVGLLLYC | 551 | KARSTPVTLSKDQLSGINNIAFSN |
| HPIV1 F | 477 | LMKARAIISAVGGWHNTEST | 497 | QIMIIIVCILIIIICGILYYLY | 520 | RVRRLLVMINSTHNSPVNAYTLESRMRNPYMGNNSN |
| RSV F-TMCT | 510 | DELLHNVNAGKSTTNIMITT | 530 | QIMIIIVCILIIIICGILYYLY | 553 | RVRRLLVMINSTHNSPVNAYTLESRMRNPYMGNNSN |

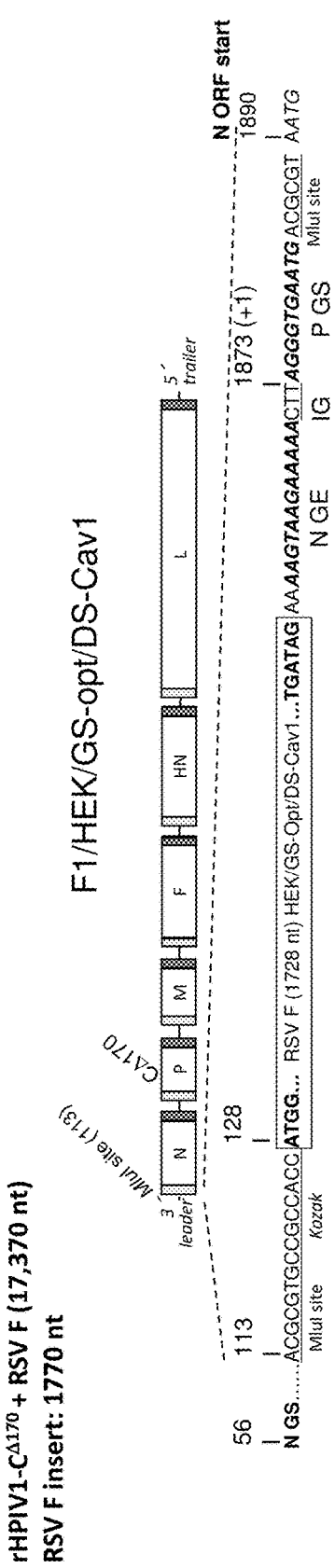
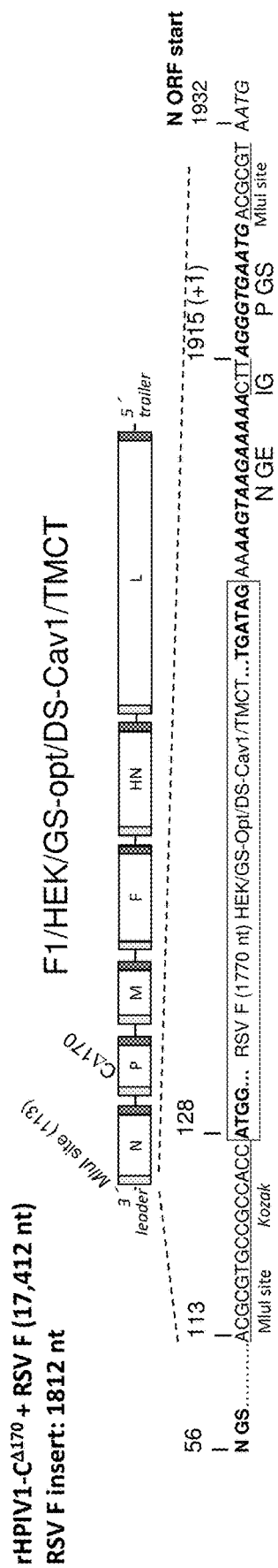
FIG. 61

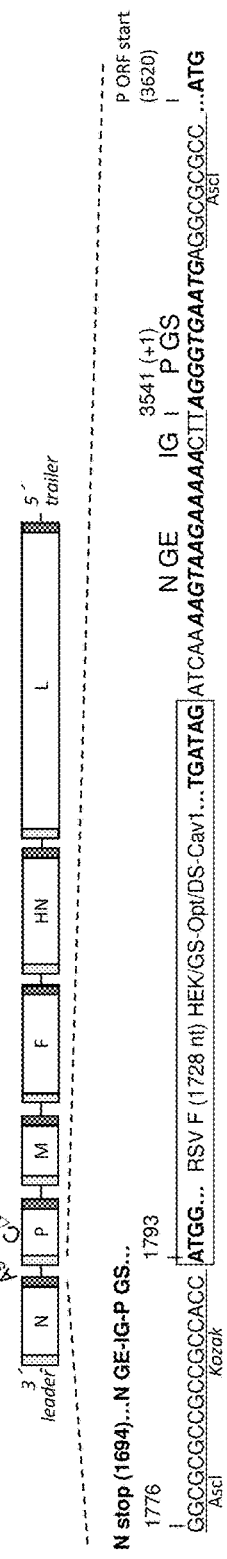
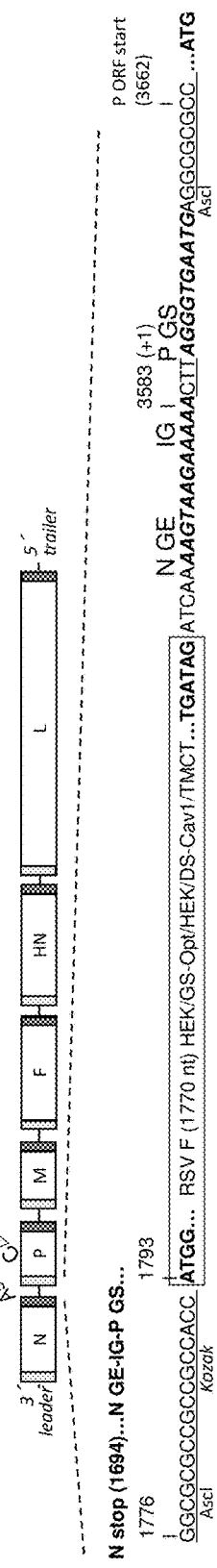
FIG. 62

FIG. 63 rHPIV1-C$^{\Delta170}$ vectors expressing RSV F/HEK/GS-opt/DS-Cav1 +/- TMCT, from the F1 or F2 position

- wt HPIV1
- rHPIV1 C$\Delta$170
- rHPIV1 C$\Delta$170-F1/DS Cav1
- rHPIV1 C$\Delta$170-F1/DS Cav1-TMCT
- rHPIV1 C$\Delta$170-F2/DS Cav1
- rHPIV1 C$\Delta$170-F2/DS Cav1-TMCT Y-axis: Virus Titer (log$_{10}$ TCID$_{50}$/ml)
X-axis: Day P.I.

FIG. 64

Lanes:
1. wt HPIV1
2. rHPIV1 C$\Delta$170
3. rHPIV1 C$\Delta$170-F1/DS-Cav1
4. rHPIV1 C$\Delta$170-F1/DS-Cav1/TMCT
5. rHPIV1 C$\Delta$170-F2/DS-Cav1
6. rHPIV1 C$\Delta$170-F2/DS-Cav1/TMCT
7. wt RSV Blots: RSV F, HPIV1 N, HPIV1 HN, HPIV1 F$_0$, HPIV1 F$_1$, RSV F$_1$

FIG. 66

RSV F and HPIV3 F TM and CT Domains

| | Ectodomain | | TM | | CT |
|---|---|---|---|---|---|
| RSV A2 F | 510 | DELLHNVNAGKSTTNIMITT | 530 | IIIVIIVILLSLIAVGLLLYC | 551 | KARSTPVTLSKDQLSGINNIAFSN |
| HPIV3 F | 474 | IRRSNQKLDSIGNWHQSSTT | 494 | IIIILIMIIILFIINITIIITIAI | 517 | KYYRIQKRNRVDQNDKPYVLTNK |
| RSV F-H3TMCT | 510 | DELLHNVNAGKSTTNIMITT | 530 | IIIILIMIIILFIINITIIITIAI | 553 | KYYRIQKRNRVDQNDKPYVLTNK |

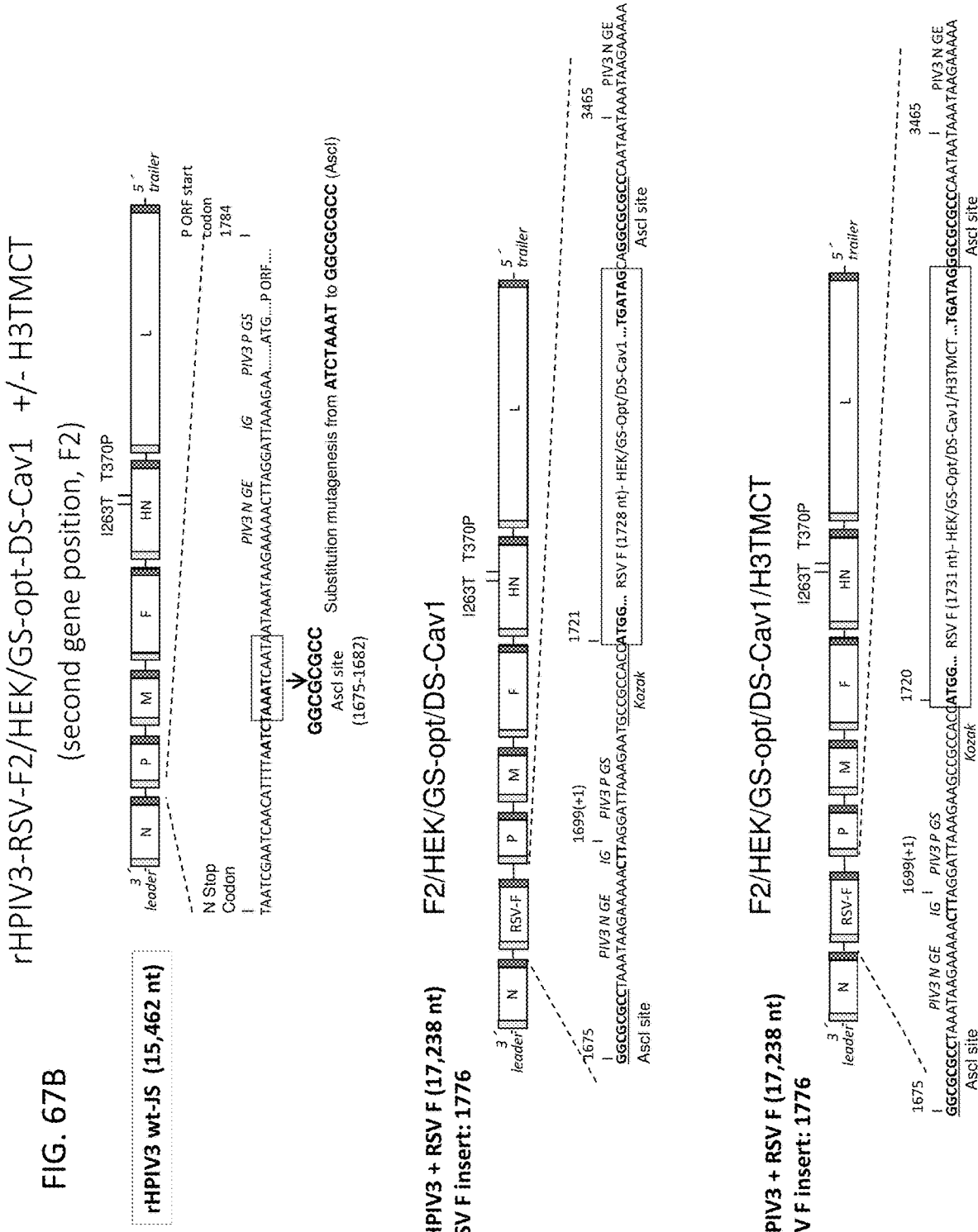

RECOMBINANT HUMAN PARAINFLUENZA VIRUS TYPE 1 EXPRESSING A CHIMERIC RSV/HPIV1 F PROTEIN AND USES THEREOF

CROSS REFERENCE TO RELATED APPLICATIONS

This application is a continuation of U.S. application Ser. No. 16/877,319, filed May 18, 2020, which is a continuation of U.S. application Ser. No. 15/545,218, filed Jul. 20, 2017, now U.S. Pat. No. 10,654,898, which is the U.S. National Stage of International Application No. PCT/US2016/014154, filed Jan. 20, 2016, which was published in English under PCT Article 21(2), which in turn claims the benefit of U.S. Provisional Application No. 62/105,667, filed Jan. 20, 2015. The contents of each of the above-listed applications are incorporated by reference herein in their entirety.

FIELD

This disclosure relates to recombinant paramyxoviruses that include a viral genome including a heterologous gene encoding an antigen of a heterologous virus. For example, the recombinant paramyxovirus can be a recombinant parainfluenza virus (PIV) that includes a genome including a heterologous gene encoding a respiratory syncytial virus (RSV) fusion (F) protein.

BACKGROUND

Paramyxoviruses are a family of negative-sense single stranded RNA viruses that account for many animal and human deaths worldwide each year. The paramyxoviruses include sub-families Paramyxovirinae and Pneumovirinae. Respiratory syncytial virus (RSV) is an enveloped non-segmented negative-strand RNA virus in the family Paramyxoviridae, genus Pneumovirinae. It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems. Passive immunization currently is used to prevent severe illness caused by RSV infection, especially in infants with prematurity, bronchopulmonary dysplasia, or congenital heart disease. Despite the burden of RSV infection in certain populations, development of an effective RSV vaccine remains elusive.

Parainfluenza virus (PIV) is another enveloped non-segmented negative-strand RNA virus that, like RSV, is in the paramyxovirus family. However, PIVs are in subfamily Paramyxovirinae. PIVs include members of the genus respirovirus (including PIV1, PIV3, Sendai virus) and rubulavirus (including PIV2, PIV4, PIV5). In addition the members of genus avulavirus (including Newcastle disease virus NDV) historically were termed PIVs and operationally can be considered the same. The human parainfluenza viruses (HPIVs, serotypes 1, 2, and 3) are second only to RSV in causing severe respiratory infections in infants and children worldwide, with HPIV3 being the most important of the HPIVs in terms of disease impact. The HPIV genome is approximately 15.5 kb, including a gene order of 3'-N-P-M-F-HN-L. Each gene encoding a separate mRNA that encodes a major protein: N, nucleoprotein; P, phosphoprotein; M, matrix protein; F, fusion glycoprotein; HN, hemagglutinin-neuramindase glycoprotein; L, large polymerase protein. The P gene contains one or more additional open reading frames (ORFs) encoding accessory proteins. Similar to RSV, development of an effective HPIV vaccine remains elusive.

SUMMARY

Recombinant paramyxoviruses including a viral genome encoding a heterologous gene are provided. In several embodiments, the recombinant paramyxovirus can be a recombinant parainfluenza virus comprising a viral genome comprising a heterologous gene encoding a type I membrane protein comprising a recombinant RSV F ectodomain linked to a cytoplasmic tail (CT), or a transmembrane domain (TM) and a CT, of an F protein of the paramyxovirus. The paramyxovirus can be, for example, a recombinant human/bovine parainfluenza virus 3 (B/HPIV3), a recombinant human parainfluenza virus 1 (HPIV1), a recombinant human parainfluenza virus 2 (HPIV2), a recombinant human parainfluenza virus 3 (HPIV3), or a recombinant bovine parainfluenza virus 3 (BPIV3).

Surprisingly, swapping the TM and CT of the heterologous RSV F protein for the corresponding TM and CT of the paramyxovirus F protein provided a multi-fold increase in RSV F ectodomain incorporation in the envelope of recombinant paramyxovirus, and dramatically increased the elicitation of an immune response to the ectodomain when the recombinant paramyxovirus was administered to a subject. Further, the induction of virus-neutralizing serum antibodies was dramatically increased both in quantity and in quality. Accordingly, in several embodiments, the disclosed recombinant paramyxoviruses can be included in immunogenic compositions for eliciting a bivalent immune response to the paramyxovirus and the heterologous RSV F protein.

The RSV F ectodomain encoded by the heterologous gene can be from a human RSV F protein. In several embodiments the RSV F ectodomain can include one or more amino acid substitutions (such as the "DS-Cav1" substitutions, S155C, S290C, S190F, and V207L) to stabilize the ectodomain in a RSV F prefusion conformation. In additional embodiments, the RSV F ectodomain can include one more amino acid substitutions to increase ectodomain expression or incorporation in the viral envelope (such as the "HEK" substitutions, K66E and Q101P).

In a non-limiting embodiment, the recombinant paramyxovirus can be a recombinant B/HPIV3 and the RSV F ectodomain is linked to a TM and CT from a BPIV3 F protein. In some such embodiments, the RSV F ectodomain linked to the TM and CT from the BPIV3 F protein comprises the amino acid sequence set forth as SEQ ID NO: 21, or an amino acid sequence at least 90% identical to SEQ ID NO: 21.

In several embodiments, the recombinant paramyxovirus is a recombinant PIV comprising a viral genome comprising, from upstream to downstream: a PIV genomic promoter followed by the N, P, M, F, HN, and L genes. In some such embodiments, the heterologous gene included in the viral genome can be located between the genomic promoter and the gene encoding the N protein, or between the genes encoding the N and the P protein.

In additional embodiments, the heterologous gene included in the viral genome of the recombinant paramyxovirus can be codon-optimized for expression in human cells. In more embodiments, the recombinant paramyxovirus can be an attenuated virus. In other embodiments, the added gene and its encoded protein can provide attenuation needed for a vaccine candidate.

Immunogenic compositions including the recombinant paramyxovirus are also provided. The compositions can further include an adjuvant. Methods of generating an immune response in a subject by administering an effective amount of a disclosed recombinant paramyxovirus to the subject are also disclosed. Further provided are isolated nucleic acid molecules including the viral genome of any of the recombinant paramyxoviruses disclosed herein.

The foregoing and other features and advantages of this disclosure will become more apparent from the following detailed description of several embodiments which proceeds with reference to the accompanying figures.

BRIEF DESCRIPTION OF THE FIGURES

FIGS. 2A and 2B. The presence of the HEK assignments in the RSV F protein resulted in increased protein expression and a reduction in protein trimer mobility in polyacrylamide gel electrophoresis compared to that of non-HEK F protein. Vero cells were infected with vectors expressing HEK or non-HEK RSV F (from GA-optimized ORFs, shown in FIG. 1) at an MOI of 10 $TCID_{50}$ at 32° C. Cell lysates were prepared at 48 hours post-infection. Equal amounts of cell lysates were analyzed by electrophoresis after being boiled and reduced (A) or without being boiled and reduced (B). Denatured and reduced RSV F monomer was detected with a commercially-obtained RSV F-specific mouse monoclonal antibody (A). Native RSV F trimer was detected with polyclonal antibodies raised in rabbits by repeated immunizations with sucrose purified RSV particles (B).

FIGS. 7A and 7B. Multi-cycle in vitro replication of rB/HPIV3 vectors expressing HEK or non-HEK RSV F protein from non-optimized or codon-optimized ORFs. (A) LLC-MK2 and (B) Vero cells were infected in triplicate at 32° C. at an MOI of 0.01 $TCID_{50}$ with empty rB/HPIV3 vector (empty B/H3) or vector expressing the RSV F ORF that was non-HEK-containing and non-optimized (Non-HEK/non-opt) or was non-HEK-containing and GA-optimized (Non-HEK/GA-opt) or was HEK-containing and GA-optimized (HEK/GA-opt) or was HEK-containing and GS-optimized (HEK/GS-opt). Aliquots of medium supernatant were collected at 24 h intervals for 6 days and viral titers were determined by limiting dilution assay on LLC-MK2 cells at 32° C. and reported as $TCID_{50}$/ml. Mean titers±SEM from three independent experiments are shown.

FIGS. 8A and 8B. Replication in hamsters of rB/HPIV3 vectors expressing HEK or non-HEK RSV F protein from non-optimized or codon-optimized ORFs. Golden Syrian hamsters were infected intranasally (IN) with 105 $TCID_{50}$ of the indicated rB/HPIV3 vectors or $10^6$ PFU of wt RSV (strain A2) in a 0.1 ml inoculum. Hamsters were euthanized (n=6 per virus per day) on day 3 and 5 post-infection and the (A) nasal turbinates and (B) lungs were removed and homogenized and viral titers were determined by limiting dilution on LLC-MK2 (rB/HPIV3 vectors) or Vero (RSV) cells at 32° C.: open and closed circles indicate titers for animals sacrificed on day 3 and 5, respectively. Each symbol represents an individual animal, and the mean titer of each group is indicated by a dashed and a solid horizontal line for day 3 and 5, respectively. The limit of detection (LOD) was 1.5 $\log_{10}$ $TCID_{50}$/g of tissue, indicated with a dotted line. The rB/HPIV3 vectors were titrated by limiting dilution assays on LLC-MK2 cells and reported as $TCID_{50}/g$; RSV was titrated by plaque assays on Vero cells and reported as PFU/g.

FIGS. 10A and 10B. Protection of immunized hamsters against RSV challenge. The hamsters (n=6 animals per virus) that had been immunized as shown in FIG. 9 with the indicated rB/HPIV3 vectors or with wt RSV, were challenged IN on day 31 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells. Each symbol represents an individual animal and mean viral titers of the groups are shown as horizontal lines. The detection limit of the assay was $log_{10}$ 2.7 PFU/g of tissue, indicated as a dashed line.

FIGS. 14A and 14B. Replication in hamsters of rB/HPIV3 vectors expressing secreted (Ecto), post-fusion, and stabilized pre-fusion forms of the RSV F protein. Hamsters were infected IN with 105 $TCID_{50}$ of the indicated rB/HPIV3 vectors or $10^6$ PFU of wt RSV in a 0.1 ml inoculum. Hamsters were euthanized (n=6 per virus per day) on days 3 and 5 post-infection and the (A) nasal turbinates and (B) lungs were removed and homogenized and viral titers were determined by limiting dilution on LLC-MK2 cells (rB/HPIV3 vectors) or Vero (RSV) cells at 32° C.: open and closed circles indicate titers for animals sacrificed on day 3 and 5, respectively. Each symbol represents an individual animal, and the mean titer of each group is indicated by a dashed or solid horizontal line for day 3 and 5, respectively. Mean values of day 5 titers are shown at the top. The rB/HPIV3 vectors were titrated by limiting dilution assays on LLC-MK2 cells and reported as $TCID_{50}/g$; RSV was titrated by plaque assays on Vero cells and reported as PFU/g. The limit of detection (LOD) is 1.5 $log_{10}$ $TCID_{50}/g$ of tissue, indicated with a dotted line. The statistical significance of difference among peak titers was determined by Tukey-Kramer test and indicated by asterisks; *, P≤0.05; , P≤0.01; or *, P≤0.001. The constructs indicated by asterisk * contained the HEK assignments and were GA-optimized for human expression.

FIGS. 15A and 15B. Serum RSV-neutralizing antibody titers from hamsters infected with rB/HPIV3 vectors expressing secreted (Ecto), post-fusion, and stabilized pre-fusion forms of the RSV F protein. Hamsters (n=6 animals per virus) were inoculated IN with 105 $TCID_{50}$ of the indicated rB/HPIV3 vectors or $10^6$ PFU of wt RSV in a 0.1 ml inoculum. Serum samples were collected at 28 days post-immunization, and RSV-neutralizing antibody titers were determined by a 60% plaque reduction neutralization test ($PRNT_{60}$) performed on Vero cells at 32° C. (A) with and (B) without added guinea pig complement. The height of each bar represents the mean titer. The values of mean titers are shown above the bars. The standard error of the mean is shown by the horizontal lines. The detection limit for the neutralization assay is indicated with a dotted line. ND means neutralization titer is below the detection limit. The statistical significance of difference among groups was determined by Tukey-Kramer test and indicated by asterisks; *, P≤0.05; , P≤0.01; or *, P≤0.001; or ns, P>0.05.

FIGS. 17A and 17B. Construction of rB/HPIV3 vectors expressing versions of RSV F protein engineered in an attempt to increase incorporation into the vector particle. (A) Structures of F proteins. (B) Sequences of the cytoplasmic tails (CT), transmembrane (TM) domains, and adjoining regions of the ectodomains of the RSV F protein (amino acid assignments in black) and BPIV3 F protein (boldface), with amino acid sequence positions indicated. Each of these modified proteins contained the HEK assignments and was expressed from a GA-optimized ORF. The HEK/GA-opt construct expressed full-length RSV F protein. "B3CT" has the CT of RSV F protein (amino acid sequence positions 551-574) replaced by the CT of BPIV3 F protein (positions 515-540, boldface). "B3TMCT" has both the TM and CT of RSV F protein (positions 530-574) replaced by the TM and CT of BPIV3 F protein (positions 494-540, boldface). "DS/B3CT", "DS/B3TMCT", "DS-Cav1/B3CT", and "DS-Cav1/B3TMCT" are versions of B3CT and B3TMCT containing the DS or DS-Cav1 mutations designed to stabilize the pre-fusion conformation. The ORFs encoding these various forms of RSV F protein were inserted into the rB/HPIV3 vector at the same position and with the same vector signals as described in FIGS. 1, 4, and 11. The sequences shown are as follows: RSV(A2)F (SEQ ID NO: 1, residues 510-574), BPIV3 F (SEQ ID NO: 151), B3CT (SEQ ID NO: 14, residues 510-576), B3TMCT (SEQ ID NO: 12, residues 510-576).

FIGS. 18A and 18B. Incorporation into the rB/HPIV3 vector particle of B3CT and B3TMCT versions of the RSV F protein. LLC-MK2 cells were infected with the indicated rB/HPIV3 vectors at an MOI of 0.01 $TCID_{50}$ at 32° C. The medium supernatants were harvested 6-7 days post-infection, clarified by low speed centrifugation, and subjected to centrifugation on 10%-30% sucrose gradients to obtain partially-purified vector particles. Additional Vero cells were infected with wt RSV at an MOI of 0.01 PFU and processed in the same way. The protein concentrations of the sucrose-purified preparations were determined by a standard commercial kit. (A) Western blot evaluation of the packaging efficiency of the RSV F protein into the rB/HPIV3 particles. To compare the relative amounts of RSV F in the particles, 0.5 g of sucrose-purified particles were lysed, denatured, reduced and subjected to Western blot analyses. The HPIV3 HN and BPIV3 N proteins of the vector particle were quantified for comparison. (B) The packaging efficiency of each form of RSV F into its respective vector particle was calculated by normalizing its band density against that of the BPIV3 N protein. The order of the lanes is the same as in part A. The packaging efficiencies of various forms of RSV F are shown relative to the native F protein set at "1". The packaging efficiency of the B3CT and B3TMCT forms of RSV F into the vector particle was judged to be similar to that of RSV F into the RSV particle because the amount of modified RSV F protein per 0.5 μg of vector particles (lanes 3, 4, 6, 7) was similar to the amount of native RSV F protein per 0.5 μg of RSV particles (lane 5). The constructs indicated by asterisk * contained the HEK assignments and were GA-codon-optimized for human expression.

FIGS. 19A-19F. Visualization of the incorporation of B3CT and B3TMCT versions of the RSV F protein into rB/HPIV3 particles by transmission electron microscopy (TEM). Sucrose purified viruses were labeled with an RSV F-specific murine monoclonal antibody and mouse-IgG-specific second antibodies that were labeled with 6 nm gold particles. Virions and gold particles were visualized with TEM. Representative images of (A) RSV, (B) empty rB/HPIV3 vector (empty B/H3), (C) vector expressing HEK/GA-opt, (D) vector expressing B3CT, (E) vector expressing B3TMCT, and (F) vector expressing DS/B3TMCT are shown. Arrows point to sporadic gold particles in HEK/GA-opt virions (C). Substantially greater amounts of gold particles associated with the vector particles are evident in D, E, and F.

FIGS. 20A and 20B. Multi-cycle in vitro replication of rB/HPIV3 vectors expressing B3CT and B3TMCT versions of the RSV F protein. (A) LLC-MK2 and (B) Vero cells were infected at 32° C. with an MOI of 0.01 $TCID_{50}$ with empty rB/HPIV3 vector (empty B/H3) or vector expressing HEK/GA-opt, or B3CT (upper panels), or B3TMCT (upper panels), or DS/B3CT (lower panels) or DS/B3TMCT (lower panels). Aliquots of medium supernatant were collected at 24 h intervals for 6 days and viral titers were determined by limiting dilution assay on LLC-MK2 cells at 32° C. and reported as $TCID_{50}$/ml. The constructs indicated by asterisk * contained the HEK assignments and were GA-codon-optimized for human expression. Multiplicity of infection in the assays was 0.01.

FIG. 26. Stability of expression of RSV F by rB/HPIV3 vectors during replication in hamsters. The percentage of recovered vector expressing RSV F in the nasal turbinates and lungs at day 3 and 5 post-immunization was determined by double-staining plaque assay of vector recovered directly from the tissue homogenates. The results are expressed for the individual animals. The percentages of rB/HPIV3 expressing RSV F protein in the tested specimens are indicated. Specimens with 100% expression of RSV F protein were colored in yellow; those with 90-99% expression of RSV F were colored in green; those with 80-89% expression of RSV F were colored in orange; those with less than 79% expression of RSV F were colored in red. Specimens that did not generate plaques due to low titer were marked as "NA". If the total number of the plaques developed with a sample was less than 10, the number of plaques was recorded as "p=X" (X equals to the number of plaques) in the bracket.

FIG. 27. Temperature sensitivity phenotypes of B/HPIV3 vectors. The indicated vectors were evaluated for the ability to form plaques on LLC-MK2 cells at the indicated temperatures. Reduction in plaque formation of ≥100-fold is indicative of temperature sensitivity. The lowest such restrictive temperature for each virus is indicated in bold, underlining, and is called the shut-off temperature.

FIG. 28. rB/HPIV3 constructs that were evaluated for attenuation and immunogenicity in non-human primates (Rhesus macaques). Rhesus macaques were infected by the combined IN and intratracheal routes with $10^6$ TCID$_{50}$ per site of the following constructs: Non-HEK/non-opt; HEK/GA-opt/DS; and HEK/GA-opt/DS/B3TMCT in groups of five, five and four animals, respectively.

FIGS. 29A and 29B. Replication of rB/HPIV3 vectors in rhesus macaques. Rhesus macaques were infected with the indicated rB/HPIV3 vectors as described in FIG. 28. Vector replication in the respiratory tract was assessed by collecting (A) nasopharyngeal swabs and (B) tracheal lavages on the indicated days and determining the viral titers by limiting dilution assay. Limit of detection is 1.2 $\log_{10}$ TCID$_{50}$/mL shown as dotted line.

(FIG. 31) RSV neutralizing antibody titers at all time points were determined by a 60% plaque reduction neutralization test (PRNT$_{60}$) in the presence of added guinea pig complement. (FIG. 32) RSV neutralizing antibody titers at day 28 post-immunization were determined by a 60% plaque reduction neutralization test (PRNT$_{60}$) in the absence of added complement. The detection limit for the neutralization assay is indicated with a dotted line. The statistical significance of difference in mean titers was determined by Tukey-Kramer test and indicated by asterisks (, P≤0.01; *, P≤0.001). The day of RSV challenge is indicated.

FIG. 33. Stability of expression of RSV F by rB/HPIV3 vectors during replication in rhesus macaques. The percentage of recovered vector expressing RSV F in nasal pharyngeal swabs from day 4, 5 and 6 post-immunization was determined by double-staining plaque assay. The percentages of rB/HPIV3 expressing RSV F in the tested specimens are indicated. Specimens with 100% of viruses expressing RSV F were colored in yellow; those with 99-90% of viruses expressing RSV F were colored in green; those that did not generate plaques due to low titer were marked as "NA".

FIG. 35. Summary of exemplary rB/HPIV3 vectors expressing RSV F, annotated to indicate constructs that have been evaluated in two different studies in hamsters and two different studies in rhesus monkeys in Example 1.

FIGS. 37A-37D. Multistep replication of HPIV1/RSV-F viruses in Vero (37A and 37C) and LLC-MK2 (37B and 37D) cells. Triplicate wells of cell monolayers in 6-well plates were infected at an MOI of 0.01 $TCID_{50}$ with HPIV1 $C^{\Delta170}$ (A and B) or $L^{Y942A}$ (C and D) viruses expressing RSV F (F1, F2, or F3), in parallel with wt HPIV1, HPIV1 $L^{Y942A}$, and HPIV1 $C^{\Delta170}$. Cultures were incubated at 32° C. Aliquots of cell culture medium were collected at 24 h intervals and virus titers ($\log_{10} TCID_{50}$/ml) were determined by serial dilution on LLC-MK2 cells and hemadsorption assay at 32° C. Mean titers with standard errors of the mean (SEM) are shown. The statistical significance of difference between the titer of each virus versus wt HPIV1 for day 2 post-infection was determined using the one-way ANOVA with Tukey's multiple comparisons test and is indicated by asterisks as follows: *, p≤0.05; , p≤0.01; *, p≤0.001; ****, p<0.0001.

FIGS. 38A-38C. Analysis of the RSV F and HPIV1 vector protein expression by Western blot. Vero cells were infected with the indicated viruses at an MOI of 5. At 48 h post-infection cells were lysed with SDS sample buffer. All samples were denatured, reduced and subjected to SDS-PAGE and Western blot. Proteins were transferred onto PVDF membranes and probed with either RSV F-specific mouse monoclonal antibody or HPIV1 N-, P-, HN-, or F-specific polyclonal antibodies that had been raised by immunizing rabbits separately with synthetic peptides representing the respective proteins. (A) Bound antibodies were visualized using corresponding anti-mouse (IRDye 680LT) and anti-rabbit (IRDye 800CW) antibodies conjugated with infra-red dye. Images were acquired by scanning the blots using the Odyssey infrared imaging system. The images shown are from a single experiment that is representative of three independent experiments. (B and C) The intensity of protein bands for the rHPIV1 $C^{\Delta170}$ (B) and the rHPIV1 $L^{Y942A}$ (C) constructs was quantified for three independent experiments and expression is shown relative to the F3 virus set at 1.0. Plots show data as mean±SEM from three independent experiments that were analyzed by one-way ANOVA with Dunnett multiple comparisons test using 95% confidence interval. Expression of the HPIV1 proteins by the F1, F2 and F3 viruses was statistically compared with that of their corresponding empty vector backbone. *, p<0.05; , p<0.01; *, p<0.001.

FIGS. 39A-39I. Formation of cytopathic effects and syncytia on LLC-MK2 cell monolayers infected with the rHPIV1 vectors expressing RSV F. MK2 cells were infected at an MOI of 0.01 $TCID_{50}$, incubated for 5 days and images were acquired at 40× magnification using phase contrast with a light microscope. Photomicrographs of (A) rHPIV1 $C^{\Delta170}$-F1; (B) rHPIV1 $C^{\Delta170}$-F2; (C) rHPIV1 $C^{\Delta170}$-F3; (D) rHPIV1 $C^{\Delta170}$; (E) rHPIV1 $L^{Y942A}$-F1; (F) rHPIV1 $L^{Y942A}$-F2; (G) rHPIV1 $L^{Y942A}$-F3; (H) rHPIV1 $L^{Y942A}$; and (I) wt HPIV1 are shown.

FIG. 42 shows a table illustrating the attenuating mutations introduced in the HPIV1 backbone in the P/C or the L ORF. Nucleotide changes (deletion or substitution) in the wt sequence are underlined.

FIG. 43 shows a table illustrating temperature sensitivity of recombinant viruses on LLC-MK2 cell monolayers. For temperature sensitivity, the underlined values in boldface indicate the virus shut-off temperature indicating a temperature sensitive phenotype defined as the lowest restrictive temperature at which the mean $\log_{10}$ reduction in virus titer at a given temperature vs. 32° C. was 2.0 $\log_{10}$ or greater than that of the wt rHPIV1 at the same two temperatures. For monolayers, serial dilutions of each of the indicated viruses on LLC-MK2 cells were incubated at various temperatures for 7 days. Virus titers were determined by hemadsorption with guinea pig erythrocytes and reported as $Log_{10}$ $TCID_{50}$/ml with a detection limit of 1.2.

FIG. 44 shows a table illustrating the percentage of virus population expressing RSV F after in vivo replication. The percentage of virus population expressing RSV F after in vivo replication (stability) was determined by an immunofluorescent double-staining plaque assay. Vero cells were infected with serially diluted tissue homogenates of the nasal turbinates or lungs of infected hamsters (n=6 per virus) collected on day 3 and 5 p.i. (total 144 samples) and incubated for 6 days under methylcellulose overlay. Virus plaques were stained with mouse monoclonal anti-RSV F and goat polyclonal anti-HPIV1 specific antibodies followed by detection with the corresponding infrared dye conjugated secondary antibodies. Percentage of plaques expressing both RSV F and HPIV1 antigens are shown. The stability of HPIV1 $C^{D170}$-F1, -F2, and F3 for lung samples and that for HPIV1 $L^{Y942A}$-F1, -F2, and F3 in the URT and lungs could not be tested due to their lack of replication in these tissues. Numbers in parenthesis indicate the RSV F expression status for the number of hamsters of the total 6 hamsters per virus. ND, no plaques were detected.

FIG. 45 shows a table listing results indicating that immunization of hamsters with rHPIV1 expressing RSV F induces serum neutralizing antibodies against RSV. Groups of six-week old hamsters (n=6) were intranasally immunized with 105 $TCID_{50}$ of each indicated virus in 0.1 ml inoculum. Serum samples were collected prior to immunization and at 28 days post immunization. Antibody titers against RSV and HPIV1 were determined by using a 60% plaque reduction neutralization test ($PRNT_{60}$) using green fluorescent protein (GFP)- or enhanced GFP (eGFP) expressing viruses (rRSV-eGFPM or HPIV1-GFP), and neutralizing antibody titers were presented as mean reciprocal $log_2 \pm SE$. Based on the initial serum dilutions used in the assay, the $PRNT_{60}$ assay has a titer detection limit of 3.3 and 1.0 reciprocal $log_2$ $PRNT_{60}$ for RSV and HPIV1, respectively. Statistical significance of difference among the groups for RSV antibody titers was determined by one-way ANOVA with Tukey's multiple comparisons test ($p<0.05$) and that for HPIV1 antibody titers was determined by Unpaired t-test. Mean neutralizing antibody titers were categorized into groups (indicated in parenthesis as A, B, C, and D). Mean antibody titers of treatment groups with different letters are statistically different from each other; titers shown with two letters are not statistically different from those indicated with either letter.

(FIG. 46) Vero and (FIG. 47) LLC-MK2 cells were infected in triplicate at 32° C. at an MOI of 0.01 $TCID_{50}$ with empty rB/HPIV3 vector (empty B/H3) or vector expressing the RSV F ORF that was HEK-containing, GA-opt, and containing the DS-Cav1 prefusion stabilizing mutations (HEK/GA-opt/DS-Cav1) or was HEK-containing, GA-opt, and containing the DS-Cav1 mutations and BPIV3-specific TM and CT domains as potential packaging signals (HEK/GA-opt/DS-Cav1/B3TMCT). Aliquots of medium supernatants were collected at 24 h intervals for 6 days and viral titers were determined by limiting dilution assay on LLC-MK2 cells at 32° C. and reported as $TCID_{50}$/ml. Mean titers±SEM from three independent experiments are shown.

FIGS. 49A-49D. Comparison of multi-cycle in vitro replication of rB/HPIV3 vectors expressing GS-opt and GA-opt RSV F. FIGS. 49A and 49B: (A) Vero and (B) LLC-MK2 cells were infected in triplicate at 32° C. at an MOI of 0.01 $TCID_{50}$ with empty rB/HPIV3 vector (empty B/H3) or vector expressing RSV F ORF that was HEK-containing, GS-opt, and bearing the DS-Cav1 mutations (HEK/GS-opt/DS-Cav1), or was HEK-containing, GA-opt, and bearing the DS-Cav1 mutations (HEK/GA-opt/DS-Cav1). FIGS. 49C and 49D: (C) Vero and (D) LLC-MK2 cells were infected at 32° C. at an MOI of 0.01 $TCID_{50}$ with empty rB/HPIV3 vector (empty B/H3) or vector expressing RSV F ORF that was HEK-containing, GS-opt, and bearing the DS-Cav1 and B3TMCT modifications (HEK/GS-opt/DS-Cav1/B3TMCT), or was HEK-containing, GA-opt, and contained the DS-Cav1 and B3TMCT modifications (HEK/GA-opt/DS-Cav1/B3TMCT). Aliquots of medium supernatant were collected at 24 h intervals for 6 days and viral titers were determined by limiting dilution assay on LLC-MK2 cells at 32° C. and reported as $TCID_{50}$/ml. Mean titers±SEM from three independent experiments are shown.

FIGS. 50A-50C. Expression of various modified forms of RSV F by rB/HPIV3 vectors in cell culture. (A) Vero and (B, C) LLC-MK2 cells were infected with empty rB/HPIV3 vector (lane 1), or rB/HPIV3 vector expressing the indicated modified forms of RSV F (lanes 2-5 and 8), or wt RSV (wt RSV, lane 6) at MOI of 3 PFU/cell, or uninfected (mock, lane 7). Infected Vero (A) and LLC-MK2 (B) cells were incubated at 32° C., and LLC-MK2 (C) cells were incubated at 37° C. Cell lysates and medium supernatant of Vero cells were collected at 48 hpi and were subjected to Western blot analysis for the expression of RSV F, which was detected as cleaved $F_1$ and/or un-cleaved $F_0$ forms. BPIV3 N was used as an internal control for the expression of vector protein; GAPDH was used as a loading control.

FIGS. 51A and 51B. Replication of rB/HPIV3 vectors in the upper and lower respiratory tract of hamsters. Hamsters were infected IN with 105 $TCID_{50}$ of the indicated rB/HPIV3 vectors or $10^6$ PFU of wt RSV in a 0.1 ml inoculum. Hamsters were euthanized (n=6 per virus per day) on days 4 and 5 post-infection and the (A) nasal turbinates and (B) lungs were removed and homogenized, and viral titers were determined by limiting dilution on LLC-MK2 cells at 32° C. and reported as $TCID_{50}$/g (rB/HPIV3 vectors) or were determined by plaque assays on Vero cells at 32° C. and reported as PFU/g (wt RSV). The limit of detection (LOD) is 1.5 $log_{10}$ $TCID_{50}$/g of tissue, indicated with a dotted line. Open and closed circles indicate titers for individual animals sacrificed on day 4 and 5, respectively. The mean titers of each group are indicated by a dashed and solid horizontal line for day 4 and 5, respectively. The values of the mean titers on day 4 and 5 are shown at the top. The mean viral titers on day 5 were assigned to different groups using the Tukey-Kramer test: mean titers with different letters are statistically different (p<0.05), whereas titers indicated with two letters are not significantly different than those indicated with either letter.

FIG. 57A: RSV neutralizing antibody titers at the indicated time points were determined by a 60% plaque reduction neutralization test (PRNT$_{60}$) in the presence of added guinea pig complement. The statistical significance of difference in mean titers of each time point was determined by pairwise student-t test (ns, P>0.05). FIG. 57A: RSV neutralizing antibody titers at day 28 post-immunization were determined by PRNT$_{60}$ in the absence of added complement. The detection limit for the neutralization assay is indicated with a dotted line. The statistical significance of difference in mean titers of each time point was determined by pairwise student-t test (ns, P>0.05).

FIGS. 58A and 58B. Construction of a rB/HPIV3 vector expressing HEK/GS-opt/DS-Cav1/B3TMCT from the pre-N position, and modification of the amino acid sequence of the HPIV3 HN protein to achieve increased phenotypic stability of the vector. FIG. 58A: Insertion of the HEK/GS-opt/DS-Cav1/B3TMCT insert into the first gene position of rB/HPIV3. FIG. 58A: Corrections of the HPIV3 HN gene that conferred increased phenotypic stability. The HN gene in the original recombinant HPIV3 made by reverse genetics (Durbin et al Virology 235:323-332 1997) had two engineered nucleotide substitutions in the HN gene at antigenome positions 7913 and 7915 that resulted in the amino acid substitution P370T, and an adventitious mutation at antigenome position 7593 that resulted in the amino acid substitution T263I. Here, these mutations were changed back to the "wild-type" assignments, i.e., that found in biologically derived HPIV3 strain JS (Genbank Z11575.1; Stokes et al Virus Res 25:91-103. 1992).

FIGS. 59A and 59B. Intracellular expression of RSV F and vector proteins by vectors expressing various versions of RSV F protein in the first gene position (pre-N) or in the second gene position (N-P). Analysis of rB/HPIV3-wt HN-HEK/GS-opt/DS-Cav1/B3TMCT/pre-N, the construct diagrammed in FIG. 58A. Vero (FIG. 59A) and LLC-MK2 (FIG. 59B) cells were infected with empty rB/HPIV3 vector (empty B/H3, lane 1), or the wtHN/HEK/GS-opt/DS-Cav1/B3TMCT/pre-N construct (pools CL20a, CL24a, lanes 3 and 4), or vector with the same version of RSV F inserted in the second (N-P) position (HEK/GS-opt/DS-Cav1/B3TMCT/N-P, lane 5), or vector with Non-HEK/non-opt version of RSV F inserted in the pre-N position (lane 6), or wt RSV (lane 2), or mock-infected (lane 7). The vectors were infected at an MOI of 10 TCID$_{50}$/cell, and wt RSV at MOI of 3 PFU/cell. Infected monolayers were incubated at 32° C. Cell lysates were collected at 48 hpi and subjected to Western blot analysis. RSV F in the forms of cleaved F$_1$ and/or uncleaved F$_0$ were detected. BPIV3 N and P proteins were used to evaluate effects on vector protein expression. GAPDH was used as a loading control.

FIG. 60. HPIV1 vector: sequences of the cytoplasmic tails (CT), transmembrane (TM) domains, and adjoining regions of the ectodomains of the RSV F protein (strain A2, amino acid assignments) and HPIV1 F protein (boldface), with the amino acid sequence positions indicated. RSV-F-TMCT is a chimeric protein consisting of the ectodomain of RSV F protein attached to the TM and CT domains of HPIV1 F protein. The sequences shown are as follows: RSV(A2)F (SEQ ID NO: 1, residues 510-574), HPIV1 F (SEQ ID NO: 152), RSV F-TMCT (SEQ ID NO: 135, residues 510-588).

FIGS. 61 and 62. Construction of HPIV1-C$^{\Delta 170}$ vectors expressing versions of RSV F protein designed to be stabilized in the prefusion conformation (DS-Cav1) and to have increased incorporation into the HPIV1 vector particle. Each of these modified RSV F inserts contained the HEK assignments (HEK) and was codon-optimized by GS for human expression (GS-opt). The RSV F insert was engineered to be stabilized in the prefusion conformation by the DS and Cav1 mutations (DS-Cav1) alone (upper construct in FIGS. 61 and 62) or with further modification by the replacement of its TMCT domain with those from HPIV1 F (TMCT, lower construct in FIGS. 61 and 62). The resulting HEK/GS-opt/DS-Cav1 and HEK/GS-opt/DS-Cav1/TMCT versions of RSV F were modified by flanking sequence and inserted into the HPIV1-C$^{\Delta170}$ vector (see Example 2 for an explanation of the HPIV1 vector and C$^{\Delta170}$ mutation) at the (FIG. 61) first gene position (MluI site), or (FIG. 62) second gene position (AscI site). In each case, the RSV F was under the control of HPIV1 transcription signals for expression as a separate mRNA. Nucleotide numbering is relative to the complete antigenome RNA sequence of the final construct. The sequences of SEQ ID NOs: 146 and 147 are shown flanking the RSV F insert under the diagrams for F1/HEK/GS-opt/DS-Cav1, F1/HEK/GS-opt/DS-Cav1/TMCT, F2/HEK/GS-opt/DS-Cav1, and F2/HEK/GS-opt/DS-Cav1/TMCT.

FIG. 63. Kinetics of multi-cycle growth in Vero cells of rHPIV1-C$^{\Delta170}$ vectors expressing RSV F stabilized in the prefusion conformation (DS-Cav1), without or with TMCT from HPIV1 F protein. Vero cells were infected with the constructs in triplicate at an MOI of 0.01 and incubated for 7 days at 32 C. At 24 h intervals, 0.5 mL of the total 3 mL culture supernatant was collected over 7 days. After sample collection, 0.5 mL fresh media was added to each culture to restore the original volume. Virus titration of the collected samples was performed on LLC-MK2 cells by hemadsorption assay and values are plotted as means±SEM.

FIG. 64. Incorporation into HPIV1-C$^{\Delta170}$ virion particles of RSV F protein stabilized in the prefusion conformation (DS-Cav1) without or with TMCT from HPIV1 F protein. The indicated virus constructs (the designations HEK/GS-opt were omitted for the sake of brevity) were grown in LLC-MK2 cells and virions were purified by sucrose gradient centrifugation. Protein concentration of the purified viruses was determined by BCA assay. 1 µg total protein from each purified virus was lysed in RIPA lysis buffer, reduced, denatured, and subjected to SDS-PAGE and Western blot analysis. RSV F (top panel) and HPIV1 proteins (second, third, and fourth panels) were detected with mouse monoclonal and rabbit polyclonal HPIV1-peptide-specific (N, F, and HN) antibodies, respectively. Infared-labeled secondary antibodies were used to detect bound primary antibodies. The chimeric RSV-F-DS-Cav1/TMCT protein in lanes 2 and 4 (fourth panel) are visible because the antipeptide serum specific to HPIV1 F protein was raised using a synthetic peptide containing the C-terminal 18 amino acids of the CT domain, and thus reacts with RSV F protein bearing the HPIV1 F protein TMCT domains.

FIG. 66. Sequences of the cytoplasmic tails (CT), transmembrane (TM) domains, and adjoining regions of the ectodomains of the RSV F protein (amino acid assignments) and HPIV3 F protein (boldface), with the amino acid sequence positions indicated. RSV-F-H3TMCT is a chimeric protein consisting of the ectodomain of RSV F protein attached to the TM and CT domains of HPIV3 F protein. The sequences shown are as follows: RSV(A2)F (SEQ ID NO: 1, residues 510-574), HPIV3 F (SEQ ID NO: 153), RSV F-H3TMCT (SEQ ID NO: 10, residues 510-575).

FIGS. 67A and 67B. Construction of rHPIV3 vectors expressing versions of RSV F protein designed to be stabilized in the prefusion conformation (DS-Cav1) and to have increased incorporation into the rHPIV3 vector particle. The vector is wild type rHPIV3 strain JS which was modified to contain the 263T and 370P amino acid assignments in the HN protein (see FIG. 58B), which were found to confer phenotypic stability to the vector. In addition, the rHPIV3 vector was modified by the creation of a BlpI site at positions 103-109 (A, top construct), for insertion of RSV F (or potentially any other insert) in gene position 1, or the creation of an AscI site at positions 1675-1682 (B, top construct), for insertion of RSV F in gene position 2. Each of the modified RSV F inserts contained the HEK assignments (HEK) and was codon-optimized by GS for human expression (GS-opt). In addition, the RSV F insert was engineered to be stabilized in the prefusion conformation by the DS and Cav1 mutations (DS Cav1) alone (A and B, second construct) or with further modification by the replacement of its TMCT domains with those from rHPIV3 F (H3TMCT, A and B, third construct). The resulting HEK/GS-opt/DS-Cav1 and HEK/GS-opt/DS-Cav1/H3TMCT versions of RSV F were modified by flanking sequence and inserted into the (A) first gene position (BlpI site), or (B) second gene position (AscI site) of wt rHPIV3 JS. In each case, the RSV F was under the control of HPIV3 transcription signals for expression as a separate mRNA. Nucleotide numbering is relative to the complete antigenome RNA sequence of the final construct. The sequence of SEQ ID NOs: 148 is shown under the diagram for rHPIV3 wt-JS. The sequences of SEQ ID NOs: 149 and 150 are shown flanking the RSV F insert under the diagrams for F1/HEK/GS-opt/DS-Cav1, F1/HEK/GS-opt/DS-Cav1/H3TMCT, F2/HEK/GS-opt/DS-Cav1, and F2/HEK/GS-opt/DS-Cav1/H3TMCT.

SEQUENCE LISTING

Figure 1:
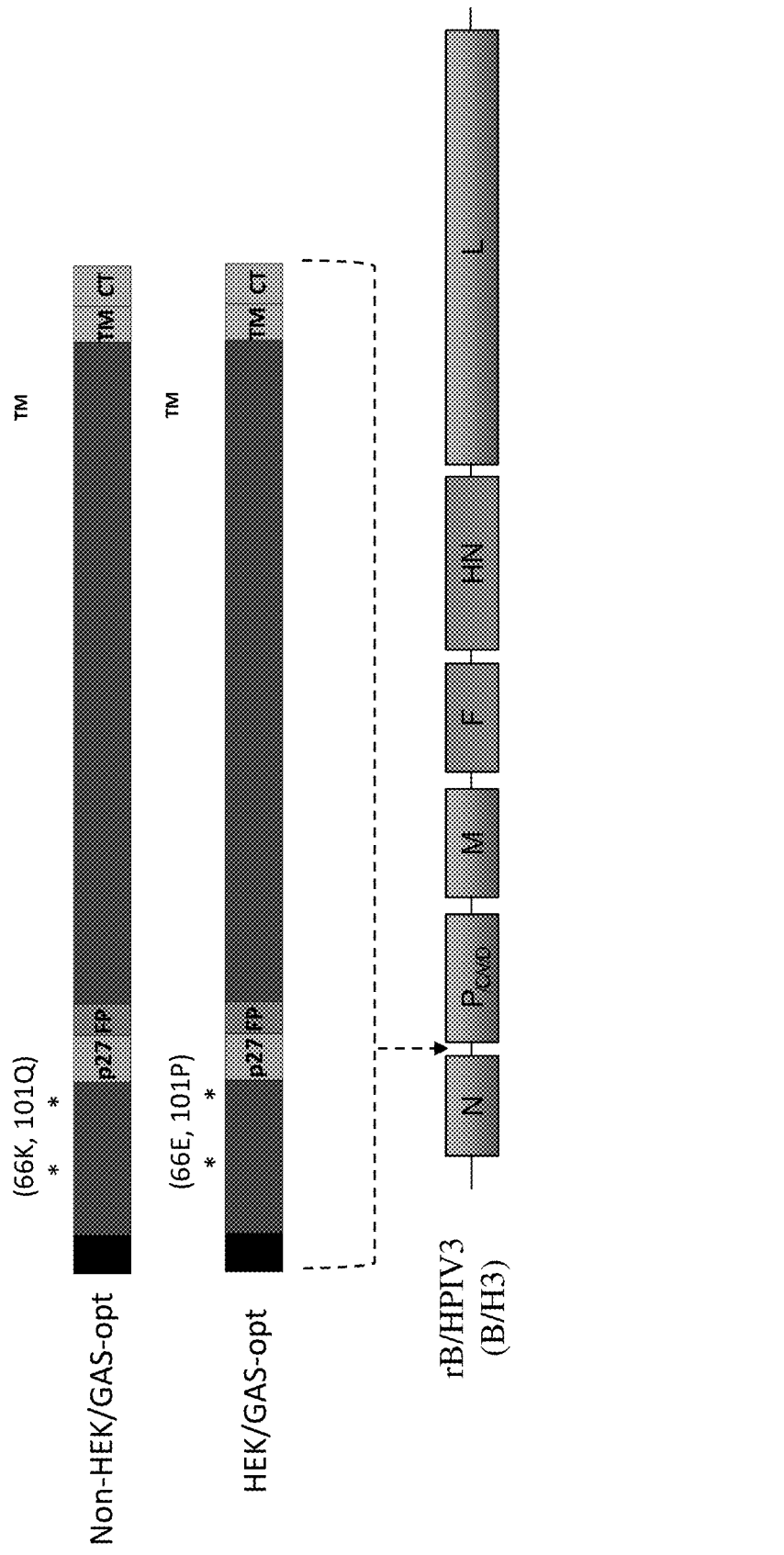
FIG. 1. Construction of rB/HPIV3 vectors expressing versions of the RSV F protein containing the non-HEK or HEK amino acid assignments. The F ORFs were codon-optimized for human expression using the GeneArt (GA) algorithm. The constructs were called non-HEK/GA-opt and HEK/GA-opt. The HEK (66E, 101P) and non-HEK (66K, 101Q) amino acid assignments are indicated by asterisks. Other annotations: S, signal sequence; p27, 27k protein fragment liberated by cleavage-activation; FP, fusion peptide; TM, transmembrane; CT, cytoplasmic tail. The RSV F ORFs were placed under the control of BPIV3 gene-start and gene-end transcription signals and inserted into the $2^{nd}$ genome position between the N and P genes of the B/HPIV3 vector. The rB/HPIV3 vector includes N, P, M, and L genes from BPIV3, and F and NH genes from HPIV3. The same vector genome position and vector transcription signals were used for all of the other rB/HPIV3 vectors expressing RSV F protein described in FIGS. 1-35.

The nucleic and amino acid sequences listed in the accompanying sequence listing are shown using standard letter abbreviations for nucleotide bases, and one letter code for amino acids, as defined in 37 C.F.R. 1.822. Only one strand of each nucleic acid sequence is shown, but the complementary strand is understood as included by any reference to the displayed strand. The Sequence Listing is submitted as an XML file with the file name "9668-93586-10_ST26_Sequence_Listing.xml" (214,795 bytes), which was generated on Jan. 23, 2023, and incorporated by reference herein.

DETAILED DESCRIPTION

A previous study (Zimmer et al J Virol 2005 79:10467-77) evaluated the expression of RSV F protein from a heterologous gene in the Sendai virus, which is a murine relative of HPIV1 and also is closely related to HPIV3. That study showed that very little RSV F protein was incorporated into the Sendai virus vector particle. The investigators replaced the CT or CT plus TM of the RSV F protein with the corresponding sequences from the Sendai F protein on the premise that this would improve the efficiency of interaction of the foreign RSV F protein with the vector particle. These modifications indeed increased incorporation of the engineered RSV F into the Sendai particle, but only if the Sendai F protein gene was also deleted. The requirement to delete the vector F protein is incompatible with the generation of infectious, attenuated viruses for vaccination and also would remove one of the vector protective antigens, which are believed to be needed to generate a bivalent vaccine.

As disclosed herein, when expressed by rB/HPIV3, HPIV3, or HPIV1, the RSV F protein including RSV F TM and CT is incorporated into the vector particle only in trace amounts. However, swapping the TM and CT of the heterologous RSV F protein for the corresponding TM and CT of the paramyxovirus F protein provided a multi-fold increase in RSV F ectodomain incorporation in the envelope of recombinant paramyxovirus, such that the packaging of RSV F into the vector was as efficient (e.g. B/HPIV3) or more efficient (e.g. HPIV1) per µg of purified virion than that of RSV itself. This was effective when the TM and CT were swapped together, or when the CT was swapped alone. However, unexpected effects of increased fusogenicity of the chimeric RSV F specific to CT alone provide guidance that TMCT is preferred.

Efficient packaging of RSV F into the vector particle dramatically increased the elicitation of an immune response to the ectodomain (bearing all of the neutralization epitopes) when the recombinant paramyxovirus was administered to a subject. Unexpectedly, the virus-neutralizing serum antibody response was dramatically increased in quality, which was assessed by comparing RSV-neutralization activity in vitro in the absence of complement (which measures strongly-neutralizing antibodies) or in its presence (which augments neutralization by weak or non-neutralizing antibodies). This unanticipated increase in antibody quality is of particular importance for RSV, which is noted for inducing incomplete immune protection. The expression and efficient packaging of a foreign glycoprotein bearing the TMCT domains of a vector glycoprotein had the obvious potential to disrupt vector replication and morphogenesis: however, constructs are provided in which this effect was minimal.

To further increase immunogenicity, stabilization of the RSV F protein in the pre-fusion conformation was evaluated. On its own, pre-fusion stabilization also resulted in an increase in titers of strongly-neutralizing antibodies, suggestive of stabilization of neutralization epitopes. In the hamster model, the effect of pre-fusion stabilization on increased immunogenicity and protection appeared to be additive to that of efficient packaging conferred by TMCT. However, when evaluated in non-human primates, the effect of packaging appeared to be greater than that of pre-fusion stabilization.

Given the challenge of achieving protection against RSV, maximal immunogenicity is desired. Extensive experimentation uncovered other aspects of vector and insert construction (e.g., use of various insertion sites, use of codon-optimization, and use of an early-passage RSV F protein sequence) that provided increased expression of RSV F and reduced the cytopathic effects of syncytia formation mediated by the highly fusogenic RSV F protein.

It is noteworthy that a prototype vaccine virus based on rB/HPIV3 expressing an unmodified RSV F protein, which in clinical trials had disappointing RSV immunogenicity (Bernstein, et al. 2012. Pediatric Infectious Disease Journal 31:109-114), was confirmed by the methods of the present disclosure to induce RSV-neutralizing serum antibodies that were of poor quality, possessing neutralization activity in vitro only in the presence of added complement. In contrast, disclosed constructs induced, in African green monkeys, high titers of serum antibodies capable of efficiently neutralizing RSV in vitro in the absence of complement.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine, published by* Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed recombinant.

Administration: The introduction of a composition into a subject by a chosen route. Administration can be local or systemic. For example, if the chosen route is intranasal, the composition (such as a composition including a disclosed recombinant paramyxovirus) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid or with no amino acid (i.e., a deletion). In some examples, an amino acid in a polypeptide is substituted with an amino acid from a homologous polypeptide, for example, and amino acid in a recombinant group A RSV F polypeptide can be substituted with the corresponding amino acid from a group B RSV F polypeptide. Reference to a "66E" amino acid in a RSV F protein refers to an RSV F protein comprising a glutamate residue at position 66. The amino acid can be present due to substitution from a reference sequence. Reference to a "K66E" substitution in an RSV F protein refers to an RSV F protein comprising a glutamate residue at position 66 that has been substituted for a lysine residue in a reference (e.g., native) sequence.

Attenuated: A paramyxovirus that is "attenuated" or has an "attenuated phenotype" refers to a paramyxovirus that has decreased virulence compared to a reference wild type paramyxovirus under similar conditions of infection. Attenuation usually is associated with decreased virus replication as compared to replication of a reference wild-type paramyxovirus under similar conditions of infection, and thus "attenuation" and "restricted replication" often are used synonymously. In some hosts (typically non-natural hosts, including experimental animals), disease is not evident during infection with a reference paramyxovirus in question, and restriction of virus replication can be used as a surrogate marker for attenuation. In some embodiments, a recombinant paramyxovirus (e.g., RSV, PIV3) that is attenuated exhibits at least about 10-fold or greater decrease, such as at least about 100-fold or greater decrease in virus titer in the upper or lower respiratory tract of a mammal compared to non-attenuated, wild type virus titer in the upper or lower respiratory tract, respectively, of a mammal of the same species under the same conditions of infection. Examples of mammals include, but are not limited to, humans, mice, rabbits, rats, hamsters, such as for example *Mesocricetus auratus*, and non-human primates, such as for example *Ceroptihecus aethiops*. An attenuated paramyxovirus may display different phenotypes including without limitation altered growth, temperature sensitive growth, host range restricted growth, or plaque size alteration.

Cytoplasmic Tail (CT): A contiguous region of a transmembrane protein that includes a terminus (either N- or C-terminus) of the protein and extends into the cytoplasm of a cell or enveloped virus from the cytoplasmic surface of the cell membrane or viral envelope. In the case of a type I transmembrane protein, the CT includes the C-terminus of the protein. In the case of a type II transmembrane protein, the CT includes the N-terminus of the protein.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Gene: A nucleic acid sequence, typically a DNA sequence, that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

Heterologous: Originating from a different genetic source. A heterologous gene included in a recombinant viral genome is a gene that does not originate from that viral genome. In one specific, non-limiting example, a heterologous gene encoding an ectodomain of a RSV F protein is included in the genome of a recombinant PIV vector. Methods for introducing a heterologous gene in a viral vector are well known in the art and also described herein.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance that can stimulate the production of antibodies or a T cell response in an animal, including compositions that are injected or absorbed into an animal. An immunogen reacts with the products of specific humoral or cellular immunity, including those induced by heterologous antigens, such as a disclosed recombinant paramyxovirus. Administration of an immunogen to a subject can lead to protective immunity against a pathogen of interest.

Immunogenic composition: A composition comprising an immunogen that induces a measurable T cell response against an antigen, or induces a measurable B cell response (such as production of antibodies) against an antigen, included on the immunogen or encoded by a nucleic acid molecule included in the immunogen. In one example, an immunogenic composition is a composition that includes a disclosed recombinant paramyxovirus that induces a measurable CTL response against RSV and/or PIV, or induces a measurable B cell response (such as production of antibodies) against RSV and/or PIV, when administered to a subject. An immunogenic composition can include an isolated recombinant paramyxovirus as disclosed herein. For in vivo use, the immunogenic composition will typically include a recombinant paramyxovirus in a pharmaceutically acceptable carrier and may also include other agents, such as an adjuvant.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linked: The terms "linked," "linkage," and "linking" refer to making two molecules into one contiguous molecule; for example, linking two polypeptides into one contiguous polypeptide by recombinant means. Reference to a gene encoding a type I membrane protein comprising a RSV F ectodomain "linked" to a TM and CT of a heterologous F protein refers to genetic linkage between the nucleic acid sequence encoding the RSV F ectodomain and the nucleic acid sequence encoding the TM and CT of the heterologous F protein in the gene by recombinant means, such that expression of the gene leads to production of a protein including, in the N- to C-terminal direction, the RSV F ectodomain, the TM, and the CT. In some embodiments, the C-terminal residue of the RSV F ectodomain can be directly linked (by peptide bond) to the N-terminal residue of the TM. In some embodiments, the C-terminal residue of the RSV F ectodomain can be indirectly linked to the N-terminal residue of the TM via a peptide linker (such as a glycine-serine linker).

Linker: A bi-functional molecule that can be used to link two molecules into one contiguous molecule. Non-limiting examples of peptide linkers include glycine-serine linkers.

Native protein, sequence, or di-sulfide bond: A polypeptide, sequence or di-sulfide bond that has not been modified, for example by selective mutation. For example, selective mutation to focus the antigenicity of the antigen to a target epitope, or to introduce a di-sulfide bond into a protein that does not occur in the native protein. Native protein or native sequence are also referred to as wild-type protein or wild-type sequence. A non-native di-sulfide bond is a disulfide bond that is not present in a native protein, for example a di-sulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Paramyxovirus: A family of enveloped non-segmented negative-sense single-stranded RNA viruses. Examples of paramyxoviruses include, but are not limited to, human parainfluenza virus (HPIV) including types 1, 2, 3, 4A, and 4B (HPIV1, HPIV2, HPIV3, HPIV4A, and HPIV4B, respectively), mouse parainfluenza type 1 (Sendai virus, MPIV1), bovine parainfluenza virus type 3 (BPIV3), parainfluenza virus 5 (PIV5, previously called simian virus 5, SV5), simian virus 41 (SV41), and mumps virus. HPIV1, HPIV3, MPIV1, and BPIV3 are classified in the genus *Respirovirus*. HPIV2, HPIV4, SV5, SV41, and mumps virus are classified in the genus *Rubulavirus*. MPIV1, PIV5, and BPIV3 are animal relatives of HPIV1, HPIV2, and HPIV3, respectively (Chancock et al., Parainfluenza Viruses, Knipe et al. (Eds.), pp. 1341-1379, Lippincott Williams & Wilkins, Philadelphia, 2001). HPIV1, HPIV2, and HPIV3 represent distinct serotypes and do not elicit significant cross immunity. HPIVs are etiological agents of respiratory infections such as croup, pneumonia, or bronchitis.

Parainfluenza virus (PIV): A number of enveloped non-segmented negative-sense single-stranded RNA viruses from family Paramyxoviridae that are descriptively grouped together. This includes all of the members of genus respirovirus (e.g., HPIV1, HPIV3) and a number of members of genus rubulavirus (e.g. HPIV2, HPIV4, PIV5). Members of genus avulavirus (e.g., NDV) historically have been called PIVs and can be considered as part of this group. HPIV serotypes 1, 2, and 3 are second only to RSV in causing severe respiratory infections in infants and children worldwide, with HPIV3 being the most important of the HPIVs in terms of disease impact. PIVs are made up of two structural modules: (1) an internal ribonucleoprotein core, or nucleocapsid, containing the viral genome, and (2) an outer, roughly spherical lipoprotein envelope. The PIV viral genome is approximately 15,000 nucleotides in length and encodes at least eight polypeptides. These proteins include the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins. The P gene contains one or more additional open reading frames (ORFs) encoding accessory proteins. The gene order is 3'-N-P-M-F-HN-L-5', and each gene encodes a separate protein encoding mRNA. Exemplary PIV strain sequences are known to the person of ordinary skill in the art, such as the sequences of the HPIV1, HPIV2, HPIV3, and BPIV3 viruses.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the primer vaccine) followed by administration of a second immunogenic composition (the booster vaccine) to a subject to induce an immune response. The booster vaccine is administered to the subject after the primer vaccine; the skilled artisan will understand a suitable time interval between administration of the primer vaccine and the booster vaccine, and examples of such timeframes are disclosed herein. Additional administrations can be included in the prime-boost protocol, for example a second boost.

Recombinant: A recombinant nucleic acid molecule is one that has a sequence that is not naturally occurring: for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Respiratory Syncytial Virus (RSV): An enveloped non-segmented negative-sense single-stranded RNA virus of the family Paramyxoviridae. The RSV genome is ~15,000 nucleotides in length and includes 10 genes encoding 11 proteins, including the glycoproteins SH, G and F. The F protein mediates fusion, allowing entry of the virus into the cell cytoplasm and also promoting the formation of syncytia. Two antigenic subgroups of human RSV strains have been described, the A and B subgroups, based primarily on differences in the antigenicity of the G glycoprotein. RSV strains for other species are also known, including bovine RSV. Exemplary RSV strain sequences are known to the person of ordinary skill in the art. Further, several models of human RSV infection are available, including model organisms infected with hRSV, as well as model organisms infected with species specific RSV, such as use of bRSV infection in cattle (see, e.g., Bern et al., *Am J, Physiol. Lung Cell Mol. Physiol.*, 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

RSV Fusion (F) protein: An RSV envelope glycoprotein that facilitates fusion of viral and cellular membranes. In nature, the RSV F protein is initially synthesized as a single polypeptide precursor approximately 574 amino acids in length, designated $F_0$. $F_0$ includes an N-terminal signal peptide that directs localization to the endoplasmic reticulum, where the signal peptide (approximately the first 22 residues of $F_0$) is proteolytically cleaved. The remaining $F_0$ residues oligomerize to form a trimer which is again proteolytically processed by a cellular protease at two conserved furin consensus cleavage sequences (approximately $F_0$ positions 109/110 and 136/137; for example, $RARR_{109}$ (SEQ ID NO: 1, residues 106-109) and $RKRR_{136}$ (SEQ ID NO: 1, residues 133-136) to excise the pep27 polypeptide and generate two disulfide-linked fragments, $F_1$ and $F_2$. The smaller of these fragments, $F_2$, originates from the N-terminal portion of the $F_0$ precursor and includes approximately residues 26-109 of $F_0$. The larger of these fragments, $F_1$, includes the C-terminal portion of the $F_0$ precursor (approximately residues 137-574) including an extracellular/lumenal region (~residues 137-529), a TM (~residues 530-550), and a CT (~residues 551-574) at the C-terminus.

Three $F_2$-$F_1$ protomers oligomerize in the mature F protein, which adopts a metastable "prefusion" conformation that is triggered to undergo a conformational change (to a "postfusion" conformation) upon contact with a target cell membrane. This conformational change exposes a hydrophobic sequence, known as the fusion peptide, which is located at the N-terminus of the $F_1$ polypeptide, and which associates with the host cell membrane and promotes fusion of the membrane of the virus, or an infected cell, with the target cell membrane.

The extracellular portion of the RSV F protein is the RSV F ectodomain, which includes the $F_2$ protein and the $F_1$ ectodomain. An RSV F ectodomain trimer includes a protein complex of three RSV F ectodomains.

The RSV F protein adopts a "prefusion" conformation prior to triggering of the fusogenic event that leads to transition of RSV F to the postfusion conformation and following processing into a mature RSV F protein in the secretory system. The three-dimensional structure of an exemplary RSV F protein in a prefusion conformation is known, and disclosed for example in WO2014160463, which is incorporated by reference herein. In the prefusion state, the RSV F protein includes an antigenic site at its membrane distal apex termed "antigenic site Ø," that includes RSV F residues 62-69 and 196-209, and also includes the epitopes of the D25 and AM22 monoclonal antibodies. Thus, a recombinant RSV F protein stabilized in a prefusion conformation can be specifically bound by an antibody that binds the pre- but not post-fusion conformation of the RSV F protein, such as an antibody that specifically binds to an epitope within antigenic site Ø, for example, the D25 or AM22 antibody. Additional RSV F prefusion specific antibodies include the 5C4 and MPE8 antibodies.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; *Needleman* & Wunsch, J. Mol. Biol. 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a polypeptide (such as a RSV F ectodomain) are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci.* USA 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89: 10915, 1989). An oligonucleotide is a linear polynucleotide sequence of up to about 100 nucleotide bases in length.

As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals. In an example, a subject is a human. In a particular example, the subject is a newborn infant. In an additional example, a subject is selected that is in need of inhibiting of an RSV infection. For example, the subject is either uninfected and at risk of RSV infection or is infected in need of treatment.

Transmembrane domain TM: An amino acid sequence that spans a lipid bilayer, such as the lipid bilayer of a cell or virus or virus-like particle. A transmembrane domain can be used to anchor an antigen to a membrane. In some examples a transmembrane domain is a RSV F transmembrane domain.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides or DNA derived from them. An attenuated vaccine is a virulent organism that has been modified to produce a less virulent form, but nevertheless retains the ability to elicit antibodies and cell-mediated immunity against the virulent form. An inactivated (killed) vaccine is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

II. Recombinant Viral Vectors

Recombinant paramyxoviruses are provided that include antigens from multiple viral pathogens, and can be used to induce an immune response to those viral pathogens. The recombinant paramyxoviruses include a genome encoding a heterologous gene. The recombinant paramyxoviruses comprise a genome comprising a heterologous gene encoding the ectodomain of a transmembrane protein (e.g., a viral glycoprotein) of a heterologous viral pathogen. The ectodomain can be linked to a CT, or a TM and a CT of an envelope protein from the paramyxovirus to allow for expression of the ectodomain of the transmembrane protein from the heterologous virus on the paramyxovirus envelope. For example, the recombinant paramyxovirus can be a recombinant PIV comprising a genome comprising a heterologous gene encoding the ectodomain of an RSV F protein linked to the TM and CT of the F protein from the PIV. Additional description of the recombinant paramyxovirus and modifications thereof is provided herein.

The paramyxovirus genome includes genes encoding N, P, M, F, HN, and L proteins. The genome also includes a genomic promoter and anti-promoter, with the order of promoter—N, P, M, F, HN, L-antipromoter. The heterologous gene included in the genome of the recombinant paramyxovirus can be located at any position between genes of the paramyxovirus genome, or between the promoter and the N gene, or the L gene and the antipromoter. The heterologous gene can be flanked by appropriate gene start and gene-end sequences to facilitate expression from the viral genome. In a preferred embodiment, the heterologous gene can be located between the promoter and the N gene, or between the N gene and the P gene.

In an embodiment, the heterologous gene included in the genome of the recombinant paramyxovirus encodes the ectodomain of a type I transmembrane protein (e.g., a type I viral glycoprotein) linked to a CT, or TM and CT, of the F protein of the paramyxovirus. In other embodiments, the heterologous gene included in the genome of the recombinant paramyxovirus encodes the ectodomain of a type II transmembrane protein (e.g., a type II viral glycoprotein) linked to a CT, or TM and CT, of the HN protein of the paramyxovirus.

The recombinant paramyxovirus can be a recombinant HPIV1, a HPIV2, a HPIV3, a BPIV3, a PIV5, a Sendai virus, or a NDV, or a chimera thereof, for example. Additional description of such recombinant paramyxovirus is provided below.

General methods of generating a recombinant paramyxovirus including a genome including a heterologous gene are known to the person of ordinary skill in the art, as are viral sequences and reagents for use in such methods. Non-limiting examples of methods of generating a recombinant PIV vector (such as a recombinant HPIV1, HPIV2, HPIV3, or H/BPIV3 vector) including a heterologous gene, methods of attenuating the vectors (e.g., by recombinant or chemical means), as well as viral sequences and reagents for use in such methods are provided in US Patent Publications 2012/0045471; 2010/0119547; 2009/0263883; 2009/0017517; 8084037; 6,410,023; 8,367,074; 7,951,383; 7,820,182; 7704509; 7632508; 7622123; 7250171; 7208161; 7201907; 7192593, and Newman et al. 2002. Virus genes 24:77-92, Tang et al., 2003. J Virol, 77(20):10819-10828; each of which is incorporated by reference herein in its entirety. Non-limiting examples of methods of generating a recombinant NDV vector including a heterologous gene, as well as viral sequences and reagents for use in such methods are provided in US Patent Publications 2012/0064112; and Basavarajappa et al. 2014 Vaccine, 32: 3555-3563, and McGinnes et al., *J. Virol.*, 85: 366-377, 2011, each of which is incorporated by reference herein in its entirety. Non-limiting examples of methods of generating a recombinant Sendai vector including a heterologous gene, as well as viral sequences and reagents for use in such methods are provided in US Patent Publications 20140186397, and Jones et al., *Vaccine*, 30:959-968, 2012, each of which is incorporated by reference herein in its entirety.

A. HPIV1 Vectors

In some embodiments, the recombinant paramyxovirus can be a recombinant HPIV1 including a viral genome encoding HPIV1 N, P, C, M, F, HN, and L proteins. Nucleic acid sequences of HPIV1 genomes, and the genes therein, are known in the art, as are structural and functional genetic elements that control gene expression, such as gene start and gene end sequences and viral genome and anti-genome promoters. An exemplary HPIV1 Washington/1964 strain genome sequence is provided as GenBank Acc. No. AF457102.1, which is incorporated by reference herein in its entirety. This exemplary HPIV1 Washington/1964 strain genome sequence encodes N, P, C, M, F, HN, and L proteins set forth as: HPIV1 N, SEQ ID NO: 24 (GenBank protein ID #AAL89400.1, incorporated by reference herein) HPIV1 P, SEQ ID NO: 25 (GenBank protein ID #AAL89402.1, incorporated by reference herein) HPIV1 C, SEQ ID NO: 26 (ORF of P, GenBank protein ID #AAL89403.1, incorporated by reference herein) HPIV1 M, SEQ ID NO: 27 (GenBank protein ID #AAL89406.1, incorporated by reference herein) HPIV1 F, SEQ ID NO: 28 (GenBank protein ID #AAL89407.1, incorporated by reference herein) HPIV1 HN, SEQ ID NO: 29 (GenBank protein ID #AAL89408.1, incorporated by reference herein) HPIV1 L, SEQ ID NO: 30 (GenBank protein ID #AAL89409.1, incorporated by reference herein)

The corresponding gene-start and gene-end sequences for these HPIV1 genes are provided below:

| Gene | Gene start | SEQ ID | Gene end | SEQ ID | Intergenic |
|---|---|---|---|---|---|
| N | agggttaaag | 54 | aagtaagaaaaa | 55 | ctt |
| P | agggtgaatg | 56 | Aattaagaaaaa | 57 | ctt |
| M | agggtcaaag | 58 | Aaataagaaaaa | 59 | ctt |
| F | agggacaaag | 60 | Aagtaagaaaaa | 55 | ctt |
| HN | agggttaaag | 61 | Gaataagaaaaa | 62 | ctt |
| L | agggttaatg | 63 | Tagtaagaaaaa | 64 | ctt |

Further, viral leader/genome promoter and trailer/antigenome promoter of the HPIV2 V94 strain as set forth in GenBank Acc. No. AF457102.1 as nucleotides 1-96 and 15544-15600, respectively.

The recombinant paramyxovirus can be a recombinant HPIV1 including a viral genome encoding HPIV1 N, P, C, M, F, HN, and L proteins as set forth above, or encoding HPIV1 N, P, C, M, F, HN, and L proteins individually having at least 90% (such as at least 95%) sequence identity to the HPIV1 N, P, C, M, F, HN, and L proteins set forth above.

In some embodiments the recombinant paramyxovirus can be a recombinant HPIV1 including a genome including a heterologous gene encoding a recombinant viral glycoprotein ectodomain from a type I membrane protein (such as RSV F ectodomain) linked to a HPIV1 F protein TM and CT as set forth below, or encoding a recombinant viral glycoprotein ectodomain from a type I membrane protein (such as RSV F ectodomain) linked to a HPIV1 F protein TM and CT having at least 90% (such as at least 95%) sequence identity to the HPIV1 F protein TM and CT as set forth below. In some embodiments the recombinant paramyxovirus can be a recombinant HPIV1 including a genome including a heterologous gene encoding a recombinant viral glycoprotein ectodomain from a type I membrane protein (such as RSV F ectodomain) linked to a HPIV1 F protein CT as set forth below, or encoding a recombinant viral glycoprotein ectodomain from a type I membrane protein (such as RSV F ectodomain) linked to a HPIV1 F protein CT having at least 90% (such as at least 95%) sequence identity to the HPIV1 F protein CT as set forth below. HPIV1 F protein TM and CT sequences are known (see, e.g., GenBank accession #AF457102.1, incorporated by reference herein). Exemplary HPIV1 F protein TM and CT sequences are set forth as:

HPIV1 F TM:
QIIMIIIVCILIIIICGILYYLY, residues 1-23 of SEQ ID NO: 31

HPIV1 F CT:
RVRRLLVMINSTHNSPVNAYTLESRMRNPYMGNNSN, residues 24-59 of SEQ ID NO: 31

HPIV1 F TM + CT:
QIIMIIIVCILIIIICGILYYLYRVRRLLVMINSTHNSPVNAYTLESRMRNPYMGNNSN, SEQ ID NO: 31

B. HPIV2 Vectors

In some embodiments the recombinant paramyxovirus vector can be a recombinant HPIV2 including a viral genome encoding HPIV2 N, P, V, M, F, HN, and L proteins. The nucleic acid sequences of the gene encoding these HPIV2 proteins are known in the art, as are structural and functional genetic elements that control gene expression, such as gene start and gene-end sequences and viral genome and anti-genome promoters. An exemplary HPIV2 V94 strain genome sequence is provided as GenBank Acc. No. AF533010.1, which is incorporated by reference herein in its entirety. This exemplary HPIV2 V94 strain genome sequence encodes N, P, V, M, F, HN, and L proteins set forth as: HPIV2 N, SEQ ID NO: 32 (encoded by GenBank No. AF533010.1, incorporated by reference herein) HPIV2 P, SEQ ID NO: 33 (encoded by GenBank No. AF533010.1, incorporated by reference herein) HPIV2 V, SEQ ID NO: 34 (ORF of P, encoded by GenBank No. AF533010.1, incorporated by reference herein) HPIV2 M, SEQ ID NO: 35 (encoded by GenBank No. AF533010.1, incorporated by reference herein) HPIV2 F, SEQ ID NO: 36 (encoded by GenBank No. AF533010.1, incorporated by reference herein) HPIV2 HN, SEQ ID NO: 37 (encoded by GenBank No. AF533010.1, incorporated by reference herein) HPIV2 L, SEQ ID NO: 38 (encoded by GenBank No. AF533010.1, incorporated by reference herein) The corresponding gene-start and gene end sequences for these HPIV2 genes are provided below:

| Gene | Gene start | SEQ ID | Gene end | SEQ ID | Intergenic | SEQ ID |
|---|---|---|---|---|---|---|
| N | Agattccggtgccg | 65 | aatttaagaaaaaa | 66 | acat | |
| P | aggcccggacgggttag | 67 | aatttaataaaaaa | 68 | ttaaaagaagttaagtaaaatttaaagaacacaat agagaaaacct | 117 |
| M | Aggtccgaaagc | 69 | aatctaacaaaaaa | 70 | ctaaacattcaataataaatcaaagttc | 118 |
| F | Aggccaaattat | 71 | aatttaagaaaaaa | 72 | cctaaaat | 119 |
| HN | Aagcacgaaccc | 73 | tatttaagaaaaaa | 74 | taatctttatataatgtaacaatactactaagattata atat | 120 |
| L | Aggccaga | 75 | tatttaagaaaaaa | 76 | | |

Further, viral leader/genome promoter and trailer/antigenome promoter of the HPIV2 V94 strain as set forth in GenBank Acc. No. AF533010.1 are set forth as nucleotides 1-175 and 15565-15654, respectively.

The recombinant paramyxovirus can be a recombinant HPIV2 including a viral genome encoding HPIV2 N, P, V, M, F, HN, and L proteins as set forth above, or encoding HPIV2 N, P, V, M, F, HN, and L proteins individually having at least 90% (such as at least 95%) sequence identity to the HPIV2 N, P, V, M, F, HN, and L proteins set forth above.

In some embodiments the recombinant paramyxovirus can be a recombinant HPIV2 including a genome including a heterologous gene encoding a recombinant viral glycoprotein ectodomain from a type I membrane protein (such as RSV F ectodomain) linked to a HPIV2 F protein TM and CT as set forth below, or encoding a recombinant viral glycoprotein ectodomain from a type I membrane protein (such as RSV F ectodomain) linked to a HPIV2 F protein TM and CT having at least 90% (such as at least 95%) sequence identity to the HPIV2 F protein TM and CT as set forth below. In some embodiments the recombinant paramyxovirus can be a recombinant HPIV2 including a genome including a heterologous gene encoding a recombinant viral glycoprotein ectodomain from a type I membrane protein (such as RSV F ectodomain) linked to a HPIV2 F protein CT as set forth below, or encoding a recombinant viral glycoprotein ectodomain from a type I membrane protein (such as RSV F ectodomain) linked to a HPIV2 F protein CT having at least 90% (such as at least 95%) sequence identity to the HPIV2 F protein CT as set forth below. HPIV2 F protein TM and CT sequences are known (see, e.g., GenBank accession #AF533010.1, incorporated by reference herein). Exemplary HPIV2 F protein TM and CT sequences from the HPIV3 JS strain are set forth as:

```
HPIV2 F TM domain:
TLYSLSAIALILSVITLVVVGLLIAYII, residues 1-28
of SEQ ID NO: 39

HPIV2 F CT:
KLVSQIHQFRALAATTMFHRENPAVFSKNNHGNIYGIS, residues
29-66 of SEQ ID NO: 39

HPIV2 F TM + CT:
TLYSLSAIALILSVITLVVVGLLIAYIIKLVSQIHQFRALAATTMFHREN
PAVFSKNNHGNIYGIS, SEQ ID NO: 39
```

C. HPIV3 Vectors

In some embodiments the recombinant paramyxovirus can be a recombinant HPIV3 including a viral genome encoding HPIV3 N, P, C, M, F, HN, and L proteins. The nucleic acid sequences of the gene encoding these HPIV3 proteins are known in the art, as are structural and functional genetic elements that control gene expression, such as gene start and gene end sequences and viral genome and antigenome promoters. An exemplary HPIV3 JS strain genome sequence is provided as GenBank Acc. No. Z11575, which is incorporated by reference herein in its entirety. For this exemplary HPIV3 JS strain genome sequence nucleic acid sequences encoding the N, P, C, M, F, HN, and L proteins are set forth below.

HPIV3 N, SEQ ID NO: 40 (encoded by nucleotides 111-1658 of GenBank No. Z11575, incorporated by reference herein)

HPIV3 P, SEQ ID NO: 41 (encoded by nucleotides 1784-3595 of GenBank No. Z11575, incorporated by reference herein)

HPIV3 C, SEQ ID NO: 114 (encoded by nucleotides 1794-2393 of GenBank No. Z11575, incorporated by reference herein)

HPIV3 M, SEQ ID NO: 42 (encoded by nucleotides 3753-4814 of GenBank No. Z11575, incorporated by reference herein), HPIV3 F, SEQ ID NO: 43 (encoded by nucleotides 5072-6691 of GenBank No. Z11575, incorporated by reference herein), HPIV3 HN, SEQ ID NO: 44 (encoded by nucleotides 6806-8524 of GenBank No. Z11575, incorporated by reference herein)

HPIV3 L, SEQ ID NO: 45 (encoded by nucleotides 8646-15347 of GenBank No. Z11575, incorporated by reference herein)

In some embodiments, the HN gene in HPIV3 vector encodes a HPIV3 HN protein comprising the amino acid sequence set forth as

```
                                        (SEQ ID NO: 101)
MEYWKHTNHGKDAGNELETSMATHGNKLTNKIIYILWTIILVLLSIVFII

VLINSIKSEKAHESLLQDINNEFMEITEKIQMASDNTNDLIQSGVNTRLL

TIQSHVQNYIPISLTQQMSDLRKFISEITIRNDNQEVLPQRITHDVGIKP

LNPDDFWRCTSGLPSLMKTPKIRLMPGPGLLAMPTTVDGCVRTPSLVIND

LIYAYTSNLITRGCQDIGKSYQVLQIGIITVNSDLVPDLNPRISHTFNIN

DNRKSCSLALLNIDVYQLCSTPKVDERSDYASSGIEDIVLDIVNYDGSIS

TTRFKNNNISFDQPYAALYPSVGPGIYYKGKIIFLGYGGLEHPINENVIC

NTTGCPGKTQRDCNQASHSTWFSDRRMVNSIIVVDKGLNSIPKLKVWTIS

MRQNYWGSEGRLLLLGNKIYIYTRSTSWHSKLQLGIIDITDYSDIRIKWT

WHNVLSRPGNNECPWGHSCPDGCITGVYTDAYPLNPTGSIVSSVILDSQK

SRVNPVITYSTATERVNELAILNRTLSAGYTTTSCITHYNKGYCFHIVEI

NHKSLNTFQPMLFKTEIPKSCS
```

An exemplary DNA sequence encoding SEQ ID NO: 101 is provided as follows:

```
                                        (SEQ ID NO: 102)
atggaatactggaagcataccaatcacggaaaggatgctggtaatgagctg gagacgtctatggctactcatggcaacaagctcactaataagataatatac atattatggacaataatcctggtgttattatcaatagtcttcatcatagtg ctaattaattccatcaaaagtgaaaaggcccacgaatcattgctgcaagac ataaataatgagtttatggaaattacagaaaagatccaaatggcatcggat aataccaatgatctaatacagtcaggagtgaatacaaggcttcttacaatt cagagtcatgtccagaattacataccaatatcattgacacaacagatgtca gatcttaggaaattcattagtgaaattacaattagaaatgataatcaagaa gtgctgccacaaagaataacacatgatgtaggtataaaacctttaaatcca gatgattttggagatgcacgtctggtcttccatctttaatgaaaactca aaaataaggttaatgccagggccgggattattagctatgccaacgactgtt gatggctgtgttagaactccgtctttagttataaatgatctgatttatgct tatacctcaaatctaattactcgaggttgtcaggatataggaaaatcatat caagtcttacagatagggataataactgtaaactcagacttggtacctgac ttaaatcctaggatctctcatacctttaacataaatgacaataggaagtca tgttctctagcactcctaaatatagatgtatatcaactgtgttcaactccc aaagttgatgaaagatcagattatgcatcatcaggcatagaagatattgta cttgatattgtcaattatgatggttcaatctcaacaacaagatttaagaat ataacataagctttgatcaaccatatgctgcactatacccatctgttgga ccagggatatactacaaaggcaaaataatatttctcgggtatggaggtctt gaacatccaataaatgagaatgtaatctgcaacacaactgggtgccccggg
```

-continued
```
aaaacacagagagactgtaatcaagcatctcatagtacttggttttcagat aggaggatggtcaactccatcattgttgttgacaaaggcttaaactcaatt ccaaaattgaaagtatggacgatatctatgcgacaaaattactgggggtca gaaggaaggttacttctactaggtaacaagatctatatatatacaagatct acaagttggcatagcaagttacaattaggaataattgatattactgattac agtgatataaggataaaatggacatggcataatgtgctatcaagaccagga aacaatgaatgtccatggggacattcatgtccagatggatgtataacagga gtatatactgatgcatatccactcaatcccacagggagcattgtgtcatct gtcatattagactcacaaaaatcgagagtgaacccagtcataacttactca acagcaaccgaaagagtaaacgagctggccatcctaaacagaacactctca gctggatatacaacaacaagctgcattacacactataacaaaggatattgt tttcatatagtagaaataaatcataaaagcttaaacacatttcaacccatg ttgttcaaaacagagattccaaaaagctgcagttaa
```

The corresponding gene-start and gene end sequences for these HPIV3 genes are provided below:

| Gene | Gene start | SEQ ID | Gene end | SEQ ID |
|------|------------|--------|----------|--------|
| N | aggattaaagac | 77 | aaataagaaaaa | 78 |
| P | Aggattaaag | 79 | aaataagaaaaa | 80 |
| M | Aggattaaag | 81 | aaataaaggataatcaaaaa | 82 |
| F | Aggacaaaag | 83 | aattataaaaa | 84 |
| HN | Aggagtaaag | 85 | aaatataaaaa | 86 |
| L | Aggagcaaag | 87 | aaagtaagaaaaa | 88 |

Further, viral genome and anti-genome promoters of the HPIV3 JS strain as set forth in GenBank Acc. No. Z11575 are provided as nucleotides 1-96 (genomic promoter) and nucleotides 15367-15462 (antigenomic promoter), respectively.

The recombinant paramyxovirus can be a recombinant HPIV3 including a viral genome encoding HPIV3 N, P, C, M, F, HN, and L proteins as set forth above, or encoding HPIV3 N, P, C, M, F, HN, and L proteins individually having at least 90% (such as at least 95%) sequence identity to the HPIV3 N, P, C, M, F, HN, and L proteins set forth above.

In some embodiments the recombinant paramyxovirus can be a recombinant HPIV3 including a genome including a heterologous gene encoding a recombinant viral glycoprotein ectodomain from a type I membrane protein (such as RSV F ectodomain) linked to a HPIV3 F protein TM and CT as set forth below, or encoding a recombinant viral glycoprotein ectodomain from a type I membrane protein (such as RSV F ectodomain) linked to a HPIV3 F protein TM and CT having at least 90% (such as at least 95%) sequence identity to the HPIV3 F protein TM and CT as set forth below. In some embodiments the recombinant paramyxovirus can be a recombinant HPIV3 including a genome including a heterologous gene encoding a recombinant viral glycoprotein ectodomain from a type I membrane protein (such as RSV F ectodomain) linked to a HPIV3 F protein CT as set forth below, or encoding a recombinant viral glycoprotein ectodomain from a type I membrane protein (such as RSV F ectodomain) linked to a HPIV3 F protein CT having at least 90% (such as at least 95%) sequence identity to the HPIV3 F protein CT as set forth below. HPIV3 F protein TM and CT sequences are known (see, e.g., protein encoded by nucleotides 5072-6691 of GenBank No. Z11575). Exemplary HPIV3 F protein TM and CT sequences from the HPIV3 JS strain are set forth as:

HPIV3 F TM domain:
IIIILIMIIILFIINITIITIAI, residues 1-23 of
SEQ ID NO: 46

HPIV3 F CT:
KYYRIQKRNRVDQNDKPYVLTNK, residues 24-46 of
SEQ ID NO: 46

HPIV3 F TM + CT:
IIIILIMIIILFIINITIITIAIKYYRIQKRNRVDQNDKPYVLTNK,
SEQ ID NO: 46

D. Bovine PIV3 and Chimeric Human/Bovine PIV3 Vectors

In some embodiments the recombinant paramyxovirus can be bovine PIV3 (BPIV3) or a chimeric paramyxovirus including a viral genome encoding a combination of N, P, C, V, M, F, HN, and L proteins from BPIV3 and HPIV3. For example, the chimeric viral genome can encode HPIV3 F and HN proteins and BPIV3 N, P, C, V, M, and L proteins. The nucleic acid sequences of the genes encoding these HPIV3 and BPIV3 proteins are known in the art, as are structural and functional genetic elements that control gene expression, such as gene start and gene end sequences and viral genome and anti-genome promoters. An exemplary BPIV3 Kansas genome sequence is provided as GenBank Acc. No. AF178654, which is incorporated by reference herein in its entirety. This exemplary BPIV3 Kansas strain genome sequence encodes N, P, C, V, M, F, HN, and L proteins set forth below:

BPIV3 N, SEQ ID NO: 47 (GenBank Acc. No.: AAF28254, encoded by nucleotides 111-1658 of GenBank No. AF178654, each of which is incorporated by reference herein)

BPIV3 P, SEQ ID NO: 48 (GenBank Acc. No.: AAF28255, encoded by nucleotides 1784-3574 of GenBank No. AF178654, each of which is incorporated by reference herein)

BPIV3 C, SEQ ID NO: 115 (encoded by nucleotide 1794-2399 of GenBank No. AF178654, incorporated by reference herein)

BPIV3 V, SEQ ID NO: 116 (encoded by nucleotide 1784-3018 of GenBank No. AF178654 with an inserted nucleotide g between nucleotide 2505-2506 at a gene editing site located at nucleotide 2500-2507)

BPIV3 M, SEQ ID NO: 49 (GenBank Acc. No.: AAF28256, encoded by nucleotides 3735-4790 of GenBank No. AF178654, each of which is incorporated by reference herein)

BPIV3 F, SEQ ID NO: 50 (GenBank Acc. No.: AAF28257, encoded by nucleotides 5066-6688 of GenBank No. AF178654, each of which is incorporated by reference herein)

BPIV3 HN, SEQ ID NO: 51 (GenBank Acc. No.: AAF28258, encoded by nucleotides 6800-8518 of GenBank No. AF178654, each of which is incorporated by reference herein)

BPIV3 L, SEQ ID NO: 52 (GenBank Acc. No.: AAF28259, encoded by nucleotides 8640-15341 of GenBank No. AF178654, each of which is incorporated by reference herein)

In some embodiments, the HPIV3 HN gene included in chimeric B/HPIV3 vector encodes a HPIV3 HN protein comprising the amino acid sequence set forth as SEQ ID NO: 101 or SEQ ID NO: 44, or a variant thereof. An exemplary DNA sequence encoding SEQ ID NO: 101 is provided SEQ ID NO: 102.

In some embodiments, the chimeric B/HPIV3 vector can include a HPIV3 F gene in place of the BPIV3 F gene, for example a gene encoding a HPIV3 F amino acid sequence set forth as SEQ ID NO: 43, or a variant thereof.

The corresponding gene-start and gene end sequences for these BPIV3 genes are provided below:

| Gene | Gene start | SEQ ID | Gene end | SEQ ID |
|------|------------|--------|----------|--------|
| N    | Aggattaaagaa | 89   | caagtaagaaaaa | 90 |
| P    | Aggattaatgga | 91   | tgattaagaaaaa | 92 |
| M    | Aggatgaaagga | 93   | gaaaaatcaaaaa | 94 |
| F    | Aggatcaaaggg | 95   | aaaagtacaaaaaa | 96 |
| HN   | Aggaacaaagtt | 97   | gaaataataaaaaa | 98 |
| L    | Aggagaaaagtg | 99   | aaagtaagaaaaa | 100 |

Further, viral genome and anti-genome promoters of the BPIV3 Kansas strain as set forth in GenBank Acc. No. AF178654 are provided as nucleotides 1-96 (genomic promoter) and nucleotides 15361-15456 (antigenomic promoter), respectively.

The recombinant paramyxovirus including a viral genome encoding N, P, C, V, M, F, HN, and L proteins from HPIV3 and BPIV3 viruses can encode a mixture of the HPIV3 and BPIV3 N, P, C, V, M, F, HN, and L proteins as set forth above, or can encode a mixture of the BPIV3 and HPIV3 N, P, C, V, M, F, HN, and L proteins individually having at least 90% (such as at least 95%) sequence identity to the BPIV3 or HPIV3 N, P, C, V, M, F, HN, and L proteins set forth above.

In some embodiments, the recombinant paramyxovirus can include a viral genome encoding HPIV3 F and HN proteins and BPIV3 N, P, C, V, M, and L proteins as set forth above, or encoding HPIV3 F and HN proteins and BPIV3 N, P, C, V, M, and L proteins individually having at least 90% (such as at least 95%) sequence identity to the corresponding HPIV3 F and HN protein or BPIV3 N, P, C, V, M, and L protein set forth above.

In some embodiments, the recombinant paramyxovirus including a genome encoding N, P, C, V, M, F, HN, and L proteins from BPIV3 can further include a heterologous gene encoding a recombinant viral glycoprotein ectodomain from a type I membrane protein (such as RSV F ectodomain) linked to a TM and CT of the BPIV3 F protein as set forth below, or linked to a TM and CT having at least 90% (such as at least 95%) sequence identity to the TM and CT of the BPIV3 F protein as set forth below. In some embodiments, the recombinant paramyxovirus including a genome encoding N, P, C, V, M, F, HN, and L proteins from BPIV3 can further include a heterologous gene encoding a recombinant viral glycoprotein ectodomain from a type I membrane protein (such as RSV F ectodomain) linked to a CT of the BPIV3 F protein as set forth below, or linked to a CT having at least 90% (such as at least 95%) sequence identity to the CT of the BPIV3 F protein as set forth below.

In some embodiments, the recombinant paramyxovirus including a genome encoding N, P, C, V, M, F, HN, and L proteins from HPIV3 and BPIV3 viruses (such as HPIV3 F and HN proteins and BPIV3 N, P, C, V, M, and L proteins) can further include a heterologous gene encoding a recombinant viral glycoprotein ectodomain from a type I membrane protein (such as RSV F ectodomain) linked to a TM and CT of the BPIV3 F protein as set forth below, or linked to a TM and CT having at least 90% (such as at least 95%) sequence identity to the TM and CT of the BPIV3 F protein as set forth below. In some embodiments, the recombinant paramyxovirus including a genome encoding N, P, C, V, M, F, HN, and L proteins from HPIV3 and BPIV3 viruses can further include a heterologous gene encoding a recombinant viral glycoprotein ectodomain from a type I membrane protein (such as RSV F ectodomain) linked to a CT of the BPIV3 F protein as set forth below, or linked to a CT having at least 90% (such as at least 95%) sequence identity to the CT of the BPIV3 F protein as set forth below. Exemplary BPIV3 F protein TM and CT sequences from the BPIV3 Kansas strain are set forth as:

BPIV3 F TM domain:
ITIIIVMIIILVIINITIIVV, residues 1-21 of SEQ ID NO: 53

BPIV3 F CT:
IIKFHRIQGKDQNDKNSEPYILTNRQ, residues 22-57 of SEQ ID NO: 53

BPIV3 F TM + CT:
ITIIIVMIIILVIINITIIVVIIKFHRIQGKDQNDKNSEPYILTNRQ, SEQ ID NO: 53

In some embodiments, the recombinant paramyxovirus including a genome encoding N, P, C, V, M, F, HN, and L proteins from HPIV3 and BPIV3 viruses (such as HPIV3 F and HN proteins and BPIV3 N, P, C, V, M, and L proteins) can further include a heterologous gene encoding a recombinant viral glycoprotein ectodomain from a type I membrane protein (such as RSV F ectodomain) linked to a TM and CT of the HPIV3 F protein as set forth above, or linked to a TM and CT having at least 90% (such as at least 95%) sequence identity to the TM and CT of the HPIV3 F protein as set forth above. In some embodiments, the recombinant paramyxovirus including a genome encoding N, P, C, V, M, F, HN, and L proteins from HPIV3 and BPIV3 viruses can further include a heterologous gene encoding a recombinant viral glycoprotein ectodomain from a type I membrane protein (such as RSV F ectodomain) linked to a CT of the HPIV3 F protein as set forth below, or linked to a CT having at least 90% (such as at least 95%) sequence identity to the CT of the HPIV3 F protein as set forth below.

E. Sendai Virus

In an embodiment, the recombinant paramyxovirus can be a recombinant Sendai virus including a recombinant viral genome encoding Sendai virus N, P, C, V, M, F, HN, and L proteins including a heterologous gene encoding a recombinant viral glycoprotein ectodomain from a type I membrane protein (such as RSV F ectodomain) linked to a TM and CT of the Sendai virus F protein, or linked to a TM and CT having at least 90% (such as at least 95%) sequence identity to the CT of the Sendai virus F protein. In an embodiment, the recombinant paramyxovirus can be a recombinant Sendai virus including a recombinant viral genome encoding Sendai virus N, P, C, V, M, F, HN, and L proteins including a heterologous gene encoding a recombinant viral glycoprotein ectodomain from a type I membrane protein (such as RSV F ectodomain) linked to a CT of the Sendai virus F protein, or linked to a CT having at least 90% (such as at least 95%) sequence identity to the CT of the Sendai virus F protein. Sendai virus F protein TM and CT sequences are known (see, e.g., GenBank accession #BAN84670, incorporated by reference herein). Exemplary Sendai virus F protein TM and CT sequences are set forth as:

```
Sendai F TM domain:
VITIIVVMVVILVVIIVIIIV
(residues 1-21 of SEQ ID NO: 103)

Sendai F CT:
LYRLRRSMLMGNPDDRIPRDTYTLEPKIRHMYTNGGFDAMAEKR
(residues 22-65 of SEQ ID NO: 103)

Sendai F TM + CT:
VITIIVVMVVILVVIIVIIIVLYRLRRSMLMGNPDDRIPRDTYTLEPKIR

HMYTNGGFDAMAEKR, SEQ ID NO: 103
```

F. NDV

In some embodiments the recombinant paramyxovirus can be a recombinant NDV virus including a recombinant viral genome encoding NDV N, P, V, M, F, HN, and L proteins including a heterologous gene encoding a recombinant viral glycoprotein ectodomain from a type I membrane protein (such as RSV F ectodomain) linked to a TM and CT of the NDV F protein as set forth below, or linked to a TM and CT having at least 90% (such as at least 95%) sequence identity to the TM and CT of the NDV F protein as set forth below. In some embodiments the recombinant paramyxovirus can be a recombinant NDV virus including a recombinant viral genome encoding NDV N, P, V, M, F, HN, and L proteins including a heterologous gene encoding a recombinant viral glycoprotein ectodomain from a type I membrane protein (such as RSV F ectodomain) linked to a CT of the NDV F protein as set forth below, or linked to a CT having at least 90% (such as at least 95%) sequence identity to the CT of the NDV F protein as set forth below. NDV virus F protein TM and CT sequences are known (see, e.g., GenBank accession #AAC28374, incorporated by reference herein). Exemplary NDV virus F protein TM and CT sequences are set forth as:

```
NDV F TM domain:
IVLTIISLVFGILSLILACYL (residues 1-21 of
SEQ ID NO: 104)

NDV F CT:
MYKQKAQQKTLLWLGNNTLDQMRATTKM (residues 22-49 of
SEQ ID NO: 104)

NDV F TM + CT:
IVLTIISLVFGILSLILACYLMYKQKAQQKTLLWLGNNTLDQMRATTKM,
SEQ ID NO: 104
```

G. Heterologous Genes

The recombinant paramyxovirus vector includes a recombinant genome including one or more heterologous genes encoding an ectodomain of one or more heterologous envelope proteins (or antigenic fragment thereof) of a heterologous viral pathogen, wherein the ectodomain is linked to a TM and CT of an envelope protein from the recombinant paramyxovirus. For example, one or more heterologous envelope proteins (or antigenic fragment thereof) from measles virus, subgroup A or subgroup B respiratory syncytial viruses, mumps virus, human papilloma viruses, type 1 or type 2 human immunodeficiency viruses, herpes simplex viruses, cytomegalovirus, rabies virus, Epstein Barr virus, filoviruses, bunyaviruses, flaviviruses, alphaviruses, human metapneumovirus, ebola viruses (such as Zaire ebola virus), influenza viruses, or highly pathogenic coronaviruses (SARS, MERS) can be expressed by the disclosed recombinant paramyxovirus. Examples of useful envelope proteins include, but are not limited to, measles virus HA and F proteins, subgroup A or subgroup B respiratory syncytial virus F, G, and SH proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus pre E, and NS1 proteins, human metapneumovirus (HMPV) G and F proteins, Ebola virus GP protein, alphavirus E protein, and SARS and MERS S protein, and antigenic domains, fragments and epitopes thereof. Exemplary methods of inserting one or more heterologous genes or transcriptional units into a paramyxovirus viral genome or antigenome are described in WO04/027037 and US2013/0052718, each of which is incorporated by reference herein.

In several embodiments, the heterologous gene included in the recombinant paramyxovirus genome encodes the ectodomain of a RSV F protein, such as a bovine RSV F protein or a human RSV F protein. Human RSV can be classified into two groups: A and B. Groups A and B include subgroups A1, A2, B1, and B2, based mainly on sequence variability of the attachment (G) and fusion (F) proteins. The RSV F ectodomain can be derived from any RSV group (such as Group A or Group B) or subgroup of RSV, such as subgroup A1, A2, B1, or B2.

Exemplary human RSV F protein sequence from subgroup A2 and corresponding GenBank reference (which is incorporated by reference herein in its entirety) are set forth below:

RSV F A2 HEK protein sequence:

```
                                        (SEQ ID NO: 1)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

KARSTPVTLSKDQLSGINNIAFSN
```

RSV F B1 HEK protein sequence, Accession No. AAB82436:

```
MELLIHRLSAIFLTLAINALYLTSSQNITEEFYQSTCSAVSRGYFSALRTG

WYTSVITIELSNIKETKCNGTDTKVKLIKQELDKYKNAVTELQLLMQNTPA

ANNRARREAPQYMNYTINTTKNLNVSISKKRKRRFLGFLLGVGSAIASGIA

VSKVLHLEGEVNKIKNALLSTNKAVVSLSNGVSVLTSKVLDLKNYINNQLL
```

PIVNQQSCRISNIETVIEFQQKNSRLLEINREFSVNAGVTTPLSTYMLTNS

ELLSLINDMPITNDQKKLMSSNVQIVRQQSYSIMSIIKEEVLAYVVQLPIY

GVIDTPCWKLHTSPLCTTNIKEGSNICLTRTDRGWYCDNAGSVSFFPQADT

CKVQSNRVFCDTMNSLTLPSEVSLCNTDIFNSKYDCKIMTSKTDISSSVIT

SLGAIVSCYGKTKCTASNKNRGIIKTFSNGCDYVSNKGVDTVSVGNTLYYV

NKLEGKNLYVKGEPIINYYDPLVFPSDEFDASISQVNEKINQSLAFIRRSD

ELLHNVNTGKSTTNIMITTIIIVIIVVLLSLIAIGLLLYCKAKNTPVTLSK

DQLSGINNIAFSK
(SEQ ID NO: 2, GenBank Accession No. AAB82436,
incorporated by reference herein in its entirety)

RSV F B1 HEK Nucleic acid sequence:

auggagcugcugauccacagguuaagugcaaucuuccuaacucuugcuauu aaugcauuguaccucaccucaagucagaacauaacugaggaguuuuaccaa ucgacauguagugcaguuagcagagguuauuuuagugcuuuaagaacaggu ugguauaccagugucauaacaauagaauuaaguaauauaaaagaaaccaaa ugcaaggaacugacacuaaaguaaaacuuaauaaaacaagaauuagauaag uauaagaaugcagugacagaauuacagcuacuuaugcaaaacacaccagcu gccaacaaccgggccagaagagaagcaccacaguauaugaacuauacaauc aauaccacuaaaaaccuaaauguaucaauaagcaagaagaggaaacgaaga uuucugggcuucuuguuaggguguaggaucugcaauagcaagugguauagcu guauccaaaguucuacaccuugaaggagaagugaacaagaucaaaaaugcu uuguuaucuacaaacaaagcuguagucagucuaucaaauggggucaguguu uuaaccagcaaaguguuagaucucaagaauuacauaaauaaccaauuauua cccauaguaaaucaacagagcugucgcaucuccaacauugaaacaguuaua gaauuccagcagaagaacagcagauuguuggaaaucaacagagaauucagu gucaaugcagguguaacaacaccuuuaagcacuuacauguuaacaaacagu gaguuacuaucauugaucaaugauaugccuauaacaaaugaucagaaaaaa uuaaugucaagcaauguucagauaguaaggcaacaaaguuauucuaucaug ucuauaauaaaggaagaaguccuugcauauguuguacagcuaccuaucuau gguguaauagauacaccuugcuggaaauuacacacaucaccucuaugcacc accaacaucaaagaaggaucaaauauuuguuuaacaaggacugauagagga ugguauugugauaaugcaggaucaguauccuucuuuccacaggcugacacu uguaaagucaccaucgaguauuuugugacauaugaacaguuugaca uuaccaagugaagucagccuuuguaacacugacauauucaauuccaaguau gacugcaaaauuaugacaucaaaaacagacauaagcagcucaguaauuacu ucucuuggagcuauagugucaugcuauggcaaaacuaaaugcacugcaucc aacaaaaaucguggauuauaaagacauuuucuaaugguugugacuaugug ucaaacaaggaguagauacugugucaguggcaacacuuuauacuauga aacaagcuggaaggcaagaaccuuuauguaaaaggggaaccuauaauaaau uacuaugacccucuagguuuccuucgaugauguuugaugcaucaauucu caagucaaugaaaaaaucaaucaaaguuuagcuuuuauucguagaucugau gaauuacuacauaaugaaauacuggcaaaucuacuacaaauauuaugaua acuacaauuauuauaguaaucauuguaguauuguuaucauuaauagcuauu gguuugcuguuguauugcaaagccaaaaacacaccaguuacacuaagcaaa gaccaacuaagugugaaucaauaauauuugcauucagcaaauag
(SEQ ID NO: 3, GenBank Accession No.: AF013254.1,
nucleotides 5666-7390,
incorporated by reference herein in its entirety)

As illustrated by the sequences above, the hRSV F protein exhibits remarkable sequence conservation, with sequence identity of more than 85% across hRSV subgroups. In view of the conservation and breadth of knowledge of RSV F sequences, the person of ordinary skill in the art can easily identify corresponding RSV F amino acid positions between different RSV F strains and subgroups. The numbering of amino acid substitutions disclosed herein is made with reference to the exemplary hRSV F protein sequence from the A2 stain set forth as SEQ ID NO: 1, unless context indicates otherwise.

For illustration purposes, the signal peptide, $F_2$ polypeptide, pep27, $F_1$, $F_1$ ectodomain, transmembrane domain, and cytosolic domain of the RSV F protein from an A2 strain (SEQ ID NO: 1), are set forth as follows:

Signal peptide (SEQ ID NO: 1, residues 1-22):
MELLILKANAITTILTAVTFCF $F_2$ polypeptide (SEQ ID NO: 1, residues 23-109):
ASGQNITEEFYQSTCSAVSKGYLSALRTGWYTSVITIELSNIKENKCNGT

DAKVKLIKQELDKYKNAVTELQLLMQSTPATNNRARR

Pep27 (SEQ ID NO: 1, residues 110-136):
ELPRFMNYTLNNAKKTNVTLSKKRKRR $F_1$ (SEQ ID NO: 1, residues 137-574):
FLGFLLGVGSAIASGVAVSKVLHLEGEVNKIKSALLSTNKAVVSLSNGVS

VLTSKVLDLKNYIDKQLLPIVNKQSCSISNIETVIEFQQKNNRLLEITRE

FSVNAGVTTPVSTYMLTNSELLSLINDMPITNDQKKLMSNNVQIVRQQSY

SIMSIIKEEVLAYVVQLPLYGVIDTPCWKLHTSPLCTTNTKEGSNICLTR

TDRGWYCDNAGSVSFFPQAETCKVQSNRVFCDTMNSLTLPSEVNLCNVDI

FNPKYDCKIMTSKTDVSSSVITSLGAIVSCYGKTKCTASNKNRGIIKTFS

NGCDYVSNKGVDTVSVGNTLYYVNKQEGKSLYVKGEPIINFYDPLVFPSD

EFDASISQVNEKINQSLAFIRKSDELLHNVNAGKSTTNIMITTIIIVIIV

ILLSLIAVGLLLYCKARSTPVTLSKDQLSGINNIAFSN $F_1$ ectodomain of mature protein (SEQ ID NO: 1,
residues 137-529):
FLGFLLGVGSAIASGVAVSKVLHLEGEVNKIKSALLSTNKAVVSLSNGVS

VLTSKVLDLKNYIDKQLLPIVNKQSCSISNIETVIEFQQKNNRLLEITRE

FSVNAGVTTPVSTYMLTNSELLSLINDMPITNDQKKLMSNNVQIVRQQSY

SIMSIIKEEVLAYVVQLPLYGVIDTPCWKLHTSPLCTTNTKEGSNICLTR

TDRGWYCDNAGSVSFFPQAETCKVQSNRVFCDTMNSLTLPSEVNLCNVDI

FNPKYDCKIMTSKTDVSSSVITSLGAIVSCYGKTKCTASNKNRGIIKTFS

NGCDYVSNKGVDTVSVGNTLYYVNKQEGKSLYVKGEPIINFYDPLVFPSD

EFDASISQVNEKINQSLAFIRKSDELLHNVNAGKSTTNIMITT

F₁ Transmembrane domain (SEQ ID NO: 1, residues 530-550):
IIIVIIVILLSLIAVGLLLYC

F₁ CT (SEQ ID NO: 1, residues 551-574):
KARSTPVTLSKDQLSGINNIAFSN

In some embodiments, the heterologous gene included in the recombinant paramyxovirus genome encodes the ectodomain of a human RSF F protein, wherein the RSV F ectodomain comprises an amino acid sequence at least 85% (such as at least 90%, or at least 95%) identical to the RSV ectodomain of one of SEQ ID NOs: 1 (WT RSV F A), 2 (WT RSV F B), 12 (A2 HEK), 14 (A2 HEK+DS), or 19 (A2 HEK+DS-Cav1), or comprises the amino acid sequence of the RSV ectodomain of SEQ ID NO: 12, 14, or 19.

In some embodiments the recombinant paramyxovirus can include a genome including a heterologous gene encoding a recombinant hRSV F protein that has been codon-optimized for expression in a human cell. For example, the gene encoding the recombinant hRSV F protein can be codon-optimized for human expression using a GA, DNA2.0 (D2), or GenScript (GS) optimization algorithm (see Example 1). Non-limiting examples of nucleic acid sequences encoding the RSV F protein that have been codon-optimized for expression in a human cell are provided as follows:

GeneArt optimized RSV F A2 HEK DNA sequence:

(SEQ ID NO: 4)
atggaactgctgatcctgaaggccaacgccatcacaacaatcctgaccgcc gtgaccttctgcttcgccagcggccagaacatcaccgaggaattctaccag agcacctgtagcgccgtgtccaagggctacctgagcgccctgagaaccggc tggtacaccagcgtgatcaccatcgagctgtccaacatcaaagaaaacaag tgcaacggcaccgacgccaaagtgaagctgatcaagcaggaactggacaag tacaagaacgccgtgaccgagctgcagctgctgatgcagtccaccccccgcc accaacaaccgggccagaagagaactgccccggttcatgaactacaccctc aacaacgccaaaaagaccaacgtgaccctgagcaagaagcggaagcggcgg ttcctgggcttcctgctgggcgtgggcagcgccattgcctctggcgtggcc gtgtctaaggtgctgcacctggaaggcgaagtgaacaagatcaagagcgcc ctgctgtccacaaacaaggccgtggtgtccctgagcaacggcgtgtccgtg ctgacctccaaggtgctggatctgaagaactacatcgacaagcagctgctg cccatcgtgaacaagcagagctgcagcatcagcaacatcgagacagtgatc gagttccagcagaagaacaaccggctgctggaaatcacccgcgagttcagc gtgaacgccggcgtgaccaccccgtgtccacctacatgctgaccaacagc gagctgctgtccctgatcaatgacatgcccatcaccaacgaccagaaaaag ctgatgagcaacaacgtgcagatcgtgcggcagcagagctactccatcatg agcatcatcaaagaagaggtgctggcctacgtggtgcagctgcccctgtac ggcgtgatcgacaccccctgctggaagctgcacaccagcccctgtgcacc accaacacaaaagagggcagcaacatctgcctgacccggaccgaccgggc tggtactgcgataatgccggcagcgtgtcattctttccacaggccgagaca tgcaaggtgcagagcaaccgggtgttctgcgacaccatgaacagcctgacc ctgccctccgaagtgaacctgtgcaacgtggacatcttcaaccctaagtac gactgcaagatcatgaccagcaagaccgacgtgtccagctccgtgatcacc tccctgggcgccatcgtgtcctgctacggcaagaccaagtgcaccgccagc aacaagaaccgggcatcatcaagaccttcagcaacggctgcgactacgtg tccaacaaggggtggacaccgtgtccgtgggcaacaccctgtactacgtg aacaaacaggaaggcaagagcctgtacgtgaagggcgagcccatcatcaac ttctacgaccccctggtgttccccagcgacgagttcgacgccagcatcagc caggtcaacgagaagatcaaccagagcctggccttcatcagaaagagcgac gagctgctgcacaatgtgaatgccggcaagagcaccacaaacatcatgatc accactatcatcatcgtgatcatcgtcatcctgctgagtctgatcgccgtg ggcctgctgctgtactgcaaggccagatccaccccctgtgaccctgtccaag gatcagctgtccggcatcaacaatatcgccttctccaactga GenScript optimized RSV F A2 HEK DNA sequence:

(SEQ ID NO: 5)
atggaactgctgatcctgaaagccaacgctattactactatcctgaccgc cgtgacattttgcttcgcatctggacagaacattactgaggaattctac agtcaacatgcagcgccgtgtccaaaggatacctgagcgccctgcggacc ggctggtatacatcagtgattactatcgagctgtccaacatcaaggaaaa caaatgtaatgggaccgacgcaaaggtgaaactgatcaagcaggagctgg ataagtacaaaaatgccgtgacagaactgcagctgctgatgcagtccaca ccagcaactaacaatcgcgcccggagagagctgccccggttcatgaacta taccctgaacaatgctaagaaaaccaatgtgacactgtccaagaaacgca agaggcgcttcctgggatttctgctgggcgtggggtctgccatcgctagt ggagtggccgtctctaaagtcctgcacctggagggcgaagtgaacaagat caaaagcgccctgctgtccactaacaaggcagtggtcagtctgtcaaatg gcgtgtccgtcctgacctctaaggtgctggacctgaaaaattatattgat aagcagctgctgcctatcgtcaacaaacagagctgctccatttctaatat cgagacagtgatcgaattccagcagaagaacaatagactgctggagatta ccagagagttcagcgtgaacgccggcgtcaccacacccgtgtccacctac atgctgacaaatagtgagctgctgtcactgattaacgacatgcctatcac caatgatcagaagaaactgatgtccaacaatgtgcagatcgtcagacagc agagttactcaatcatgtctatcattaaggaggaagtcctggcctacgtg gtccagctgccactgtatggcgtgatcgacacccctgctggaaactgca tacatctcctctgtgcactaccaacacaaaggaaggaagtaatatctgcc tgactcgaaccgaccggggatggtactgtgataacgcaggcagcgtgtcc ttctttccacaggccgagacctgcaaggtccagagcaacagggtgttctg tgacactatgaatagcctgaccctgccttccgaagtcaacctgtgcaatg tggacatctttaatccaaagtacgattgtaagatcatgactagcaagacc gatgtcagctcctctgtgattacttctgggggccatcgtgagttgcta cggaaagacaaaatgtactgccagcaacaaaaatcgcggcatcattaaga

```
ccttctccaacgggtgcgactatgtctctaacaagggcgtggatacagtg agtgtcgggaacactctgtactatgtcaataagcaggagggaaaaagcct gtacgtgaagggcgaacccatcattaacttctatgaccccctggtgttcc cttccgacgagtttgatgcatctattagtcaggtgaacgaaaaaatcaat cagagtctggcctttattcggaagtcagatgagctgctgcacaacgtgaa tgctggcaaatctacaactaacatcatgatcaccacaatcatcatcgtga ttatcgtcattctgctgtcactgatcgctgtggggctgctgctgtactgt aaggcaagaagcaccccagtcactctgtcaaaagaccagctgtcagggat taacaacattgccttcagtaactga
```

Additional examples of codon-optimized (for human expression) sequences are provided below.

The RSV F protein encoded by the heterologous gene can include one or more amino acid substitutions that improve expression of the RSV F protein, availability of the RSV F protein on the virion envelope, or stability of the RSV F protein, for example, in a prefusion conformation. In some embodiments, the RSV F protein can include a glutamic acid substitution at position 66, a proline substitution at position 101, or both. For example the RSV F protein can include the "HEK" substitutions of a K66E substitution and a Q101P substitution. Exemplary DNA and protein sequences for a RSV F protein from the A2 subgroup including the HEK amino acid substitutions are set forth below.

RSV F A2 protein with HEK substitutions (RSV F_A2_HEK): SEQ ID NO: 1
GeneArt optimized RSV F_A2_HEK DNA sequence:

```
                                         (SEQ ID NO: 6)
atggaactgctgatcctgaaggccaacgccatcacaacaatcctgaccgc cgtgaccttctgcttcgccagcggccagaacatcaccgaggaattctacc agagcacctgtagcgccgtgtccaagggctacctgagcgccctgagaacc ggctggtacaccagcgtgatcaccatcgagctgtccaacatcaaagaaaa caagtgcaacggcaccgacgccaaagtgaagctgatcaagcaggaactgg acaagtacaagaacgccgtgaccgagctgcagctgctgatgcagtccacc cccgccaccaacaacgggccagaagagaactgccccggttcatgaacta cacccctcaacaacgccaaaaagaccaacgtgaccctgagcaagaagcgga gcggcggttcctggcttcctgctgggcgtgggcagcgccattgcctct ggcgtggccgtgtctaaggtgctgcacctggaaggcgaagtgaacaagat caagagcgccctgctgtccacaaacaaggccgtggtgtccctgagcaacg gcgtgtccgtgctgacctccaaggtgctggatctgaagaactacatcgac aagcagctgctgcccatcgtgaacaagcagagctgcagcatcagcaacat cgagacagtgatcgagttccagcagaagaacaaccggctgctggaaatca cccgcgagttcagcgtgaacgccggcgtgaccaccccgtgtccacctac atgctgaccaacagcgagctgctgtccctgatcaatgacatgcctatcac caacgaccagaaaaagctgatgagcaacaacgtgcagatcgtgcggcagc agagctactccatcatgagcatcatcaaagaagaggtgctggcctacgtg gtgcagctgcccctgtacggcgtgatcgacacccctgctggaagctgca
```

```
caccagcccctgtgcaccaccaacacaaaagagggcagcaacatctgcc tgacccggaccgaccggggctggtactgcgataatgccggcagcgtgtca ttctttccacaggccgagacatgcaaggtgcagagcaaccgggtgttctg cgacaccatgaacagcctgaccctgcccctccgaagtgaacctgtgcaacg tggacatcttcaaccctaagtacgactgcaagatcatgaccagcaagacc gacgtgtccagctccgtgatcacctccctgggcgccatcgtgtcctgcta cggcaagaccaagtgcaccgccagcaacaagaaccggggcatcatcaaga ccttcagcaacggctgcgactacgtgtccaacaaggggtggacaccgtg tccgtgggcaacaccctgtactacgtgaacaaacaggaaggcaagagcct gtacgtgaagggcgagcccatcatcaacttctacgaccccctggtgttcc ccagcgacgagttcgacgccagcatcagccaggtcaacgagaagatcaac cagagcctggccttcatcagaaagagcgacgagctgctgcacaatgtgaa tgccggcaagagcaccacaaacatcatgatcaccactatcatcatcgtga tcatcgtcatcctgctgagtctgatcgccgtgggcctgctgctgtactgc aaggccagatccacccctgtgaccctgtccaaggatcagctgtccggcat caacaatatcgccttctccaactga
```

GenScript optimized RSV F_A2_HEK DNA sequence:

```
                                         (SEQ ID NO: 7)
atggaactgctgatcctgaaagccaacgctattactactatcctgaccgc cgtgacattttgcttcgcatctggacagaacattactgaggaattctacc agtcaacatgcagcgccgtgtccaaaggatacctgagcgccctgcggacc ggctggtatacatcagtgattactatcgagctgtccaacatcaaggaaaa caaatgtaatgggaccgacgcaaaggtgaaactgatcaagcaggagctgg ataagtacaaaaatgccgtgacagaactgcagctgctgatgcagtccaca ccagcaactaacaatcgcgcccggagagagctgccccggttcatgaacta taccctgaacaatgctaagaaaaccaatgtgacactgtccaagaaacgca agaggcgcttcctgggatttctgctgggcgtggggtctgccatcgctagt ggagtggccgtctctaaagtcctgcacctggagggcgaagtgaacaagat caaaagcgccctgctgtccactaacaaggcagtggtcagtctgtcaaatg gcgtgtccgtcctgacctctaaggtgctggacctgaaaaattatattgat aagcagctgctgcctatcgtcaacaaacagagctgctccatttctaatat cgagacagtgatcgaattccagcagaagaacaatagactgctggagatta ccagagagttcagcgtgaacgccggcgtcaccacacccgtgtccacctac atgctgacaaatagtgagctgctgtcactgattaacgacatgcctatcac caatgatcagaagaaactgatgtccaacaatgtgcagatcgtcagacagc agagttactcaatcatgtctatcattaaggaggaagtcctggcctacgtg gtccagctgccactgtatggcgtgatcgacacccctgctggaaactgca tacatcctctgtgcactaccaacacaaaggaaggaagtaatatctgcc tgactcgaaccgaccggggatggtactgtgataacgcaggcagcgtgtcc ttctttccacaggccgagacctgcaaggtccagagcaacagggtgttctg
```

-continued

```
tgacactatgaatagcctgaccctgccttccgaagtcaacctgtgcaatg tggacatctttaatccaaagtacgattgtaagatcatgactagcaagacc gatgtcagctcctctgtgattacttctctgggggccatcgtgagttgcta cggaaagacaaaatgtactgccagcaacaaaaatcgcggcatcattaaga ccttctccaacgggtgcgactatgtctctaacaagggcgtggatacagtg agtgtcgggaacactctgtactatgtcaataagcaggagggaaaaagcct gtacgtgaagggcgaacccatcattaacttctatgaccccctggtgttcc cttccgacgagtttgatgcatctattagtcaggtgaacgaaaaaatcaat cagagtctggcctttattcggaagtcagatgagctgctgcacaacgtgaa tgctggcaaatctacaactaacatcatgatcaccacaatcatcatcgtga ttatcgtcattctgctgtcactgatcgctgtggggctgctgctgtactgt aaggcaagaagcaccccagtcactctgtcaaaagaccagctgtcagggat taacaacattgccttcagtaactga
```

In additional embodiments, the RSV F protein can include one or more amino acid substitutions that stabilize the ectodomain of the RSV F protein in a prefusion conformation. For example, the RSV F protein can include the "DS" substitution of a pair of cysteine substitutions at positions 155 and 290 that form a non-natural disulfide bond to stabilize the RSV F protein in its prefusion conformation. In some embodiments, the RSV F protein can include one or more cavity filling amino acid substitutions at positions 190 and/or 207 to stabilize the protein in a prefusion conformation. For example, the RSV F protein can include a 190F substitution and/or a 207L substitution. In some embodiments, the RSV F protein can include the "Cav1" substitutions of S190F and a F207L. In some embodiments, the RSV F protein can include the DS-Cav1 substitutions of S155C, S290C, S190F, and V207L to stabilize the protein in a prefusion conformation. Exemplary DNA and protein sequences for an RSV F protein (with a chimeric TM and/or CT domain) from the A2 subgroup including the DS-Cav1 amino acid substitutions are set forth as SEQ ID NOs: 10-11 and 21-23.

Additional amino acid substitutions and protein modifications that can be used to stabilize the RSV F ectodomain in a prefusion conformation are disclosed, for example, in WO2014160463, which is incorporated by reference in its entirety. The HEK substitutions can be combined with any of the amino acid substitutions for stabilizing the RSV F protein in a prefusion conformation.

In several embodiments, the heterologous gene included in the recombinant paramyxovirus genome encodes a recombinant RSV F ectodomain linked to a TM and CT of the F protein of the recombinant paramyxovirus.

In an embodiment, the recombinant paramyxovirus is a recombinant HPIV1 including a recombinant HPIV1 genome including a heterologous gene encoding a recombinant hRSV F ectodomain. The RSV F ectodomain can be linked to a TM and CT from HPIV1 F protein, for example as set forth as residues 1-23 of SEQ ID NO 31 (TM), residues 24-59 of SEQ ID NO: 31 (CT), or SEQ ID NO: 31 (TM+CT). Exemplary sequences are provided below:
hRSV F protein from an A2 strain including HEK and DS-Cav1 substitutions, and HPIV1 F CT domain (RSV F A2_HEK_DS-Cav1_H1CT) is provided as SEQ ID NO: 133 GenScript optimized RSV F A2_HEK_DS-Cav1_H1CT DNA sequence is provided as SEQ ID NO: 134
hRSV F protein from an A2 strain including HEK and DS-Cav1 substitutions, and HPIV1 F TM and CT domains (RSV F A2_HEK_DS-Cav1_H1TMCT):

(SEQ ID NO: 135)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTQIIMIIIVCILIIIICGILYY

LYRVRRLLVMINSTHNSPVNAYTLESRMRNPYMGNNSN

GenScript optimized RSV F A2_HEK_DS-Cav1_H1TMCT DNA sequence:

(SEQ ID NO: 136)
```
atggaactgctgatcctgaaagccaacgctattactactatcctgaccgc cgtgacattttgcttcgcatctggacagaacattactgaggaattctacc agtcaacatgcagcgccgtgtccaaaggatacctgagcgccctgcggacc ggctggtatacatcagtgattactatcgagctgtccaacatcaaggaaaa caaatgtaatgggaccgacgcaaaggtgaaactgatcaagcaggagctgg ataagtacaaaaatgccgtgacagaactgcagctgctgatgcagtccaca ccagcaactaacaatcgcgcccggagagagctgccccggttcatgaacta taccctgaacaatgctaagaaaaccaatgtgacactgtccaagaaacgca agaggcgcttcctgggatttctgctgggcgtggggtctgccatcgctagt ggagtggccgtctgcaaagtcctgcacctggagggcgaagtgaacaagat caaaagcgccctgctgtccactaacaaggcagtggtcagtctgtcaaatg gcgtgtccgtcctgaccttcaaggtgctggacctgaaaaattatattgat aagcagctgctgcctatcctgaacaaacagagctgctccatttctaatat cgagacagtgatcgaattccagcagaagaacaatagactgctggagatta ccagagagttcagcgtgaacgccggcgtcaccacacccgtgtccacctac atgctgacaaatagtgagctgctgtcactgattaacgacatgcctatcac caatgatcagaagaaactgatgtccaacaatgtgcagatcgtcagacagc agagttactcaatcatgtgcatcattaaggaggaagtcctggcctacgtg gtccagctgccactgtatggcgtgatcgacacccctgctggaaactgca tacatctcctctgtgcactaccaacacaaaggaaggaagtaatatctgcc tgactcgaaccgaccggggatggtactgtgataacgcaggcagcgtgtcc ttctttccacaggccgagacctgcaaggtccagagcaacagggtgttctg
```

-continued

```
tgacactatgaatagcctgaccctgccttccgaagtcaacctgtgcaatg tggacatctttaatccaaagtacgattgtaagatcatgactagcaagacc gatgtcagctcctctgtgattacttctctgggggccatcgtgagttgcta cggaaagacaaaatgtactgccagcaacaaaaatcgcggcatcattaaga ccttctccaacgggtgcgactatgtctctaacaagggcgtggatacagtg agtgtcgggaacactctgtactatgtcaataagcaggagggaaaaagcct gtacgtgaagggcgaacccatcattaacttctatgaccccctggtgttcc cttccgacgagtttgatgcatctattagtcaggtgaacgaaaaaatcaat cagagtctggcctttattcggaagtcagatgagctgctgcacaacgtgaa tgctggcaaatctacaactaacatcatgatcaccacacagatcattatga tcattatcgtgtgcattctgattatcattatctgtggcatcctgtactat ctgtaccgagtgcggagactgctggtcatgattaacagcacccacaattc ccccgtcaacgcctacacactggagtctaggatgcgcaatccttatatgg ggaacaatagcaactgatag
```

In an embodiment, the recombinant paramyxovirus is a recombinant HPIV2 including a recombinant HPIV2 genome including a heterologous gene encoding a recombinant hRSV F ectodomain. The RSV F ectodomain can be linked to a TM and CT from a HPIV2 F protein, for example as set forth as residues 1-28 of SEQ ID NO: 39 (TM), residues 29-66 of SEQ ID NO: 39 (CT), or SEQ ID NO: 39 (TM+CT).

In an embodiment, the recombinant paramyxovirus can be a recombinant HPIV3 including a 50 genome including a heterologous gene encoding a recombinant hRSV F ectodomain. The recombinant RSV F ectodomain can be linked to a TM and CT from a HPIV3 F protein, for example as set forth as residues 1-23 of SEQ ID NO 46 (TM), residues 24-46 of SEQ ID NO: 46 (CT), or SEQ ID NO: 46 (TM+CT). Exemplary sequences are provided below:

hRSV F protein from an A2 strain including HEK and DS-Cav1 substitutions, and HPIV3 F CT domain (RSV F_HEK_DS-Cav1_H3CT) protein sequence is provided as SEQ ID NO: 8

GenScript optimized RSV F_HEK_DS-Cav1_H3CT DNA sequence is provided as SEQ ID NO: 9 hRSV F protein from an A2 strain including HEK and DS-Cav1 substitutions, and HPIV3 F TM and CT domains (RSV F_HEK_DS-Cav1_H3TMCT) protein sequence:

```
(SEQ ID NO: 10)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIILIMIIILFIINITIITI

AIKYYRIQKRNRVDQNDKPYVLTNK
```

GenScript optimized RSV F_HEK_DS-Cav1_H3TMCT DNA sequence:

```
(SEQ ID NO: 11)
atggaactgctgatcctgaaagccaacgctattactactatcctgaccgc cgtgacatttttgcttcgcatctggacagaacattactgaggaattctacc agtcaacatgcagcgccgtgtccaaaggatacctgagcgccctgcggacc ggctggtatacatcagtgattactatcgagctgtccaacatcaaggaaaa caaatgtaatgggaccgacgcaaaggtgaaactgatcaagcaggagctgg ataagtacaaaaatgccgtgacagaactgcagctgctgatgcagtccaca ccagcaactaacaatcgcgcccggagagagctgcccggttcatgaacta taccctgaacaatgctaagaaaaccaatgtgacactgtccaagaaacgca agaggcgcttcctgggatttctgctgggcgtggggtctgccatcgctagt ggagtggccgtctgcaaagtcctgcacctggaggcgaagtgaacaagat caaaagcgccctgctgtccactaacaaggcagtggtcagtctgtcaaatg gcgtgtccgtcctgaccttcaaggtgctggacctgaaaaattatattgat aagcagctgctgcctatcctgaacaaacagagctgctccatttctaatat cgagacagtgatcgaattccagcagaagaacaatagactgctggagatta ccagagagttcagcgtgaacgccggcgtcaccacacccgtgtccacctac atgctgacaaatagtgagctgctgtcactgattaacgacatgcctatcac caatgatcagaagaaactgatgtccaacaatgtgcagatcgtcagacagc agagttactcaatcatgtgcatcattaaggaggaagtcctggcctacgtg gtccagctgccactgtatggcgtgatcgacacccctgctggaaactgca tacatctcctctgtgcactaccaacacaaaggaaggaagtaatatctgcc tgactcgaaccgaccggggatggtactgtgataacgcaggcagcgtgtcc ttctttccacaggccgagacctgcaaggtccagagcaacagggtgttctg tgacactatgaatagcctgaccctgccttccgaagtcaacctgtgcaatg tggacatctttaatccaaagtacgattgtaagatcatgactagcaagacc gatgtcagctcctctgtgattacttctctgggggccatcgtgagttgcta cggaaagacaaaatgtactgccagcaacaaaaatcgcggcatcattaaga ccttctccaacgggtgcgactatgtctctaacaagggcgtggatacagtg agtgtcgggaacactctgtactatgtcaataagcaggagggaaaaagcct gtacgtgaagggcgaacccatcattaacttctatgaccccctggtgttcc cttccgacgagtttgatgcatctattagtcaggtgaacgaaaaaatcaat cagagtctggcctttattcggaagtcagatgagctgctgcacaacgtgaa tgctggcaaatctacaactaacatcatgatcaccacaatcatcatcatct tgatcatgatcatcatcctgttcatcatcaacatcacaatcatcaccatc
```

```
gctatcaagtactaccgtatccagaagaggaacagagttgaccagaacga taagccatacgtgctcactaacaagtga
```

In an embodiment, the recombinant paramyxovirus is a chimeric PIV including a recombinant viral genome encoding HPIV3 F and HN proteins and BPIV3 N, P, C, V, M, and L proteins, wherein the viral genome further includes a heterologous gene encoding a recombinant hRSV F ectodomain linked to a TM and/or CT from a BPIV3 F protein, for example as set forth as residues 1-21 of SEQ ID NO 53 (TM), residues 22-57 of SEQ ID NO: 53 (CT) or SEQ ID NO: 53 (TM+CT). Exemplary DNA and protein sequences for recombinant RSV F proteins of the A2 subgroup that include the HEK, DS, and/or Cav1 substitutions, as well as a heterologous TM and/or CT domains from BPIV3 F protein that can be used in a disclosed recombinant paramyxovirus are set forth below.

hRSV F protein from an A2 strain including HEK substitutions, and BPIV3 F TM and CT domains (RSV F_A2_HEK_B3TMCT) protein sequence:

```
                                         (SEQ ID NO: 12)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTITIIIVMIIILVIINITIIVV

IIKFHRIQGKDQNDKNSEPYILTNRQ
```

GeneArt optimized RSV F_A2_HEK_B3TMCT DNA sequence:

```
                                         (SEQ ID NO: 13)
atggaactgctgatcctgaaggccaacgccatcaccaccatcctgaccgc cgtgaccttctgctttgccagcggccagaacatcaccgaggaattctacc agagcacctgtagcgccgtgtccaagggctacctgagcgccctgagaacc ggctggtacaccagcgtgatcaccatcgagctgagcaacatcaaagaaaa caagtgcaacggcaccgacgccaaagtgaagctgatcaagcaggaactgg acaagtacaagaatgccgtgaccgaactgcagctgctgatgcagagcacc cccgccaccaacaacgggccagaagagaactgcccagattcatgaacta cacccctgaacaacgccaaaaagaccaacgtgaccctgagcaagaagcgga agcggcggttcctgggctttctgctgggagtgggaagcgccattgctagc ggagtggccgtgtctaaggtgctgcacctggaaggcgaagtgaacaagat caagtccgccctgctgagcaccaacaaggccgtggtgtctctgagcaacg
```

```
gcgtgtccgtgctgaccagcaaggtgctggatctgaagaactacatcgac aaacagctgctgcccatcgtgaacaagcagagctgcagcatcagcaacat cgagacagtgatcgagttccagcagaagaacaaccggctgctggaaatca cccgcgagttcagcgtgaacgctggcgtgaccaccccgtgtccacctac atgctgaccaacagcgagctgctgtccctgatcaacgacatgcccatcac caacgaccagaaaaagctgatgagcaacaacgtgcagatcgtgcggcagc agagctactccatcatgagcattatcaaagaagaggtgctggcctacgtg gtgcagctgcctctgtacggcgtgatcgacacccctgctggaagctgca caccagccctctgtgcaccaccaacaccaagagggctccaacatctgcc tgacccggaccgacagaggctggtactgcgataatgccggctccgtctca ttctttccacaagccgagacatgcaaggtgcagagcaacgggtgttctg cgacaccatgaacagcctgaccctgcctccgaagtgaatctgtgcaacg tggacatcttcaaccctaagtacgactgcaagatcatgacctccaagacc gacgtgtccagctccgtgatcacaagcctgggcgccatcgtgtcctgcta cggcaagaccaagtgcaccgccagcaacaagaaccggggcatcatcaaga ccttcagcaacggctgcgactacgtgtccaacaaggggtggacaccgtg tctgtgggcaacaccctgtactacgtgaacaaacaggaaggcaagagcct gtacgtgaagggcgagcccatcatcaacttctacgacccctggtgttcc ccagcgacgagttcgatgccagcatctcccaagtgaacgagaagatcaac cagagcctggccttcatcagaaagtccgatgagctgctgcacaatgtgaa cgccggcaagtccaccaccaatatcatgatcaccacaatcaccatcatca ttgtgatgattatcatcctcgtgatcatcaacatcacaatcatcgtcgtg attattaagttccaccggatccagggcaaggaccagaacgacaagaactc cgagccctacatcctgacaaaccggcagtga
``` hRSV F protein from an A2 strain including HEK and DS substitutions, hRSV F TM domain and BPIV3 F CT domain (RSV F_A2_HEK_DS_B3CT) protein sequence is provided as SEQ ID NO: 14

GeneArt optimized RSV F_A2_HEK_DS_B3CT DNA sequence is provided as SEQ ID NO: 15:

hRSV F protein from an A2 strain including HEK and DS-Cav1 substitutions, hRSV F TM domain and BPIV3 F CT domain (RSV F_A2_HEK_DS-Cav1_B3CT) protein sequence:

```
                                         (SEQ ID NO: 16)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT
```

-continued

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

IIKFHRIQGKDQNDKNSEPYILTNRQ

GeneArt optimized RSV F_A2_HEK_DS-Cav1_B3CT DNA sequence:

(SEQ ID NO: 17)
atggaactgctgatcctgaaggccaacgccatcaccaccatcctgaccgc cgtgaccttctgctttgccagcggccagaacatcaccgaggaattctacc agagcacctgtagcgccgtgtccaagggctacctgagcgccctgagaacc ggctggtacaccagcgtgatcaccatcgagctgagcaacatcaaagaaaa caagtgcaacggcaccgacgccaaagtgaagctgatcaagcaggaactgg acaagtacaagaatgccgtgaccgaactgcagctgctgatgcagagcacc cccgccaccaacaaccgggccagaagagaactgcccagattcatgaacta caccctgaacaacgccaaaaagaccaacgtgaccctgagcaagaagcgga agcggcggttcctgggctttctgctgggagtggggaagcgccattgctagc ggagtggccgtgtgcaaggtgctgcacctggaaggcgaagtgaacaagat caagtccgccctgctgagcaccaacaaggccgtggtgtctctgagcaacg gcgtgtccgtgctgaccttcaaggtgctggatctgaagaactacatcgac aaacagctgctgcccatcttgaacaagcagagctgcagcatcagcaacat cgagacagtgatcgagttccagcagaagaacaaccggctgctggaaatca cccgcgagttcagcgtgaacgctggcgtgaccaccccccgtgtccacctac atgctgaccaacagcgagctgctgtccctgatcaacgacatgcccatcac caacgaccagaaaaagctgatgagcaacaacgtgcagatcgtgcggcagc agagctactccatcatgtgcatcatcaaagaagaggtgctggcctacgtg gtgcagctgcctctgtacggcgtgatcgacaccccctgctggaagctgca caccagccctctgtgcaccaccaacaccaaagagggctccaacatctgcc tgacccggaccgacagaggctggtactgcgataatgccggctccgtctca ttctttccacaagccgagacatgcaaggtgcagagcaacgggtgttctg cgacaccatgaacagcctgaccctgccctccgaagtgaatctgtgcaacg tggacatcttcaaccctaagtacgactgcaagatcatgacctccaagacc gacgtgtccagctccgtgatcacaagcctgggcgccatcgtgtcctgcta cggcaagaccaagtgcaccgccagcaacaagaaccggggcatcatcaaga ccttcagcaacggctgcgactacgtgtccaacaagggggtggacaccgtg tctgtgggcaacaccctgtactacgtgaacaaacaggaaggcaagagcct gtacgtgaagggcgagcccatcatcaacttctacgaccccctggtgttcc ccagcgacgagttcgatgccagcatctcccaagtgaacgagaagatcaac cagagcctggccttcatcagaaagtccgatgagctgctgcacaatgtgaa cgccggcaagtccaccaccaatatcatgatcaccacaatcatcatcgtga ttatcgtgatcctgctgagcctgatcgccgtgggcctgctgctgtactgt atcatcaagttccaccggatccagggcaaggaccagaacgacaagaactc cgagccctacatcctgacaaaccggcagtga GenScript optimized RSV F_A2_HEK_DS-Cav1_B3CT DNA sequence:

(SEQ ID NO: 18)
atggaactgctgatcctgaaagccaacgctattactactatcctgaccgc cgtgacattttgcttcgcatctggacagaacattactgaggaattctacc agtcaacatgcagcgccgtgtccaaaggatacctgagcgccctgcggacc ggctggtatacatcagtgattactatcgagctgtccaacatcaaggaaaa caaatgtaatgggaccgacgcaaaggtgaaactgatcaagcaggagctgg ataagtacaaaaatgccgtgacagaactgcagctgctgatgcagtccaca ccagcaactaacaatcgcgcccggagagagctgccccggttcatgaacta tacccctgaacaatgctaagaaaaccaatgtgacactgtccaagaaacgca agaggcgcttcctgggatttctgctgggcgtgggtctgccatcgctagt ggagtggccgtctgcaaagtcctgcacctggagggcgaagtgaacaagat caaaagcgccctgctgtccactaacaaggcagtggtcagtctgtcaaatg gcgtgtccgtcctgaccttcaaggtgctggacctgaaaaattatattgat aagcagctgctgcctatcctgaacaaacagagctgctccatttctaatat cgagacagtgatcgaattccagcagaagaacaatagactgctggagatta ccagagagttcagcgtgaacgccggcgtcaccacacccgtgtccacctac atgctgacaaatagtgagctgctgtcactgattaacgacatgcctatcac caatgatcagaagaaactgatgtccaacaatgtgcagatcgtcagacagc agagttactcaatcatgtgcatcattaaggaggaagtcctggcctacgtg gtccagctgccactgtatggcgtgatcgacaccccctgctggaaactgca tacatctcctctgtgcactaccaacacaaaggaaggaagtaatatctgcc tgactcgaaccgaccggggatggtactgtgataacgcaggcagcgtgtcc ttctttccacaggccgagacctgcaaggtccagagcaacagggtgttctg tgacactatgaatagcctgaccctgccttccgaagtcaacctgtgcaatg tggacatctttaatccaaagtacgattgtaagatcatgactagcaagacc gatgtcagctcctctgtgattacttctctgggggccatcgtgagttgcta cggaaagacaaaatgtactgccagcaacaaaaatcgcggcatcattaaga ccttctcaacgggtgcgactatgtctctaacaagggcgtggatacagtg agtgtcgggaacactctgtactatgtcaataagcaggagggaaaaagcct gtacgtgaagggcgaacccatcattaacttctatgacccctggtgttcc cttccgacgagtttgatgcatctattagtcaggtgaacgaaaaaatcaat cagagtctggcctttattcggaagtcagatgagctgctgcacaacgtgaa tgctggcaaatctacaactaacatcatgatcaccacaatcatcatcgtga ttatcgtcattctgctgtcactgatcgctgtgggctgctgctgtactgt atcattaagttccaccggatccagggcaaggaccagaacgataaaaatag cgagccctacattctgaccaacagacag hRSV F protein from an A2 strain including HEK and DS substitutions, and BPIV3 F TM and CT domains (RSV F_A2_HEK_DS_B3TMCT) protein sequence:

(SEQ ID NO: 19)
MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVCKVLHLEGEVNKIKSALLSTNKAVVSLSNGVSVLTSKVLDLKNYID
KQLLPIVNKQSCSISNIETVIEFQQKNNRLLEITREFSVNAGVTTPVSTY
MLTNSELLSLINDMPITNDQKKLMSNNVQIVRQQSYSIMCIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLHNVAGKSTTNIMITTITIIIVMIIILVIINITIIVV
IIKFHRIQGKDQNDKNSEPYILTNRQ

GeneArt optimized RSV F_A2_HEK_DS_B3TMCT DNA sequence:

(SEQ ID NO: 20)
atggaactgctgatcctgaaggccaacgccatcaccaccatcctgaccgc
cgtgaccttctgctttgccagcggccagaacatcaccgaggaattctacc
agagcacctgtagcgccgtgtccaagggctacctgagcgccctgagaacc
ggctggtacaccagcgtgatcaccatcgagctgagcaacatcaagaaaa
caagtgcaacggcaccgacgccaaagtgaagctgatcaagcaggaactgg
acaagtacaagaatgccgtgaccgaactgcagctgctgatgcagagcacc
cccgccaccaacaacgggccagaagagaactgcccagattcatgaacta
caccctgaacaacgccaaaaagaccaacgtgaccctgagcaagaagcgga
agcggcggttcctgggctttctgctgggagtggggaagcgccattgctagc
ggagtggccgtgtgcaaggtgctgcacctggaaggcgaagtgaacaagat
caagtccgccctgctgagcaccaacaaggccgtggtgtctctgagcaacg
gcgtgtccgtgctgaccagcaaggtgctggatctgaagaactacatcgac
aaacagctgctgcccatcgtgaacaagcagagctgcagcatcagcaacat
cgagacagtgatcgagttccagcagaagaacaaccggctgctggaaatca
cccgcgagttcagcgtgaacgctggcgtgaccacccccgtgtccacctac
atgctgaccaacagcgagctgctgccctgatcaacgacatgcccatcac
caacgaccagaaaaagctgatgagcaacaacgtgcagatcgtgcggcagc
agagctactccatcatgtgcatcatcaaagaagaggtgctggcctacgtg
gtgcagctgcctctgtacggcgtgatcgacacccctgctggaagctgca
caccagccctctgtgcaccaccaacaccaaagagggctccaacatctgcc
tgacccggaccgacagaggctggtactgcgataatgccggctccgtctca
ttctttccacaagccgagacatgcaaggtgcagagcaaccgggtgttctg
cgacaccatgaacagcctgaccctgccctccgaagtgaatctgtgcaacg
tggacatcttcaaccctaagtacgactgcaagatcatgacctccaagacc
gacgtgtccagctccgtgatcacaagcctgggcgccatcgtgtcctgcta
cggcaagaccaagtgcaccgccagcaacaagaaccggggcatcatcaaga
ccttcagcaacggctgcgactacgtgtccaacaaggggtggacaccgtg
tctgtgggcaacaccctgtactacgtgaacaaacaggaaggcaagagcct
gtacgtgaagggcgagcccatcatcaacttctacgacccccctggtgttcc
ccagcgacgagttcgatgccagcatctcccaagtgaacgagaagatcaac
cagagcctggccttcatcagaaagtccgatgagctgctgcacaatgtgaa
cgccggcaagtccaccaccaatatcatgatcaccacaatcaccatcatca
ttgtgatgattatcatcctcgtgatcatcaacatcacaatcatcgtcgtg
attattaagttccaccggatccagggcaaggaccagaacgacaagaactc
cgagccctacatcctgacaaaccggcagtga Genescript optimized RSV F_A2_HEK_DS_B3TMCT DNA sequence:

(SEQ ID NO: 137)
atggaactgctgatcctgaaagccaacgctattactactatcctgaccgc
cgtgacattttgcttcgcatctggacagaacattactgaggaattctacc
agtcaacatgcagcgccgtgtccaaaggatacctgagcgccctgcggacc
ggctggtatacatcagtgattactatcgagctgtccaacatcaaggaaaa
caaatgtaatgggaccgacgcaaaggtgaaactgatcaagcaggagctgg
ataagtacaaaaatgccgtgacagaactgcagctgctgatgcagtccaca
ccagcaactaacaatcgcgcccggagagagctgccccggttcatgaacta
taccctgaacaatgctaagaaaaccaatgtgacactgtccaagaaacgca
agaggcgcttcctgggatttctgctgggcgtggggtctgccatcgctagt
ggagtggccgtctgcaaagtcctgcacctggagggcgaagtgaacaagat
caaaagcgccctgctgtccactaacaaggcagtggtcagtctgtcaaatg
gcgtgtccgtcctgacctccaaggtgctggacctgaaaaattatattgat
aagcagctgctgcctatcgtcaacaaacagagctgctccatttctaatat
cgagacagtgatcgaattccagcagaagaacaatagactgctggagatta
ccagagagttcagcgtgaacgccggcgtcaccacacccgtgtccacctac
atgctgacaaatagtgagctgctgtcactgattaacgacatgcctatcac
caatgatcagaagaaactgatgtccaacaatgtgcagatcgtcagacagc
agagttactcaatcatgtgcatcattaaggaggaagtcctggcctacgtg
gtccagctgccactgtatggcgtgatcgacacccctgctggaaactgca
tacatctcctctgtgcactaccaacacaaaggaaggaagtaatatctgcc
tgactcgaaccgaccggggatggtactgtgataacgcaggcagcgtgtcc
ttctttccacaggccgagacctgcaaggtccagagcaacagggtgttctg
tgacactatgaatagcctgaccctgccttccgaagtcaacctgtgcaatg
tggacatctttaatccaaagtacgattgtaagatcatgactagcaagacc
gatgtcagctcctctgtgattacttctggggggccatcgtgagttgcta
cggaaagacaaaatgtactgccagcaacaaaaatcgcggcatcattaaga
ccttctccaacgggtgcgactatgtctctaacaaggcgtggatacagtg
agtgtcgggaacactctgtactatgtcaataagcaggagggaaaaagcct

```
gtacgtgaagggcgaacccatcattaacttctatgacccctggtgttcc
cttccgacgagtttgatgcatctattagtcaggtgaacgaaaaaatcaat
cagagtctggcctttattcggaagtcagatgagctgctgcacaacgtgaa
tgctggcaaatctacaactaacatcatgatcaccacaatcaccatcatta
tcgtgatgattatcattctggtcatcattaacatcacaatcattgtggtc
atcattaagttccaccggattcagggcaaggaccagaacgataaaaatag
cgagccctacatcctgaccaatagacagtga
``` hRSV F protein from an A2 strain including HEK and DS-Cav1 substitutions, and BPIV3 F TM and CT domains (RSV F_A2_HEK_DS-Cav1_B3TMCT) protein sequence:

(SEQ ID NO: 21)
```
MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVCKVLHLEGEVNKIKSALLSTNKAVVSLSNGVSVLTFKVLDLKNYID
KQLLPILNKQSCSISNIETVIEFQQKNNRLLEITREFSVNAGVTTPVSTY
MLTNSELLSLINDMPITNDQKKLMSNNVQIVRQQSYSIMCIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLHNVNAGKSTTNIMITTITIIIVMIIILVIINITIIVV
IIKFHRIQGKDQNDKNSEPYILTNRQ
```

GeneArt optimized RSV F_A2_HEK_DS-Cav1_B3TMCT DNA sequence:

(SEQ ID NO: 22)
```
atggaactgctgatcctgaaggccaacgccatcaccaccatcctgaccgc
cgtgaccttctgctttgccagcggccagaacatcaccgaggaattctacc
agagcacctgtagcgccgtgtccaagggctacctgagcgccctgagaacc
ggctggtacaccagcgtgatcaccatcgagctgagcaacatcaaagaaaa
caagtgcaacggcaccgacgccaaagtgaagctgatcaagcaggaactgg
acaagtacaagaatgccgtgaccgaactgcagctgctgatgcagagcacc
cccgccaccaacaaccgggccagaagagaactgcccagattcatgaacta
caccctgaacaacgccaaaaagaccaacgtgaccctgagcaagaagcgga
agcggcggttcctgggctttctgctgggagtggggaagcgccattgctagc
ggagtggccgtgtgcaaggctgcacctggaaggcgaagtgaacaagat
caagtccgccctgctgagcaccaacaaggccgtggtgtctctgagcaacg
gcgtgtccgtgctgaccttcaaggtgctggatctgaagaactacatcgac
aaacagctgctgcccatcttgaacaagcagagctgcagcatcagcaacat
cgagacagtgatcgagttccagcagaagaacaaccggctgctggaaatca
cccgcgagttcagcgtgaacgctggcgtgaccacccccgtgtccacctac
atgctgaccaacagcgagctgctgtccctgatcaacgacatgcccatcac
caacgaccagaaaagctgatgagcaacaacgtgcagatcgtgcggcagc
agagctactccatcatgtgcatcatcaaagaagaggtgctggcctacgtg
gtgcagctgcctctgtacggcgtgatcgacacccccctgctggaagctgca
caccagccctctgtgcaccaccaacaccaaagagggctccaacatctgcc
tgacccggaccgacagaggctggtactgcgataatgccggctccgtctca
ttctttccacaagccgagacatgcaaggtgcagagcaaccgggtgttctg
cgacaccatgaacagcctgaccctgccctccgaagtgaatctgtgcaacg
tggacatcttcaaccctaagtacgactgcaagatcatgacctccaagacc
gacgtgtccagctccgtgatcacaagcctgggcgccatcgtgtcctgcta
cggcaagaccaagtgcaccgccagcaacaagaaccggggcatcatcaaga
ccttcagcaacggctgcgactacgtgtccaacaaggggtggacaccgtg
tctgtgggcaacaccctgtactacgtgaacaaacaggaaggcaagagcct
gtacgtgaagggcgagcccatcatcaacttctacgaccccctggtgttcc
ccagcgacgagttcgatgccagcatctcccaagtgaacgagaagatcaac
cagagcctggccttcatcagaaagtccgatgagctgctgcacaatgtgaa
cgccggcaagtccaccaccaatatcatgatcaccacaatcaccatcatca
ttgtgatgattatcatcctcgtgatcatcaacatcacaatcatcgtcgtg
attattaagttccaccggatccagggcaaggaccagaacgacaagaactc
cgagccctacatcctgacaaaccggcagtga
```

GenScript optimized RSV F_A2_HEK_DS-Cav1_B3TMCT DNA sequence:

(SEQ ID NO: 23)
```
atggaactgctgatcctgaaagccaacgctattactactatcctgaccgc
cgtgacattttgcttcgcatctggacagaacattactgaggaattctacc
agtcaacatgcagcgccgtgtccaaaggatacctgagcgccctgcggacc
ggctggtatacatcagtgattactatcgagctgtccaacatcaaggaaaa
caaatgtaatgggaccgacgcaaaggtgaaactgatcaagcaggagctgg
ataagtacaaaaatgccgtgacagaactgcagctgctgatgcagtccaca
ccagcaactaacaatcgcgcccggagagagctgccccggttcatgaacta
tacgctgaacaatgctaagaaaccaatgtgacactgtccaagaaacgca
agaggcgcttcctgggatttctgctgggcgtggggtctgccatcgctagt
ggagtggccgtctgcaaagtcctgcacctggagggcgaagtgaacaagat
caaaagcgccctgctgtccactaacaaggcagtggtcagtctgtcaaatg
gcgtgtccgtcctgaccttcaaggtgctggacctgaaaaattatattgat
aagcagctgctgcctatcctgaacaaacagagctgctccatttctaatat
cgagacagtgatcgaattccagcagaagaacaatagactgctggagatta
ccagagagttcagcgtgaacgccggcgtcaccacccgtgtccacctac
atgctgacaaatagtgagctgctgtcactgattaacgacatgcccatcac
caatgatcagaagaaactgatgtccaacaatgtgcagatcgtcagacagc
```

```
                    -continued
agagttactcaatcatgtgcatcattaaggaggaagtcctggcctacgtg gtccagctgccactgtatggcgtgatcgacaccccctgctggaaactgca tacatctcctctgtgcactaccaacacaaaggaaggaagtaatatctgcc tgactcgaaccgaccggggatggtactgtgataacgcaggcagcgtgtcc ttctttccacaggccgagacctgcaaggtccagagcaacagggtgttctg tgacactatgaatagcctgaccctgccttccgaagtcaacctgtgcaatg tggacatctttaatccaaagtacgattgtaagatcatgactagcaagacc gatgtcagctcctctgtgattacttctctgggggccatcgtgagttgcta cggaaagacaaaatgtactgccagcaacaaaaatcgcggcatcattaaga ccttctccaacgggtgcgactatgtctctaacaagggcgtggatacagtg agtgtcgggaacactctgtactatgtcaataagcaggagggaaaaagcct gtacgtgaagggcgaacccatcattaacttctatgacccctggtgttcc cttccgacgagtttgatgcatctattagtcaggtgaacgaaaaaatcaat cagagtctggcctttattcggaagtcagatgagctgctgcacaacgtgaa tgctggcaaatctacaactaacatcatgatcaccacaatcaccatcatta tcgtgatgattatcattctggtcatcattaacatcacaatcattgtggtc atcattaagttccaccggattcagggcaaggaccagaacgataaaaatag cgagccctacatcctgaccaatagacagtga
```

In an embodiment, the recombinant paramyxovirus includes a recombinant Sendai virus genome including a heterologous gene encoding a recombinant hRSV F ectodomain. In such embodiments, the TM and CT linked to the RSV F ectodomain can be from a Sendai virus F protein, for example as set forth as residues 1-21 of SEQ ID NO: 103 (TM), residues 22-65 of SEQ ID NO: 103 (CT), or SEQ ID NO: 103 (TM+CT). For example, in some embodiments, the recombinant hRSV F ectodomain linked to the Sendai virus TM and/or CT can include the amino acid sequence set forth as one of SEQ ID NOs: 105-108:

hRSV F protein from an A2 strain including HEK substitutions, and Sendai virus F CT domain (RSV F_A2_HEK_SeVCT) protein sequence.

```
                                    (SEQ ID NO: 105)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

LYRLRRSMLMGNPDDRIPRDTYTLEPKIRHMYTNGGFDAMAEKR
``` hRSV F protein from an A2 strain including HEK substitutions, and Sendai virus F TM and CT domains (RSV F_A2_HEK_SeVTMCT) protein sequence.

```
                                    (SEQ ID NO: 106)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTVITIIVVMVVILVVIIVIIIV

LYRLRRSMLMGNPDDRIPRDTYTLEPKIRHMYTNGGFDAMAEKR
``` hRSV F protein from an A2 strain including HEK and DS-Cav1 substitutions, and Sendai virus F CT domains (RSV F_A2_HEK_SeVCT) protein sequence

```
                                    (SEQ ID NO: 107)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

LYRLRRSMLMGNPDDRIPRDTYTLEPKIRHMYTNGGFDAMAEKR
``` hRSV F protein from an A2 strain including HEK and DS-Cav1 substitutions, and Sendai virus F TM and CT domains (RSV F_A2_HEK_SeVTMCT) protein sequence

```
                                    (SEQ ID NO: 108)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS
```

-continued

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTVITIIVVMVVILVVIIVIIIV

LYRLRRSMLMGNPDDRIPRDTYTLEPKIRHMYTNGGFDAMAEKR

In an embodiment, the recombinant paramyxovirus includes a recombinant NDV genome including a heterologous gene encoding a recombinant hRSV F ectodomain. In such embodiments, the TM and CT linked to the RSV F ectodomain can be from a NDV virus F protein, cytoplasmic tail, for example as set forth as residues 1-21 of SEQ ID NO: 104 (TM), residues 22-49 of SEQ ID NO: 104 (CT), or SEQ ID NO: 104 (TM+CT). For example, in some embodiments, the recombinant hRSV F ectodomain linked to the NDV TM and/or CT can include the amino acid sequence set forth as one of SEQ ID NOs: 109-113:

hRSV F protein from an A2 strain including HEK substitutions, and NDV F CT domains (RSV F_A2_HEK_NDVCT) protein sequence (SEQ ID NO: 109)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

MYKQKAQQKTLLWLGNNTLDQMRATTKM hRSV F protein from an A2 strain including HEK substitutions, and NDV F TM and CT domains (RSV F_A2_HEK_NDVTMCT) protein sequence (SEQ ID NO: 110)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIVLTIISLVFGILSLILACYL

MYKQKAQQKTLLWLGNNTLDQMRATTKM hRSV F protein from an A2 strain including HEK and DS-Cav1 substitutions, and NDV F CT domains (RSV F_A2_HEK_NDVCT) protein sequence (SEQ ID NO: 112)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

MYKQKAQQKTLLWLGNNTLDQMRATTKM hRSV F protein from an A2 strain including HEK and DS-Cav1 substitutions, and NDV F TM and CT domains (RSV F_A2_HEK_NDVTMCT) protein sequence (SEQ ID NO: 113)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTVITIIVVMVVILVVIIVIIIV

LYRLRRSMLMGNPDDRIPRDTYTLEPKIRHMYTNGGFDAMAEKR

H. Additional Description of Recombinant Paramyxovirus

Particular Embodiments

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the NDV F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the PIV5 F protein.

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the NDV F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the PIV5 F protein.

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the NDV F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the PIV5 F protein.

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the NDV F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the PIV5 F protein.

In any of the embodiments of a recombinant paramyxovirus disclosed herein that includes a viral genome including a heterologous gene encoding an RSV F ectodomain (such as any of the recombinant paramyxoviruses discussed above, the heterologous gene encoding the recombinant RSV F ectodomain can encodes a polypeptide sequence comprising RSV F positions 1-529.

Additional Description

The disclosed recombinant paramyxoviruses are self-replicating, that is they are capable of replicating following infection of an appropriate host cell. In several embodiments, the recombinant paramyxoviruses have an attenuated phenotype, for example when administered to a human subject.

Attenuation of the recombinant paramyxoviruses can be achieved using various methods known in the art, for example, by introduction of one or more mutations that cause a change in the biological function of the recombinant paramyxoviruses result in the attenuated phenotype. Insertion of the heterologous gene can also result in an attenuated phenotype. Preferably, the paramyxovirus comprising a genome encoding a heterologous gene is attenuated about 100 to 5000 fold or more in a cell or mammal compared to wild type paramyxovirus.

The disclosed recombinant paramyxoviruses can be tested in well-known and in vitro and in vivo models to confirm adequate attenuation, resistance to phenotypic reversion, and immunogenicity. In in vitro assays, the modified paramyxovirus can be tested for one or more desired phenotypes, such as, for example, temperature sensitive replication. The disclosed recombinant paramyxoviruses can also be tested in animal models of infection with PIV and/or the viral pathogen of the heterologous gene included in the recombinant virus (e.g., RSV). A variety of animal models are known.

The recombinant attenuated paramyxoviruses are preferably attenuated about 100 to 5000 fold in a cell or mammal compared to wild type paramyxovirus. In some embodiments, it is preferred that the level of viral replication in vitro is sufficient to provide for production of viral vaccine for use on a wide spread scale. In some embodiments, it is preferred that the level of viral replication of attenuated paramyxovirus in vitro is at least $10^6$, more preferably at least $10^7$, and most preferably at least 10 per ml. The attenuating mutation is preferably one that is stable. A recombinant paramyxovirus with at least two, three, four or ever more attenuating mutations is likely to be more stable.

Ongoing preclinical studies have identified a number of mutations or modifications that are attenuating for HPIV1, HPIV2, and HPIV3, and which can be introduced by reverse genetics to produce attenuated strains as potential vaccines and vector backbones. The inclusion of a foreign gene into an HPIV backbone also is attenuating on its own. This may due to a variety of effects including the increase in genome length and gene number as well as the effects of the foreign protein. Whatever the cause, the attenuating effect of the insert also has to be taken into account when attempting to achieve the appropriate level of attenuation.

Attenuated strains of HPIV1, 2, and 3 have been in or are presently in clinical studies in seronegative infants and children (Karron, et al. 2012. Vaccine 30:3975-3981; Schmidt, et al. 2011. Expert Rev. Respir. Med. 5:515-526). These attenuated HPIV1, HPIV2, and HPIV3 strains, or versions thereof, are potential vectors for expressing the heterologous RSV F protein.

Examples of modifications to the genome of a paramyxovirus that provide for an attenuated phenotype are known in the art and have been described, for example, in US Patent Publications 2012/0045471; 2010/0119547; 2009/0263883; 2009/0017517; 8084037; 6,410,023; 8,367,074; 7,951,383; 7,820,182; 7704509; 7632508; 7622123; 7250171; 7208161; 7201907; 7192593; 2012/0064112; 20140186397; and Newman et al. 2002. Virus genes 24:77-92, Tang et al., 2003. J Virol, 77(20):10819-10828; Basavarajappa et al. 2014 Vaccine, 32: 3555-3563; McGinnes et al., J. Virol., 85: 366-377, 2011; and Jones et al., *Vaccine,* 30:959-968, 2012, each of which is incorporated by reference herein in its entirety. For example, attenuation of PIV3 can be achieved by the presence of BPIV3-derived genes, which confers a host range restriction in primates including humans, such as the B/HPIV3 virus that contains BPIV3 genes except for the F and HN from HPIV3 (Skiadopoulos M H et al J Virol 77:1141-8, 2003). Sendai virus also is restricted in primates due to a host range restriction (Jones B G et al Vaccine 30:959-968 2012). Another means of attenuation is exemplified by missense mutations that can occur in multiple genes, such as in the cp45 HPIV3 virus (Skiadopoulos M H et al J Virol 73:1374-81 1999). Other examples of attenuating point mutations are provided for HPIV1 in Example 2, below. Deletion of one or several codons also can confer an attenuation phenotype, as exemplified by HPIV1 in Example 2. As also exemplified in Example 1, the presence of vector TM plus CT, or CT domains linked to a heterologous ectodomain can strongly attenuate the vector. Other examples of attenuating mutations in HPIV1 are described by Bartlett E J et al Virol J 4:67 2007), and for HPIV2 by Nolan S M et al, Vaccine 23:4765-4774 2005). The deletion of all or part of one or more accessory genes also is a means of attenuation (Durbin A Virology 261:319-330 1999).

Immunogenicity of a recombinant attenuated paramyxovirus can be assessed in an animal model (such as a non-human primate, for example an African green monkey) by determining the number of animals that form antibodies to the paramyxovirus after one immunization and after a second immunization, and by measuring the magnitude of that response. In some embodiments, a recombinant paramyxovirus has sufficient immunogenicity if about 60 to 80% of the animals develop antibodies after the first immunization and about 80 to 100% of the animals develop antibodies after the second immunization. Preferably, the immune response protects against infection by both the originating paramyxovirus and the viral pathogen from which the heterologous gene included in the recombinant paramyxovirus is derived.

I. Additional Vectors

It will be appreciated that the recombinant RSV F proteins and nucleic acid molecules encoding same can be included (or expressed) on vectors other than a PIV vector. For example, plasmid vectors, as well as other viral vectors can be used, for example, for expression of the recombinant RSV F protein or fragment thereof in a host cell, or for immunization of a subject as disclosed herein. In some embodiments, the vectors can be administered to a subject as part of a prime-boost vaccination. In several embodiments, the vectors are included in a vaccine, such as a primer vaccine or a booster vaccine for use in a prime-boost vaccination.

In several examples, the vector can be a viral vector that is replication-competent and/or attenuated. The viral vector also can be conditionally replication-competent. In other examples, the viral vector is replication-deficient in host cells.

A number of viral vectors have been constructed, that can be used to express the recombinant RSV F protein or immunogenic fragment thereof, including polyoma, i.e., SV40 (Madzak et al., 1992, *J. Gen. Virol.*, 73: 15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158:67-90; Johnson et al., 1992, *J. Virol.*, 66: 29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 52,217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed recombinant RSV F protein or immunogenic fragment thereof (such as the RSV F ectodomain). Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., *Vaccine*, 27:1293-1300, 2009).

Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/022311.

III. Recombinant Methods, Vectors, and Host Cells

The recombinant paramyxoviruses and polynucleotides disclosed herein can be produced by synthetic and recombinant methods. Accordingly, polynucleotides encoding infectious paramyxovirus clones and host cells including the infectious clone, as well as methods of making such vectors and host cells by recombinant methods are also provided.

Isolated nucleic acid molecules encoding any of the recombinant RSV F proteins disclosed herein are also provided.

As discussed above, the disclosed paramyxovirus or polynucleotides may be synthesized or prepared by techniques well known in the art. See, for example, WO94/027037 and US20130052718. Nucleotide sequences for wild type paramyxovirus genomes are known and readily available, for example, on the Internet at GenBank (accessible at ncbi-nlm-nihgov/entrez). The nucleotide sequences encoding the disclosed recombinant paramyxovirus may be synthesized or amplified using methods known to those of ordinary skill in the art including utilizing DNA polymerases in a cell free environment. Further, one of skill in the art can readily use the genetic code to construct a variety of functionally equivalent nucleic acids, such as nucleic acids which differ in sequence but which encode the same protein sequence.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4$^{th}$ ed, Cold Spring Harbor, New York, 2012, and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

The genome of the recombinant paramyxovirus can include one or more variations (for example, mutations that cause an amino acid deletion, substitution, or insertion) as long as the resulting recombinant paramyxovirus retains the desired biological function, such as a level of attenuation or immunogenicity. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, 4$^{th}$ ed., Cold Spring Harbor, New York, 2012) and Ausubel et al. (In Current Protocols in Molecular Biology, John Wiley & Sons, New York, through supplement 104, 2013, both of which are incorporated herein by reference in their entirety.

Modifications can be made to a nucleic acid encoding described herein without diminishing its biological activity. Amino acid substitutions, insertions, and deletions can be made using known recombinant methods such as oligonucleotide-mediated (site-directed) mutagenesis, alanine scanning, PCR mutagenesis, site-directed mutagenesis, cassette mutagenesis, restriction selection mutagenesis, and the like (see, e.g., Sambrook et al. (*Molecular Cloning: A Laboratory Manual*, 4$^{th}$ ed, Cold Spring Harbor, New York, 2012, and Ausubel et al. (*In Current Protocols in Molecular Biology*, John Wiley & Sons, New York, through supplement 104, 2013). Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional nucleotides placed on either terminus to create conveniently located restriction sites.

"Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The disclosed recombinant paramyxovirus can be produced from virus isolated from biological samples. The polynucleotides and vectors may be produced by standard recombinant methods known in the art, such as polymerase chain reaction (Sambrook et al. (Molecular Cloning: A Laboratory Manual, 4$^{th}$ ed, Cold Spring Harbor, New York, 2012, and Ausubel et al. (In Current Protocols in Molecular Biology, John Wiley & Sons, New York, through supplement 104, 2013). Methods of altering or modifying nucleic acid sequences are also known to those of skill in the art.

The paramyxovirus genome may be assembled from polymerase chain reaction cassettes sequentially cloned into a vector including a selectable marker for propagation in a host. Such markers include dihydrofolate reductase or neomycin resistance for eukaryotic cell culture and tetracycline or ampicillin resistance genes for culturing in *E. coli* and other bacteria.

The polynucleotide may be inserted into a replicable vector for cloning using standard recombinant methods. Various vectors are publicly available. The vector may, for example, be in the form of a plasmid, cosmid, viral particle, or phage. The appropriate nucleic acid sequence may be inserted into the vector by a variety of procedures. In general, a nucleic acid is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors including one or more of these components employs standard ligation techniques that are known to the skilled artisan.

Examples of suitable replicable vectors include, without limitation, pUC19 or pTM1. The polynucleotide can be operably linked to an appropriate promoter such as, for example, T7 polymerase promoter, cytomegalovirus promoter, cellular polymerase II promoter, or SP1 promoter. The replicable vectors may further include sites for transcription initiation, transcription termination, and a ribosome binding site for translation.

Introduction of a recombinant vector composed of a paramyxovirus genome or polynucleotide encoding a paramyxovirus protein into a host cell, such as for example a bacterial cell or eukaryotic cell, can be affected by calcium phosphate transfection, DEAE-dextran mediated transfection, cationic lipid-mediated transfection, electroporation, electrical nuclear transport, chemical transduction, electrotransduction, infection, or other methods. Such methods are described in standard laboratory manuals such as Sambrook et al. (Molecular Cloning: A Laboratory Manual, 4$^{th}$ ed, Cold Spring Harbor, New York, 2012, and Ausubel et al. (In Current Protocols in Molecular Biology, John Wiley & Sons, New York, through supplement 104, 2013. Commercial transfection reagents, such as Lipofectamine (Invitrogen, Carlsbad, Calif.) and FuGENE 6 ™ (Roche Diagnostics, Indianapolis, Ind.), are also available. Suitable host cells include, but are not limited to, HEp-2 cells, FRhL-DBS2 cells, LLC-MK2 cells, MRC-5 cells, and Vero cells.

IV. Immunogenic Compositions

Immunogenic compositions comprising a recombinant paramyxoviruses as described herein (such as a recombinant PIV including a genome encoding a heterologous recombinant RSV F protein) and a pharmaceutically acceptable carrier are also provided. Such compositions can be administered to subjects by a variety of administration modes known to the person of ordinary skill in the art, for example, by an intranasal route. Actual methods for preparing administrable compositions will be known or apparent to those skilled in the art and are described in more detail in such publications as *Remingtons Pharmaceutical Sciences*, $19^{th}$ Ed., Mack Publishing Company, Easton, Pennsylvania, 1995.

Thus, a recombinant paramyxovirus described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The pharmaceutical composition may optionally include an adjuvant to enhance the immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the composition can include a recombinant paramyxovirus encoding an RSV F ectodomain from one particular RSV subgroup or strain and also a recombinant paramyxovirus encoding an RSV F ectodomain from a different RSV subgroup or strain. For example, the composition can include recombinant paramyxovirus including recombinant RSV F proteins from subtype A and subtype B RSV. The different vectors can be in an admixture and administered simultaneously, or administered separately. Due to the phenomenon of cross-protection among certain strains of RSV, immunization with one paramyxovirus encoding a RSV F ectodomain from a first strain may protect against several different strains of the same or different subgroup.

In some instances it may be desirable to combine a recombinant viral vector, or a composition thereof, with other pharmaceutical products (e.g., vaccines) which induce protective responses to other agents, particularly those causing other childhood illnesses. For example, a composition including a recombinant paramyxovirus as described herein can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age). These additional vaccines include, but are not limited to, IN-administered vaccines. As such, a recombinant paramyxovirus including a recombinant RSV F protein described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

Recombinant paramyxoviruses for use in an immunogenic composition, such as for example a vaccine, are selected based on their attenuation and immunogenicity. These vaccine selection criteria are determined according to well-known methods. Preferably, candidate viruses have a stable attenuation phenotype, exhibit replication in an immunized host, and effectively elicit production of an immune response in a recipient, preferably a protective immune response. Preferably, the candidate viruses stimulate and expand the immune response, e.g., induce an immune response against different viral strains or subgroups and/or stimulate an immune response mediated by a different immunologic basis (e.g., secretory versus serum immunoglobulins, cellular immunity, and the like).

The pharmaceutical composition typically contains a effective amount of a disclosed paramyxovirus and can be prepared by conventional techniques. Typically, the amount of recombinant virus in each dose of the immunogenic composition is selected as an amount which induces an immune response without significant, adverse side effects. In some embodiments, the composition can be provided in unit dosage form for use to induce an immune response in a subject, for example, to prevent PIV and/or RSV infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

V. Methods of Eliciting an Immune Response

Provided herein are methods of eliciting an immune response in a subject by administering one or more of the disclosed recombinant paramyxoviruses to the subject. In a particular example, the subject is a human. The immune response can be a protective immune response, for example a response that prevents or reduces subsequent infection with the paramyxovirus or the virus of the heterologous gene included in the recombinant paramyxovirus. Elicitation of the immune response can also be used to treat or inhibit viral infection and illnesses associated therewith. In several embodiments, the method includes administration of an immunogenic composition including an attenuated recombinant parainfluenza virus including a viral genome including a heterologous gene encoding a recombinant RSV F ectodomain linked to a PIV F protein transmembrane (TM) domain and cytoplasmic tail.

A subject can be selected for treatment that has, or is at risk for developing a paramyxovirus infection, such as a RSV and/or a PIV infection, for example because of exposure or the possibility of exposure to RSV and/or PIV. Following administration of a disclosed immunogen, the subject can be monitored for paramyxovirus infection or symptoms associated therewith, or both.

Methods of intra-nasal administration of recombinant paramyxovirus to a subject are known to the person of ordinary skill in the art, as are methods of selecting subjects for administration, preparing immunogenic compositions including the recombinant paramyxovirus for intranasal administration, and evaluating the subject for an immune response to the recombinant paramyxovirus. Exemplary description of such methods can be found, for example, in Karron et al, 2012. *Vaccine,* 30(26), 3975-3981, which is incorporated by reference herein in its entirety.

Typical subjects intended for treatment with therapeutics and methods of the present disclosure include humans, as well as non-human primates and other animals. Because nearly all humans are infected with RSV and PIV by the age of 5, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age. The scope of this disclosure is meant to include maternal immunization. In several embodiments, the subject is a human subject that is seronegative for RSV or PIV3 specific antibodies. In additional embodiments, the subject is no more than one year old, such as no more than 6 months old, no more than 3 months, or no more than 1 month old.

Subjects at greatest risk of RSV and/or PIV infection with severe symptoms (e.g. requiring hospitalization) include children with prematurity, bronchopulmonary dysplasia, and congenital heart disease are most susceptible to severe disease. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. Thus, these subjects can be selected for administration of a disclosed recombinant paramyxovirus.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize paramyxovirus infection. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a disclosed recombinant paramyxovirus can be for prophylactic or therapeutic purpose. When provided prophylactically, the immunogen can be provided in advance of any symptom, for example in advance of infection. The prophylactic administration serves to elicit an immune response that can prevent or ameliorate any subsequent infection. In some embodiments, the methods can involve selecting a subject at risk for contracting a paramyxovirus infection, and administering an effective amount of a disclosed recombinant paramyxovirus to the subject. The recombinant paramyxovirus can be provided prior to the anticipated exposure to paramyxovirus so as to elicit an immune response that can attenuate the anticipated severity, duration or extent of an infection and/or associated disease symptoms, after exposure or suspected exposure to the virus, or after the actual initiation of an infection. In some examples, treatment using the methods disclosed herein prolongs the time of survival of the subject.

Administration of the disclosed recombinant paramyxoviruses including RSV and PIV antigens to a subject can elicit the production of an immune response that is protective against serious lower respiratory tract disease, such as pneumonia and bronchiolitis, or croup, when the subject is subsequently infected or re-infected with a wild-type RSV or PIV. While the naturally circulating virus is still capable of causing infection, particularly in the upper respiratory tract, there is a reduced possibility of rhinitis as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup. To achieve higher levels of cross-protection, for example, against heterologous strains of another subgroup, subjects can be vaccinated with a composition including recombinant viral vectors including RSV F proteins from at least one predominant strain of both RSV subgroups A and B.

The recombinant viral vectors described herein, and immunogenic compositions thereof, are provided to a subject in an amount effective to induce or enhance an immune response against the antigens included in the virus in the subject, preferably a human. An effective amount will allow some growth and proliferation of the virus, in order to produce the desired immune response, but will not produce viral-associated symptoms or illnesses. Based on the guidance provided herein and knowledge in the art, persons skilled in the art will readily be able to determine the proper amount of virus to use in the live vaccine. The precise amounts will depend on several factors, for example, the subject's state of health and weight, the mode of administration, the degree of attenuation of the virus, the nature of the formulation, and whether the immune system of the subject is compromised.

An immunogenic composition including one or more of the disclosed recombinant paramyxoviruses can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to RSV and PIV proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

It is contemplated that there can be several boosts, and that each boost can be a different disclosed immunogen. It is also contemplated in some examples that the boost may be the same immunogen as another boost, or the prime.

Upon administration of a disclosed recombinant paramyxovirus the immune system of the subject typically responds to the immunogenic composition by producing antibodies specific for viral protein. Such a response signifies that an immunologically effective dose was delivered to the subject.

For each particular subject, specific dosage regimens can be evaluated and adjusted over time according to the individual need and professional judgment of the person administering or supervising the administration of the immunogenic composition. In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of therapeutic agent administered to the individual can be at least partially based on the antibody titer level. The antibody titer level can be based on, for example, an immunobinding assay which measures the concentration of antibodies in the serum which bind to an antigen including, for example, an RSV F protein. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes. In one embodiment, a general range of virus administration is about 103 to about 10 plaque forming units (PFU) or more of virus per human subject, including about 104 to about 105 PFU virus per human subject.

Administration of an immunogenic composition that induces an immune response to reduce or prevent an infection, can, but does not necessarily completely, eliminate such an infection, so long as the infection is measurably diminished, for example, by at least about 50%, such as by at least about 70%, or about 80%, or even by about 90% the infection in the absence of the agent, or in comparison to a reference agent. Those in need of treatment include the general population and/or patients infected with or at risk of infection with a paramyxovirus, such as RSV and/or PIV In one example, a desired response is to inhibit or reduce or prevent RSV and/or PIV infection or reinfection. The RSV and/or PIV infection does not need to be completely eliminated or reduced or prevented for the method to be effective. For example, administration of an effective amount of a disclosed recombinant paramyxovirus can decrease subsequence RSV and/or PIV infection (for example, as measured by infection of cells, or by number or percentage of subjects infected by RSV and/or PIV) by a desired amount, for example by at least 10%, at least 20%, at least 50%, at least 60%, at least 70%, at least 80%, at least 90%, at least 95%, at least 98%, or even at least 100% (elimination or prevention of detectable RSV and/or PIV infection, as compared to a suitable control.

The dosage and number of doses will depend on the setting, for example, in an adult or any one primed by prior paramyxovirus infection or immunization, a single dose may be a sufficient booster. In naïve subjects, in some examples, at least two doses can be given, for example, at least three doses. In some embodiments, an annual boost is given, for example, along with an annual influenza vaccination.

Following immunization of a subject, serum can be collected from the subject at appropriate time points, frozen, and stored for assay of antibody titer and/or neutralization testing. Quantification of antibody levels can be performed by subtype-specific Neutralization assay or ELISA. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of RSV or PIV pseudoviruses. Virus-neutralizing antibody titres were determined in serum samples by a PRVN assay as described previously (de Graaf et al., *J. Virol Methods,* 143: 169-174, 2007). In brief, serum samples can be diluted and incubated for 60 min at 37° C. with approximately 50 p.f.u. of NL/1/00 or NL/1/99, expressing an enhanced green fluorescent protein. Subsequently, the virus-serum mixtures are added to Vero-118 cells in 24-well plates and incubated at 37° C. After 2 h, the supernatants are replaced by a mixture of equal amounts of infection medium and 2% methyl cellulose. Six days later, fluorescent plaques are counted using a Typhoon 9410 Variable Mode Imager (GE Healthcare). Antibody titres are expressed as the dilution resulting in 50% reduction of the number of plaques, calculated according to the method of Reed & Muench, *Am. J. Hyg.,* 27, 493-497, 1938.

Additional Embodiments

Clause 1. A recombinant paramyxovirus, comprising (a) a viral genome comprising a heterologous gene encoding the ectodomain of a type I transmembrane protein of a heterologous virus linked to the transmembrane domain TM and cytoplasmic tail (CT) of the F protein of the paramyxovirus; or (b) a viral genome comprising a heterologous gene encoding the ectodomain of a type II transmembrane protein of a heterologous virus linked to the TM and CT of the HN protein of the paramyxovirus.

Clause 2. The recombinant paramyxovirus of clause 1, wherein the recombinant paramyxovirus is a recombinant human/bovine parainfluenza virus 3 (B/HPIV3), a recombinant human parainfluenza virus 1 (HPIV1), a recombinant human parainfluenza virus 1 (HPIV2), a recombinant human parainfluenza virus 1 (HPIV3), a recombinant parainfluenza virus 5 (PIV5) a recombinant Sendai virus, or a recombinant Newcastle disease virus (NDV).

Clause 3. The recombinant paramyxovirus of clause 2, comprising: a recombinant parainfluenza virus (PIV) comprising a viral genome comprising a heterologous gene encoding a recombinant respiratory syncytial virus (RSV) F ectodomain linked to a PIV F protein TM and CT; a recombinant NDV comprising a viral genome comprising a heterologous gene encoding a recombinant RSV F ectodomain linked to a NDV F protein TM and CT; or a recombinant Sendai virus comprising a viral genome comprising a heterologous gene encoding a recombinant RSV F ectodomain linked to a Sendai virus F protein TM and CT.

Clause 4. The recombinant paramyxovirus of any of clauses 1-3, comprising: a recombinant PIV comprising a viral genome comprising a heterologous gene encoding a recombinant RSV F ectodomain linked to a PIV F protein TM and CT.

Clause 5. The recombinant paramyxovirus of clause 4, wherein the RSV F ectodomain is from a human RSV (hRSV) F protein.

Clause 6. The recombinant paramyxovirus of clause 4 or claim 5, wherein the hRSV F protein is from a subtype A hRSV or subtype B hRSV.

Clause 7. The recombinant paramyxovirus of any one of clauses 4-6, wherein the RSV F ectodomain is stabilized in a RSV F prefusion-conformation by one or more amino acid substitutions compared to a native RSV F protein sequence.

Clause 8. The recombinant paramyxovirus of any one of clauses 4-7, wherein the RSV F ectodomain comprises amino acids set forth as: (a) 66E; (b) 101P; (c) 155C and 290C; (d) 190F; (e) 207L; or (f) a combination of (a) and (b); (a) and (c); (a) and (d); (a) and (e); (a), (d), and (e); (a), (c), (d), and (e); (a), (b), and (c); (a), (b), and (d); (a), (b), and (e); (a), (b), (e), and (d); (a), (b), (c), (d), and (e); (c) and (d); or (c) and (e); or (c), (d), and (e), wherein the amino acid numbering corresponds to the RSV F protein sequence set forth as SEQ ID NO: 1.

Clause 9. The recombinant paramyxovirus of clause 8, wherein the RSV F ectodomain comprises amino acid substitutions are set forth as: (a) K66E; (b) Q101P; (c) S155C and S290C; (d) S190F; (e) V207L; or (f) a combination of (a) and (b); (a) and (c); (a) and (d); (a) and (e); (a), (d), and (e); (a), (c), (d), and (e); (a), (b), and (c); (a), (b), and (d); (a), (b), and (e); (a), (b), (e), and (d); (a), (b), (c), (d), and (e); (c) and (d); or (c) and (e); or (c), (d), and (e).

Clause 10. The recombinant paramyxovirus of clause 8 or clause 9, wherein the RSV F ectodomain comprises 66E, 101P, 115C, 290C, 190F, and 207L.

Clause 11. The recombinant paramyxovirus of any one of clauses 4-10, wherein the RSV F ectodomain comprises an amino acid sequence at least 85% identical to the RSV ectodomain of one of SEQ ID NOs: 1 (WT RSV F A), 2 (WT RSV F B), 12 (A2 HEK), 14 (A2 HEK+DS), or 21 (A2 HEK+DS-Cav1), or comprises the amino acid sequence of the RSV ectodomain of SEQ ID NO: 12, 14, or 21.

Clause 12. The recombinant paramyxovirus of any one of clauses 4-11, wherein the PIV is a recombinant PIV1, a recombinant PIV2, or a recombinant PIV3.

Clause 13. The recombinant paramyxovirus of clause 12, wherein the recombinant PIV is: a recombinant PIV1, and the TM and CT linked to the RSV F ectodomain are from a PIV1 F protein; a recombinant PIV2, and the TM and CT linked to the RSV F ectodomain are from a PIV2 F protein; or a recombinant PIV3, and the TM and CT linked to the RSV F ectodomain are from a PIV3 F protein.

Clause 14. The recombinant paramyxovirus of clause 12 or clause 13, wherein the recombinant PIV is: a recombinant HPIV1 and the PIV F TM and CT linked to the RSV F ectodomain are from a HPIV1 F protein; a recombinant HPIV2 and the PIV F TM and CT linked to the RSV F ectodomain are from a HPIV2 F protein; a recombinant HPIV3 and the PIV F TM and CT linked to the RSV F ectodomain are from a HPIV3 F protein; or a recombinant B/HPIV3 and the PIV F TM and CT linked to the RSV F ectodomain are from a BPIV3 F protein.

Clause 15. The recombinant paramyxovirus of any one of clauses 4-14, wherein the RSV F ectodomain is from a hRSV F protein, and the TM and CT are from a BPIV3 F protein.

Clause 16. The recombinant paramyxovirus of any one of clauses 4-15, wherein the recombinant PIV is: a recombinant HPIV1 and the PIV F TM and CT linked to the RSV F ectodomain comprise the amino acid sequence set forth as SEQ ID NO: 31, or an amino acid sequence at least 90% identical to SEQ ID NO: 31; a recombinant HPIV2 and the PIV F TM and CT linked to the RSV F ectodomain comprise the amino acid sequence set forth as SEQ ID NO: 39, or an amino acid sequence at least 90% identical to SEQ ID NO: 39; a recombinant HPIV3 and the PIV F TM and CT linked to the RSV F ectodomain comprise the amino acid sequence set forth as SEQ ID NO: 46, or an amino acid sequence at least 90% identical to SEQ ID NO: 46; or a recombinant B/HPIV3 and the PIV F TM and CT linked to the RSV F ectodomain comprise the amino acid sequence set forth as SEQ ID NO: 53, or an amino acid sequence at least 90% identical to SEQ ID NO: 53.

Clause 17. The recombinant paramyxovirus of any one of clauses 4-16, wherein the recombinant PIV is: a recombinant HPIV3 and the heterologous gene encodes a hRSV F ectodomain linked to a HPIV3 F TM and CT comprising the amino acid sequence set forth as SEQ ID NO: 10, or an amino acid sequence at least 90% identical thereto; or a recombinant B/HPIV3 and the heterologous gene encodes a hRSV F ectodomain linked to a BPIV3 F TM and CT comprising the amino acid sequence set forth as SEQ ID NO: 21, or an amino acid sequence at least 90% identical thereto.

Clause 18. The recombinant paramyxovirus of any one of clauses 4-17, wherein the RSV F ectodomain is from a hRSV F protein and the recombinant PIV comprises a viral genome encoding: HPIV3 F and HN proteins and BPIV3 N, P, C, V, M, and L proteins, and wherein the TM and CT linked to the RSV F ectodomain are from a BPIV3 F protein; HPIV1 N, P, C, M, F, HN and L proteins, and wherein the TM and CT linked to the RSV F ectodomain are from a HPIV1 F protein; HPIV2 N, P, V, M, F, HN and L proteins, and wherein the TM and CT linked to the RSV F ectodomain are from a HPIV2 F protein; or HPIV3 N, P, C, M, F, HN and L proteins, and wherein the TM and CT linked to the RSV F ectodomain are from a HPIV3 F protein.

Clause 19. The recombinant paramyxovirus of any one of clauses 4-18, wherein the recombinant RSV F ectodomain linked to the PIV TM and CT is encoded by the first or second gene downstream of a genomic promoter of the PIV genome.

Clause 20. The recombinant paramyxovirus of clause 18 or clause 19, wherein the viral genome comprises, from upstream to downstream: a PIV genomic promoter followed by the N, P, C/V, M, F, HN, and L genes; and wherein the gene encoding the recombinant RSV F ectodomain linked to the PIV TM and CT is located between the genomic promoter and the gene encoding the N protein, or between the genes encoding the N and the P protein.

Clause 21. The recombinant paramyxovirus of any one of clauses 18-19, comprising a viral genome encoding: HPIV3 F and HN genes and BPIV3 N, P, C, V, M, and L genes comprising the amino acid sequences set forth as SEQ ID NOs: 21, 101, 47, 48, 49, 52, respectively, or sequences at least 90% identical thereto.

Clause 22. The recombinant paramyxovirus of any one of the prior clauses, wherein the heterologous gene is codon-optimized for expression in human cells.

Clause 23. The recombinant paramyxovirus of clause 22, wherein the recombinant paramyxovirus is: a recombinant HPIV3 and the heterologous gene encodes an RSV F ectodomain linked to a HPIV3 F TM and CT, and comprises the nucleotide sequence set forth as SEQ ID NO: 11 (GenScript RSV F_HEK_DS-Cav1_H3TMCT); or a recombinant B/HPIV3 and the heterologous gene encodes an RSV F ectodomain linked to a BPIV3 F TM and CT, and comprises the nucleotide sequence set forth as SEQ ID NO: 22 (GenArt RSV F_HEK_DS-Cav1_B3TMCT) or SEQ ID NO: 23 (GenScript RSV F_HEK_DS-Cav1_B3TMCT).

Clause 24. A recombinant viral vector, comprising: a viral genome comprising a heterologous gene encoding a RSV F ectodomain linked to the TM and CT of a type I membrane protein of the viral genome.

Clause 25. The viral vector of clause 24, wherein the RSV F ectodomain comprises K66E and Q101P amino acid substitutions.

Clause 26. A recombinant viral vector, comprising a viral genome comprising a heterologous gene encoding a RSV F ectodomain comprising K66E and Q101P amino acid substitutions.

Clause 27. The viral vector of any one of clauses 24-26, wherein the RSV F protein is stabilized in a prefusion or a postfusion conformation by one or more amino acid substitutions.

Clause 28. The viral vector of any one of clauses 24-27, wherein the RSV F ectodomain is stabilized in the prefusion conformation by S155C, S290C, S190F, and V207L amino acid substitutions Clause 29. The viral vector of any one of clauses 26-28, wherein the RSV F ectodomain is soluble and can be secreted from a host cell comprising the viral vector.

Clause 30. The viral vector of any one of clauses 24-29, wherein the viral vector is a recombinant human/bovine parainfluenza virus 3 (B/HPIV3), a recombinant human parainfluenza virus 1 (HPIV1), a recombinant human parainfluenza virus 1 (HPIV2), a recombinant human parainfluenza virus 1 (HPIV3), a recombinant parainfluenza virus 5 (PIV5) a recombinant Sendai virus, or a recombinant Newcastle disease virus (NDV).

Clause 31. The viral vector of any one of clauses 24-30, wherein the RSV F ectodomain is from a human RSV (hRSV) F protein.

Clause 32. The viral vector of any one of clauses 24-31, wherein the heterologous gene encoding the RSV F protein comprises the nucleic acid sequence set forth as nucleotides 1-1587 of SEQ ID NO: 18. (ectodomain encoded by GenScript optimized RSV F_A2_HEK_DS-Cav1_B3CT DNA sequence) Clause 33. The recombinant paramyxovirus or viral vector of any one of the prior clauses, wherein at least 90% of viral particles produced by a host cell infected with the recombinant paramyxovirus or viral vector comprise a viral envelope comprising the ectodomain encoded by the heterologous gene.

Clause 34. The recombinant paramyxovirus or viral vector of any one of the previous clauses, wherein the recombinant paramyxovirus or viral vector is attenuated.

Clause 35. An immunogenic composition comprising the recombinant paramyxovirus or viral vector of any one of the prior clauses and a pharmaceutically acceptable carrier.

Clause 36. The immunogenic composition of clause 35, further comprising an adjuvant.

Clause 37. A method of eliciting an immune response to a virus and a heterologous antigen encoded thereby in a subject comprising administering a therapeutically effective amount of the immunogenic composition of clause 35 or clause 36 to the subject.

Clause 38. A method of eliciting an immune response to a paramyxovirus and a heterologous antigen encoded thereby in a subject comprising administering a therapeutically effective amount of the immunogenic composition of clause 35 or clause 36 to the subject, wherein the immunogenic composition comprises a recombinant paramyxovirus comprising a heterologous gene encoding the heterologous antigen.

Clause 39. A method of eliciting an immune response to RSV and PIV in a subject, comprising administering an immunogenic composition comprising a therapeutically effective amount of the immunogenic composition of clause 35 or clause 36 to the subject, wherein the immunogenic composition comprises a recombinant paramyxovirus comprising a heterologous gene encoding an RSV antigen.

Clause 40. The method of any one of clauses 37-39, wherein the immune response is a protective immune response.

Clause 41. The method of any one of clauses 37-40, comprising a prime-boost administration of the immunogenic composition.

Clause 42. The method of any one of clauses 37-41, comprising intranasal or parenteral administration of the immunogenic composition.

Clause 43. The method of any one of clauses 37-42, wherein the subject is a human or a veterinary subject.

Clause 44. The method of any one of clauses 37-43, wherein the subject is at risk of or has a RSV or a PIV infection.

Clause 45. The method of any one of clauses 37-44, wherein the subject is less than one year old.

Clause 46. A nucleic acid molecule comprising the genome of the recombinant paramyxovirus of any one of clauses 1-25.

Clause 47. A recombinant RSV F protein or immunogenic fragment thereof comprising K66E and Q101P amino acid substitutions.

Clause 48. The recombinant RSV F protein or immunogenic fragment thereof of clause 47, further comprising: (a) S155C and S290C; (b) S190F; (c) V207L; or (f) a combination of (a) and (b); (a) and (c); (b) and (c); or (a), (b), and (c).

Clause 49. The immunogenic fragment of the recombinant RSV F protein of clause 47 or clause 48, comprising the RSV F ectodomain.

Clause 50. A nucleic acid molecule encoding the recombinant RSV F protein of any one of clauses 47-49.

EXAMPLES

The following examples are provided to illustrate particular features of certain embodiments, but the scope of the claims should not be limited to those features exemplified.

Example 1

Improved Expression and Immunogenicity of the Respiratory Syncytial Virus (RSV) Fusion (F) Glycoprotein Expressed by an Attenuated Parainfluenza Virus Vector This example describes approaches to enhance the immunogenicity and stability of RSV F expressed by a recombinant B/HPIV3 by using RSV F sequence from an early passage virus, by codon-optimization, by using stable and highly immunogenic pre-fusion and post-fusion forms of RSV F, and by engineering the RSV F protein TM and CT so that it was more efficiently incorporated into vector particles.

Introduction. Live attenuated RSV strains administered represent one strategy for an RSV vaccine, and these are currently under development (Hurwitz. 2011. Expert. Rev. Vaccines. 10:1415-1433; Collins and Melero. 2011. Virus Res. 162:80-99; Karron, et al. 2013. Current Topics Microbiology and Immunology 372:259-284). A live attenuated RSV strain typically would be administered by the intranasal (IN) route. However attenuation generally results in reduced antigen synthesis, resulting in reduced immunogenicity. Obtaining a suitable balance between attenuation and immunogenicity has been challenging for RSV.

Complete, infectious HPIVs can be generated entirely from cloned cDNAs in transfected cell culture (using reverse genetics). A foreign gene designed for expression would be modified so that it is flanked by HPIV transcription signals (called the gene-start and gene-end signals, located at the beginning and end of each gene, respectively) and would be inserted as an additional gene into the HPIV genome by reverse genetics. The foreign gene would then be transcribed into a separate mRNA, like the other HPIV genes. HPIVs can accommodate and express several added foreign genes (Skiadopoulos, et al. 2002. Virology 297:136-152). However, multiple genes can be overly attenuating and can collect point mutations (Skiadopoulos, et al. 2002. Virology 297:136-152).

HPIV transcription initiates at a single promoter at the 3' end of the genome and proceeds sequentially. A fraction of the polymerase disengages from the template at each gene junction, resulting in a negative gradient of gene transcription. Therefore, promoter-proximal genes are expressed more frequently than downstream genes. Placement of a foreign gene close to the promoter would increase expression, but has the potential to affect expression of downstream vector genes. Other features, such as differences in the efficiency of gene-start or gene-end transcription signals or effects of other structural features in the RNA template that sometimes are present but are poorly understood, also can unpredictably affect expression of an inserted gene or open reading frame (ORF) (Whelan, et al. 2004. Current Topics Microbiology and Immunology 283:61-119). In addition, in some cases the properties of viral constructs can be greatly affected by factors that remain unidentified; for example, the insertion of the RSV F gene into the P-M gene junction of a PIV3 vector resulted in a virus that was substantially temperature-sensitive and attenuated (Liang B, et al. 2014. J Virol 88:4237-4250). Thus, while the broad details of expression from HPIV genomes is generally known, specific constructions can give unpredictable results.

In previous studies, the B/HPIV3 vector was used as a vector to express the RSV G gene and F proteins from added genes in the first and second genome positions after the promoter or to express the RSV F gene from an added gene in the second genome position between the N and P genes. The latter virus, called MEDI-534, has been evaluated in clinical studies in seronegative children and was attenuated, well tolerated, and infectious but was less immunogenic against RSV than hoped (Bernstein, et al. 2012. Pediatric Infectious Disease Journal 31:109-114). Analysis of shed vaccine virus from vaccine recipients showed that ~50% of specimens contained vaccine virus with mutations that would be predicted to perturb RSV F expression. This likely reduced immunogenicity. Retrospective analysis of the clinical trial material (CTM) showed that 2.5% of this virus did not express RSV F (Yang, et al. 2013. *Vaccine* 31:2822-2827). In addition, the observation that the RSV F insert accumulated mutations that inactivated its expression at the protein level, and that these mutations were amplified during growth, suggests that there was a selective advantage to silencing expression of the RSV F protein. This likely could be due to the highly fusogenic nature of the RSV F protein, which efficiently mediates syncytium formation. In vitro, this results in destruction of the cell substrate, which could reduce vector replication. In addition, the synthesis of high levels of a foreign glycoprotein could interfere with the synthesis, processing and transport of the vector glycoproteins through the endoplasmic reticulum and exocytic pathway, and could interfere sterically with virion morphogenesis, among other things. These effects might occur both in vitro and in vivo.

Expression of an early-passage (HEK) version of the RSV F protein and codon-optimized versions of the RSV F open reading frame (ORF). Increased expression of viral antigen typically provides enhanced immunogenicity. Codon-optimization of the ORF encoding a vectored antigen can increase its expression and in turn enhance its immunogenicity, for example as has been shown with human immunodeficiency virus antigens expressed from viral or DNA vectors (Gao, et al. 2003. AIDS research and human retroviruses 19:817-823; Carnero, et al. 2009. *J Virol* 83:584-597). However, these sequence changes can have effects beyond improving translation, such as effects on mRNA stability and transport, and so the effects of altering the nucleotide sequence of an mRNA can be complex and unpredictable. Therefore, a codon-optimized version of the RSV F sequence was designed using GeneArt (GA) algorithms and was evaluated to determine whether it conferred protein expression.

When designing this codon-optimized ORF, the amino acid sequence of an early-passage version of RSV strain A2 from the 1960s was mistakenly used (Connors, et al. 1995. Virology 208:478-484; Whitehead, et al. 1998. J Virol 72:4467-4471). This early-passage (or low-passage) strain from the 1960s is called HEK after the human embryonic kidney (HEK) cell culture used in its propagation. The HEK virus differed from current, highly passaged laboratory version of RSV strain A2 by two amino acid assignments (Connors, et al. 1995. Virology 208:478-484; Whitehead, et al. 1998. *J Virol* 72:4467-4471). The HEK version had assignments 66E and 101P whereas the highly passaged laboratory A2 strain had assignments 66K and 101Q (hereafter called "non-HEK" assignments) (FIG. 1). However, the occurrence of sequence differences between virus strains or between stocks of a given strain is common for RNA viruses given their high mutation rate, and the HEK differences previously had no known importance. Further, the presence of the HEK assignments in an attenuated RSV vaccine candidate called RSV NIH ΔM2-2 was associated with a small reduction in the efficiency of replication in cell culture. Additionally, the HEK assignment at position 66 was identified to affect syncytium formation during RSV infection. Thus, it was intended to avoid the HEK assignments given their association with reduced replication. However, because the version of RSV F containing the HEK assignments was accidentally used for the initial codon optimization, a parallel GA-optimized non-HEK version was constructed and the two versions were compared (FIG. 1). The two versions of RSV F were placed under the control of BPIV3 gene-start and gene-end transcription signals and inserted into the $2^{nd}$ position of the rB/HPIV3 vector (FIG. 1). The transcription signals and insert position were used in all subsequent rB/HPIV3 constructs expressing RSV F so as to provide direct comparisons throughout.

Vero cells were infected with the two different vectors (called "HEK/GA-opt" and "non-HEK/GA-opt"), cell lysates were prepared 48 h post-infection, and the proteins were subjected to gel electrophoresis in the presence of denaturing detergent and under reducing or non-reducing conditions. The separated proteins were transferred to membranes by Western blotting and were analyzed using antibodies specific to RSV F (FIG. 2). This showed that the presence of the HEK assignments was associated with a small (~2-fold) but consistent increase in the expression of RSV F protein (FIG. 2). One non-limiting explanation for this finding is that the HEK assignments increased F protein stability although an effect on protein synthesis is possible but seems less likely given that the HEK and non-HEK versions of the F ORF were identical except for two codons. In addition, when analyzed under non-reducing conditions, the presence of the HEK assignments was associated with a reduction in the gel mobility of the RSV F trimer (FIG. 2). This suggested that these assignments altered the F protein trimer structure. More strikingly, expression of the HEK version of RSV F was associated with a drastic reduction in syncytium formation compared to the non-HEK version (FIG. 3) even though the HEK version was expressed at a slightly increased level, as already noted. This assay takes advantage of the general lack of evident syncytia induced in cells infected by the rB/HPIV3 empty vector, whereas the expression of the RSV F protein from the vector results in syncytium formation that is generally proportional to the amount of expression of RSV F protein. This provides an assay for the quantity and functionality of RSV F protein expressed from a PIV vector. These observations concerning HEK indicated that the HEK assignments were associated with differences in synthesis/stability, structure, and fusogenic activity of RSV F, and that these effects occurred in the absence of any other RSV proteins and thus were directly relevant to expression from a heterologous vector.

Because the HEK assignments are from a low-passage stock of RSV strain A2 from the 1960s, they are likely to be representative of the original clinical isolate, whereas the non-HEK assignments had appeared during extensive passage in vitro over subsequent decades. This suggests that the hypo-fusogenic phenotype of the HEK version of F is more representative of the original biological virus. The non-HEK version may represent a hyper-fusogenic variant that was selected for during passage in cell culture. A hyper-fusogenic version of RSV F might be less favored in nature because it might destabilize the virus, but might be selected for in a laboratory setting of rapid growth in a cell monolayer. 226 sequences of RSV F from clinical isolates in the GenBank database were examined and it was found that clinical isolates usually contained the HEK assignments. This is consistent with these assignments being representative of circulating RSV. In any event, the HEK assignments provided a modest increase in F protein expression and provided a form of RSV F that was hypo-fusogenic. The reduction in syncytium formation is advantageous because it reduces cytopathogenicity that might otherwise interfere with HPIV vector replication and favor selection of vector in which the RSV F insert was silenced. Therefore, the HEK assignments have the triple advantage of representing a more native and clinically relevant form of the F protein, providing a modest increase in protein expression, and reducing selective pressure to silence the RSV F insert.

Figure 4:
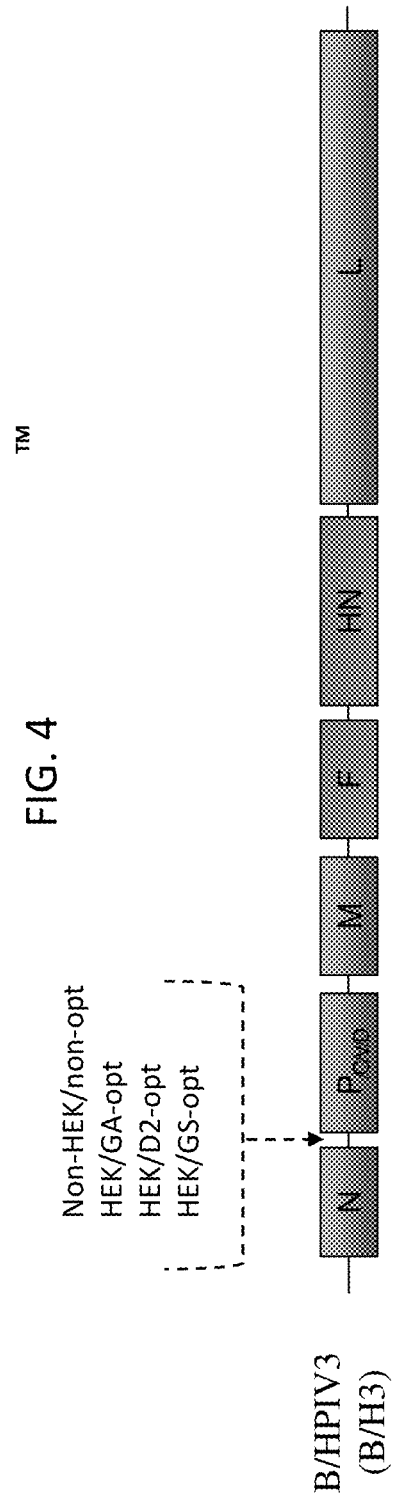
FIG. 4. Construction of rB/HPIV3 vectors expressing RSV F ORFs that were codon-optimized (for human expression) by different algorithms and contained the HEK assignments. The ORF encoding the RSV F protein with HEK assignments was optimized for human codon usage with the GA algorithm (HEK/GA-opt, shown in FIG. 1), the DNA2.0 algorithm (HEK/D2-opt), or the GenScript (GS) algorithm (HEK/GS-opt). These codon-optimized ORFs were compared with the non-HEK, non-optimized version of the RSV F ORF (Non-HEK/non-opt). These RSV F ORFs were inserted into the rB/HPIV3 vector in exactly the same position and with the same vector signals as in FIG. 1.
Figures 5A, 5B:
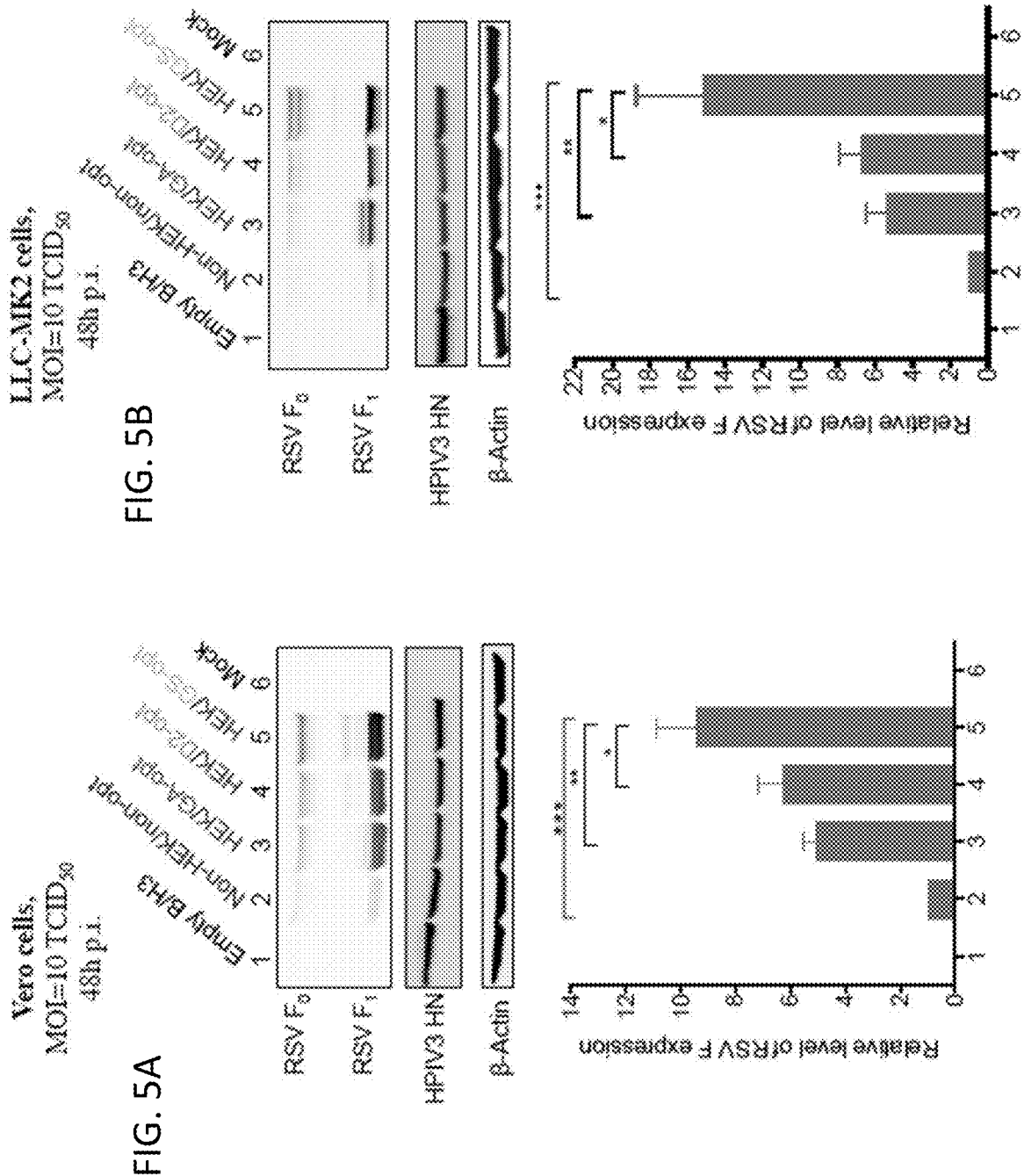
FIGS. 5A and 5B. Increased in vitro expression of RSV F protein from rB/HPIV3 vectors due to the HEK assignments and codon optimization. Expression of RSV F in (A) Vero and (B) LLC-MK2 cells was evaluated by Western blot analysis. Cells were infected at an MOI of 10 $TCID_{50}$ at 32° C. with the indicated rB/HPIV3 vectors, and cell lysates were harvested at 48 hours post-infection. Lysates were subjected to gel electrophoresis under reducing and denaturing conditions and analyzed by Western blotting. Proteins were visualized by reaction with fluorescent antibodies and detected by infrared imaging. The experiment was performed with a total of three wells per virus. A monoclonal antibody specific to RSV F detected the uncleaved $F_0$ precursor and cleaved $F_1$ subunit. RSV $F_1$ band densities were quantified and normalized to the band density of the Non-HEK/non-opt samples indicated as "1". Expression of the HPIV3 HN protein also was determined as an internal control for vector protein expression and to ensure equivalence of MOI and replication; β-actin was used as the loading control.

The effect of codon-optimization on RSV F expression and immunogenicity was also evaluated. The HEK-containing and GA-optimized version (HEK/GA-opt) described above was used along with two other codon-optimized RSV HEK F sequences made by two other different algorithms. Evaluation of multiple optimized versions is not a typical practice, since it increases the expense and inconvenience and had not been shown to be useful. The two other sources were DNA2.0 (D2) and GenScript (GS) algorithms; also included for comparison was the non-HEK, non-codon-optimized version (FIG. 4). Codon optimization resulted in significantly enhanced RSV F protein synthesis that, surprisingly, differed in magnitude for the different versions. The highest expression was observed for the HEK-containing GenScript-optimized F protein (HEK/GS-opt), which was 10-fold (Vero cells) and 16-fold (LLC-MK2 cells) higher than the unmodified RSV F (non-HEK/non-opt) (FIG. 5). The levels of expression with the more efficient ORFs were so high that progressively increasing levels of syncytium formation were evident in association with increasing levels of F expression despite the presence of the HEK assignments (FIG. 6), although it can be presumed that syncytium formation would have been even faster and more extensive in the absence of the HEK assignments.

Codon-pair optimization was also evaluated as a means to increase F protein expression, using an algorithm that was previously described (Coleman, et al. 2008. *Science* 320: 1784-1787). Codon-pair optimization increases the frequency of codon pairs associated with high expression. However, this did not confer any increase in expression in the case of RSV F.

Contrary to expectations, the 10- to 16-fold increase in RSV F expression and concomitant increase in syncytium formation did not have a significant negative impact on vector replication in cell culture (FIG. 7). It might have been anticipated that high levels of RSV F expression and syncytium formation would have interfered with the vector at any of a number of steps, as already noted, including vector glycoprotein synthesis, processing, exocytosis, vector particle formation, and cell viability, but this was not the case. This was particularly surprising because, as already noted, the accumulation and amplification of mutations that silenced expression of the RSV F gene in MEDI-534 suggested that there was a substantial selective pressure against expression of RSV F protein. Compared with the empty vector, all vectors with RSV F insert were moderately attenuated (FIG. 7)—perhaps involving a common attenuating effect such as the increase in genome length and gene number—but replicated with similar kinetics to each other and grew to high peak titers that were slightly lower than the peak titer of empty vector (FIG. 7). Modest variance of peak titers likely represents experimental variability.

In vivo replication, immunogenicity, and protective efficacy of the rB/HPIV3 vectors was evaluated in a hamster model. Groups of hamsters were immunized intranasally with the rB/HPIV3 vectors at a dose of $10^5$ tissue-culture-infection-dose-50 units ($TCID_{50}$) per animal. In addition, wildtype (wt) RSV given at a dose of $10^6$ plaque forming units (pfu) was included as positive control for the induction of RSV-specific immunity. The wt RSV control was included with the caveat that wt RSV was a non-attenuated virus whereas the vectors were attenuated and might be relatively less immunogenic for that reason. Six animals per virus per day were euthanized on days 3 and 5 post-infection, and nasal turbinates and lungs were collected for virus titration to measure replication in vivo. This showed that vectors bearing the RSV F insert were moderately attenuated in the nasal turbinates (upper respiratory tract), and substantially attenuated in the lungs (lower respiratory tract) as compared with the empty vector (FIG. 8). Increased attenuation compared to the empty vector was evident by the lower values for virus shedding. It also was evident by comparison of the day 3 and day 5 titers: for the empty vector, the titers on days 3 and 5 were comparable, whereas for the vectors bearing RSV F, the day 3 titers were lower than the day 5 titers, indicating that these constructs took longer to achieve their maximum titers. Surprisingly, among the vectors with RSV F insert, those with enhanced RSV F expression were not more attenuated than the one with less RSV F expression, i.e., non-HEK/non-opt. Thus, the addition of the RSV F insert to the rB/HPIV3 vector was attenuating in vivo—perhaps due to some common feature such as the increase in genome length or gene number—but this did not appear to be substantially influenced by the level of synthesis of the RSV F protein.

Figure 9:
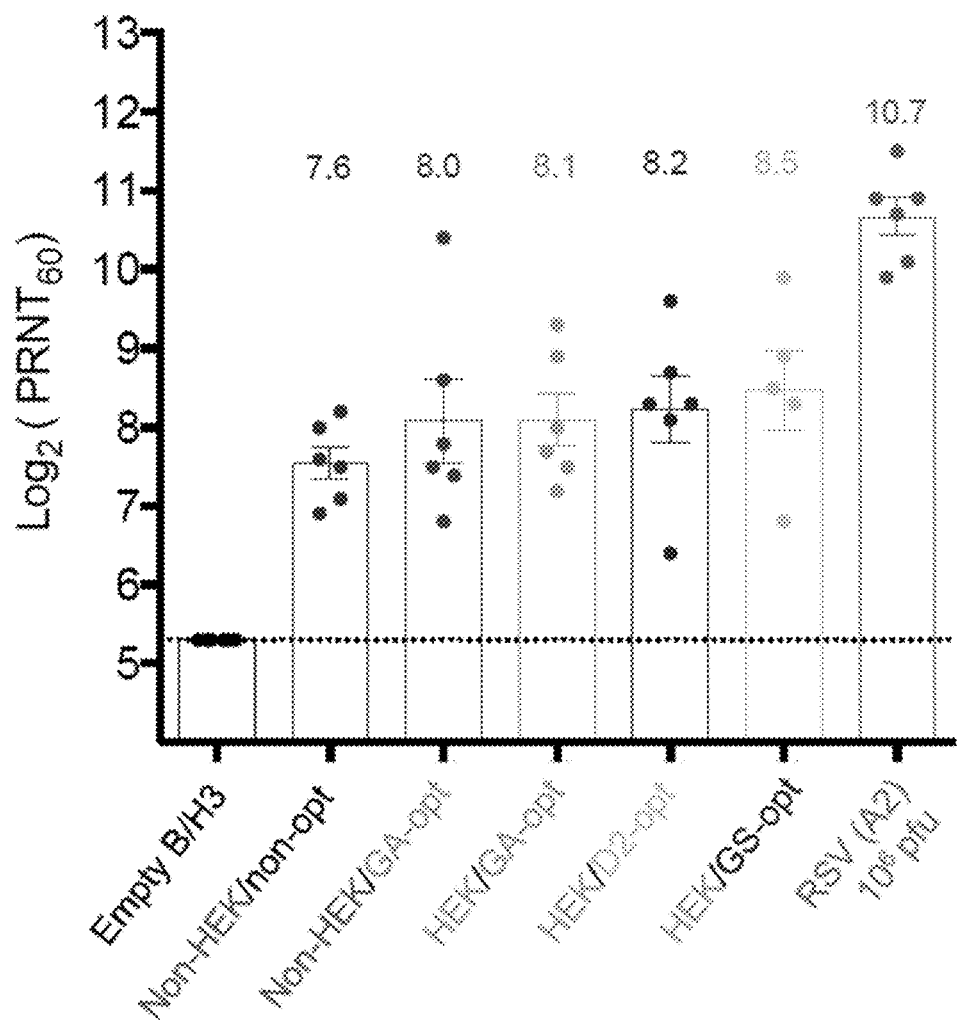
FIG. 9. Serum RSV-neutralizing antibody titers from hamsters infected with rB/HPIV3 vectors expressing HEK or non-HEK RSV F protein from non-optimized or codon-optimized ORFs. Hamsters (n=6 animals per virus) were inoculated IN with 105 $TCID_{50}$ of the indicated rB/HPIV3 vectors or $10^6$ PFU of wt RSV in a 0.1 ml inoculum. Serum samples were collected at 28 days post-immunization, and RSV-neutralizing antibody titers were determined by using a 60% plaque reduction neutralization test ($PRNT_{60}$) performed on Vero cells at 32° C. in the presence of guinea pig complement. Each symbol represents an individual animal. The height of each bar represents the mean titer of each group. The values of mean titers are shown above the bars. The standard error of the mean is shown by the horizontal lines. The detection limit for the neutralization assay was 5.3 reciprocal $log_2$ $PRNT_{60}$, indicated with a dotted line.

The immunogenicity of the vectors was assessed by measuring the serum titers of RSV-neutralizing antibodies by a 60% plaque reduction assay supplemented with guinea pig complement, which is a standard assay. All vectors expressing RSV F induced similarly high titers of RSV-neutralizing serum antibodies, irrespective of HEK assignments or codon-optimization (FIG. 9). There was a modest progressive increase in neutralizing titers associated with increasing RSV F expression, but the differences were not statistically significant. WT RSV that had been infected in parallel as a control induced significantly higher titers of RSV-neutralizing antibodies than the vectors. However, it is important to note that the neutralizing antibodies induced by RSV infection included contributions from both the F and G neutralization antigens, whereas the vectors only had F-specific antibodies contributing to the neutralizing titers. In addition, the non-attenuated wt RSV control replicated more efficiently than the attenuated vectors, especially in the lungs (FIG. 8), which would have increased its immunogenicity compared to that of the vectors.

In order to assess the protective efficacy of these vectors, immunized hamsters in groups of 6 animals, from the experiment in FIG. 9, were challenged 30 days post-immunization by intranasal infection with $10^6$ pfu of wt RSV per animal. Nasal turbinates and lungs were collected from euthanized animals at 3 days post-challenge, and tissue homogenates were prepared and evaluated by plaque assay to measure the levels of challenge RSV replication. Vectors expressing RSV F conferred almost complete protection in the lungs and intermediate levels of protection in the nasal turbinates, while wt RSV conferred almost complete protection in both anatomical sites (FIG. 10). There was no significant difference among the vectors expressing RSV F in the protective efficacy against RSV challenge. It should be noted that the protection conferred by RSV would include contributions from neutralizing antibodies against both the F and G proteins as well as cellular immunity against potentially all of the RSV proteins, whereas protection conferred by the vectors would include humoral and cellular immunity against solely the F protein. In addition, as noted, the RSV control was a non-attenuated wt virus that replicated to higher titers than the vectors during immunization (FIG. 8), especially in the lungs, which would increase its immunogenicity and protective efficacy.

These results showed that the 10- to 16-fold increase in expression of the RSV F protein expression resulting from the use of the HEK assignments and codon-optimized sequence did not result in a significant increase in the induction of RSV-neutralizing serum antibodies (although a trend towards an increase was observed) or a significant increase in protection against wt RSV challenge. In contrast, a similar level of increase in expression for human immunodeficiency virus antigens had resulted in enhanced protection with other viral vectors and DNA vaccines in different animal models (Gao, et al. 2003. AIDS research and human retroviruses 19:817-823; Carnero, et al. 2009. J Virol 83:584-597). Previously, it had also been observed that a 30- to 69-fold difference in the expression of RSV F due to insertion at positions 1 or 2 versus 6 in the rB/HPIV3 vector induced significant differences in the protective efficacy in hamsters (Liang B, et al. 2014. *J Virol* 88:4237-4250). Thus, it is generally thought that an increase in antigen synthesis would confer an increase in immunogenicity. However in some cases this effect might not be of sufficient magnitude to be detected unambiguously, or it may be that a given in vivo model might not be sufficiently sensitive. Thus, the 10- to 16-fold difference in the present study might not be sufficient to induce an effect of sufficient magnitude to be statistically significant in the semi-permissive hamster model. The beneficial effect of higher RSV F expression might be more prominent in combination with other features, or in a permissive host, i.e. primates and humans, with a larger sample size in a pre-clinical and clinical evaluation.

In particular, the 10- to 16-fold increase in F protein expression observed in this study was in Vero (African green monkey) or LLC-MK2 (rhesus monkey) cells, in which codon-optimization for human use would likely be effective given the relatively close phylogenetic relatedness of these primates to humans. In contrast, the in vivo immunogenicity assay employed hamsters, in which codon optimization for human use might not be effective in increasing expression and, thereby, immunogenicity.

Evaluation of the immunogenicity of the pre-fusion and post-fusion forms of RSV F expressed by the rB/HPIV3 vector. Like all paramyxovirus F proteins, the RSV F protein initially assembles into a pre-fusion conformation that is the version that initially accumulates on the surface of infected cells and is incorporated into virions. Pre-fusion F can be triggered, such as by contact with an adjacent target cell membrane, to undergo massive conformational changes that mediate membrane fusion, with the F protein ending in a post-fusion conformation (Calder, et al. 2000. Virology 271:122-131; McLellan, et al. 2013. Science 340:1113-1117; McLellan, et al. 2011. J Virol 85:7788-7796; Swanson, et al. 2011. Proc. Nat'l Acad. Sci. U.S.A. 108:9619-9624). The RSV F protein is notable among the paramyxoviruses for being highly susceptible to triggering and can readily be triggered prematurely, which may contribute to the marked instability of RSV infectivity. There also is evidence that much of the RSV F protein that accumulates in infected cells is conformationally heterogeneous, which may act as a decoy to reduce the induction of virus-neutralizing antibodies (Sakurai, et al. 1999. J Virol 73:2956-2962). Therefore, it would be advantageous for more than one reason to express RSV F in a stabilized conformation.

Recently, a stable post-fusion form of RSV F was described (McLellan, et al. 2011. J Virol 85:7788-7796; Swanson, et al. 2011. Proc. Nat'l Acad. Sci. U.S.A. 108: 9619-9624). This stable post-fusion form was generated recombinantly by truncation of the hydrophobic fusion peptide and removal of the C-terminal transmembrane domain TM and cytoplasmic tail (CT) (Ruiz-Arguello, et al. 2004. J General Virology 85:3677-3687). With the lack of the TM and CT, this post-fusion form would not be membrane-anchored and would be secreted. The post-fusion form of RSV F has been shown to be immunogenic and protective in mice (Swanson, et al. 2011. Proc. Nat'l Acad. Sci. U.S.A. 108:9619-9624).

However, it is thought that the pre-fusion form of RSV F is much more immunogenic than the post-fusion form (McLellan, et al. 2013. Science 340:1113-1117). This is based on the observation that the vast majority of the neutralizing activity in convalescent animal and human sera was conferred by antibodies that do not bind to the post-fusion F protein and presumably are specific to the pre-fusion form (McLellan, et al. 2013. Science 340:1113-1117; Magro, et al. 2012. Proc Nat'l Acad. Sci. U.S.A. 109:3089-3094). Recently, the structure of the pre-fusion form of RSV F was determined, and it became possible to stabilize this pre-fusion conformation through structure-based mutations: one of these involves the introduction of a disulfide bond (DS), and another involves amino acid substitutions in a predicted cavity in the timer structure (Cav1), and the combination of these is called DS-Cav1 (McLellan, et al. 2013. Science 342:592-598). The recombinant DS and DS-Cav1 forms of the RSV F protein were evaluated as subunit vaccines in mice and macaques and were shown to induce significantly higher levels of RSV neutralizing serum antibodies than the post-fusion form, with the DS-Cav1 form being more immunogenic than the DS form (McLellan, et al. 2013. Science 342:592-598).

Figure 11:
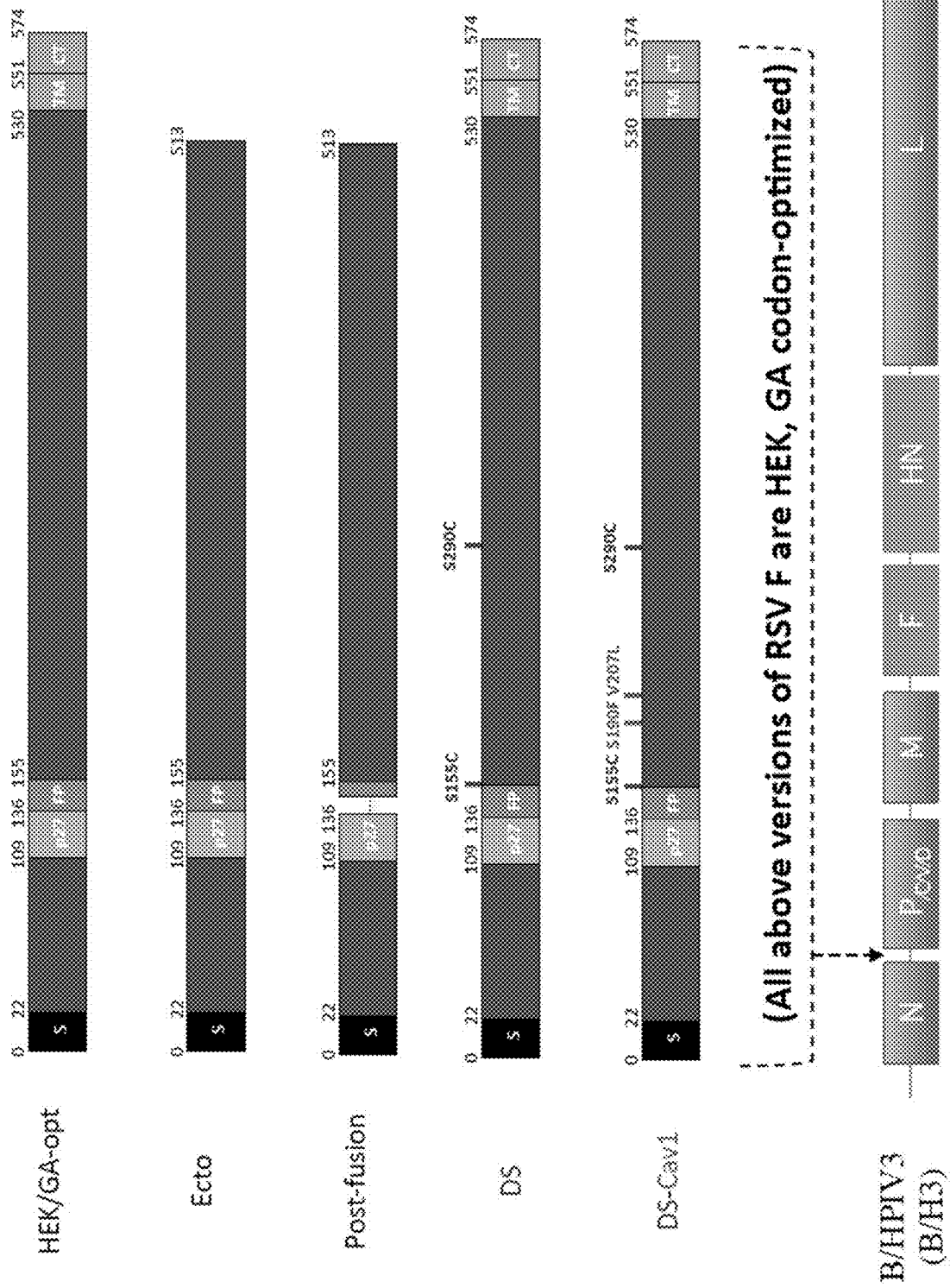
FIG. 11. Construction of rB/HPIV3 vectors expressing secreted (Ecto), post-fusion, and stabilized pre-fusion forms of the RSV F protein. Each of these modified proteins contained the HEK assignments and was expressed from a GA-optimized (for human expression) ORF. Annotations: S, signal sequence; p27, 27k protein fragment liberated by cleavage-activation; FP, fusion peptide; TM, transmembrane; CT, cytoplasmic tail. The HEK/GA-opt construct expresses full-length RSV F. The ectodomain or "ecto" form consisted of amino acids 1-513 of the RSV F protein; it lacks the CT and TM anchor and would be available for secretion. The "post-fusion" form was derived from the ectodomain (1-513aa) by the further deletion of the first 10 aa from the N-terminal end of the fusion peptide (FP; 137-146aa) (McLellan et al, 2011, J Virol 85:7788-96). "DS" and "DS-Cav1" are two versions of full-length RSV F protein stabilized in the pre-fusion form by the S155C/S290C mutations (DS) or by the DS and S190F/V207L (Cav1) mutations (McLellan et al, 2013, Science 342:931). The ORFs encoding these various forms of RSV F were inserted into the rB/HPIV3 vector at the same position and with the same vector signals as described in FIGS. 1 and 4.

The immunogenicity of post-fusion and pre-fusion forms of RSV F when expressed from the live attenuated rB/HPIV3 vector was evaluated. The post-fusion and stabilized pre-fusion forms (DS and DS-Cav1) of RSV F with HEK assignments were GA codon-optimized and inserted into the $2^{nd}$ genome position of the rB/HPIV3 vector (FIG. 11). These were compared with HEK/GA-opt as well as with a version of HEK-containing, GA-optimized F protein from which the CT and TM had been deleted, leaving the ectodomain (Ecto)(FIG. 11). These constructs were also compared to the non-HEK/non-opt construct.

GA-optimized F ORF was used in the data presented in FIG. 11 and subsequent experiments. Parallel constructs with the GS-optimized ORF have been constructed in some instances (see FIG. 35) but remain to be evaluated. Given the superior expression of the GS-optimized ORF (FIG. 5), GS-optimized versions may be more immunogenic and protective. Also, the identifiers "HEK" and "GA-opt" are sometimes omitted from construct names in in FIG. 11 and subsequent Figures and in the subsequent text for the sake of simplicity, but the presence of these features is indicated in the Figures (i.e. "All above versions of RSV F are HEK, GA-optimized", FIG. 11).

Figure 12B:
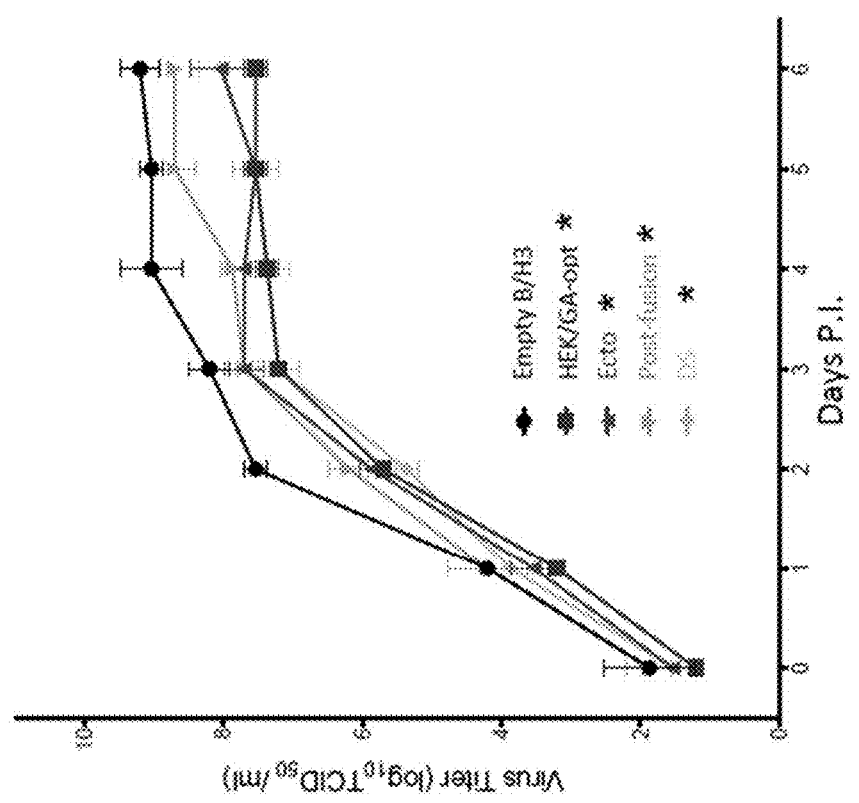
FIGS. 12A and 12B. Multi-cycle in vitro replication of rB/HPIV3 vectors expressing secreted, post-fusion, and stabilized pre-fusion forms of the RSV F protein. (A) LLC-MK2 and (B) Vero cells were infected at an MOI of 0.01 $TCID_{50}$ with empty rB/HPIV3 vector (empty B/H3) or with the indicated constructs: HEK/GA-opt; Ecto; Post-fusion; and DS (see FIG. 11 for descriptions). Viral replication during a period of 6 days at 32° C. was determined by collecting medium supernatant samples at 24-h intervals and performing virus titration by limiting dilution on LLC-MK2 cells. See FIG. 11 for diagrams of the mutant proteins. The asterisk * indicates that all of these RSV F constructs were HEK and GA-optimized.
Figure 12A:
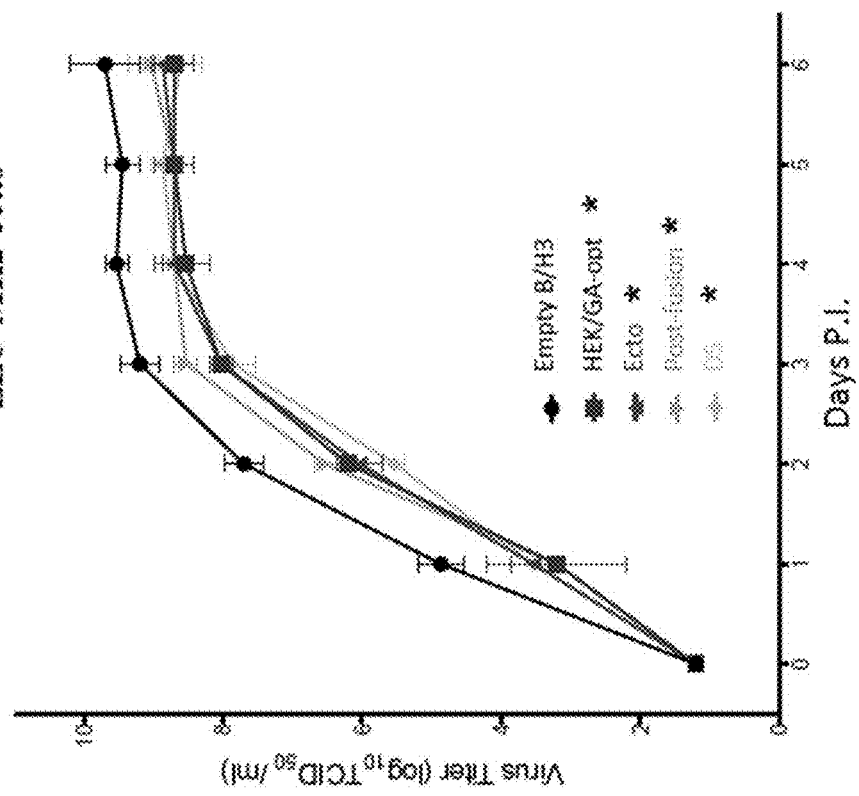

Vectors with these various forms of RSV F were rescued, and each grew to high, similar titers in vitro (FIG. 12). These were generally slightly attenuated in terms of growth kinetics and final yield compared to the empty rB/HPIV3 vector, as was noted previously for other vector constructs (see FIG. 7).

Figure 13B:
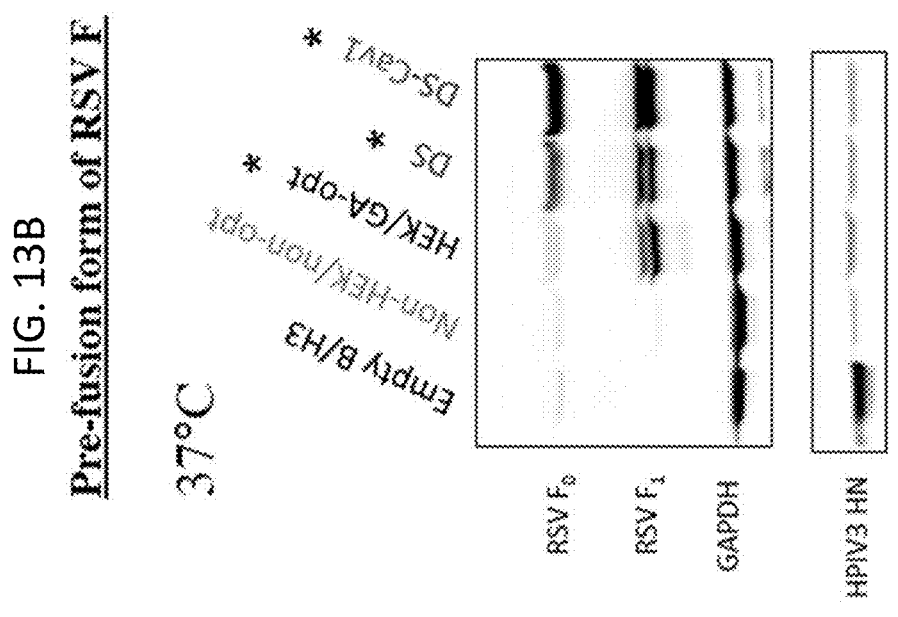
FIGS. 13A and 13B. In vitro expression of secreted (Ecto), post-fusion, and stabilized pre-fusion forms of the RSV F protein from rB/HPIV3 vectors. Vero cells were infected with the indicated rB/HPIV3 vectors at an MOI of 10 $TCID_{50}$ or with wt RSV at an MOI of 10 PFU. Infected cells were incubated at (A) 32° C. or (B) 37° C. for 48 h. (A) Medium supernatants and lysates of cells infected with the rB/HPIV3 vectors expressing post-fusion, Ecto, or HEK/GA-opt, or with wt RSV, and (B) lysates of cells infected with rB/HPIV3 vectors with non-HEK/non-opt, HEK/GA-opt, DS, or DS-Cav1 forms of RSV F were harvested and analyzed for RSV F expression by Western blot. The constructs indicated by asterisk * contained the HEK assignments and were GA-optimized.
Figure 13A:
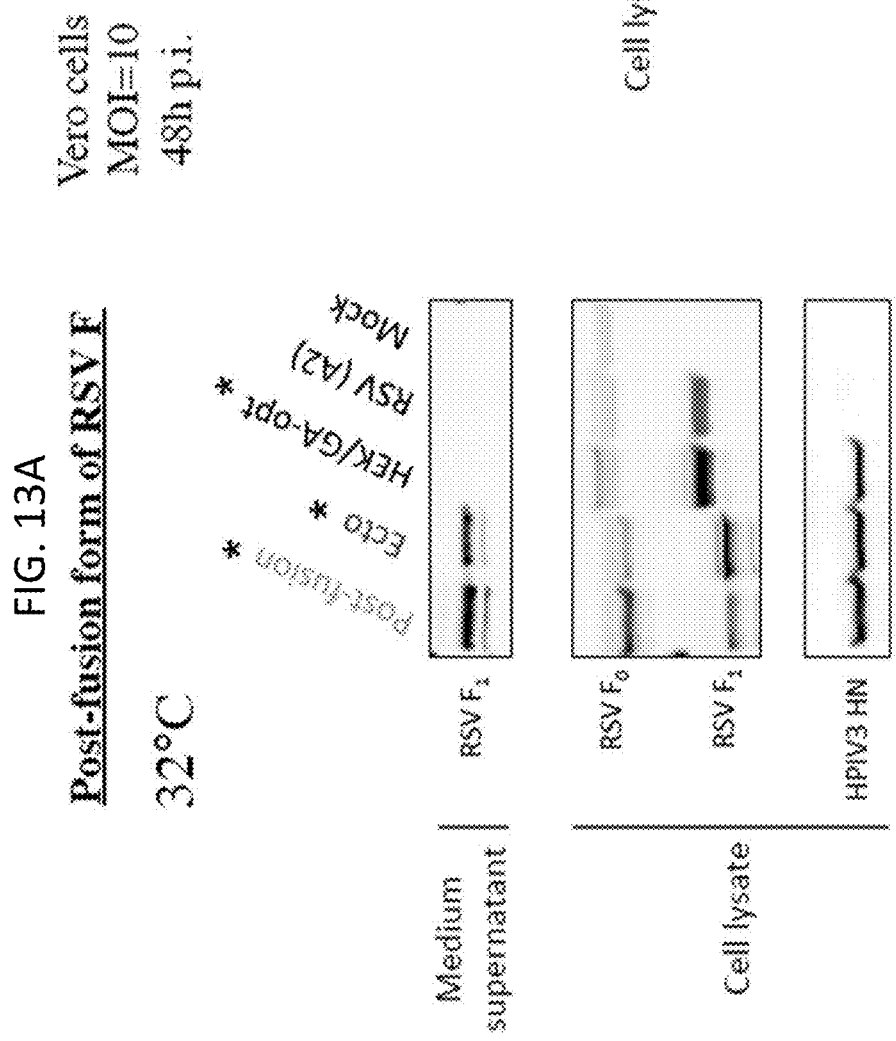

The efficiency of expression of the various forms of RSV F protein was evaluated in Vero and LLC-MK2 cells infected with the various constructs (FIGS. 13A and B). Infected cell cultures were harvested 48 h post-infection and analyzed by Western blotting. The native form of RSV F (i.e., HEK/GA-opt) was cell-associated, as expected. The post-fusion and Ecto forms were found to be secreted as well as to be cell-associated. The secretion of post-fusion F was consistently more efficient than that of the Ecto form: the latter might remain more cell-associated because it contained a higher content of hydrophobic sequence. Unexpectedly, the DS and DS-Cav1 forms of F were expressed more efficiently (FIG. 13B). Since these viruses replicated at similar kinetics and since the ORFs were similarly GA-optimzed, this increase in expression likely reflected increased protein stability of the DS and DS-Cav1 forms. Protein engineering can substantially affect the expression, processing, and stability of a glycoprotein, and often in a negative way, and so the efficient expression of DS and DS-Cav1 by this live vector was an essential property that could not have been reliably predicted.

Replication of these vectors in vivo was evaluated in hamsters (FIG. 14). In the nasal turbinates, all vectors with RSV F inserts were moderately more attenuated than the empty vector (FIG. 14A). Increased attenuation compared to the empty vector was evident by the lower values for virus shedding. It also was evident by comparison of the day 3 and day 5 titers: for the empty vector, these values were comparable, whereas for the vectors bearing RSV F, the day 5 titers were higher than the day 3 titers, indicating that these constructs took longer to achieve their maximum titers. The vector with post-fusion F replicated to a higher titer than those with other forms of F whereas the vector with pre-fusion F (DS) replicated to a lower titer, which might represent experimental variability or might represent authentic disparate effects on vector replication. In the lungs, all vectors with RSV F insert were substantially more attenuated than the empty vector (FIG. 14B). Consistent with the nasal turbinates, the vector with post-fusion F also replicated to somewhat higher titer than other vectors in the lungs whereas the vector expressing the pre-fusion (DS) version appeared to be somewhat more attenuated. The RSV control, which is a fully wt virus, replicated more efficiently than the attenuated rB/HPIV3 vectors expressing RSV F; for example, wt RSV replicated to 100- and 1000-fold higher titers in the nasal turbinates and lungs, respectively, than the vector expressing pre-fusion (DS) F. RSV-neutralizing serum antibody titers were determined by a 60% plaque reduction assay. This was performed in two ways: (i) in the presence of added complement (which is the usual practice, as already shown in FIG. 9), and (ii) in the absence of added complement (FIGS. 15 A and B, respectively). The presence of added complement provides for the most sensitive detection of virus-specific antibodies, since complement potentially confers viral-lysis capability to all antibodies that bound to the virion, and also can exert steric effects (Yoder et al 2004 J Med Virol 72:688-694). In contrast, the complement-independent neutralization assay would detect only high quality neutralizing antibodies that are able to neutralize RSV without involving the viral-lysis function or steric effects of the complement proteins. It has been suggested that "neutralization assays performed without complement may be most reflective of physiologic conditions in the respiratory tract" (Yoder et al 2004 J Med Virol 72:688-694). In the complement-containing assay (FIG. 15A), vector with post-fusion F was poorly immunogenic among the vectors even though it replicated to the highest titers in hamsters; while the vector with pre-fusion (DS) F was the most immunogenic among the tested vectors even though it was the most attenuated. In the complement-independent assay (FIG. 15B), among the vectors, only the one expressing pre-fusion (DS) F induced high titers of neutralizing antibodies. None of the other vectors with unmodified, post-fusion, or Ecto F were effective at inducing high quality neutralizing antibodies. The wt RSV control was efficient at inducing antibodies that were neutralizing in both the complement-containing and complement-independent assays. Remarkably, the vector with pre-fusion (DS) F was statistically similar to wt RSV in inducing high-quality RSV neutralizing antibodies (FIG. 15B). This is noteworthy because this attenuated vector replicated 100 to 1000 times less efficiently than non-attenuated wt RSV and the neutralizing activity conferred by wt RSV had the additional contribution from the RSV G protein. This suggested that the vector expressing pre-fusion (DS) form of RSV F was very potent and highly immunogenic in inducing very effective neutralizing antibodies.

Figure 16A:
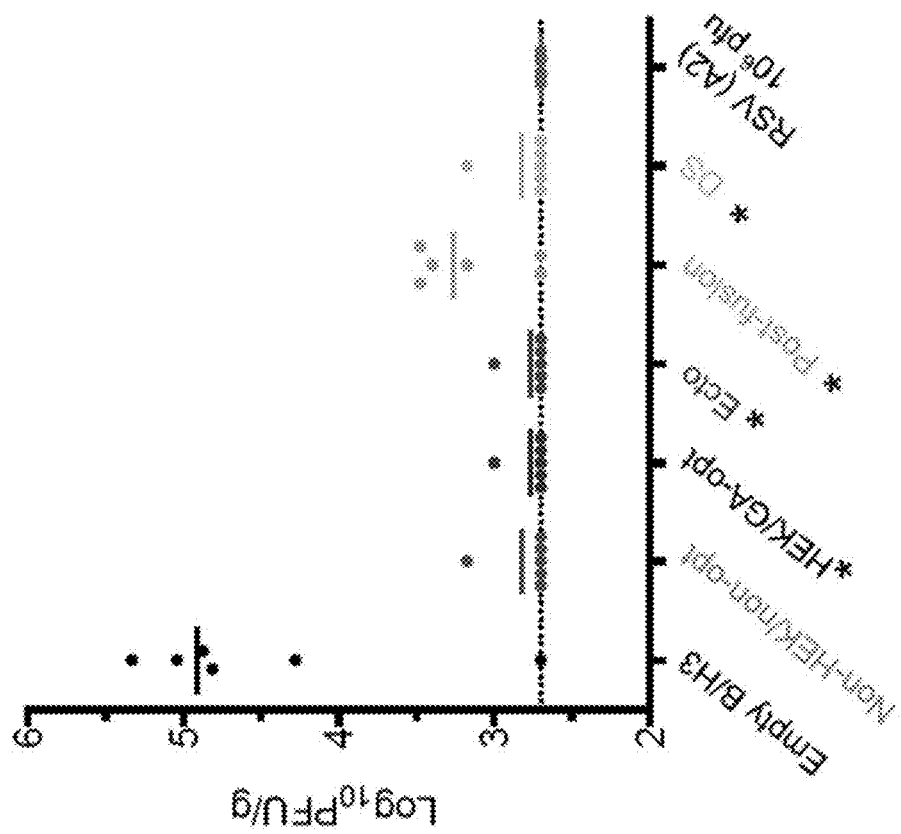
FIGS. 16A and 16B. Protection of immunized hamsters against RSV challenge. The hamsters (n=6 animals per virus) that had been immunized as shown in FIG. 15 were challenged IN on day 31 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells at 32° C. Each symbol represents an individual animal and mean viral titers of the groups are shown as horizontal lines. The detection limit of the assay was $\log_{10}$ 2.7 PFU/g of tissue, indicated as a dotted line.
Figure 16B:
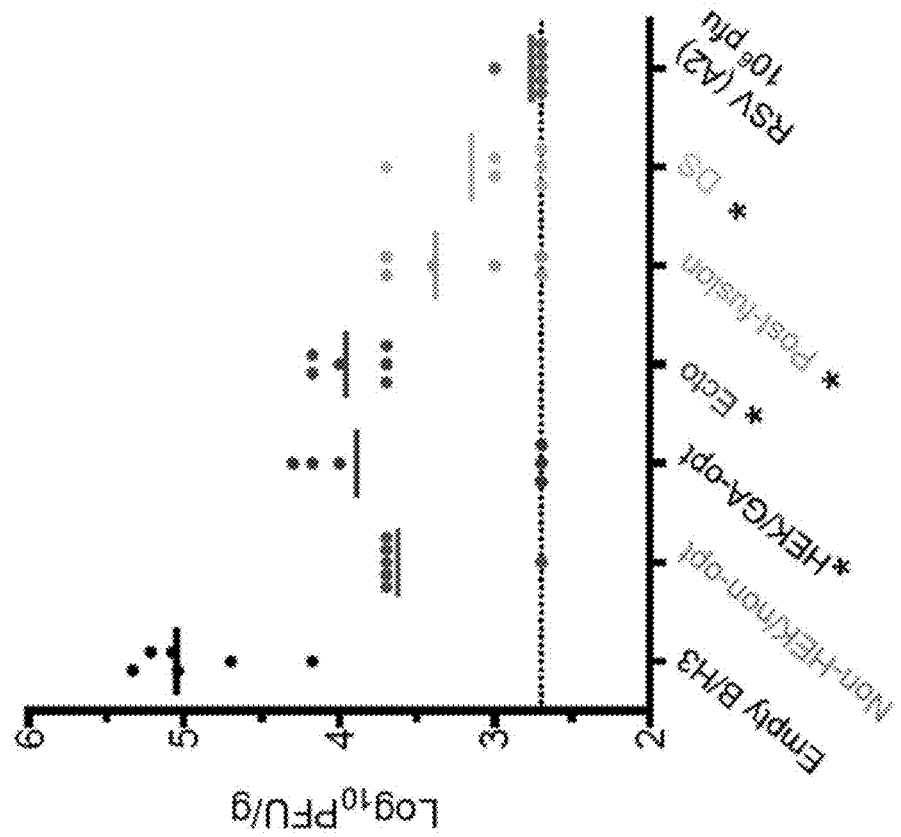

In order to assess the protective efficacy of these vectors, immunized hamsters from the experiment in FIG. 15 were challenged 30 days post-immunization by intranasal infection with $10^6$ pfu of wt RSV per animal. The animals were sacrificed 3 days post infection and nasal turbinates and lungs were harvested and processed into tissue homogenates that were assayed by plaque titration (FIG. 16). In the nasal turbinates (FIG. 16A), constructs expressing non-HEK/non-opt F, or HEK/GA-opt, or Ecto F, conferred a moderate level of protection, whereas post-fusion F and especially pre-fusion (DS) F were somewhat more protective. In the lungs (FIG. 16B), all of the vector constructs provided substantial protection against RSV challenge, except the post-fusion form, which conferred the least protection (FIG. 16B). The wt RSV control provided nearly-complete protection in the nasal turbinates and complete protection in the lungs; however, as already noted, wt RSV had the advantage of expressing both the F and G neutralization antigens, in addition to expressing all of the RSV proteins as potential antigens for cellular immunity, as well as replicating up to 1000-fold more efficiently (FIG. 14).

Figure 6:
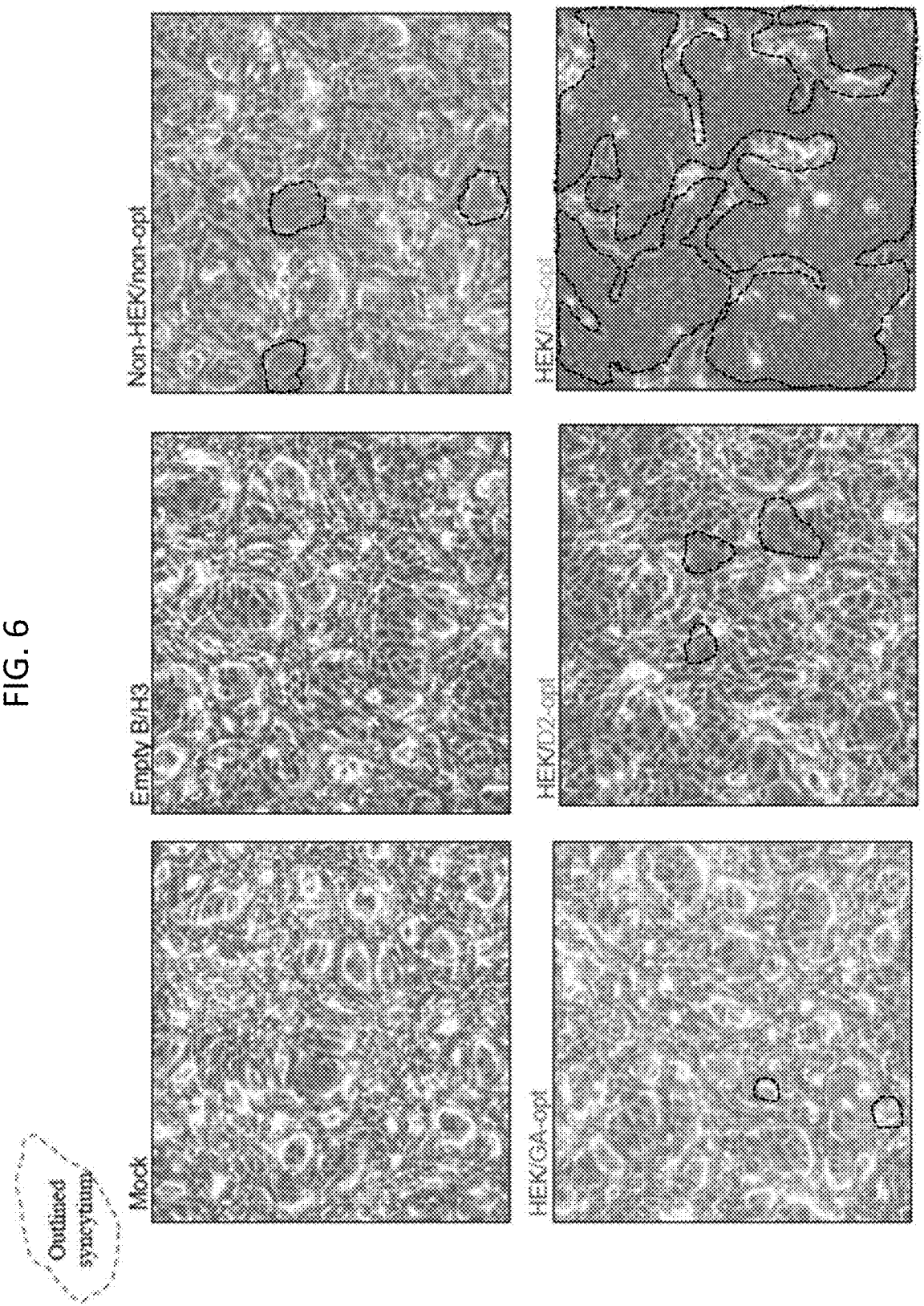
FIG. 6. Effects of HEK and codon-optimization of the F ORF on the formation of syncytia in vector-infected Vero cell monolayers. Cells were mock-infected (mock) or infected with empty rB/HPIV3 vector (empty B/H3) or with rB/HPIV3 vector expressing the RSV F ORF that was non-HEK and non-optimized (Non-HEK/non-opt) or was HEK and GA-optimized (HEK/GA-opt) or HEK and DNA2.0-optimized (HEK/D2-opt) or HEK and GS-optimized (HEK/GS-opt). Infections were performed at an MOI of 10 $TCID_{50}$ at 32° C. and images were acquired at 48 hours post-infection. Representative syncytia are indicated with dashed outline in some of the panels.

The addition of the Cav-1 mutations to the DS construct provided increased immunogenicity as a subunit vaccine (McLellan, et al. 2013. Science 342:592-598) and is anticipated to further enhance the immunogenicity of the pre-fusion RSV F expressed from a viral vector. Also, the DS and DS-Cav1 forms of RSV F remain to be evaluated for immunogenicity and protective efficacy in the context of the GS-optimization, which provided the greatest increase in expression (FIGS. 5 and 6). These further constructs have been constructed and recovered and prepared as working pools (FIG. 35).

Enhancing the immunogenicity of RSV F protein by facilitating its incorporation into the virion particle of the rB/HPIV3 vector. The incorporation of antigens into virus like particles (VLP) or adeno-associated virus particles has been shown to increase their immunogenicity (Rybniker, et al. 2012. J Virol 86:13800-13804; McGinnes, et al. 2011. J Virol 85:366-377). But whether the incorporation of a heterologous antigen into the viral envelope of an infectious virus could enhance its immunogenicity was unclear. When expressed by rB/HPIV3, the native RSV F protein (i.e., HEK/GA-opt) is incorporated into the vector particle only in trace amounts (see below).

A previous study by Zimmer et al (Zimmer et al *J Virol* 2005 79:10467-77) evaluated the expression of RSV F protein from an added gene in Sendai virus, which is a murine relative of HPIV1 and also is closely related to HPIV3. That study showed that, as with rB/HPIV3, very little RSV F protein was incorporated into the Sendai virus vector particle. The investigators replaced the CT or CT plus TM of the RSV F protein with the corresponding sequences from the Sendai F protein on the premise that this would improve the efficiency of interaction of the foreign RSV F protein with the vector particle. These modifications indeed increased incorporation of the engineered RSV F into the Sendai particle, but only if the Sendai F protein gene was deleted. That requirement to delete the vector F protein would be undesirable in the present study because deleting the vector F protein from rB/HPIV3 would have the potential of substantially altering its replicative properties, especially in vivo, and also would remove one of the HPIV3 protective antigens.

Figure 17A:
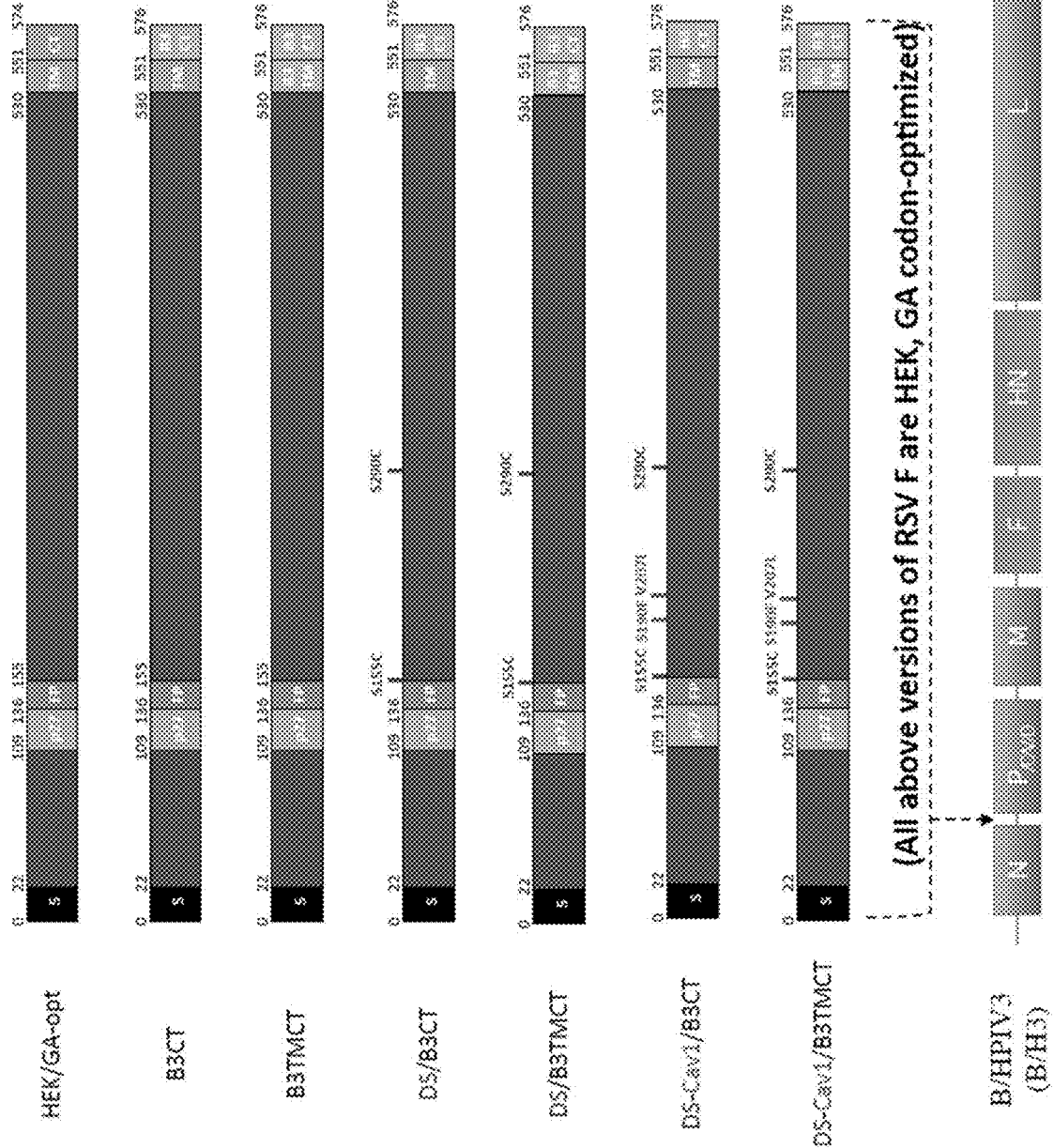

Despite this clear precedent indicating that this strategy would be not be suitable, rB/HPIV3 constructs were made in which the RSV F protein had CT or CT plus TM replaced with that of the vector (PIV) F protein (resulting in constructs called B3CT and B3TMCT, respectively, FIG. 17). The TM and CT regions from rB/HPIV3 were 21 and 26 amino acids in length respectively. The constructions in the present study were done with the version of the F protein that contained the HEK assignment and GA optimization in native F protein (HEK/GA-opt), and also with the pre-fusion DS and DS-Cav1 forms (FIG. 17). (The GA-optimized F ORF was used). All chimeric F genes were inserted into the $2^{nd}$ position of rB/HPIV3 for direct comparison with the constructs described above.

All of the viruses were readily recovered by reverse genetics. To quantify the packaging efficiency of RSV F and its modified derivatives, sucrose-purified viruses were prepared for Western blot analysis to determine the amount of RSV F in the particle (FIG. 18). Equal amounts of each sucrose-purified stock (0.5 ug protein per sample) were subjected to denaturing, reducing gel electrophoresis and analyzed by Western blotting. This showed that non-chimeric F protein (from HEK/GA-opt) had relatively poor incorporation into the rB/HPIV3 virions (FIG. 18, lane 2). However, the B3CT and B3TMCT modifications dramatically enhanced the incorporation efficiency by 19- to 20-fold (FIG. 18, lanes 3 and 4). Indeed, when compared to an equal protein mass of wt RSV virions (FIG. 18, lane 5), the amount of incorporated B3CT and B3TMCT F protein in the vector particles appeared to be equal to the amount of native F in the RSV particles. Similarly enhanced efficiency of packaging also was observed for the chimeric pre-fusion (DS) form of RSV F with B3CT or B3TMCT (FIG. 18, lanes 6 and 7). Thus, efficient packaging of RSV F B3CT and B3TMCT into the rB/HPIV3 vector did not require deletion of the vector F protein, and thus differed dramatically from the Sendai precedent.

Figure 19D:
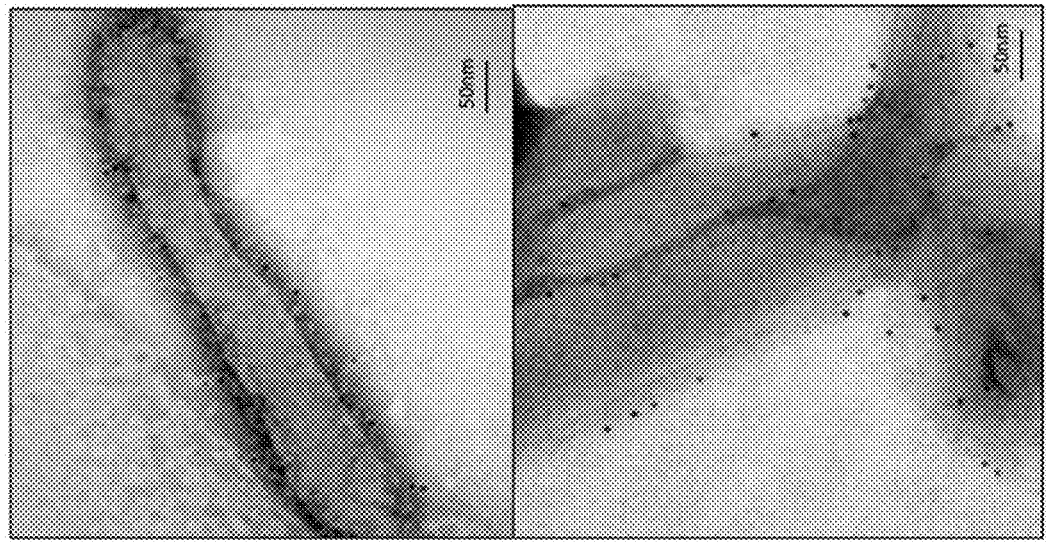
Figure 19E:
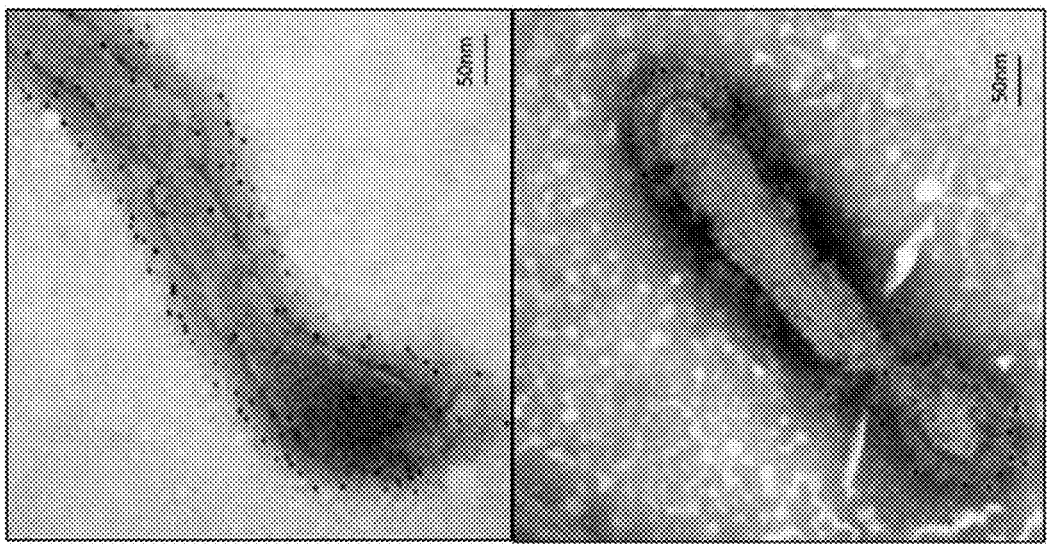
Figure 19F:
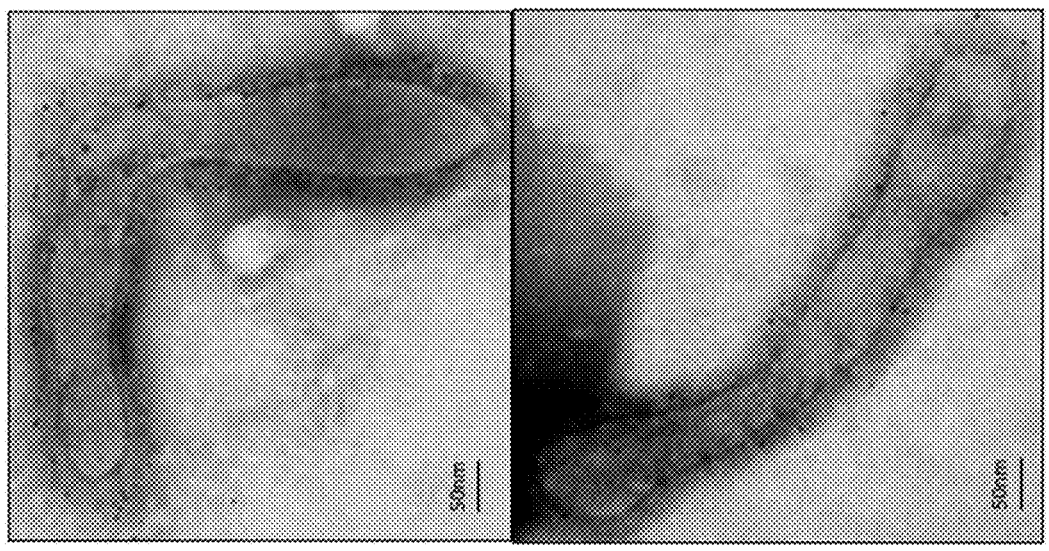

Packaging of RSV F also was examined with transmission electron microscopy (TEM) using RSV-specific antibody and immune-gold labeling (FIG. 19 A-F). RSV F spikes on the surface of RSV particles were labeled (FIG. 19A), while no labeling could be observed on the surface of the empty rB/HPIV3 vector (FIG. 19B). Very limited labeling of native RSV F was detected in the vector envelope (FIG. 19C), consistent with the results in FIG. 18 showing that very little native F was detected in purified rB/HPIV3 virions by Western blot analysis. In contrast, vectors expressing chimeric F with B3CT or B3TMCT showed enhanced labeling (FIGS. 19D and E), indicating efficient packaging of these chimeric forms into the vector envelope. Likewise, the pre-fusion (DS) RSV F with B3TMCT also was efficiently packaged into the vector particles (FIG. 19F). This confirmed that the B3CT and B3TMCT modifications resulted in dramatically increased incorporation of RSV F into the rB/HPIV3 particles. In addition, this showed that the incorporated RSV F protein was present in immunologically active surface spikes similar in appearance to those of authentic RSV particles. Furthermore, stabilized pre-fusion DS F protein also efficiently appeared at the virion surface.

The high efficiency of packaging of RSV F B3CT and B3TMCT into the vector particles raised the possibility that this would be attenuating to vector replication, since it is generally assumed that a virion surface is organized for efficiency and is limited in its capacity for surface proteins, so that changes in the composition of surface proteins could be attenuating, especially since the modified B3CT and B3TMCT RSV F proteins contained the CT or the TMCT regions of vector F protein that are thought to interact with internal viral proteins. For example, efficient incorporation of RSV F into the vector envelope might displace vector HN and F glycoproteins, or might interfere with interactions between vector components (such as between the vector F and HN glycoproteins and the internal M protein during virion assembly, or between the vector F and HN proteins that must interact to efficiently initiate virus entry). Surprisingly, it was found that all of the vectors bearing RSV F B3CT and B3TMCT replicated efficiently in vitro to high titers that were indistinguishable from those of vector with RSV F protein that was unmodified with respect to TM and CT (HEK/GA-opt, FIG. 20). Thus, there was no evidence of any reduction in replication in vitro due to the increased incorporation of RSV F into the vector particle. This is important because efficient vector replication in vitro would be essential for efficient vaccine manufacturing and clinical evaluation. It also suggests that the high efficiency of incorporation will not place a strong selective pressure for mutations that silence expression of RSV F.

Figure 21B:
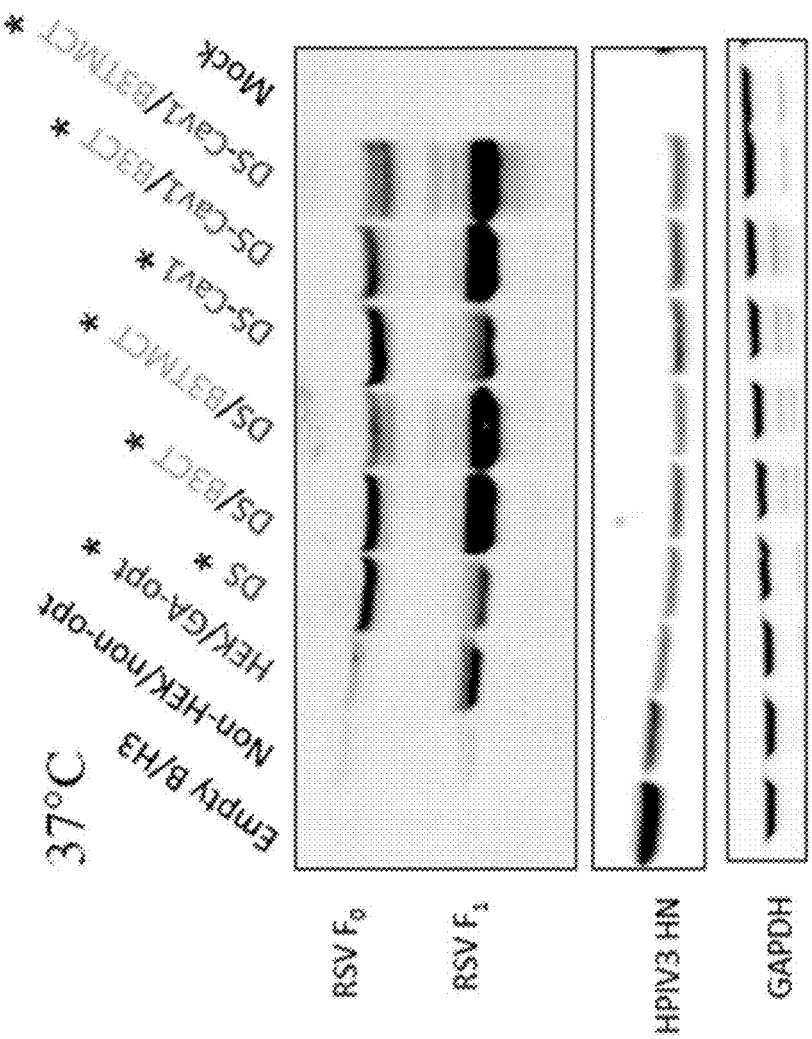
FIGS. 21A and 21B. In vitro expression of B3CT and B3TMCT versions of the RSV F protein with or without the DS or DS-Cav1 mutations that stabilize the pre-fusion form of RSV F protein. Expression of (A) B3CT and B3TMCT; and (B) DS and DS-Cav1 in combination with B3CT and B3TMCT. Vero cells were infected with the indicated rB/HPIV3 vectors at an MOI of 10 $TCID_{50}$, or with RSV at an MOI of 10 PFU. Infected cells were incubated at (A) 32° C. or (B) 37° C. for 48 h. Cell lysates were analyzed for RSV F expression by Western blot. HPIV3 HN protein was used as a control to show equivalence of vector replication; GAPDH was used as loading control. The constructs indicated by asterisk * contained the HEK assignments and were GA-codon-optimized for human expression.
Figure 21A:
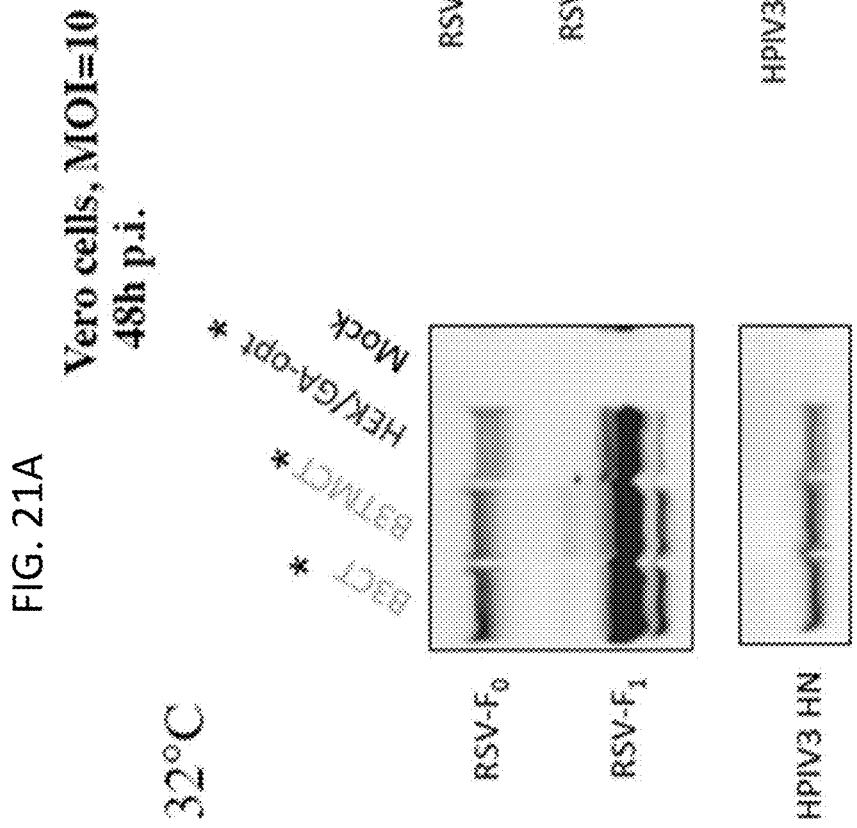

The intracellular expression of the chimeric forms of RSV F by the rB/HPIV3 vectors was examined by Western blotting. This was evaluated in Vero cells that were harvested 48 h post-infection (FIG. 21). Interestingly, the B3CT and B3TMCT versions of F were both expressed efficiently, and indeed appeared to be expressed slightly more efficiently than the native F (i.e., HEK/GA-opt) (FIG. 21A). In addition, the DS or DS-Cav1 modifications appeared to further increase expression (FIG. 21B), as noted previously (FIG. 13B). These effects appeared to be additive, since the DS or DS-Cav1 constructs with B3CT or B3TMCT were expressed even more efficiently than those with DS or DS-Cav1 alone. This increased expression would be advantageous for vaccine purposes since it provides a higher level of antigen. As noted, protein engineering and domain swapping have the potential to negatively affect the expression, processing, and stability of a glycoprotein, and so the efficient expression of these glycoproteins with DS, DS-Cav1, B3CT, and B3TMCT modifications by this live vector was a property that could not have been reliably predicted.

Figure 3B:
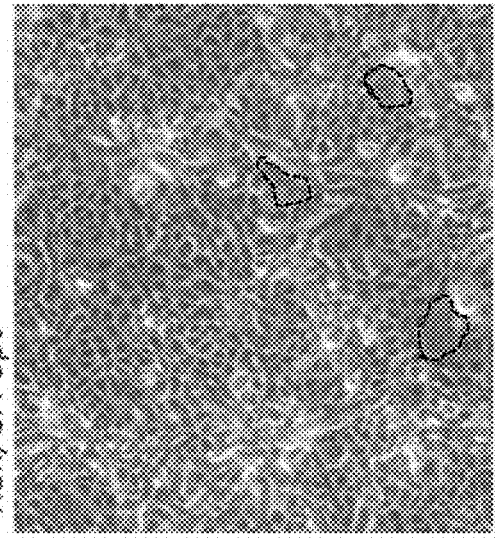
FIGS. 3A and 3B. Formation of syncytia in Vero cell monolayers infected with rB/HPIV3 vectors expressing non-HEK or HEK RSV F protein. Cells were infected with rB/HPIV3 expressing GA-codon-optimized RSV F (see FIG. 1) with (A) non-HEK or (B) HEK assignments at an MOI of 10 $TCID_{50}$ at 32° C. Images of the infected cells were acquired at 48 hours post-infection. Representative syncytia are marked with dashed outline.
Figure 3A:
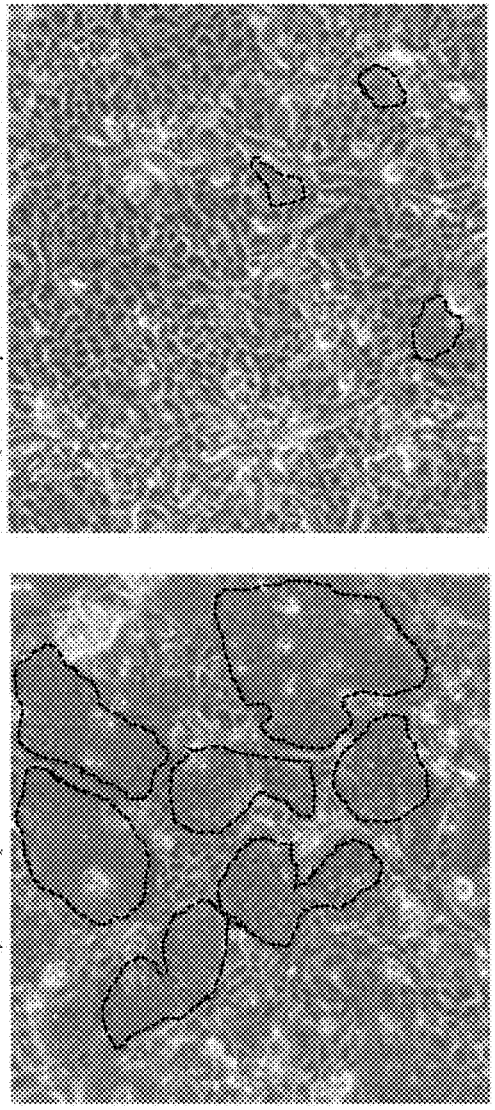
Figure 22:
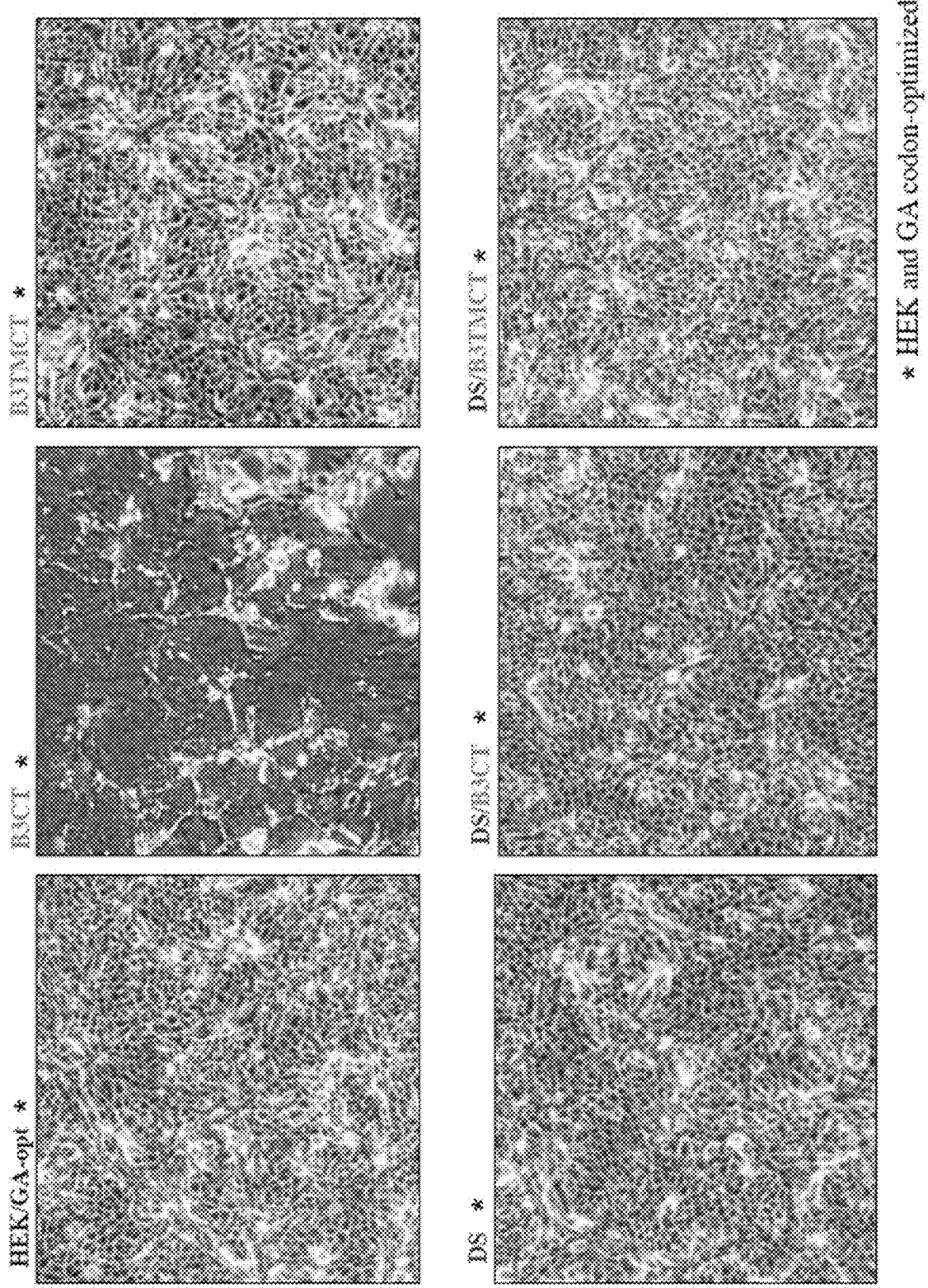
FIG. 22. Formation of syncytia in Vero cell monolayers infected with rB/HPIV3 vectors expressing the B3CT or B3TMCT version of the RSV F protein with or without the DS mutations that stabilize the pre-fusion form of RSV F protein. Vero cells were infected at an MOI of 10 $TCID_{50}$ with rB/HPIV3 vectors expressing the indicated versions of RSV F protein and incubated at 32° C. Images were acquired at 48 h post-infection. The constructs indicated by asterisk * contained the HEK assignments and were GA-codon-optimized for human expression.

The ability of these constructs to induce syncytium formation in Vero cells was assayed. Unexpectedly, RSV F bearing the B3CT substitution exhibited a hyper-fusogenic phenotype, while that bearing the B3TMCT substitution resembled native F (e.g., HEK/GA-opt) in being hypofusogenic (FIG. 22; also see FIG. 3). Upon extended incubation, B3TMCT did induce syncytium formation in the cell monolayer, indicating it was still functional and thus was conformationally intact. These findings suggested that, between the B3CT and B3TMCT constructs, the latter would be preferred since extensive syncytium formation and resulting cytopathology might reduce vector production in vitro and in vivo by prematurely destroying the cell substrate, and also might interfere with the stability of infectivity due to premature triggering. None of the pre-fusion DS forms induced syncytia in the cell monolayers. This was not completely unexpected, since a stabilized version of the pre-fusion F protein should be less able to undergo the massive conformation changes needed to mediate fusion. These findings suggest that the pre-fusion DS form of RSV F indeed was substantially stabilized in the context of vector-infected cells.

Figure 23B:
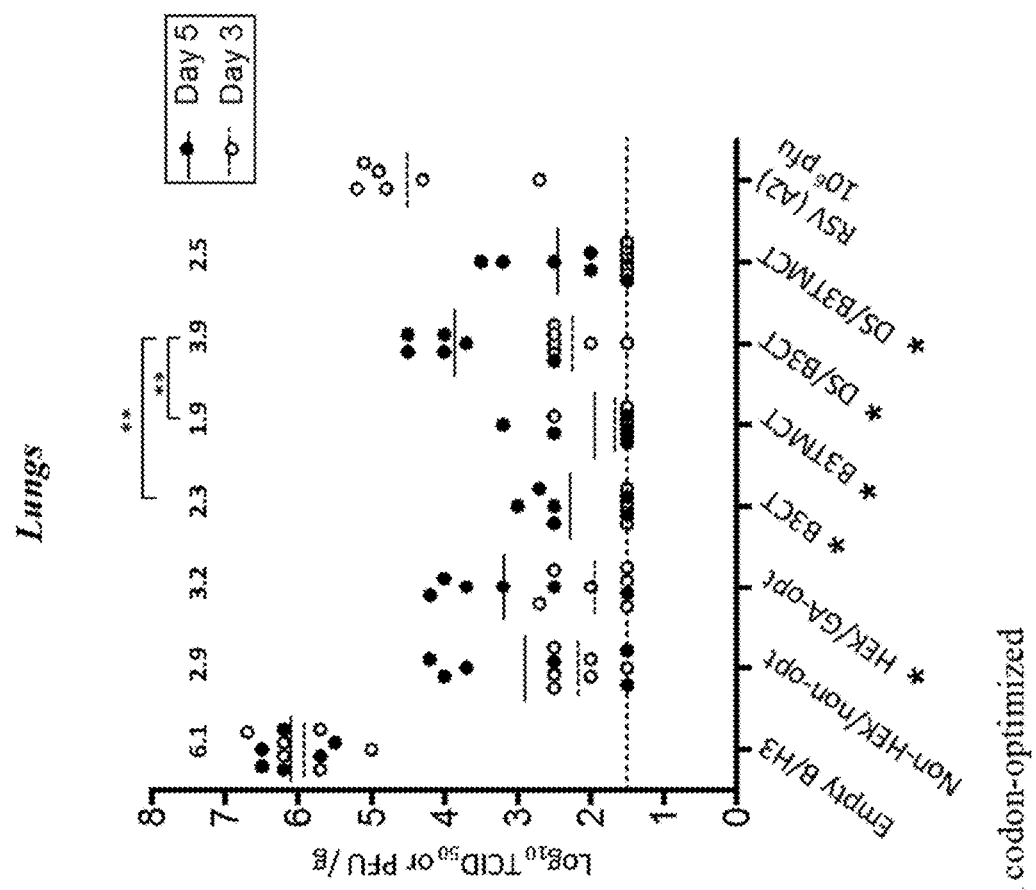
FIGS. 23A and 23B. Replication in hamsters of rB/HPIV3 vectors expressing the B3CT or B3TMCT version of the RSV F protein with or without the DS mutations that stabilize the pre-fusion form of RSV F protein. Hamsters were infected IN with 105 $TCID_{50}$ of rB/HPIV3 vectors or $10^6$ PFU of wt RSV in a 0.1 ml inoculum. Hamsters were euthanized (6 per virus per day) on day 3 and 5 post-infection and the (A) nasal turbinates and (B) lungs were removed and homogenized and viral titers were determined by limiting dilution on LLC-MK2 (rB/HPIV3 vectors) or Vero (RSV) cells at 32° C.: open and closed circles indicate titers for animals sacrificed on day 3 and 5, respectively. Each symbol represents an individual animal, and the mean titer of each group is indicated by a dashed or solid horizontal line for day 3 and 5, respectively. Mean values of day 5 titers are shown at the top. The rB/HPIV3 vectors were titrated by limiting dilution assays on LLC-MK2 cells and reported as $TCID_{50}$/g; RSV was titrated by plaque assays on Vero cells and reported as PFU/g. The limit of detection (LOD) is 1.5 $\log_{10}$ $TCID_{50}$/g of tissue, indicated with a dotted line. The statistical significance of difference among peak titers was determined by Tukey-Kramer test and indicated by asterisks (*, P≤0.05; , P≤0.01; or *, P≤0.001). The constructs indicated by asterisk * along the x-axis contained the HEK assignments and were GA-codon-optimized for human expression. Constructs containing the DS-Cav1 modification were not examined because they were not available at the time of this experiment.
Figure 23A:
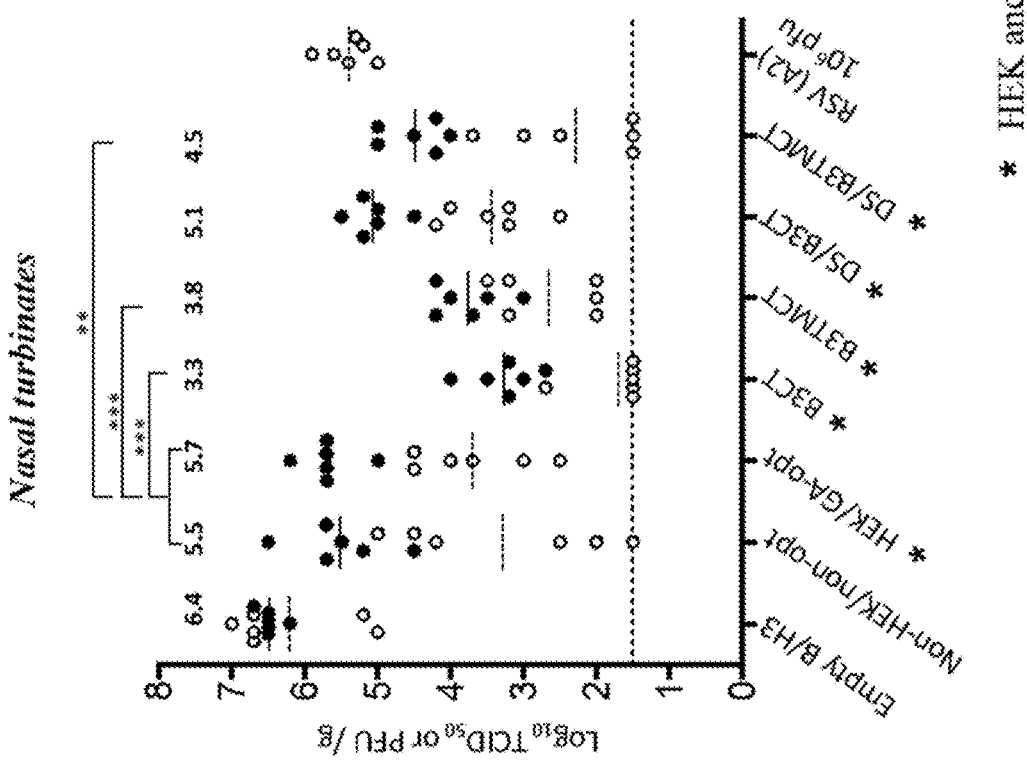

Replication of vectors expressing the B3CT and B3TMCT RSV F constructs was examined in hamsters by intranasal infection (FIG. 23). Vectors with F that was non-HEK non-optimized (non-HEK/non-opt) or F that was HEK and GA-optimized (HEK/GA-opt) were somewhat more attenuated in the nasal turbinates compared to empty rB/HPIV3 vector, illustrating the attenuating effect of the insert. Increased attenuation compared to the empty vector was evident by the lower values for virus shedding. It also was evident by comparison of the day 3 and day 5 titers: for the empty vector, these values were comparable, whereas for the vectors bearing RSV F, the day 3 titers were lower than the day 5 titers, indicating that these constructs took longer to achieve their maximum titers.) The vectors expressing B3CT, or B3TMCT, or pre-fusion F (DS) with B3CT (DS/B3CT) or B3TMCT (DS/B3TMCT) were substantially (and in most cases significantly) more attenuated in the nasal turbinates (FIG. 23A). This likely reflects an attenuating effect of the incorporation of the RSV F protein into the vector particle: this attenuating effect was not observed in vitro (FIG. 20). In the lungs, all of the vectors expressing RSV F were substantially more attenuated compared to empty vector (FIG. 23B). It is noteworthy that the hyperfusogenic B3CT construct was significantly more attenuated in both the nasal turbinates and the lungs than the parallel stabilized DS/B3CT construct, suggesting that increased fusion indeed was attenuating (i.e., interfered with replication) in vivo under these conditions. If this was evident in a semi-permissive host such as the hamster, it might be substantially more pronounced in the human host. The non-attenuated wt RSV (A2) control replicated to 100- to 1000-fold higher titer in nasal turbinates, and 1000 to 10,000-fold higher titer in lungs, compared to the attenuated vectors.

Figure 24A:
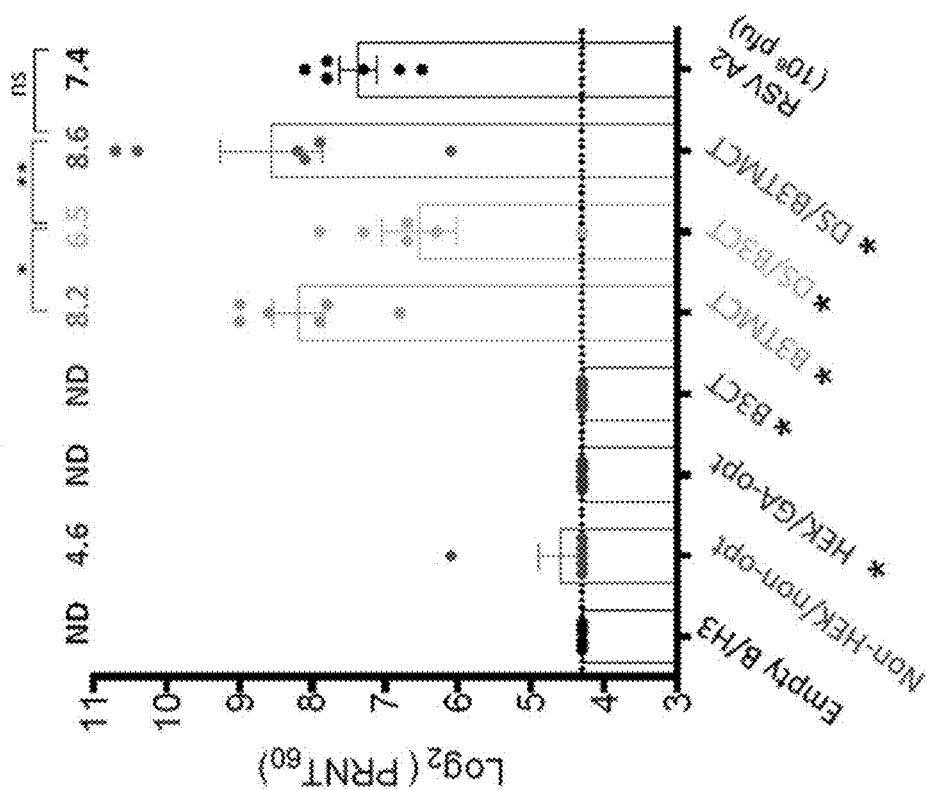
FIGS. 24A and 24B. Serum RSV-neutralizing antibody titers from hamsters infected with rB/HPIV3 vectors expressing the B3CT or B3TMCT version of the RSV F protein with or without the DS mutations that stabilize the pre-fusion form of RSV F protein. Hamsters (n=6 animals per virus) were inoculated IN with $10^5$ TCID$_{50}$ of the indicated rB/HPIV3 vectors or $10^6$ PFU of wt RSV in a 0.1 ml inoculum. Serum samples were collected at 28 days post-immunization, and antibody titers were determined by a 60% plaque reduction neutralization test (PRNT$_{60}$) with (A) or without (B) added guinea pig complement. The height of each bar represents the mean titer shown along with the SEM. The values of mean titers are shown above the bars. The detection limit for the neutralization assay is indicated with a dotted line. The statistical significance of difference in the mean titers was determined by Tukey-Kramer test and indicated by asterisks (*, P≤0.05; **, P≤0.01; ns, P≥0.05). ND, neutralization titer was below the detection limit. The constructs indicated by asterisk * along the x-axis contained the HEK assignments and were GA-codon-optimized for human expression.

The immunogenicity of the vectors was determined by analyzing hamster sera for RSV-neutralizing antibodies by a 60% plaque reduction assay in the presence or absence of added complement (FIGS. 24 A and B, respectively). All of the constructs expressing F protein with B3CT or B3TMCT modifications induced substantial titers of RSV-neutralizing serum antibodies detected in the presence of complement (FIG. 24A). The constructs that combined B3CT or B3TMCT with the prefusion DS mutations gave somewhat higher levels of neutralizing antibodies compared to the parallel constructs without the DS mutations. When assayed in the presence of complement (FIG. 24A), all of the attenuated vector constructs induced lower titers of RSV-neutralizing antibodies compared to non-attenuated wt RSV, although as noted wt RSV has the advantage of the further contribution of the G neutralization antigen and replicated 100- to 10,000-fold more efficiently than the attenuated vectors.

Figure 24B:
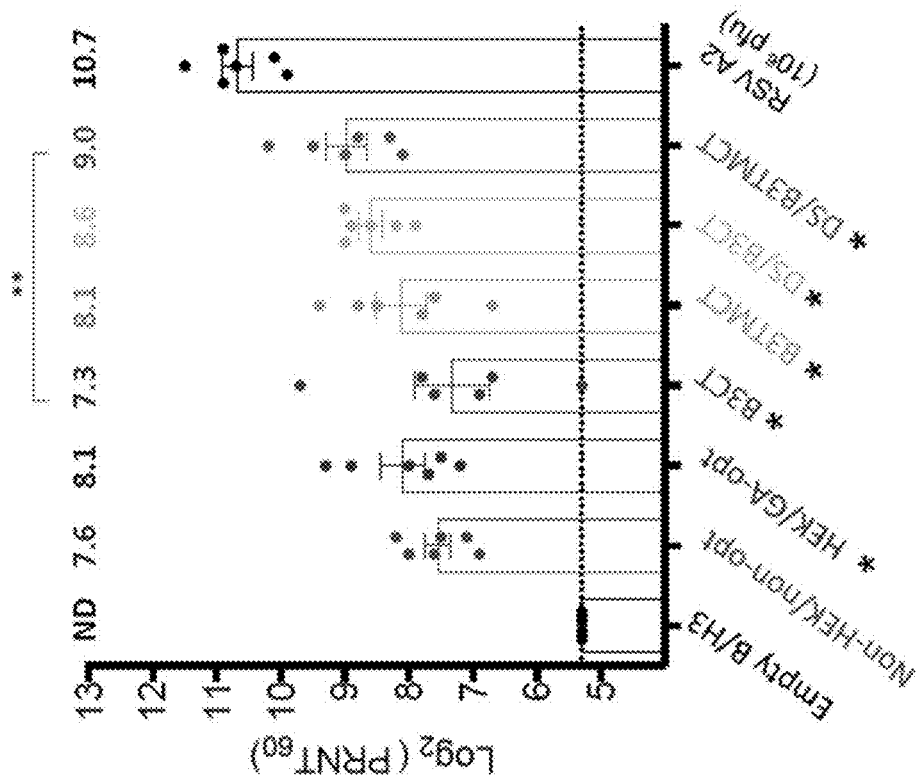

In the version of the assay performed without complement (FIG. 24B) three vectors efficiently induced RSV-neutralizing antibodies detected under these conditions, namely the one expressing B3TMCT F and the ones expressing prefusion DS F containing the B3CT and B3TMCT modifications. The B3TMCT and DS/B3TMCT constructs induced somewhat more high-quality RSV-neutralizing serum antibodies than wt RSV, although this difference was not significant. Nonetheless, this finding was remarkable given that the vectors expressed only one of the two RSV neutralizing antigens and replicated 10- to 10,000-fold less efficiently compared to wt RSV (FIG. 22). In contrast to the B3TMCT vectors, B3CT did not induce a significant antibody response when assayed in the absence of complement (FIG. 24B), even though it was incorporated in the virions at a similar efficiency as the B3TMCT (FIG. 18). Similarly, DS/B3CT also was less immunogenic than B3TMCT, DS (FIG. 24B). This indicated that B3TMCT may be a structurally or antigenically superior form of RSV F compared to B3CT, or it may be that the hyperfusogenic phenotype of B3CT reduced its expression and immunogenicity in vivo. These studies clearly showed that B3TMCT greatly enhanced the immunogenicity of RSV F.

Figure 25A:
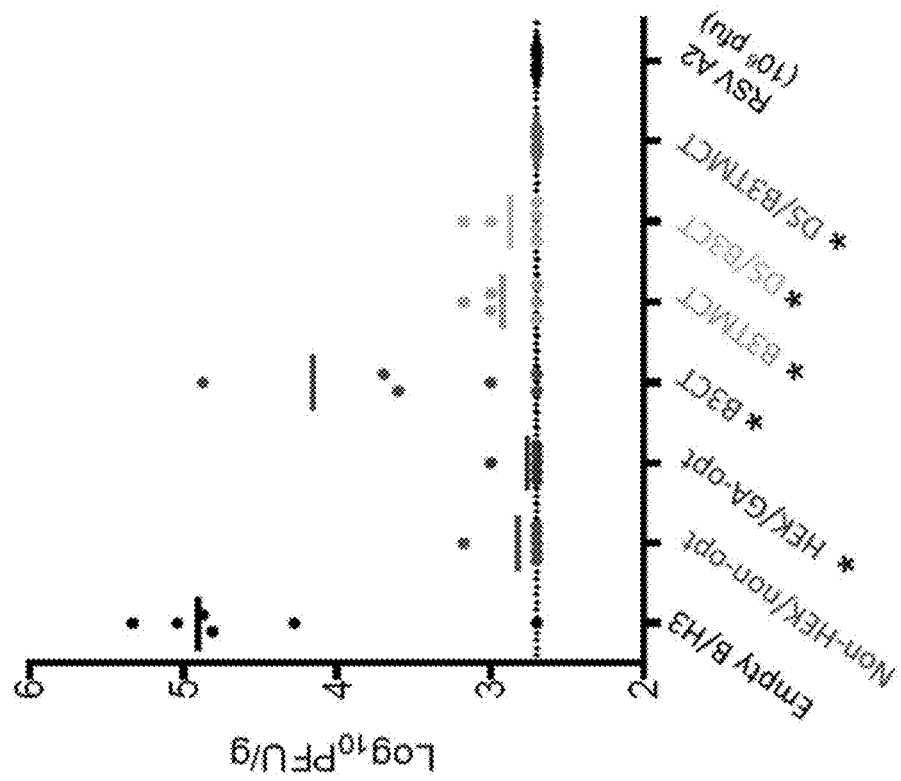
FIGS. 25A and 25B. Protection of immunized hamsters against RSV challenge. The hamsters (n=6 animals per virus) that had been immunized as shown in FIG. 24 were challenged IN on day 31 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells at 32° C. Each symbol represents an individual animal and mean viral titers of the groups are shown as horizontal lines. The detection limit of the assay was $\log_{10}2.7$ PFU/g of tissue, indicated as a dotted line.
Figure 25B:
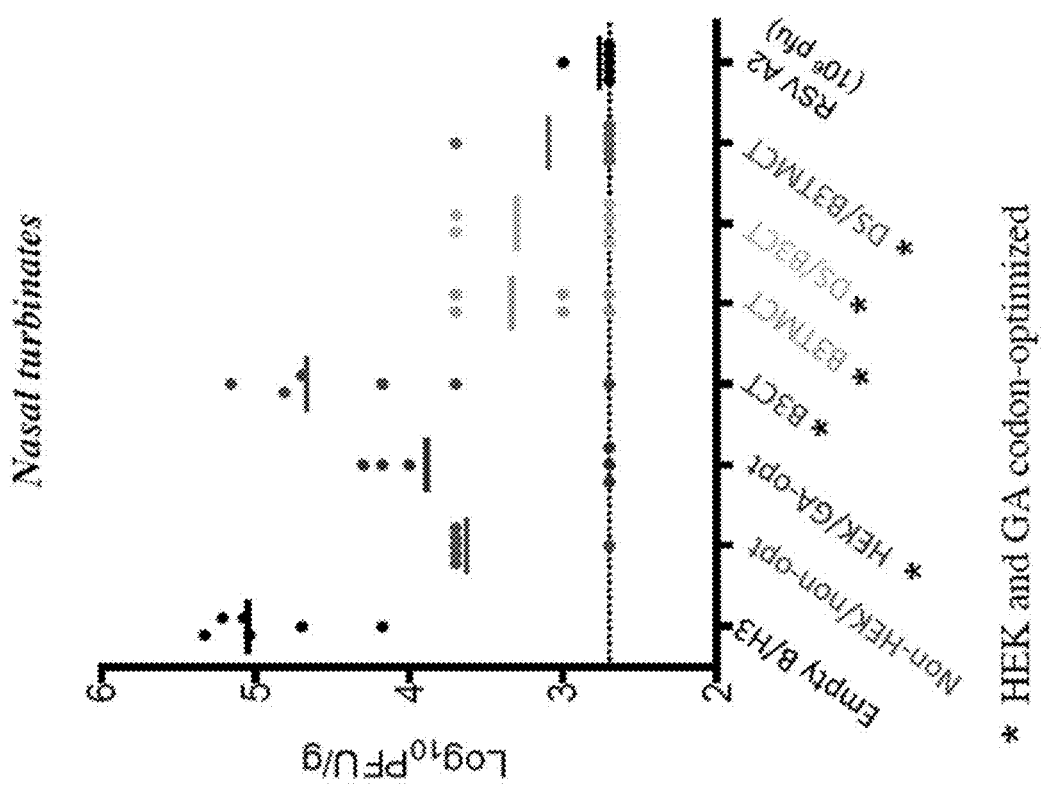

To evaluate the protective efficacy of the vectors, immunized hamsters were challenged intranasally with $10^6$ pfu of wt RSV at 30 days post-immunization (FIG. 25). In agreement with the immunogenicity data, B3CT was less protective in both the nasal turbinates and the lungs. B3TMCT was more protective against RSV challenge, and DS/B3TMCT was the most protective of the vector constructs (although the difference was small), with only one immunized hamster showing detectable RSV replication in the nasal turbinates and all being completely protected in the lungs, providing protection similar to that conferred by the non-attenuated wt RSV control (FIG. 24). The comparable level of protective efficacy between the DS/B3TMCT construct and wt RSV was particularly noteworthy because the latter replicated to 2-4 log titers higher than DS/B3TMCT, expressed both the F and G RSV neutralization antigens, and expressed all of the RSV proteins as potential antigens for cellular immunity. This indicates that rB/HPIV3 vector with packaged prefusion form of RSV F (DS/B3TMCT) is very highly immunogenic and protective.

Stability of the rB/HPIV3-RSV-F constructs in hamsters. Give the experience with the genetic instability of MEDI-534 in clinical studies (Yang et al 2013 Vaccine 31:2822-2827), a key issue was whether expression of the RSV F insert remained stable during replication in vivo. The genetic stability of all of the 12 different rB/HPIV3-RSV-F constructs that had been analyzed in hamsters in FIGS. 8, 14, and 23 was assayed. Tissue homogenates of the lungs and nasal turbinates that were collected on days 3 and 5 following infection were analyzed by a fluorescence double-staining plaque assay that can simultaneously detect the expression of the RSV F protein and the vector proteins in the viral plaques (FIG. 26). In this assay, RSV F expression was detected with an F-specific antibody visualized by red fluorescence, and expression of PIV3 antigen was detected with an HPIV3-specific antiserum (from rabbits that were hyperimmunized with purified HPIV3 virions) visualized by green fluorescence. When merged, rB/HPIV3 plaques that maintained expression of RSV F appeared yellow while those that have lost expression of the RSV F insert remained green (FIG. 26). This analysis showed that the RSV F insert generally was stable during replication in hamsters (FIG. 26). For majority of the samples, all of recovered viruses in higher dilution wells (in which individual plaques could be discerned) appeared as yellow plaques and thus expressed RSV F protein. In a subset of other specimens there was sporadic loss of expression of RSV F in a subset of plaques, resulting in a small percentage of green plaques (usually <12%). In addition, there was no evidence that loss of expression of RSV F increased progressively with time; in other words, there was not a higher frequency of loss of expression on specimens from day 5 compared to day 3. In a single case, there was a high level of loss of expression in a single nasal turbinate specimen from day 3 (14% remaining expression, hamster #511 in group #9), whereas the lung specimen from the same animal had 100% expression. In general, this indicated that expression of the RSV F insert was substantially stable for all of the tested constructs. It also showed that none of the constructs appeared to be disproportionately unstable. Thus, high levels of expression of RSV F and syncytium formation, or expression of stabilized forms of RSV, or high levels of incorporation of modified F into the vector particles that was attenuating for the rB/HPIV3 vector, did not appear to favor the emergence of mutants in which expression of RSV F was silenced.

The 12 rB/HPIV3 constructs described and evaluated in FIGS. 1-26 were further evaluated for possible temperature sensitivity phenotype. For each vector, equal aliquots were plaqued under methylcellulose at 32, 35, 36, 37, 38, 39, and 40° C. (FIG. 27). A reduction in plaque formation of ≥100-fold was indicative of temperature sensitivity at that temperature. The empty rB/HPIV3 vector was temperature sensitive (ts) at 40° C. (FIG. 27), whereas neither HPIV3 nor BPIV3 is ts at this temperature. This indicates that chimerization (i.e., the replacement of the HPIV3 F and HN genes into the BPIV3 backbone) conferred a slight ts phenotype. Every vector that in addition contained the RSV F insert was ts at 37-38° C., indicating that the presence of the additional gene augmented the ts phenotype. The constructs that were the most ts were B3CT, B3TMCT, and DS/B3CT (#7, 8, 12 in FIG. 27). This implied that packaging of RSV F into the virus particle augmented this phenotype. One possible explanation would be that the presence of RSV F in the vector made the particle somewhat unstable and susceptible to elevated temperature. The remaining construct with efficient packaging of RSV F, namely DS/B3TMCT (construct 13 in FIG. 27), was slightly less ts, suggesting that the hypo-fusogenic phenotypes associated with DS and B3TMCT ameliorated the instability to some extent. Taken together, these findings provide a means to confer attenuation or to mitigate attenuation, depending on the construct design, and in any event provide information important in designing vaccine viruses.

Evaluation of selected rB/HPIV3-RSV-F constructs in rhesus macaques. To further investigate the effects of the "DS" and "B3TMCT" mutations on vector replication, immunogenicity, and protective efficacy, two candidates (HEK/GA-opt/DS and HEK/GA-opt/DS/B3TMCT) were evaluated for replication and immunogenicity in rhesus macaques (FIG. 28). The B/HPIV3 vector with unmodified RSV F (non-HEK/non-opt) was included as a baseline control for comparison. A limited number of constructs were evaluated given the expense and ethical consideration of studies in primates. Monkeys were immunized with a total of $2\times10^6$ TCID$_{50}$ of each rBHPIV3 vector by the combined IN and intratracheal (IT) routes. Nasopharyngeal swabs and tracheal lavage samples were collected on indicated days (FIG. 29) to monitor virus shedding as a measure of replication. Sera were collected on day 0, 14, 21, and 28 days. All animals were challenged on day 28 with wt RSV IN and IT, with $10^6$ pfu per site, and serum samples were collected on days 35 and 56.

The non-HEK/non-opt and HEK/GA-opt/DS viruses replicated to peak titers of approximately 105 and 103 TCID$_{50}$ units per ml in the upper and lower respiratory tracts (FIGS. 29A and B, respectively). In contrast, the HEK/GA-opt/DS/B3TMCT construct was dramatically more attenuated in both the upper and lower respiratory tracts of rhesus monkeys (FIGS. 29 A and B). This indicated that B3TMCT conferred substantial attenuation to the rB/HPIV3 construct, whereas the DS mutations did not appear to confer significant attenuation. Thus, the mild tendency of the B3TMCT modification to confer attenuation in hamsters (FIG. 23) was substantially greater in non-human primates.

Figure 30:
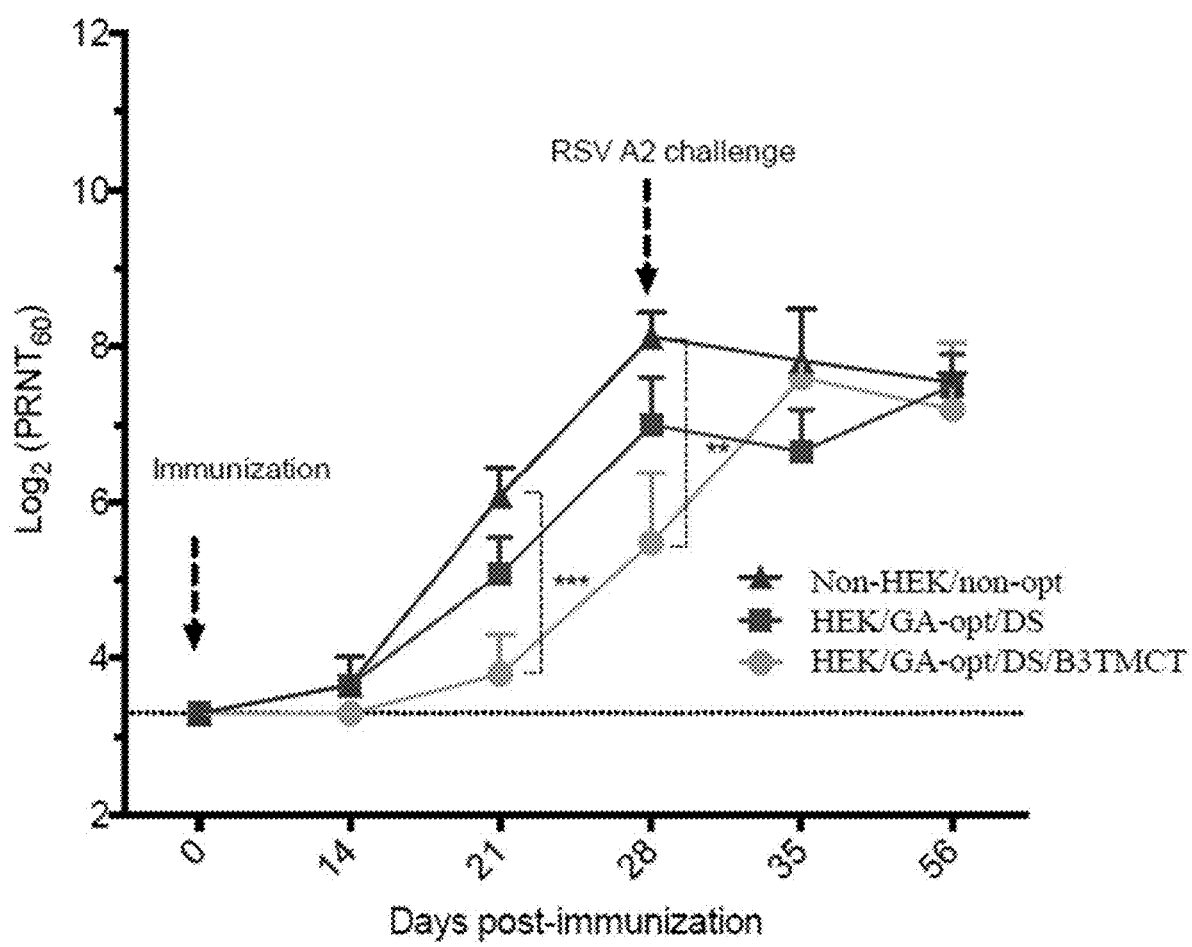
FIG. 30. Serum HPIV3-neutralizing antibody titers induced by rB/HPIV3 vectors. Monkey sera were collected at 0, 14, 21, 28, 35 and 56 days post-immunization and HPIV3-neutralizing antibody titers were determined by a 60% plaque reduction neutralization test (PRNT$_{60}$) in the presence of added guinea pig complement. The detection limit for the neutralization assay is indicated with a dotted line. The day of RSV challenge is indicated.

As noted, sera were collected on days 0, 14, 21, 28, 35, and 56. Serum antibodies specific to the rB/HPIV3 vector were analyzed by a 60% plaque reduction assay against HPIV3 (FIG. 30). This showed that the vector-specific neutralizing serum antibody response to the highly attenuated HEK/GA-opt/DS/B3TMCT construct was slower and somewhat reduced compared to the non-HEK/non-opt and HEK/GA-opt/DS constructs. This is consistent with the expectation that reduced antigenic load would reduce immunogenicity. After 28 days the titers became more similar and, as expected, there was no boost in vector-specific immunity from the RSV challenge on day 28 (since RSV did not contain any vector antigens).

Figure 32:
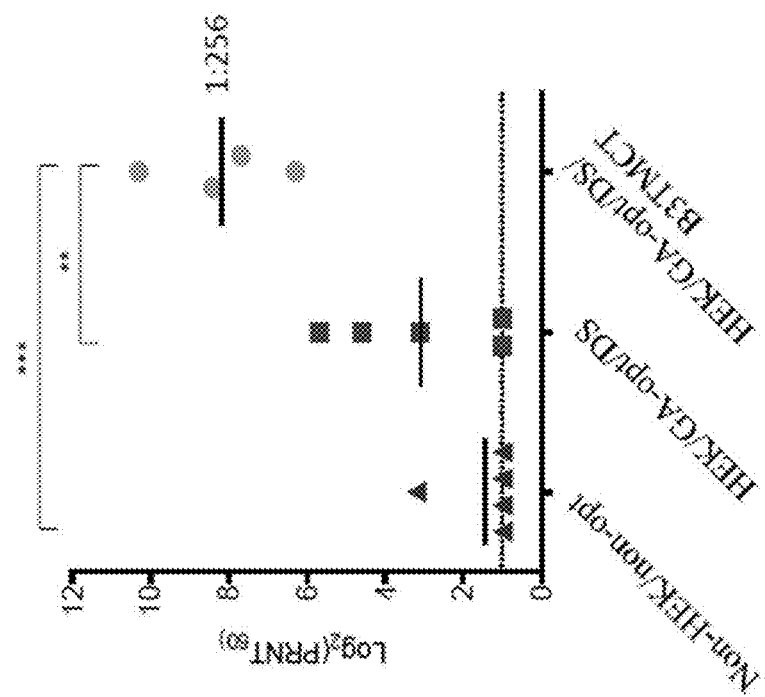
FIGS. 31 and 32. Serum RSV-neutralizing antibody titers induced by rB/HPIV3 vectors. Monkey sera were collected at 0, 14, 21, 28, 35 and 56 days post-immunization.
Figure 31:
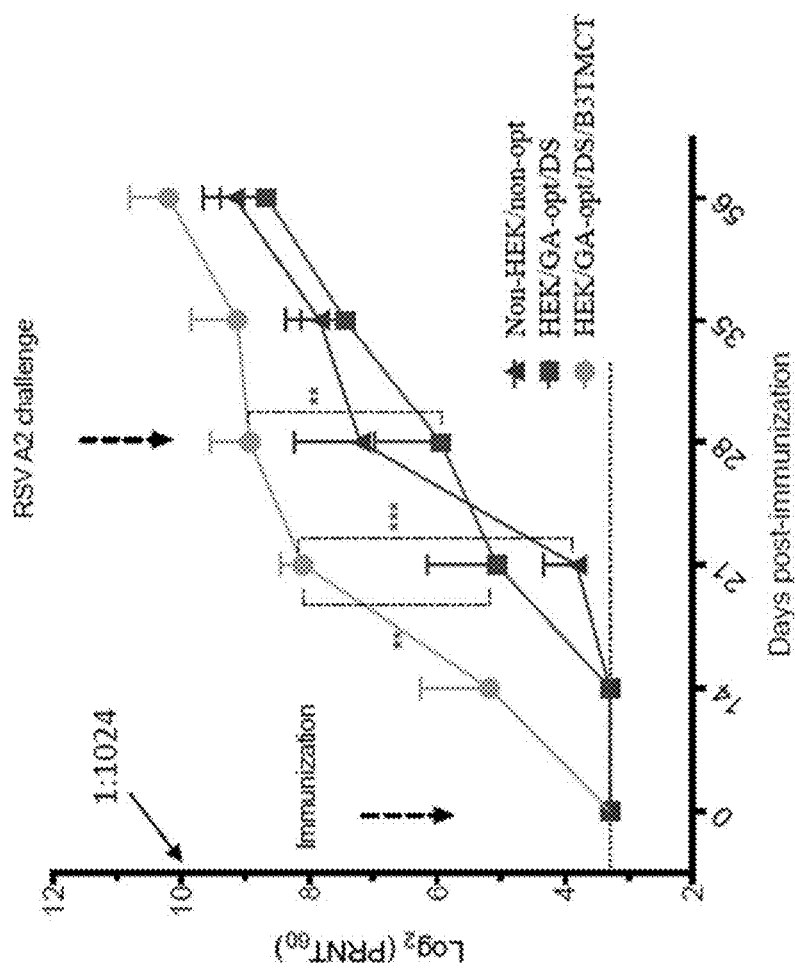
Figure 34:
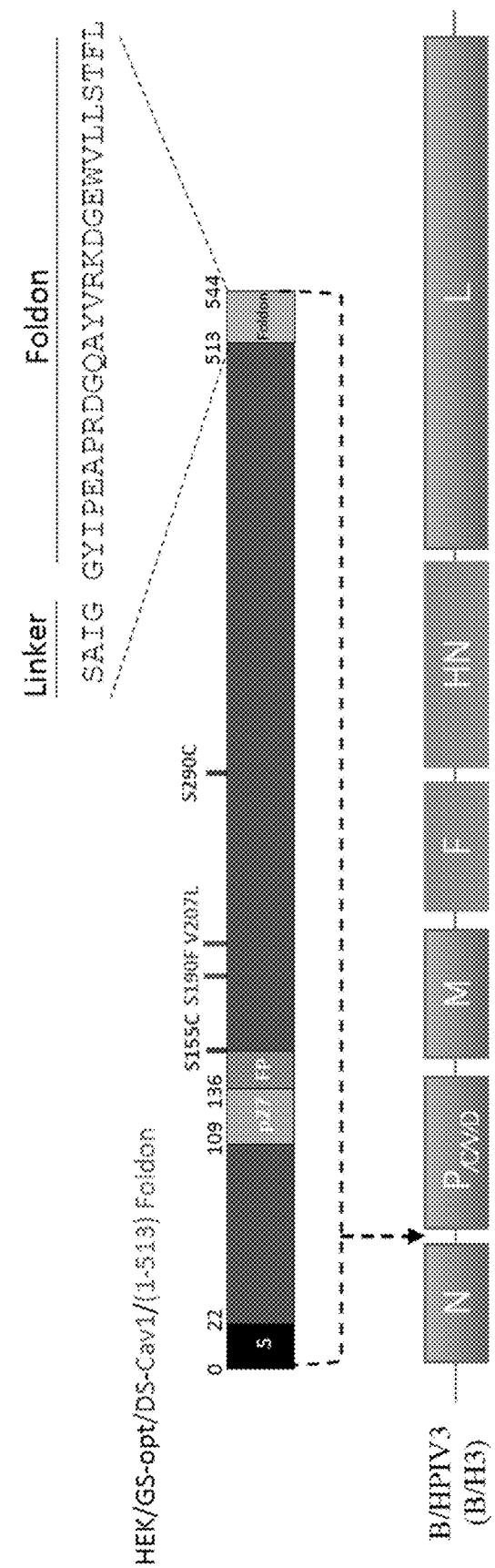
FIG. 34. Construction of an rB/HPIV3 vector expressing a secreted version of HEK/GS-opt/DS-Cav1 RSV F protein that contains a C-terminal "foldon" sequence. RSV F protein containing the HEK assignments and expressed from a GS-codon-optimized (for human expression) ORF with DS-Cav1 mutations was engineered to contain the N-terminal 513 amino acids of the F protein (i.e., lacking the TM and CT domains), fused to the indicated 4-amino acid linker and the indicated 27-amino acid foldon sequence from T4 phage (SEQ ID NO: 132, see Efimov et al. 1994, J Mol Biol 242:470-486; Miroshnikov et al 1998 Protein Eng. 11:329-332). The ORF was inserted into the rB/HPIV3 vector at the same position and with the same vector signals as described in FIGS. 1, 4, 11, and 17.

The RSV-specific neutralizing serum antibody responses were quantified by a plaque reduction assay performed in the presence and absence of complement (FIGS. 31 and 32, respectively). The assay in the presence of complement showed that RSV-neutralizing serum antibodies were induced more rapidly and to significantly higher titer in response to the HEK/GA-opt/DS/B3TMCT construct than for the other two constructs (FIG. 31). This greater induction of RSV-specific neutralizing serum antibodies was noteworthy and surprising since this construct was much more highly restricted in replication (FIG. 29). When assayed previously in hamsters (FIG. 24), this construct had given an apparent increase compared to HEK/GA-opt/DS that was not statistically significant: the greater increase observed in non-human primates is consistent with the idea that the hamster model is a less sensitive model for these human and bovine/human viruses. For example, The greater induction of RSV-neutralizing serum antibodies in the rhesus macaques in response to the HEK/GA-opt/DS/B3TMCT construct also was observed when the assay was performed in the absence of complement to measure high-quality antibodies on day 28: indeed, the difference in titer for this construct versus the other two constructs was substantially greater than what was observed in the presence of complement (FIG. 32). Taken together, these results indicated that the DS mutation did not substantially increase the quantity of RSV-neutralizing serum antibodies (FIG. 31) but did increase the quality (FIG. 32), while the further addition of the B3TMCT modification dramatically increased both the quantity (FIG. 31) and quality (FIG. 32) of the RSV-neutralizing serum antibodies.

The RSV challenge virus administered on day 28 was completely restricted by all vectors and no infectious challenge RSV could be recovered from the nasopharyngeal swabs and tracheal lavage samples from any animal, and therefore this experiment did not provide further information on the comparative properties of these viruses. Complete protection against short-term RSV challenge in experimental animals is sometimes observed because the semi-permissive nature of RSV replication in these models facilitates restriction of replication. The RSV-specific antibody responses continued to increase following day 28, but it is not clear whether this response was due to the primary infection or the challenge.

The fluorescence double-staining plaque assay was used to analyze virus recovered from the rhesus macaques on days 4, 5, and 6, which was the time of peak shedding, for the expression of RSV F protein. A summary of the data is shown in FIG. 33. This analysis showed that the RSV F inserts generally were stable during replication in monkeys. The results were very similar to those shown in FIG. 26 for the hamster study. For majority of the samples from the rhesus monkeys, nearly all of recovered viruses appeared as yellow plaques and thus expressed RSV F protein. There was sporadic loss of RSV F expression in some specimens, typically <10% of recovered plaques in a given specimen. There was no evidence that loss of expression increased significantly with time, and sometimes evidence of loss of expression was observed at an early time point but not at a later time point from the same animal. There also was no evidence that a particular construct was associated with disproportionately greater loss of RSV F expression versus another construct. For example, even though the expression of HEK/GA-opt/B3TMCT was highly attenuating for the rB/HPIV3 vector, there was no evidence of increased selection of virus in which expression of RSV F was lost.

A rB/HPIV3 vector expressing the ectodomain of RSV F (amino acids 1-513, lacking the TM and CT domains) with GenScript (GS) optimization, and containing the HEK assignments and the DS-Cav1 modifications was also generated. The ectodomain was fused to a 4-amino acid linked followed by a trimer-stabilizing foldon sequence at its C-terminus, i.e. construct #19 (HEK/GS-opt/DS-Cav1/[1-513] Foldon). This form of pre-fusion RSV F was previously evaluated as subunit vaccine in mice and rhesus monkeys (McLellan, et al. 2013. Science 342:592-598). This RSV F protein should be expressed as a partially secreted form, resembling construct #8 (HEK/GA-opt/Ecto), but with the improvements of more efficient translation due to the GS optimization, better immunogenicity due to the DS-Cav1 modifications, and greater trimer stability due to the foldon stabilization domain. This construct can be used to compare how immunogenic the secreted DS-Cav1 form is compared with the membrane anchored form, i.e. #16 (HEK/GS-opt/DS-Cav1) and the virion-incorporated form, i.e. #18 (HEK/GS-opt/DS-Cav1/B3TMCT).

Points from this study: (1) The hamster model, while convenient, may be somewhat insensitive to changes in replication, expression, and immunogenicity with the various constructs, and it may be that the effects associated with these constructs, such as attenuation and immunogenicity, would be substantially greater in the human host for which these vaccine constructs are intended. For example, while the presence of the B3TMCT modification in the HEK/GA-opt/DS/B3TMCT construct conferred only a modest increase in attenuation in the hamster model (FIG. 23), it was substantially more attenuating in rhesus macaque (FIG. 29), which is more closely related to the authentic human host. Furthermore, the difference in immunogenicity for RSV-neutralizing antibodies between HEK/GA-opt/DS/B3TMCT and the other constructs was substantially greater in rhesus macaques (FIG. 31) than in hamsters (FIG. 24), even though that construct was substantially more attenuated in rhesus macaques (FIG. 29). Thus, the inherent immunogenicity per pfu of HEK/GA-opt/DS/B3TMCT appeared to be much greater in rhesus macaques than in hamsters, and thus might similarly be greater in humans. This apparent insensitivity in the hamster may explain, for example, why the hamster model did not reliably provide a difference in immunogenicity associated with a 16-fold increase in RSV F expression (FIG. 9). It also should be noted that codon-optimization for human use might not provide comparable increases in expression in hamsters as compared to primate cells (and the human vaccine), which might contribute to reduced immunogenicity in the hamster model compared to primates. (2) Another theme was the desirability to reduce the amount of syncytium formation induced by RSV F. In vitro, syncytium formation did not appear to restrict replication in monolayer cultures, although it is possible that it might become a factor in microcarrier cell culture systems used for manufacture, and so it seems prudent to control syncytium formation. With most of the constructs, the HEK assignments were present, which strongly suppressed syncytium formation. The DS and DS-Cav1 constructs, like the HEK assignments, also strongly suppressed syncytium formation and thus provided an unexpected benefit. One construct that was associated with up-regulated syncytium formation, namely HEK/GA-opt/B3CT, did exhibit reduced replication (FIG. 23) and immunogenicity (FIG. 24) in hamsters, giving an indication that increased syncytium formation can be deleterious in vivo. This might be more pronounced in a primate host. Therefore, the combination of GS-opt, HEK, DS or DS-Cav1, and B3TMCT was identified as a combination that would give the highest level of expression of RSV F (due to HEK plus GS-opt, plus stabilization of the pre-fusion F protein that appeared to provide increased F protein accumulation) in the context of two suppressors of syncytium formation (HEK and DS-Cav1), and in the presence of packaging signals that were not hyper-fusogenic (B3TMCT). (3) Two features (namely B3TMCT and the DS mutations) independently were associated with substantial induction of high quality RSV-neutralizing serum antibodies. The rhesus macaque study suggested that the B3TMCT was the more important of these two factors in a primate host, relevant to anticipated vaccine performance in humans (FIG. 32). Importantly, the B3TMCT modification also dramatically increased the quantity (FIG. 31) of the RSV-neutralizing serum antibody response. (4) Unexpectedly and fortuitously, the features that improved the expression and packaging of RSV F did not appear to confer a significant selective pressure for loss of expression of RSV F, when evaluated by a dual immunofluorescence assay. As already noted, loss of expression of the RSV F insert was a problem with MEDI-534, but a number of features were employed in the present study to down-regulate fusion that were not employed in MEDI-534, and this may have played a major role in stabilizing the RSV F insert. In addition, by evaluating two overlapping sets of packaging signals, it was possible to identify and avoid one that was hyperfusogenic, and to identify and choose one that had substantially reduced fusion. (5) The B3TMCT modification in particular emerged as an important factor in increasing immunogenicity. The HEK, GA-opt or GS-opt, and DS or DS-Cav1 modifications emerged as secondary improvements. B3TMCT had the effect of strongly attenuating the vector in rhesus macaques, as noted. The use of this modification in the context of the highly attenuated rB/HPIV3 vector resulted in a vector that appeared to be substantially over-attenuated. However, using reverse genetics, the B3TMCT F protein (with HEK, plus GA- or GS-opt, plus DS or DS-Cav1 modifications, as desired) can be combined with a less-attenuated vector backbone, such as wild type HPIV1, 2, or 3 or versions bearing one or more known, stabilized attenuating mutations, to create a construct that is less attenuated. Since the B3TMCT construct in rB/HPIV3 was very highly immunogenic despite being very over-attenuated, a construct expressing this protein that replicates 10- to 100-fold better should be suitably attenuated and substantially more immunogenic.

Additional Assays with Recombinant rB/HPIV3 Vectors Expressing Modified Versions of the RSV F ORF and Protein.

Additional assays were preformed to evaluate: (i) GS-opt versions of constructs including the DS prefusion stabilization mutations and the B3TMCT packaging signal, and (ii) the DS-Cav1 prefusion stabilization mutations, which include the two cavity-filling mutations S190F and V270L combined with the DS mutations. The F proteins assayed also contain the two HEK amino acid assignments that result in an amino acid sequence identical to that of an early passage (called HEK-7) of the A2 strain, as described above. These assays show that:

1. DS-Cav1 and B3TMCT independently confer the ability to induce significant levels of complement-independent RSV-neutralizing antibodies, which are considered to be the most relevant for in vivo protection.
2. The combination of DS-Cav1 plus B3TMCT gives a further increase in immunogenicity.
3. The two most immunogenic constructs were HEK/GA-opt/DS-Cav1/B3TMCT (FIG. 53, group #7) and HEK/GS-opt/DS-Cav1/B3TMCT (group #10), which differ only in the source of codon optimization, with GS-opt appearing to be the most immunogenic.
4. Although HEK/GA-opt/DS-Cav1/B3TMCT (group #7) and HEK/GS-opt/DS-Cav1/B3TMCT (FIG. 53, group #10) were not statistically distinguishable in a pair-wise comparison, the latter was significantly more immunogenic than wt RSV. These findings show that HEK/GS-opt/DS-Cav1/B3TMCT (group #10) was the most immunogenic construct in the hamster model, particularly for highly-efficient neutralizing antibodies detected without the need to add complement (FIG. 53), and thus the further modification with GS-opt and DS-Cav1 appeared to increase immunogenicity. This also was the most protective construct in the hamster challenge study.

5. The propensity for the rB/HPIV3 vector to acquire mutations conferring a large-plaque phenotype and attenuation was essentially eliminated by three nucleotide and two amino acid mutations in the vector HN protein.

6. The HEK/GS-opt/DS-Cav1/B3TMCT insert was expressed from the first gene position (pre-N), resulting in a construct that replicated efficiently in Vero cells, could be obtained in a preparation with a high percentage of RSV F expression, and efficiently expressed the RSV F protein.

Figure 57A:
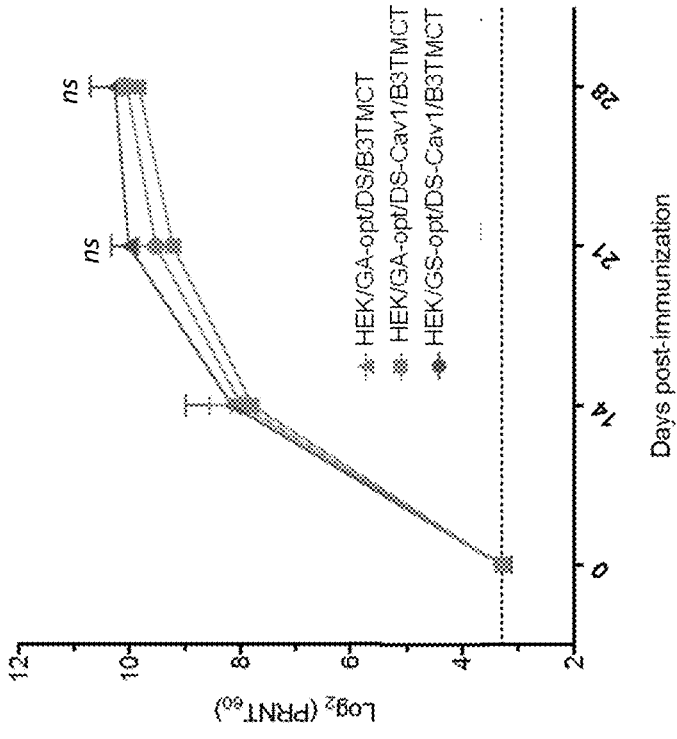
FIGS. 57A and 57B. Serum RSV-neutralizing antibody titers induced by rB/HPIV3 vectors. From the experiment shown in FIGS. 55 and 56, sera were collected at 0, 14, 21, and 28 days post-immunization.
Figure 57B:
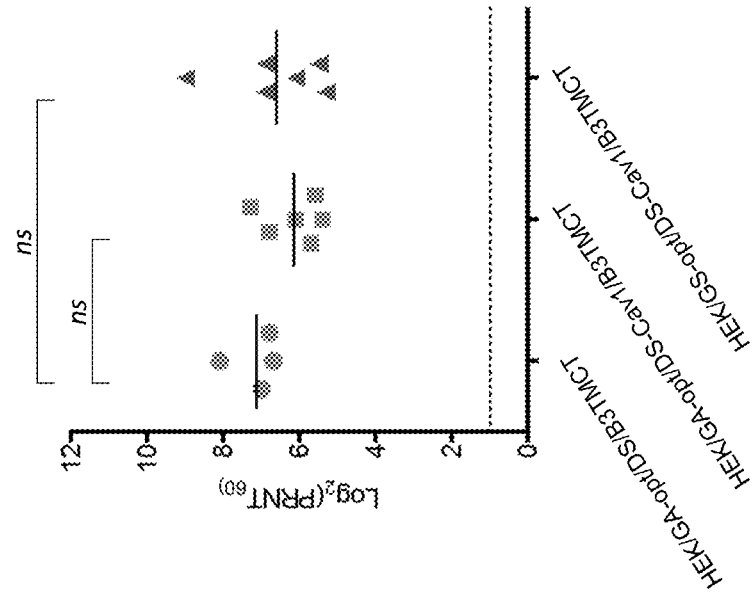

Summary of animal studies. FIG. 35 indicates the constructs that have been evaluated in two different studies in hamsters and two different studies in rhesus monkeys, as indicated: the "1$^{st}$ hamster study" encompasses FIGS. 8-9, 14-16, and 23-26; the "1$^{st}$ NHP study" encompasses FIGS. 29-33; the "2$^{nd}$ hamster study" encompasses FIGS. 51-54; the "2$^{nd}$ NHP study" encompasses FIGS. 55 and 57.

Figure 46:
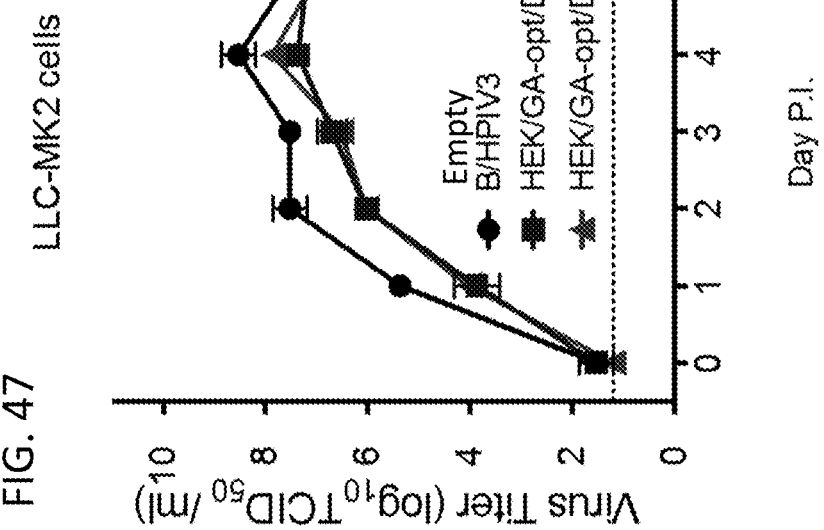
FIGS. 46 and 47. Multi-cycle in vitro replication of rB/HPIV3 vectors expressing GA-optimized (GA-opt) prefusion form of RSV F with DS-Cav1 mutations.
Figure 47:
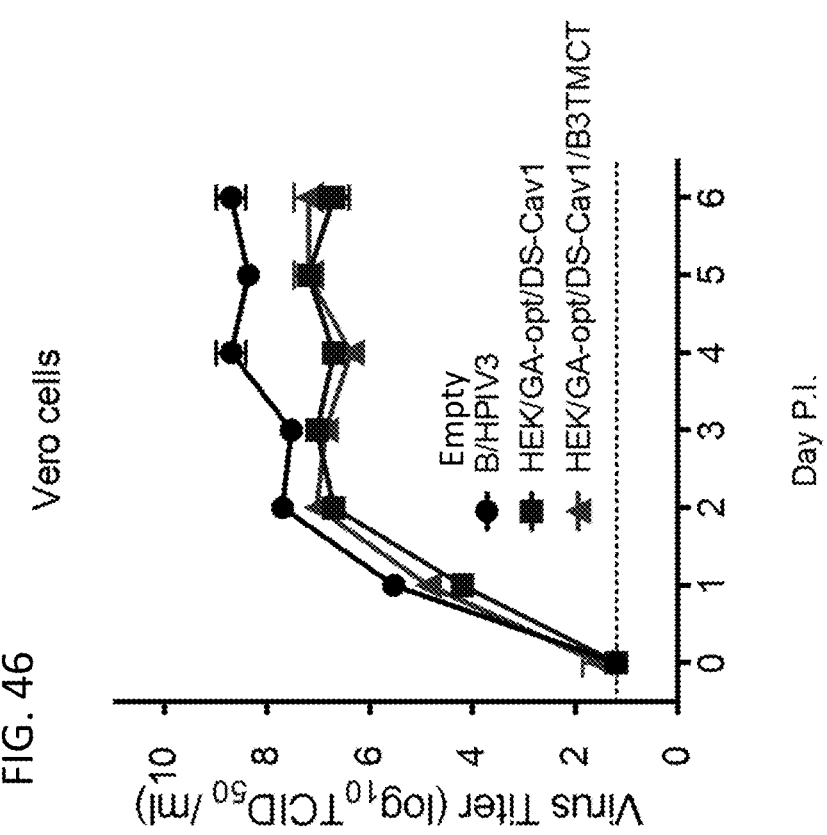

Multi-cycle replication in vitro of GA-opt viruses. FIGS. 46 and 47 illustrate multi-cycle replication of the HEK/GA-opt/DS-Cav1 construct on its own or with the further addition of the B3TMCT packaging signal (constructs #13 and 15 in FIG. 35), compared to the empty vector. This was done in African Green monkey kidney Vero cells (FIG. 46), which is the cell substrate used for vaccine manufacture, and in rhesus monkey kidney LLC-MK2 cells (B), which is a common laboratory cell line that, unlike Vero cells, typically is induced by virus infection to express type I interferons. This experiment showed that the two DS-Cav1-containing constructs (with or without B3TMCT) replicated efficiently and similarly to each other, and were modestly attenuated compared to the empty vector. Despite this modest attenuation, both DS-Cav1-containing constructs replicated to titers higher than $10^7$ TCID$_{50}$/ml. This pattern of modest attenuation is very similar to results obtained with other rB/HPIV3 vectors expressing different versions of RSV F (e.g. FIGS. 7, 12, and 20). Thus, these results showed that rB/HPIV3 bearing these modified inserts replicated in an efficient manner that is fully satisfactory for vaccine manufacture.

Figure 48A:
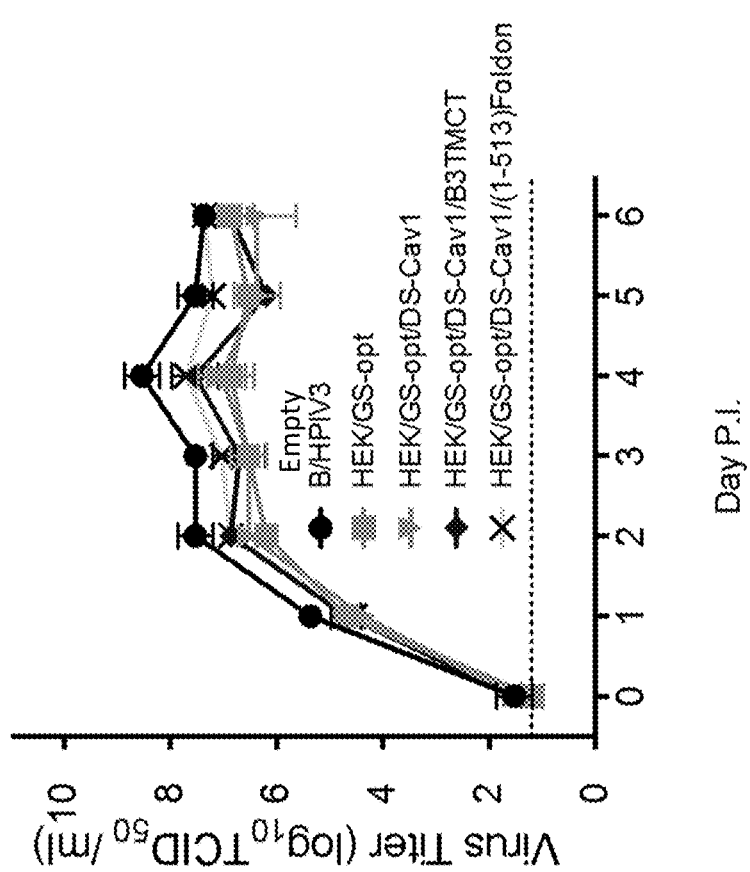
FIGS. 48A and 48B. Multi-cycle in vitro replication of rB/HPIV3 vectors expressing GS-optimized (GS-opt) RSV F with different modifications. (A) Vero and (B) LLC-MK2 cells were infected in triplicate at 32° C. at an MOI of 0.01 $TCID_{50}$ with empty rB/HPIV3 vector (empty B/H3) or vector expressing the RSV F ORF that was HEK-containing and GS-opt RSV F (HEK/GS-opt), or was HEK-containing, GS-opt and bearing DS-Cav1 prefusion stabilizing mutations (HEK/GS-opt/DS-Cav1), or was HEK-containing, GS-opt, and bearing the DS-Cav1 mutations and BPIV3-specific TM and CT domains (HEK/GS-opt/DS-Cav1/B3TMCT), or was a truncated RSV F with amino acids from 1 to 513 that was fused to a four-amino acid linker and 27-amino acid oligomerization sequence from T4 phage, which was HEK-containing, GS-opt and bearing DS-Cav1 mutations (HEK/GS-opt/DS-Cav1/(1-513) Foldon). Aliquots of medium supernatants were collected at 24 h intervals for 6 days and viral titers were determined by limiting dilution assay on LLC-MK2 cells at 32° C. and reported as $TCID_{50}$/ml. Mean titers±SEM from three independent experiments are shown.
Figure 48B:
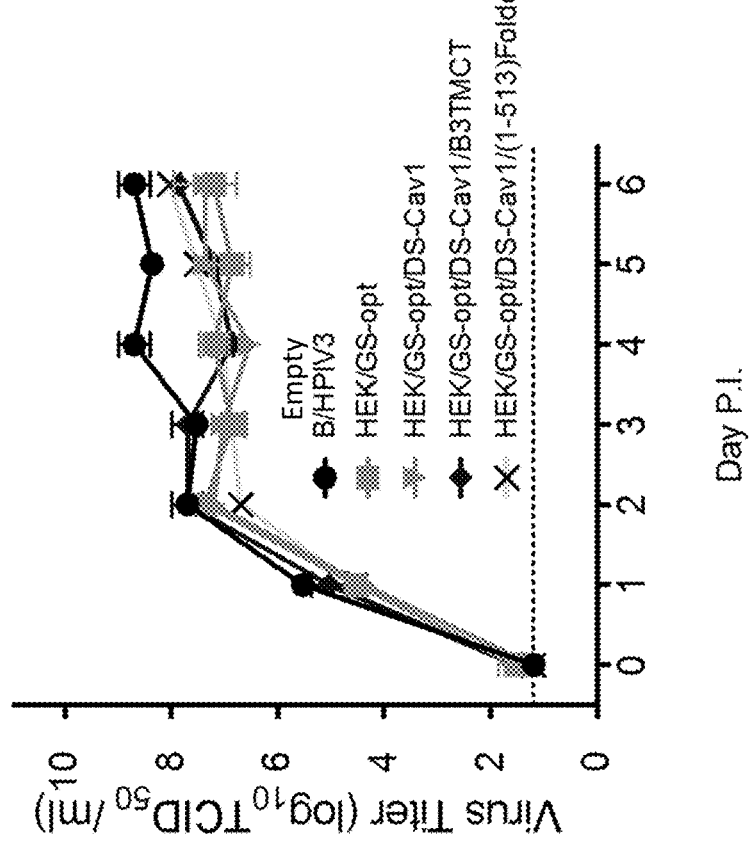

Multi-cycle replication in vitro of GS-opt viruses. FIG. 48 illustrates multi-cycle replication of the HEK/GS-opt backbone (construct #5 in FIG. 35) compared with versions with the further additions of DS-Cav1 (#16), the combination of DS-Cav1/B3TMCT (#18), and the combination of DS-Cav1, ectodomain 1-513, and a C-terminal "foldon" domain to promote ectodomain oligomerization (#19), with empty vector for comparison. Evaluation in Vero (FIG. 48A) and LLC-MK2 (B) cells showed that the vectors expressing the various forms of RSV F replicated with very similar kinetics and yield, and were modestly attenuated compared to the empty vector. They all replicated to titer higher than $10^7$ TCID$_{50}$/mL in cell culture. These results showed that rB/HPIV3 bearing these modified inserts replicated in an efficient manner that is fully satisfactory for vaccine manufacture.

Multi-cycle replication in vitro of GA- and GS-opt viruses. FIG. 49 illustrates multi-cycle replication of pairs of constructs that differ in being GA-optimized or GS-optimized: specifically: HEK/GS-opt/DS-Cav1 versus HEK/GA-opt/DS-Cav1 (top panels, constructs #16 and 13 respectively from FIG. 35), and HEK/GS-opt/DS-Cav1/B3TMCT versus HEK/GA-opt/DS-Cav1/B3TMCT (bottom panels, constructs #18 and 15 respectively from FIG. 35). The two pairs of constructs were each evaluated in Vero (FIGS. 49A, C) and LLC-MK2 (B, D) cells. The GS-opt constructs sometimes replicated marginally more efficiently than the GA-opt constructs (e.g. FIGS. 49C and 49D), especially during the first 3-4 days of incubation.

Expression of RSV F in vitro. FIG. 50 illustrates expression of RSV F and vector proteins by rB/HPIV3 constructs in Vero and LLC-MK2 cells. This compares expression by HEK/GA-opt (FIG. 50, lane 2; FIG. 35, construct #3) versus HEK/GS-opt (FIG. 50, lane 3; FIG. 35, construct 5): consistent with results described in Example 1 (FIG. 5), the GS-optimization resulted in somewhat greater expression of RSV F protein. The HEK/GS-opt construct also was compared to versions that, in addition, contained DS-Cav1 (FIG. 50, lane 3; FIG. 35, construct #16), or DS-Cav1/B3TMCT (FIG. 50, lane 5; FIG. 35, construct #18), or DS-Cav1/(1-513) Foldon (FIG. 50, lane 8; FIG. 35, construct #19). Also included for comparison were cells infected with wt RSV (FIG. 50, lane 6) or mock-infected (lane 7). The results showed that each of the GS-opt constructs directed efficient expression of RSV F, and indeed expressed much more RSV F than did wt RSV (FIG. 50, lane 6). Cells infected with the three GS-opt constructs encoding full-length DS-Cav1 F protein (FIG. 50, lanes 4, 5, and 8) had a somewhat greater accumulation of the F$_0$ precursor of RSV F protein, suggesting that its prefusion stabilization may have marginally reduced the efficiency of cleavage. In general, however, each of the constructs was very efficient in expressing the RSV F protein. The prefusion Foldon construct, HEK/GS-opt/DS-Cav1/(1-513) Foldon (FIG. 50, lane 8), was only partly secreted into the medium (FIG. 50A, lower panel), and the secreted form was entirely the cleaved F$_1$ chain (FIG. 4A, lower panel, lane 8), whereas all of the cell-associated form was uncleaved F$_0$ (FIG. 4A, upper panel, B and C, lane 8). None of other tested forms of RSV F was detected in the medium supernatant, indicating they were not secreted. The inefficient cleavage and secretion of the DS-Cav1/(1-513) Foldon construct was unexpected, since this trimerization domain had been successfully used previously to prepare purified F protein (McLellan et al Science 2013 Nov. 1; 342(6158):592-8. doi: 10.1126/science.1243283). This illustrates that expression of foreign proteins by vectored constructs can be unpredictable, whereas the detailed evaluation of multiple constructs herein provides comprehensive evaluation leading to the identification of a number of suitable, successful constructs.

Hamster studies. A number of GA-opt and GS-opt constructs that contained the further additions of B3TMCT, DS, and DS-Cav1 (the constructs are identified in FIG. 35 as the "2$^{nd}$ hamster study") were evaluated in hamsters for efficiency of replication (FIG. 51), stability of expression of RSV F protein, stimulation of RSV-neutralizing serum antibodies (FIGS. 52 and 53), and protective efficacy against RSV challenge (FIG. 54).

Replication in hamsters. GA-opt and GS-opt constructs were evaluated for replication in the upper (nasal turbinates) and lower (lungs) respiratory tract of hamsters (FIG. 51). In the nasal turbinates, HEK/GA-opt/B3TMCT (group #5) and HEK/GA-opt/DS/B3TMCT (group #6) were more restricted than others. In the lungs, GA-opt constructs with B3TMCT (HEK/GA-opt/B3TMCT, group #5, HEK/GA-opt/DS/B3TMCT, group #6, and HEK/GA-opt/DS-Cav1/B3TMCT, group #7) were more restricted. Similarly, GS-opt constructs with B3TMCT, i.e., HEK/GS-opt/DS-Cav1/B3TMCT (group #10) was also more attenuated than HEK/GS-opt/DS-Cav1 (group #9). These observations suggested that B3TMCT increases the level of attenuation. In addition, GA-opt constructs appeared to be more attenuated than GS-opt constructs. For example, GS-opt constructs of DS-Cav1 and DS-Cav1/B3TMCT, i.e., HEK/GS-opt/DS-Cav1 (group #9) and HEK/GS-opt/DS-Cav1/B3TMCT (group #10) replicated to mean peak titers of 5.0 and 4.2 $\text{Log}_{10}$ $\text{TCID}_{50}$/g in the LRT, which was higher than the mean titers of equivalent GA-opt constructs, i.e. 4.0 and 3.4 $\text{Log}_{10}$ $\text{TCID}_{50}$/g (groups #4 and 7). This suggested that GS-opt RSV F inserts were less attenuating than GA-opt RSV F.

Stability of expression of RSV F protein. The stability of RSV F expression by rB/HPIV3 vectors during their replication in vivo was evaluated with double-staining plaque assay by analyzing nasal turbinate and lung samples of immunized hamsters harvested on day 5 post-immunization. Most of samples (92 out of 107) had more than 90% of replicated vectors still expressing RSV F; 6 out of 107 had 89-80% vectors expressing RSV F; 9 out of 107 had less than 79% of replicated vectors expressing RSV F; only 7 samples had >50% of vectors losing RSV F expression. Among these seven samples with >50% vectors losing RSV F expression, four were GA-opt constructs, three were GS-opt constructs. There was no evidence that GA-opt, or GS-opt, or DS, or DS-Cav1, or TMCT were associated with any particular increase in instability. It is likely that the varying levels of instability among individual preparations reflect sporadic mutations that are largely independent of the specific construct, and thus evaluation of several independent preparations of each construct likely would identify one or more with a very high percentage of expression of RSV F protein.

Figure 52:
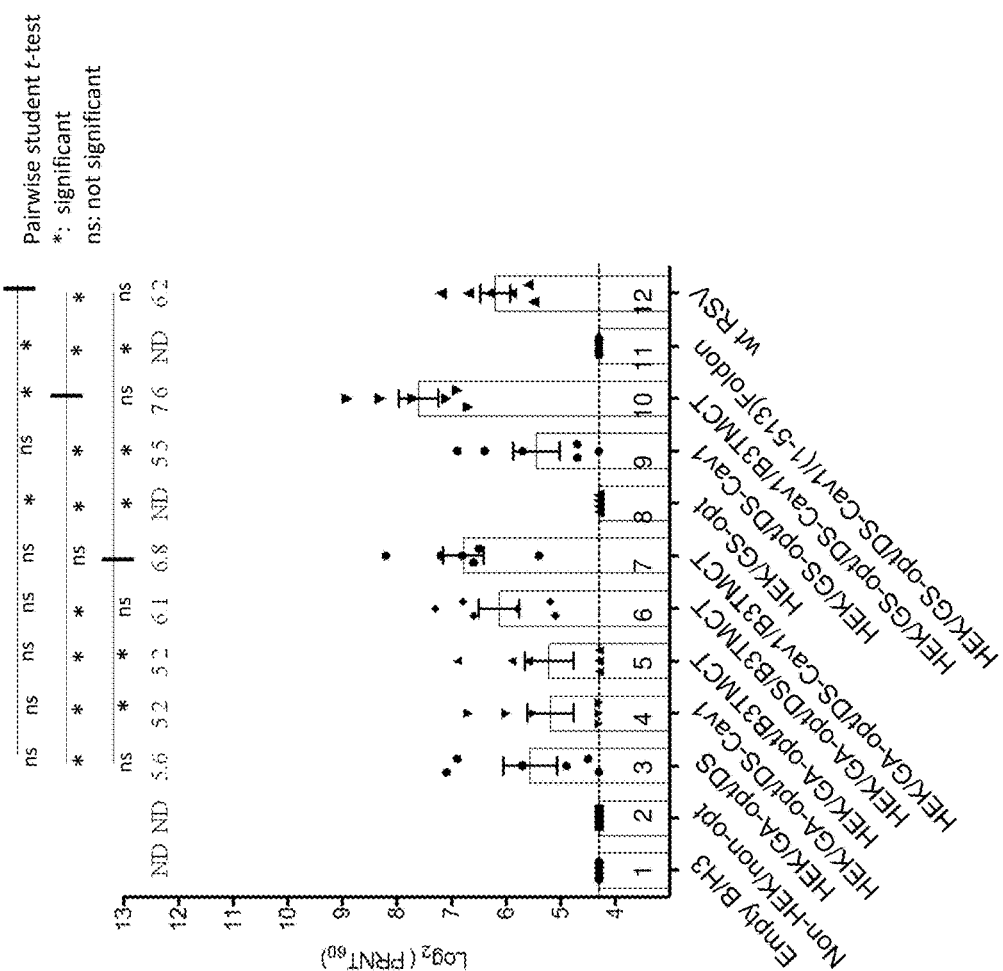
FIGS. 52 and 53. Serum RSV-neutralizing antibody titers from hamsters infected with the indicated rB/HPIV3 vectors expressing the GA-opt or GS-opt RSV F protein with or without the DS or DS-Cav1 or B3TMCT modifications. Hamsters (n=6 animals per virus) were inoculated IN with $10^5$ TCID$_{50}$ of the indicated rB/HPIV3 vectors or $10^6$ PFU of wt RSV in a 0.1 ml inoculum. Serum samples were collected at 28 days post-immunization, and antibody titers were determined by a 60% plaque reduction neutralization test (PRNT$_{60}$) with (FIG. 52) or without (FIG. 53) added guinea pig complement. The height of each bar represents the mean titer shown along with the SEM. The values of mean titers are shown above the bars. The pairwise student t-test was used to evaluate the statistical significance of differences between values: in each of the three horizontal lines over the mean titers, the value indicated with a vertical bar was compared pair-wise to each of the others and recorded as being significantly (*, p≤0.05) or not significantly (ns) different. The detection limit for the neutralization assay is indicated with a dotted line. ND, neutralization titer was below the detection limit.
Figure 53:
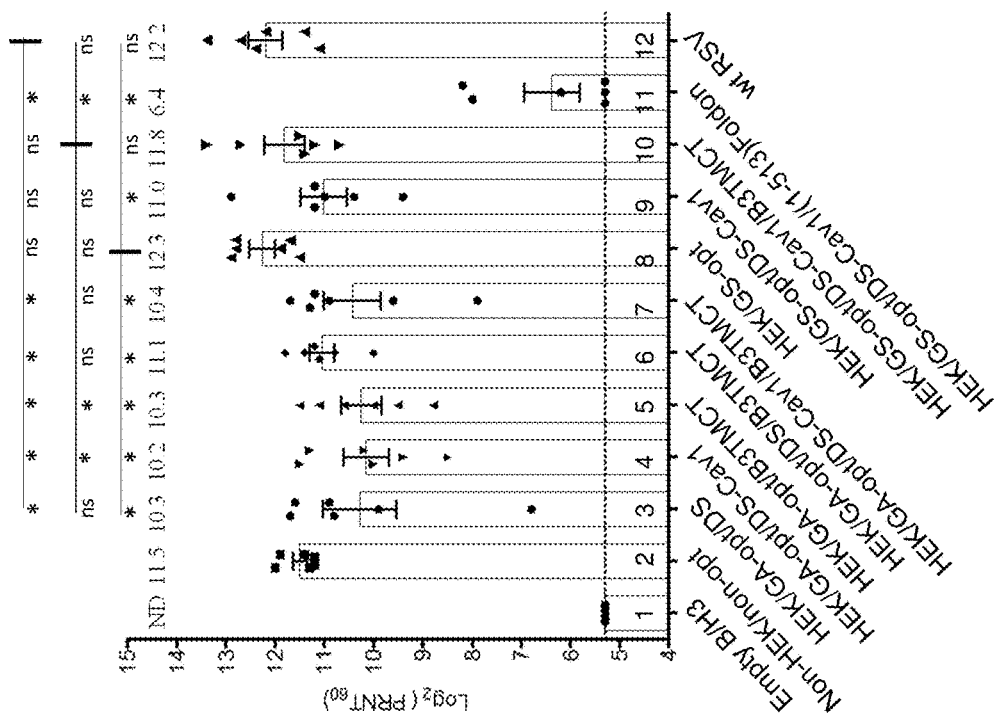

Titers of RSV-neutralizing serum antibodies. RSV neutralizing serum antibody titers were determined by RSV neutralization assays with added guinea pig complement (FIG. 52) or in the absence of complement (FIG. 53). The assay performed with added complement is commonly used for RSV and HPIV3 neutralization assays because it allows sensitive detection of virus-specific antibodies, since complement can confer viral-lysis and steric-hindrance capabilities to antibodies that otherwise might not be neutralizing in vitro (Yoder et al J Med Virol 72:688-694, 2004). In contrast, antibodies that neutralize RSV in vitro in the absence of complement have been suggested to be the most relevant for protection (Yoder et al J Med Virol 72:688-694, 2004), and in prior studies have associated with a higher level of protection against RSV challenge (Liang et al J Virol 89:9499-9510, 2015). Antibodies that neutralize in vitro independent of added complement are considered to be "high quality" and to be indicative of qualitatively superior immunogenicity.

In the complement-dependent assay (FIG. 52), all rB/HPIV3 vectors expressing RSV F induced high titers of RSV neutralizing antibodies except for the poorly immunogenic HEK/GS-opt/DS-Cav/(1-513) Foldon construct. GS-opt constructs induced higher titers of RSV serum neutralizing antibodies than their counterparts of GA-opt constructs (11.0 $\text{Log}_2$ $\text{PRNT}_{60}$ for HEK/GS-opt/DS-Cav1, group #9 versus 10.2 $\text{Log}_2$ $\text{PRNT}_{60}$ for HEK/GA-opt/DS-Cav1 group #4; 11.8 $\text{Log}_2$ $\text{PRNT}_{60}$ for HEK/GS-opt/DS-Cav1/B3TMCT, group #10 versus 10.4 $\text{Log}_2$ $\text{PRNT}_{60}$ for HEK/GA-opt/DS-Cav1/B3TMCT, group #7). In the complement-dependent assay (FIG. 52), it was noteworthy that the three constructs that were statistically as immunogenic as wt RSV (the gold standard) were the GS-opt constructs HEK/GS-opt (group #8), HEK/GS-opt/DS-Cav1 (group #9), and HEK/GS-opt/DS-Cav1/B3TMCT (group #10).

In the complement-independent assay (FIG. 53), vectors expressing native forms of RSV F (Non-HEK/non-opt and HEK/GS-opt) did not induce detectable RSV neutralizing antibodies, confirming and extending results from Example 1. Prefusion stabilizing mutations (DS, DS-Cav1) and the packaging signal B3TMCT independently increased immunogenicity for high quality RSV-neutralizing antibodies (e.g., constructs with DS and/or Cav1 in the absence of B3TMCT are exemplified by groups #3, 4, and 9, whereas a construct with B3TMCT in the absence of DS/Cav-1 is exemplified by group #5). The combination of prefusion stabilizing mutations plus B3TMCT had additive improvement in immunogenicity, which was observed with GA-opt as well as GS-opt constructs (e.g., groups 6, 7, and 10). In the complement-independent assay, the HEK/GS-opt/DS-Cav1/B3TMCT construct (group #10) induced significantly higher titers of RSV-neutralizing serum antibodies (7.6 $\text{Log}_2$ $\text{PRNT}_{60}$) than that induced by any of the other vectors except for its GA-opt counterpart HEK/GA-opt/DS-Cav1/B3TMCT (group #7) which induced a lower titer (6.8 $\text{Log}_2$ $\text{PRNT}_{60}$) but was not significantly lower. However, the antibody titer induced by HEK/GS-opt/DS-Cav1/B3TMCT construct (group #10), but not HEK/GA-opt/DS-Cav1/B3TMCT (group #7) was significantly higher than that of wt RSV (group 12), and therefore the HEK/GS-opt/DS-Cav1/B3TMCT construct (group #10) was the most immunogenic among the vectors and wt RSV for high quality RSV-neutralizing antibodies.

Figure 54A:
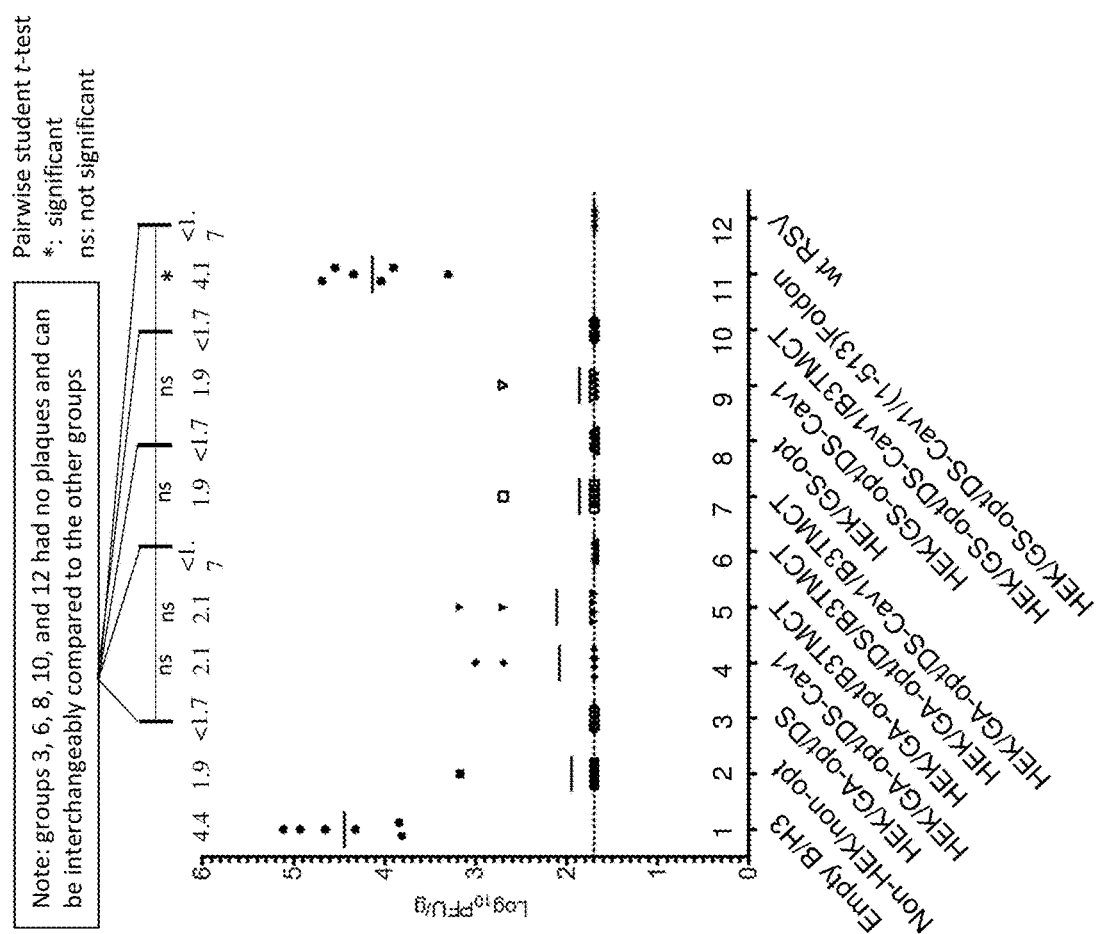
FIGS. 54A and 54B. Protection against RSV challenge of hamsters immunized with the indicated rB/HPIV3 vectors. The hamsters (n=6 animals per immunization group) that had been immunized as shown in FIG. 53 were challenged IN on day 30 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells at 37° C. Each symbol represents an individual animal and mean values of viral titers of the groups are shown above the symbols and indicated as short horizontal lines. The pairwise student t-test was used to evaluate the statistical significance of differences between values: in each of the horizontal lines over the mean titers, the value(s) indicated with a vertical bar(s) was compared pair-wise to each of the others and recorded as being significantly (*, p<0.05) or not significantly (ns) different. The detection limit of the assay was log$_{10}$ 1.7 PFU/g of tissue, indicated as a dotted line.
Figure 54B:
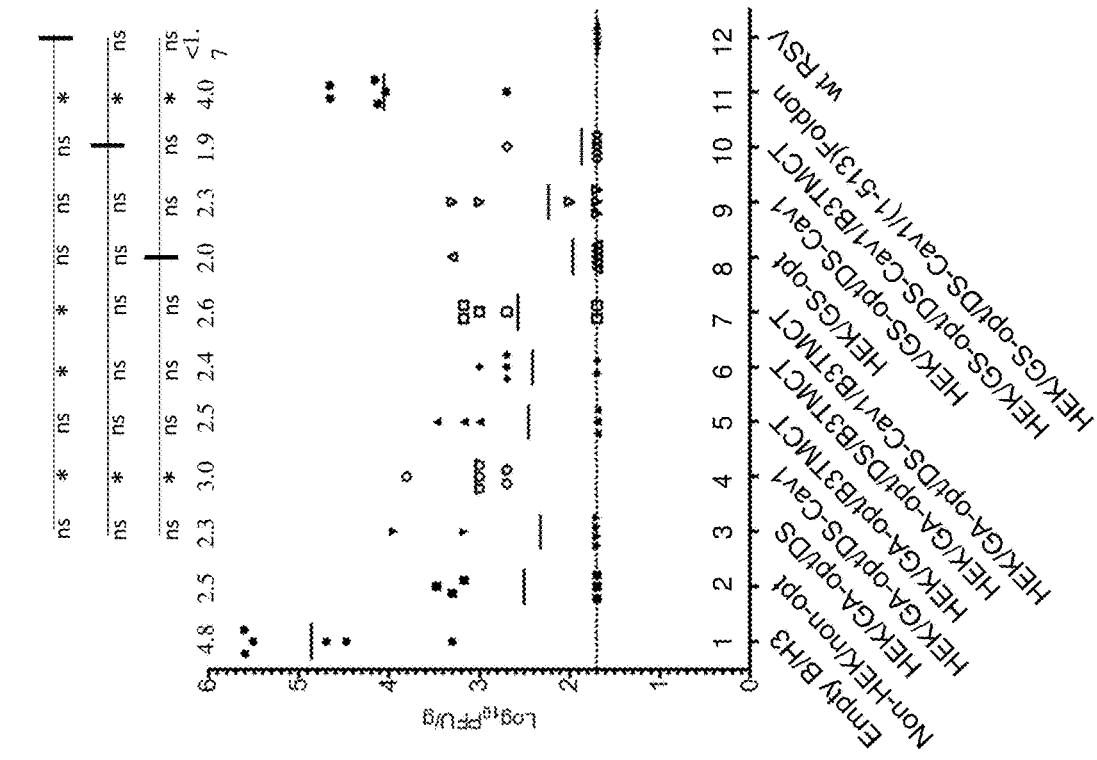

RSV challenge. The immunized hamsters were challenged IN with wt RSV to evaluate protective efficacy (FIG. 54). As shown in FIG. 54, all of the RSV F-expressing vectors, except for the DS-Cav1/(1-513) Foldon construct, induced significant protection in the URT (FIG. 54A) and LRT (FIG. 54B). The lack of protection by DS-Cav1/(1-513) Foldon was in line with its poor immunogenicity shown in the RSV serum neutralization assays (FIGS. 52 and 53). Compared with the sterile immunity conferred by wt RSV, the HEK/GS-opt/DS-Cav1/B3TMCT conferred the greatest protection among all tested vectors and was nearly equivalent to wt RSV: only one hamster immunized by this vector had detectable wt RSV, and only at very low level in the nasal turbinates. The protective efficacy of HEK/GS-opt/DS-Cav1/B3TMCT (group #10) was statistically indistinguishable from that of wt RSV (group #12) in the nasal turbinates, whereas HEK/GA-opt/DS-Cav1/B3TMCT (group #7) was significantly less protective, supporting the idea that the former construct is the most immunogenic construct. This equivalence in protection to wt RSV is remarkable because wt RSV expresses two neutralization antigens, G and F, and also expresses all of the viral proteins as potential antigens for cellular immunity, whereas the vectors express only the RSV F protein. Cellular immunity has been shown to confer potent protection in RSV challenge studies in rodents (e.g., Connors et al J Virol 66:1277-1281 1992).

Figure 55:
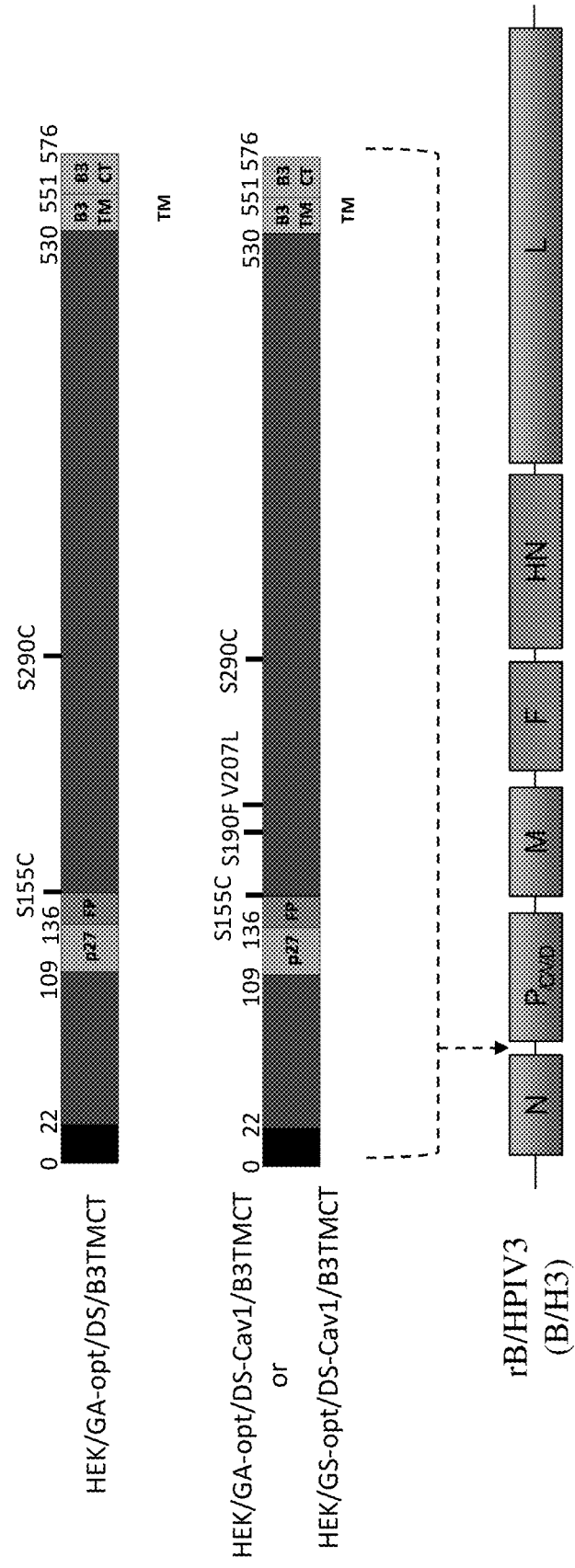
FIG. 55. rB/HPIV3 constructs that were evaluated for attenuation and immunogenicity in non-human primates (Rhesus macaques). Rhesus macaques were infected by the combined IN and intratracheal routes with $10^6$ TCID$_{50}$ per site of the following constructs: HEK/GA-opt/DS/B3TMCT; HEK/GA-opt/DS-Cav1/B3TMCT; and HEK/GS-opt/DS-Cav1/B3TMCT in groups of four, six and six animals, respectively.

Evaluation in rhesus monkeys. Three vectors with greatest immunogenicity in hamsters were selected to evaluate their replication and immunogenicity in rhesus monkeys (FIG. 55). These constructs included HEK/GA-opt/DS/B3TMCT (the construct at the top of FIG. 55), which was identified as particularly effective in the $1^{st}$ NHP study (FIGS. 28-32, in Example 1). The second construct was HEK/GA-opt/DS-Cav1/B3TMCT, which is the same as the first construct except that it has DS-Cav1 instead of DS. The third construct was HEK/GS-opt/DS-Cav1/B3TMCT, which differs from the previous construct in having GS-opt instead of GA-opt. These latter two constructs induced the highest titers of "high quality" RSV-neutralizing serum antibodies in FIG. 53.

Figure 56B:
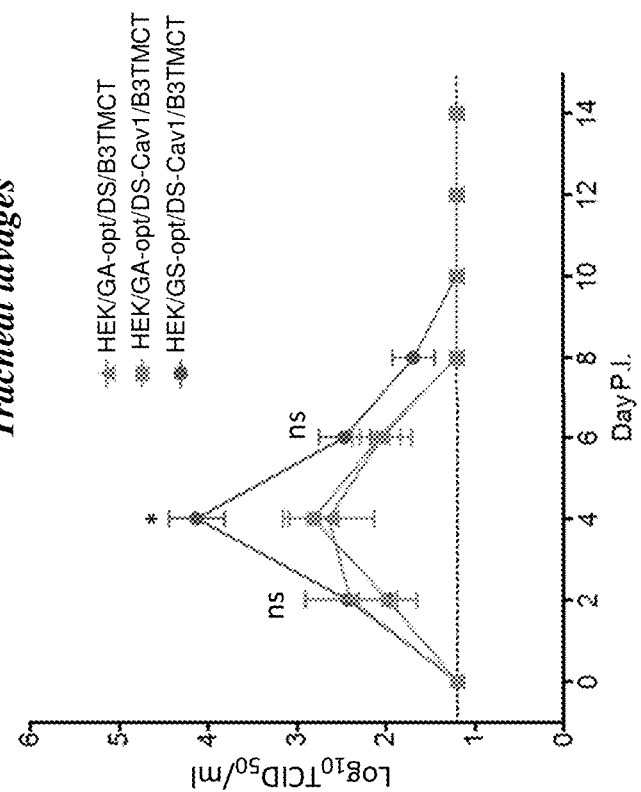
FIGS. 56A and 56B. Replication of rB/HPIV3 vectors in rhesus macaques. Rhesus macaques were infected with the rB/HPIV3 vectors indicated in FIG. 55. Vector replication in the respiratory tract was assessed by collecting (A) nasopharyngeal swabs and (B) tracheal lavages on the indicated days and determining the viral titers by limiting dilution assay. Limit of detection is 1.2 log$_{10}$ TCID$_{50}$/mL shown as dotted line.
Figure 56A:
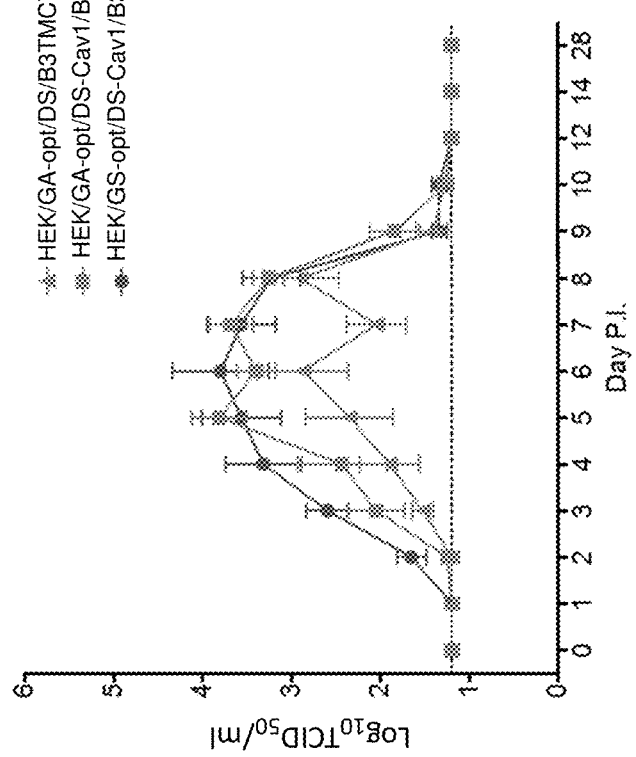

Replication in rhesus monkeys. The parallel constructs with GA-opt and GS-opt versions of HEK/DS-Cav1/B3TMCT replicated in similar kinetics in the URT, as sampled by nasopharyngeal swabs (FIG. 56A). However, this equivalency was not observed in the LRT, as sampled by tracheal lavage: the GS-opt version was less attenuated than GA-opt version (FIG. 56B). These results are consistent with what was observed in hamsters in FIG. 51. With regard to the comparison of parallel constructs with DS versus DS-Cav1 (HEK/GA-opt/DS/B3TMCT versus HEK/GA-opt/DS-Cav1/B3TMCT), the former virus was more attenuated in the URT (FIG. 56A); but they replicated at similar efficiency in the LRT (FIG. 56B). These results also are consistent with what was observed in hamsters in FIG. 51. It is noticeable that the HEK/GA-opt/DS/B3TMCT replicated to significantly higher titers (~10-fold higher) in both URT and LRT in this study, compared to the same construct tested in the 1$^{st}$ NHP study (FIG. 29, Example 1). The monkeys in the previous study (FIG. 29) were 6 years older and 2-3 times bigger in weight than monkeys used in FIG. 56. It may be that replication of these viruses is more efficient in younger monkeys, or the difference might reflect variability between these two experiments.

RSV-neutralizing serum antibodies. Although the three vectors in FIG. 56 replicated at slightly different efficiencies in rhesus monkeys, they induced comparably high levels of RSV-neutralizing serum antibodies determined by complement-dependent (FIG. 57A) and complement-independent (FIG. 57B) assays.

Insertion of RSV F at the first gene position. All of the previous B/HPIV3-RSV-F constructs in Examples 1 and the present Example involved an RSV gene inserted in the second gene position, between the vector N and P genes. Insertion of unmodified RSV F at the first position was not associated with any evident problems of impaired growth or reduced stability of expression of RSV F protein. Whether an optimized, engineered form of RSV F could be efficiently and stably expressed from the first gene position was investigated. Specifically, the HEK/GS-opt/DS-Cav1/B3TMCT version of RSV F was inserted into the pre-N position (FIG. 58A).

Identification and modification of two amino acid assignments in HN that conferred phenotypic instability of the vector. The rB/HPIV3 vector was previously noted to exhibit phenotypic instability upon passage in vitro (Liang et al J Virol 88:4237-4250). Specifically, a substantial proportion of vector acquired a large-plaque phenotype during passage. This occurred with different inserts as well as with empty vector, indicating that it was a property of the vector alone and not specific to the foreign gene. Whole-genome sequence analysis of six cloned large-plaque viruses showed that each had acquired an H552Q missense mutation in HN, as well as one of three different missense mutations in F, and in some cases one or two missense mutations in L (Liang et al J Virol 88:4237-4250). Partial sequencing of 11 additional large-plaque clones showed that seven of these contained the H552Q mutation in HN, while the other four each contained one of four other missense mutation in HN (N240K, P241L, R242K, or F558L). Comparison with the crystal structure of the HPIV3 HN protein (Lawrence et al J Mol Biol 335: 1343-1357 2004) indicated that all of these HN mutations are located in the dimer interface of the HN globular head. In addition, the H552Q mutation had previously been described in an HPIV3 variant that had been selected by growth on neuraminidase-treated cells, and which had a large-plaque phenotype, had higher avidity to sialic acid-containing receptor, had enhanced triggering of F protein, and was attenuating in rodents (Moscona et al J Virol 67:6463-6468; Porotto et al J Virol 81:3216-3228; Palermo et al J Virol 83:6900-6908). This suggested that the adventitious mutations in the HPIV3 HN gene in the rB/HIPIV3 vector were similar and probably were selected for because they increased the binding affinity of the rB/HPIV3 vector for Vero cells. However, the observation by others (Moscona et al J Virol 67:6463-6468; Porotto et al J Virol 81:3216-3228; Palermo et al J Virol 83:6900-6908) that the large-plaque phenotype was associated with substantial attenuation in vivo would be disadvantageous for the present vectors because this likely would lead to over-attenuation. The HPIV3 reverse genetic system contained two mutations in the HN gene: there was an adventitious C7589T nucleotide mutation (relative to the complete antigenome sequence) in the cDNA clone leading to a T263I missense mutation, and C7913A and A7915T mutations leading to a P370T mutation that had been purposefully introduced as a marker (Durbin et al Virology 235:323-332, 1997). This latter missense mutation had been designed to ablate an epitope recognized by two available HPIV3-neutralizing monoclonal antibodies (MAbs 423/6 and 170/7). These mutations were restored to their wild-type assignments, namely 7593C (263T) and 7913C+7915A (370P) (FIG. 58B). Remarkably, these changes prevented acquisition of the large-plaque phenotype during passage in Vero cells (not shown). Therefore, further vector constructs bearing the HPIV3 HN gene (including but not limited to rB/HPIV3- and HPIV3-based vectors) preferably should contain these assignments. For example, the I263T and T370P mutations were incorporated into the HEK/GS-opt/DS-Cav1/B3TMCT/pre-N construct shown in FIG. 58A. All vectors of interest that bear the HPIV3 HN gene will be modified to contain the 263T and 370P assignments.

Virus recovery. The rB/HPIV3 vector with HEK/GS-opt/DS-Cav1/B3TMCT inserted in the pre-N position (FIG. 58A) was recovered and grew to titers up to 8.2 log$_{10}$ TCID$_{50}$/mL, and thus had little or no growth restriction with regard to viral yield, which is important for vaccine manufacture. The plaque size of this virus was generally smaller than the same version of RSV F inserted in the second position (not shown), indicating that there was a modest restriction on growth that was not evident in the virus yield.

Stability of expression of RSV F protein. Two preparations of viruses were analyzed by a double-staining plaque assay, to evaluate stability of expression of the RSV F protein. Double-staining plaque phenotype of two independent rescued virus pools, designated CL20a and CL24a, were performed. Plaque assay was carried out on Vero monolayer in 24-well plates infected with 10-fold serially diluted virus. Infected monolayers were overlaid with medium containing 0.8% methylcellulose and incubated at 32° C. for 6 days. After fixing in ice-cold 80% methanol, the monolayers were incubated with a mixture of three mouse monoclonal antibodies against RSV F (1129, 1109, 1243) and a rabbit anti-HPIV3 hyperimmune serum, followed by incubation with IRDye 680 (red, detecting RSV F) conjugated goat anti-mouse and IRDye 800 (green, detecting HPIV3) conjugated goat anti-rabbit antibodies.

One preparation was stable after passaging in cell culture, whereas a second preparation had green staining in ~40% of viruses and thus had evidence of loss of RSV F expression. These results indicated that loss of RSV F expression can occur and can be amplified in the virus preparation, but it appeared to be sporadic and careful monitoring can identify preparations with a high proportion of expression.

Intracellular protein expression. Expression of RSV F from the pre-N position was analyzed in Vero (FIG. 59A) and LLC-MK2 (FIG. 59B) cells. In Vero cells, HEK/GS-opt/DS-Cav1/B3TMCT version of RSV F was expressed as $F_1$ and $F_0$ chains (FIG. 59A), and the total expression from the pre-N position was comparable to that expressed from the N-P position. But in LLC-MK2 cells (FIG. 59B), this version of RSV F was predominantly expressed as $F_0$ chain, and expression from pre-N was substantially more efficient than that from N-P position (FIG. 59B, lane 3, 4, 5). In both types of cells, this version of RSV F was expressed at a much higher level than unmodified RSV F (Non-HEK/non-opt, FIG. 59A, 59B, lanes 3 and 4 versus lane 6).

Example 2

Attenuated Human Parainfluenza Virus Type 1 (HPIV1) Expressing the Fusion F Glycoprotein of Human Respiratory Syncytial Virus (RSV) as a Bivalent HPIV1/RSV Vaccine This example illustrates the development and pre-clinical evaluation of a live attenuated rHPIV1 vectored RSV vaccine expressing RSV F antigen from three genome positions of the two attenuated rHPIV1 backbones. Pre-clinical evaluation in hamsters indicated that the rHPIV1 $C^{\Delta 170}$F1 vector, bearing attenuating deletion mutation ($C^{\Delta 170}$) in the P/C gene and expressing RSV F from the pre-N position was sufficiently attenuated, stable and immunogenic against RSV and HPIV1 and provided significant protection against RSV challenge infection. This study demonstrated that rHPIV1 could be used as an RSV vaccine vector to achieve bivalent protection against two major childhood diseases.

Introduction. Compared to an RSV vaccine comprising an attenuated strain of RSV, an RSV vaccine comprising a live attenuated HPIV vector (such as one developed from HPIV1) expressing the RSV F protein offers several advantages. One advantage is that it provides a bivalent vaccine against RSV and the HPIV serotype used as a vector. This is important because, as noted, the HPIVs also are important, uncontrolled agents of pediatric respiratory tract disease, with characteristics of epidemiology and pathogenesis that overlap those of RSV. Thus, a combined HPIV/RSV vaccine is a logical combination that would broaden the coverage against pediatric respiratory tract disease. In addition, RSV infectivity is notorious for being prone to instability during handling, which complicates vaccine development, manufacture, and delivery. The HPIVs are substantially more stable, which may be critical for extending RSV vaccines to developing countries where their need is the greatest. RSV grown in vitro often forms long filaments that complicate manufacture, whereas the HPIVs form smaller spherical particles. It also may be that RSV is inherently more pathogenic and even possibly immunosuppressive compared to the HPIVs, which would be another advantage of an HPIV-vectored RSV vaccine. It has also been have found that, in rodents, the use of an HPIV-vectored vaccine as a boost administered subsequent to a live attenuated RSV strain was more immunogenic than a second dose of the same attenuated RSV strain. Thus, RSV-specific immunity resulting from a primary immunization might be expected to restrict replication of a second dose of an attenuated RSV strain more efficiently than that of an HPIV-vectored virus, and indicates another potential advantage of HPIV-vectored RSV vaccines.

The HPIV1 genome is a single strand of negative sense RNA. It consists of a short 3' leader region followed by 6 genes encoding the N, P, C, M, F, HN, and L proteins, and a short trailer region. Each gene encodes a major viral protein: N, nucleoprotein; P, phosphoprotein; M, internal matrix protein; F, fusion glycoprotein; HN, hemagglutinin-neuraminidase glycoprotein; and L, major polymerase subunit. In addition, the P gene carries an overlapping ORF expressing a set of carboxy-co-terminal C accessory proteins that inhibit the host interferon (IFN) response and block apoptosis (Bartlett, et al. 2008. J virology 82:8965-8977). Like other nonsegmented negative strand RNA viruses, HPIV1 transcription initiates at the 3' end promoter and proceeds down the genome in a start-stop process regulated by the gene end (GE)-intergenic (IG)-gene start (GS) signals to generate a series of monocistronic mRNAs. There is a 3' to 5' gradient of decreasing transcription, with the promoter-proximal genes expressed at higher levels (Nagai. 1999. Reviews in medical virology 9:83-99). Like other paramyxoviruses, complete infectious, replication-competent HPIV1 can be recovered in cell culture from transfected cDNAs (reverse genetics).

Previous studies have described the development of a chimera of bovine and human PIV3 as a vector for RSV F protein (Schmidt et al 2000 J Virol 74:8922-8929; Schmidt et al 2001 J Virol 75:4594-4603; Schmidt et al 2002 J Virol 76:1088-1089; Tang et al 2002 J Virol 78:11198-11207; Bernstein et al 2012 Pediatr Infect Dis 31:109-114; see also Example 1). This virus, called rB/HPIV3, consists of BPIV3 in which the F and HN genes were replaced using reverse genetics with those of HPIV3, combining the attenuation phenotype of BPIV3 in primates with the major neutralization antigens of HPIV3 (Schmidt et al 2001 J Virol 75:4594-4603; Schmidt et al 2002 J Virol 76:1088-1089; Tang et al 2002 J Virol 78:11198-11207; Bernstein et al 2012 Pediatr Infect Dis 31:109-114) rB/HPIV3 was shown to efficiently express the RSV F and G genes. Clinical evaluation of a lead rB/HPIV3/RSV-F construct as a bivalent vaccine for RSV and HPIV3 in seronegative children showed that it was infectious, well tolerated, and attenuated, but was less immunogenic against RSV F than hoped (Bernstein et al 2012 Pediatr Infect Dis 31:109-114). This appeared to be due at least in part to genetic instability in the clinical trial material that silenced expression of the RSV F insert (Yang, et al. 2013. Vaccine 31:2822-2827). However, further studies are underway to stabilize the RSV F insert and to obtain increased immunogenicity by characterizing and optimizing various parameters of vector construction (Liang, et al. 2014. J virology 88:4237-4250). HPIV1 is another attractive vector for expressing RSV F antigen. In particular, HPIV1 infects somewhat later in childhood than RSV or HPIV3 (Counihan, et al. 2001. Pediatric infectious disease journal 20:646-653; Reed, et al. 1997. J Infect Dis 175:807-813), and so an HPIV1-vectored RSV vaccine might be used subsequent to a live attenuated RSV or rB/HPIV3-vectored vaccine to boost immune responses to RSV.

In the present study, two parameters for developing an HPIV1-vectored vaccine expressing RSV F protein were evaluated (FIGS. 36 and 42): (i) two different attenuated HPIV1 backbones were compared, and (ii) insertion of the RSV F gene at the first, second, and third genome positions of the HPIV1 vector was compared. The first parameter, the level of attenuation, is important because it is linked to safety and, inversely, to immunogenicity. Specifically, the HPIV1 vector must be sufficiently attenuated so as to be non-pathogenic and well tolerated, but must replicate and express antigens sufficiently well to be satisfactorily immunogenic. The addition of a foreign gene, such as RSV F, to an HPIV vector also typically confers attenuation and also can confer the temperature-sensitivity (ts) phenotype (Liang, et al. 2014. J virology 88:4237-4250), and so the combined effect of the insert and specific attenuating mutation(s) had to be determined. The two different HPIV1 backbones used in the present study each contained a single attenuating mutation ($C^{\Delta 170}$ or $L^{Y942A}$) developed in previous studies (1, 3, 25). Each of these mutations has been shown to be moderately attenuating in vivo (Bartlett, et al. 2006. Vaccine 24:2674-2684; Bartlett, et al. 2007. Virology J 4:67; Newman, et al. 2004. J Virol 78:2017-2028). The $C^{\Delta 170}$ mutation is non-temperature sensitive. It reduces the ability of C proteins to inhibit the host type I interferon response and apoptosis (Bartlett, et al. 2006. Vaccine 24:2674-2684; Bartlett, et al. 2008. J virology 82:8965-8977; Newman, et al. 2004. J Virol 78:2017-2028) resulting in virus attenuation. The mechanism of attenuation has the potential to increase the inherent immunogenicity of the construct because this mutation in C increases the host interferon response and apoptosis response, both of which have the potential to increase immunogenicity. The $C^{\Delta 170}$ mutation consists of a 6-nucleotide deletion in the overlapping P and C ORFs. In the C ORF, this results in the deletion of two amino acids and the substitution of a third amino acid (specifically, the triplet 168-RDF-170 was changed to the single amino acid S), whereas in the overlapping P ORF it results in deletion of two amino acids (172-GF-173). Deletion mutations are thought to have increased stability because they offer greater genotypic and phenotypic stability due to low risk of same site reversion. The $L^{Y942A}$ mutation is temperature-sensitive. It is a missense mutation (942-Y to A) in the L ORF that was designed to involve 3 nt substitutions so as to be highly resistant to de-attenuation (FIG. 42), as has been directly documented (McAuliffe et al 2004. J Virol 78:2029-2036). (ii) The second parameter investigated in the present study, the position of insertion of the foreign gene in the HPIV genome, is important because it affects the level of expression of the foreign gene as well as its attenuating impact on the vector. In an HPIV genome, insertion of the RSV F gene closer to the promoter would be expected to provide a higher level of expression, due to the transcription gradient. However, the closer the foreign gene is to the promoter, the greater the number of downstream vector genes it can impact, because each of these vector genes is now one position further removed from the promoter and consequently is expressed less efficiently. In addition, placement of the foreign gene in the first position has the potential to affect the functioning of the promoter. The insertion of the foreign gene also can have unpredictable effects. It also can be attenuating through effects such as the increase in genome length and gene number.

Six viruses, representing three different insertion sites for RSV F in two different attenuated HPIV1 backbones, were constructed, rescued by reverse genetics, and analyzed for in vitro replication and expression of RSV F and vector proteins. The hamster model was used to assess in vivo replication (upper and lower respiratory tract), vaccine virus stability, immunogenicity, and protection against wt RSV challenge.

Materials and Methods

Cells and Viruses. LLC-MK2 (ATCC CCL-7) rhesus monkey kidney and Vero (ATCC CCL-81) African green monkey kidney cell lines were maintained in Opti-MEMI medium with GlutaMAX (Life Technologies, Grand Island, NY) supplemented with 5% fetal bovine serum (FBS; HyClone/Logan, UT) and 1 mM L-glutamine (Life Technologies). BSR T7/5 cells are baby hamster kidney 21 (BHK-21) cells that constitutively express T7 RNA polymerase (Buchholz, et al. 1999. J Virol 73:251-259). These cells were maintained in Glasgow minimal essential medium (GMEM; Life Technologies) supplemented with 10% FBS, 2 mM L-glutamine and 2% MEM amino acids (Life Technologies). Medium was also supplemented with 2% Geneticin (Life Technologies) at every other passage to select for cells that posses the T7 polymerase construct.

HPIV1 was propagated in LLC-MK2 cells. Before virus inoculation, LLC-MK2 cells, grown in media containing 5% FBS, were washed twice with 1× phosphate buffered saline (PBS) to remove FBS. Infection with HPIV1 was always performed in serum-free Opti-MEMI media containing 1.2% trypsin (TrypLE Select; Life Technologies), 100 U/ml Penicillin, 100 µg/ml Streptomycin (Life Technologies) and 1 mM L-glutamine. Infected cells were incubated at 32° C. till the appearance of cytopathic effects. For virus stock harvest, culture supernatant was harvested and clarified by centrifugation at 1500 rpm for 10 min at 4° C. Aliquots of virus stocks were snap-frozen on dry ice and stored at −80° C. HPIV1 titers were determined by 10-fold serial dilutions in 96-well plates on LLC-MK2 cells with serum-free Opti-MEMI media containing 1.2% trypsin as described above followed by incubation at 32° C. for 7 days. Infected cells were detected by hemadsorption (HAD) using guinea pig erythrocytes and titers were calculated as $\log_{10}$ tissue culture infective dose 50% ($TCID_{50}$/ml) as previously described (Bartlett, et al. 2006. Vaccine 24:2674-2684). The temperature sensitivity (ts) phenotype of each of the virus was studied by evaluating their efficiency of replication at 32, 35, 36, 37, 38, 39, and 40° C. as previously described Skiadopoulos, et al. 1999. Vaccine 18:503-510). Titration of each virus was performed in 96-well replicate plates of LLC-MK2 cells, as described above, and incubated in sealed containers in temperature-controlled water baths at various temperatures for 7 days. Titers were determined by HAD and reported as $TCID_{50}$/ml.

Design of rHPIV1-$C^{\Delta 170}$ and rHPIV1-$L^{Y942A}$ viruses expressing the RSV F antigen. The rHPIV1 viruses were constructed using the reverse genetic system derived from the wild type (wt) HPIV1 strain Washington/20993/1964 (GenBank accession AF457102) (Newman, et al. 2002. Virus Genes 24:77-92). The recombinant full-length antigenomic cDNA clone (pFLC) of HPIV1 was modified by site-directed mutagenesis to contain 3 additional unique restriction sites: MluI (ACGCGT, pre-N position, nucleotide numbers 113-118), AscI (GGCGCGCC, N-P position, nucleotide numbers 1776-1783) and NotI (GCGGCCGC, P-M position, nucleotide numbers 3609-3616). Two attenuated cDNA backbones were generated by introducing either the $C^{\Delta 170}$ (Bartlett, et al. 2007. Virology J 4:67) or the $L^{Y942A}$ (Bartlett, et al. 2007. Virology J 4:67; McAuliffe, et al. 2004. J virology 78:2029-2036) mutation into the P/C or L ORF, respectively, using the QuikChange Lightning Mutagensis Kit (Agilent, Santa Clara, CA) as per manufacturer's instructions. The following mutagenesis primers were used to generate the attenuated HPIV1 backbones. For HPIV1 $C^{\Delta 170}$ mutation, the forward primer was AAGAAGAC-CAAGTTGAGCCAGAAGAGGTACGAAG (SEQ ID NO: 121) and the reverse primer was CTTCGTACCTCTTCTGGCTCAACTTGGTCTTCTT (SEQ ID NO: 122). These primers introduced a 6-nucleotide deletion (GGATTT) between positions 17 and 18 compared to the P/C ORF (FIG. 42) keeping with the rule of six (Calain, et al. 1993. J Virol 67:4822-4830; Kolakofsky, et al. 1998. J Virol 72:891-899). As previously described (Bartlett, et al. 2007. Virology J 4:67), the $C^{\Delta 170}$ deletion in the P/C ORF includes an R168S substitution and a deletion of D and F from position 169-170 resulting in a change in the amino acid sequence of C protein from RDF to S. This mutation also affects the P ORF involving a deletion of two residues G and F from position 172-173. For the L$^{Y942A}$ mutation, the forward primer was CCAGCTAACATAGGAGGGTT-CAACGCGATGTCTACAGCTAGATGTTTTGTC (SEQ ID NO: 123) and the reverse primer was GACAAAA-CATCTAGCTGTAGACATCGCGTTGAACCCTC CTATGTTAGCTGG (SEQ ID NO: 124). In these primer sequences the mutation site TAT (Y) to GCG (A) at aa 942 in the L ORF is underlined. Mutagenesis primer pairs were PAGE 2-Step purified (Operon, Huntsville, AL). Clones with the desired mutation, as determined by sequencing, were then purified by plasmid maxiprep (EndoFree Plasmid Maxi Kit; Qiagen) and sequenced in entirety. The rHPIV1 pFLCs with either the C$^{Δ170}$ or the L$^{Y942A}$ mutation were digested with MluI, AscI, or NotI enzymes (New England Biolabs, Ipswich MA), treated with Calf Intestinal Phosphatase (New England Biolabs), and purified by gel extraction (QIAEX II Gel Extraction Kit; Qiagen, Valencia CA).

Figure 36:
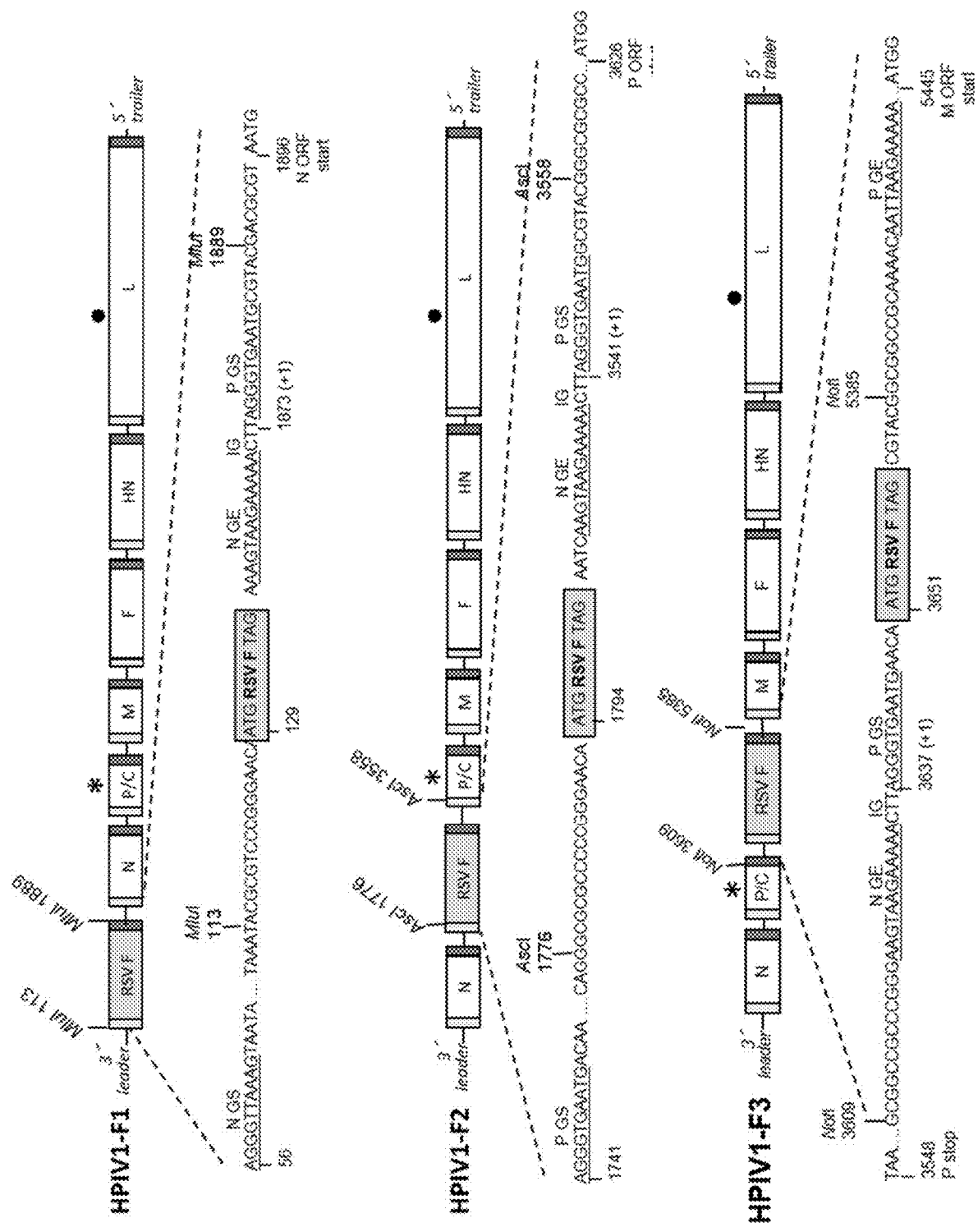
FIG. 36. Construction of antigenomic cDNAs of the HPIV1 $C^{D170}$ and $L^{Y942A}$ mutants containing the RSV F gene insert at the first (F1), second (F2), or third (F3) genome positions. The rHPIV1 backbones used for RSV F expression contained either of the two attenuating mutations: namely the $C^{D170}$ mutation (indicated by *) in the P/C gene or the $L^{Y942A}$ mutation (indicated by •) in L gene. For the HPIV1-F1 constructs, the RSV F gene was inserted at the first genome position before the HPIV1 N gene at the MluI site located in the upstream non-translated region of the N gene. In case of HPIV1-F2, the RSV F gene was inserted between the HPIV1 N and P genes at the AscI site located in the upstream non-translated region of the P gene. For the HPIV1-F3, the RSV F gene was cloned between the HPIV1 P and M genes at the NotI site situated in the downstream non-translated region of the P gene. For all constructs, the RSV F ORF was codon optimized for human expression and contained HEK amino acid assignments. A copy of the N gene-end (GE), intergenic (IG) CTT triplet, and P gene-start (GS) sequence was added following (F1, F2) or before (F3) the RSV F insert so that it was under the control of a set of HPIV1 transcription signals. The sequences of SEQ ID NOs: 138-140 are shown flanking the RSV F insert under HPIV1-F1; the sequences of SEQ ID NOs: 141-143 are shown flanking the RSV F insert under HPIV1-F2, and the sequences of SEQ ID NOs: 144-145 are shown flanking the RSV F insert under HPIV1-F3.

The RSV F gene from strain A2 with HEK amino acid assignments: Glu and Pro at aa position 66 and 101, respectively (Whitehead, et al. 1998. *J virology* 72:4467-4471) was optimized for human codon usage (GeneArt, Life Technologies, Grand Island, NY). RSV F gene insert was designed (FIG. 36) to include the HPIV1 transcriptional regulatory sequences: gene end (GE)-intergenic (IG)-gene start (GS) signals to allow for RSV F expression as an independent transcript. For all constructs, the RSV F gene insert was designed to include HPIV1 N GE (AAGTAAGAAAAA, SEQ ID NO: 125) and P GS (AGGGTGAATG, SEQ ID NO: 126) sequences along with the conserved IG sequence (CTT), while keeping the +1 phasing for the P GS. RSV F inserts were generated by PCR with the corresponding flanking MluI, AscI, or NotI restriction sites complimentary to those in the HPIV1 FLCs for insertion in the first Pre-N (F1), second N-P (F2), or third P-M (F3) positions, respectively (FIG. 36). The following PCR primers were used to generate the RSV F inserts. For RSV F fragments containing MluI restriction sites for insertion into the first F1 gene position the forward primer was ACGCGTCCCGG-GAACAATGG AACTGCTGATCCTGAAGGC-CAACGCC (SEQ ID NO: 127) and the reverse primer was ACGCGTCGTACGCATTCACCCTAAGTTTTTCT-TACTTTCTATCAGTTGGAGAAGGCGATATT GTT-GATGCCGG (SEQ ID NO: 128). For RSV F fragments containing the AscI restriction sites for insertion into the second F2 gene position the forward primer was (SEQ ID NO: 129)
GGCGCGCCCCGGGAACAATGGAACTGCTGATCCTGAAGGCCAACGCC and the reverse primer was (SEQ ID NO: 130)
GGCGCGCCCGTACGCATTCACCCTAAGTTTTTCTTACTTGATT*CTATCA*

GTTGGAGAAGGCGATATTGTTGATGCCGG.

For RSV F fragments containing the NotI restriction sites for insertion into the third F3 gene position the forward primer was (SEQ ID NO: 131)
GCGGCCGCCCGGGAAGTAAGAAAAACTTAGGGTGAATGAACAATGGAAC

TGCTGATCCTGAAGGCCAACGCC and the reverse primer was (SEQ ID NO: 111)
GCGGCCGCCGTACGCTATCAGTTGGAGAAGGCGATATTGTTGATGCCGG.

Recovery of rHPIV1 C$^{Δ170}$ and rHPIV1 L$^{Y942A}$ viruses expressing the RSV F antigen. The rHPIV1 C$^{Δ170}$ backbones expressing RSV F from the first (HPIV1 C$^{Δ170}$-F1), second (HPIV1 C$^{Δ170}$-F2), and third (HPIV1 C$^{Δ170}$-F3) positions and the rHPIV1 L$^{Y942A}$ viruses expressing RSV F from the first (HPIV1 L$^{Y942A}$-F1), second (HPIV1 L$^{Y942A}$-F2), and third (HPIV1 L$^{Y942A}$-F3) positions were rescued from cDNA by using the HPIV1 reverse genetics system (Newman, et al. 2002. Virus Genes 24:77-92) in BSR T7/5 cells constitutively expressing T7 RNA polymerase (Buchholz et al. 1999. J. Virology 73:251-259). This rHPIV1 cDNA is derived from the Washington/20993/1964 (HPIV1 WASH/64) clinical isolate. The BSR T7/5 cells were grown to 90% confluency in 6-well plates and co-transfected with the antigenome pFLC plasmid (5 ug) to be rescued along with pTM-N (0.8 ug), pTM-P (0.8 ug) and pTM-L (0.1 ug) support plasmids expressing HPIV1 N, P and L proteins, respectively, using Lipofectamine 2000 (20 ul) (Life Technologies) as previously described (Bartlett, et al. 2005. *Vaccine* 23:4631-4646; Newman, et al. 2002. Virus Genes 24:77-92). Transfected cells were incubated overnight at 37° C., washed twice with OptiMEM media (Life Technologies, Grand Island, NY) and fresh OptiMEM containing 1 mM L-glutamine and 1.2% trypsin was added to the cells followed by incubation at 32° C. At 48 h post-transfection, cells were harvested by scraping into the medium and the cell suspension was added to 50% confluent monolayers of LLC-MK2 cells in OptiMEM, 1 mM L-glutamine, 1.2% trypsin (Life Technologies) and incubated at 32° C. Virus was harvested after 7 days and was further amplified by one (HPIV1-C$^{Δ170}$) or two (HPIV1-L$^{Y942A}$) passages in LLC-MK2 cells at 32° C. Virus titers were determined by 10-fold serial dilutions on LLC-MK2 cells in 96-well plates as described above. All recombinant viruses were sequenced to confirm the lack of adventitious mutations. For this, viral RNA was extracted (QiaAmp Viral RNA Mini Kit; Qiagen, Valencia, CA) from virus stocks and treated with RNase free DNase I (Qiagen) to remove the plasmid DNA used for virus rescue. RNA was reverse transcribed (SuperScript First-Strand Synthesis System for RT-PCR; Invitrogen/Life Technologies) and overlapping genome regions were amplified by RT-PCR (Advantage-HF 2 PCR Kit; Clontech Laboratories). RT-PCR controls lacking the reverse transcriptase were included for all viruses, which showed that the amplified products were derived from viral RNA and not from the pFLC cDNA used for virus recovery. The genome sequence of each virus construct was determined by direct Sanger sequencing of the overlapping amplified RT-PCR products. Sequence reads were aligned and the genome sequence was assembled using Sequencher program-version 5.1 (Gene Codes Corporation, Ann Arbor, MI).

Replication of chimeric rHPIV1 viruses in Vero and LLC-MK2 cells. Triplicate wells of Vero or LLC-MK2 cell monolayers in 6-well plates were infected at a multiplicity of infection (MOI) of 0.01 TCID$_{50}$ with HPIV1 (C$^{Δ170}$ or L$^{Y942A}$) viruses expressing RSV F (F1, F2, or F3), or the empty HPIV1 C$^{Δ}$170 or HPIV1 L$^{Y942A}$ vector, or wt HPIV1. Cultures were incubated at 32° C. Aliquots of 0.5 ml from a total 2 ml cell culture supernatant medium were collected at 24 h intervals from each well and replaced by fresh media. The samples were flash frozen and stored at −80° C. Virus titers ($\log_{10}$ TCID$_{50}$/ml) were determined by serial dilution on LLC-MK2 cells followed by detection of infected cells by HAD as described above.

Analysis of RSV F and HPIV1 vector protein expression by Western blotting. Vero cells ($1 \times 10^6$) were infected with HPIV1 C$^{\Delta 170}$ or HPIV1 L$^{Y942A}$ constructs expressing RSV F from either of the three genome positions (F1, F2, or F3). Empty HPIV1 C$^{\Delta 170}$ and HPIV1 L$^{Y942A}$ vector, wt HPIV1, and mock treated cells were used as controls. Infections were performed at an MOI of 5 TCID$_{50}$ per cell and incubated at 32° C. At 48 h post-infection (post-infection), monolayers were washed twice with PBS and lysed with 400 ul of 1×LDS sample buffer (Life Technologies). For electrophoresis, lysates were reduced and denatured by mixing with 1× reducing reagent (Life Technologies) and incubation at 37° C. for 30 min. Reduced denatured lysate (40 µl) was loaded onto 4 to 12% Bis-Tris NuPAGE gels (Novex-Life Technologies) and electrophoresis performed in 1×MOPS buffer. Proteins were transferred onto PVDF membranes using the iBlot protein transfer system (Life Technologies). Membranes were blocked for 1 h in Licor blocking buffer (Licor Inc. Lincoln, NE) and probed with a murine monoclonal RSV F specific antibody (ab43812; Abcam, Cambridge, MA) and a rabbit polyclonal HPIV1 N specific antibody (HPIV1-N-485) at 1:1000 dilution in blocking buffer. HPIV1-N-485 was generated by immunization of rabbits with the KLH-conjugated N peptide spanning the amino acid (aa) residues 485-499 of N as previously described (Bartlett, et al. 2010. Vaccine 28:767-779). Replicate blots performed with the same set of lysates were probed with the rabbit polyclonal antisera for HPIV1 P (SKIA-1), F (SKIA-15), or HN (SKIA-13) which were also raised by repeated immunization of rabbits with the KLH-conjugated peptide, and were used at 1:200 dilution. After overnight incubation with the above antibodies, the membranes were washed 4×, 5 min each, followed by incubation with the secondary antibodies, diluted in the Licor blocking buffer, for 1 h. The corresponding infra-red dye-conjugated secondary antibodies were goat anti-mouse IRDye 680LT and goat anti-rabbit IRDye 800CW (LiCor). Membranes were scanned and the blot images were acquired using an Odyssey infrared imaging system (LiCor). Fluorescence intensities of the protein bands, derived from three independent experiments, were quantified by using the Licor image analysis suite (Image Studio) and reported as expression of RSV F or HPIV1 vector proteins (N, P, F, and HN) relative to F3 viruses.

Percentage of virions expressing RSV F determined by fluorescent double-staining plaque assay. An infrared fluorescence based two-color plaque assay was developed to simultaneously detect the expression of RSV F and HPIV1 proteins in the plaques formed by the HPIV1 vectors expressing RSV F on Vero cell monolayers. Each virus was 10-fold serially diluted in OptiMEM media containing 1 mM L-glutamine and 1.2% trypsin and 100 µl of each dilution was added in duplicate to Vero cell monolayers grown in 24-well plates. Inoculated cells were incubated for 2 h at 32 C on a rocker after which an overlay OptiMEMI media containing 0.8% methylcellulose (Sigma Aldrich, St. Louis, MO), 1 mM L-glutamine, 4% trypsin, 100 U/ml Penicillin, and 100 µg/ml Streptomycin was added to each well. For animal tissue derived virus samples, Timentin (200 mg/ml), Ampicillin (100 mg/ml), Cleocin (150 mg/ml), and Amphotericin B (250 µg/ml) were included in the methylcellulose overlay instead of Penicillin and Streptomycin. After incubation for 6 days at 32 C, cells were fixed twice with 80% cold methanol. The rHPIV1-RSV F plaques were detected on infected Vero cell monolayers by co-immunostaining with a mixture of three RSV F-specific monoclonal antibodies at a 1:2000 dilution each, as previously described (Murphy, et al. 1990. Vaccine 8:497-502) and an HPIV1 specific goat polyclonal antibody (ab20791; Abcam) at a 1:1600 dilution in Licor blocking buffer. After 1 h incubation, cells were washed once with 1 ml blocking buffer and incubated with the secondary antibody mixture containing infrared dye-conjugated goat anti-mouse 680LT and the donkey anti-goat 800CW (LiCor) each at a 1:800 dilution in the blocking buffer. Cells were washed twice with 1×PBS and images of the co-stained plaques were acquired by scanning the plates on an Odyssey infrared imaging system (LiCor). Wells containing fewer than 50 plaques were chosen for analysis and the percentage of rHPIV1 plaques positive for RSV F expression was determined. This assay was employed to assess the stability of RSV F expression by determining the percent population expressing RSV F in the vaccine inoculum as well as in the virus isolated from hamsters after in vivo replication.

Hamster Studies

Virus replication in hamsters. All animal studies were approved by the National Institutes of Health (NIH) Institutional Animal Care and Use Committee (IACUC). In vivo replication of each virus at 3 and 5 days post-infection as well as the immunogenicity was assessed in hamsters. Six-week old Golden Syrian hamsters were confirmed to be seronegative for HPIV1 and RSV by analyzing pre-immune sera by hemagglutination inhibition (HAI) assay and an RSV neutralization assay, respectively (Coates, et al. 1966. Am J Epidemiol 83:299-313; Coates, et al. 1966. J Bacteriol 91:1263-1269; van Wyke Coelingh, et al. 1988. J Infect Dis 157:655-662). Groups of 6 hamsters per virus were anesthetized and inoculated intranasally with 0.1 ml L15 medium (Life Technologies) containing $10^5$ TCID$_{50}$ of the virus per animal. To evaluate replication, hamsters were euthanized on days 3 and 5 post-infection and nasal turbinates and lungs were collected for virus titration. Tissue homogenates in L15 medium containing Timentin (200 mg/ml), Ampicillin (100 mg/ml), Cleocin (150 mg/ml), and Amphotericin B (250 ug/ml) were titrated by serial dilution on LLC-MK2 cells followed by detection of virus infection by HAD. Virus titers were reported as TCID$_{50}$/gram of hamster tissue. Tissue homogenates were also titrated by plaque assay on Vero cells and stained for the expression of RSV F and HPIV1 proteins by using the fluorescent double staining plaque assay as described above. Results were reported as percent HPIV1 plaques expressing RSV F.

Immunogenicity

Induction of virus neutralizing antibodies (NAbs) in serum against RSV and HPIV1 [60% plaque reduction neutralization test (PRNT$_{60}$)]. To assess immunogenicity of the vaccine candidates, hamsters were immunized as described above and sera were collected from hamsters at day 28 after immunization. Titers of RSV specific neutralizing antibodies (NAbs) were determined by PRNT$_{60}$ on Vero cells as previously described (Coates, et al. 1966. Am J Epidemiol 83:299-313) using the eGFP-expressing RSV (Munir, et al. 2008. J Virol 82:8780-8796). Hamster sera were incubated at 56° C. for 30 min to inactivate the complement proteins followed by serial dilution in Opti-MEMI, 2% FBS, 1× Gentamicin media in 96-well plates. RSV-eGFP diluted in Opti-MEM, 2% FBS, 1× Gentamicin, 10% guinea pig complement (Yoder, et al. 2004. J medical virology 72:688-694) (Lonza, Walkersville, MD) was further diluted 1:1 by mixing with an equal volume of serially diluted serum samples followed by 30 min incubation at 37°

C. A volume of 100 µl of serum-virus mix was added to Vero cells grown in 24-well plates and virus was allowed to adsorb for 2 h on the rocker at 32° C. An overlay of Opti-MEMI, 8% methylcellulose, 2% FBS, 1× Gentamicin was added and incubated for 5-6 days to allow plaque formation. RSV plaques on monolayers were visualized by scanning and acquiring images using Typhoon Imager (GE Healthcare, Piscataway, NJ). Plaque counts for each sample were determined and the NAb titer was determined as described (Coates, et al. 1966. Am J Epidemiol 83:299-313). Titers of HPIV1-specific NAbs were also determined by 60% plaque reduction assay on Vero cells, using the methods as described for RSV, using GFP-expressing rHPIV1 with the following modifications: First, in case of HPIV1 neutralization assay, guinea pig complement was not used as it was found to neutralize the virus, second, the inoculated Vero cells were washed twice with 1×PBS after virus adsorption to remove serum, and third a methylcellulose overlay medium containing 4% trypsin and lacking FBS was used.

The ability of vaccine candidates to protect against RSV infection was tested by challenge infection of hamsters at 30 days post-immunization by intranasal inoculation with 0.1 ml L15 medium containing $10^6$ PFU of wt RSV strain A2. Hamsters were euthanized and nasal turbinates and lungs were harvested 3 days post-challenge and viral loads of challenge RSV in these tissues were determined by plaque assay on Vero cells (Durbin, et al. 2003. Clinical infectious diseases 37:1668-1677; Luongo, et al. 2013. J virology 87:1985-1996).

Results

Creation of two attenuated HPIV1 backbones (rHPIV1 $C^{\Delta 170}$ and rHPIV1 $L^{Y942A}$) expressing the RSV F protein from three different genome locations. Two attenuated HPIV1 backbones were prepared that each contained a different, previously identified attenuating mutation (namely, $C^{\Delta 170}$ and $L^{Y942A}$) that had been designed for stability against de-attenuation (Introduction, FIGS. 36 and 42). The $C^{\Delta 170}$ mutation did not confer temperature-sensitivity while the $L^{Y942A}$ mutation was a temperature sensitivity mutation. Next, the RSV F ORF of strain A2 was codon-optimized for human expression and engineered to be under the control of HPIV1 gene-start and gene-end signals, and was inserted into the rHPIV1 $C^{\Delta 170}$ and rHPIV1 $L^{Y942A}$ backbones at three different, parallel genome locations: namely at the first gene position (Pre-N, yielding rHPIV1 $C^{\Delta 170}$-F1 and rHPIV1 $L^{Y942A}$-F1); at the second gene position (N-P, yielding rHPIV1 $C^{\Delta 170}$-F2 and rHPIV1 $L^{Y942A}$-F2): and at the third gene position (P-M, yielding rHPIV1 $C^{\Delta 170}$-F3 and rHPIV1 $L^{Y942A}$-F3) (FIG. 36). Each construct conformed to the "rule of six" (Calain, et al. 1993. J Virol 67:4822-4830). Each vector gene maintained its original hexamer spacing, while the F1, F2, and F3 inserts assumed the original hexamer spacing of the N, P, and P genes, respectively. The RSV F protein also carried the HEK amino acid assignments, Glu and Pro at residues 66 and 101, respectively (Whitehead, et al. 1998. *J virology* 72:4467-4471) which matches with the sequence of RSV F from early passages of strain A2 and also is consistent with most other clinical isolates.

The rHPIV1/RSV F viruses were recovered by reverse genetics. All viruses were rescued readily except for the rHPIV1 $L^{Y942A}$-F2 construct, which appeared to be recovered with low efficiency and required multiple passages to make a working pool. The complete sequence of each virus was determined to verify the absence of adventitious mutations. All of the rHPIV1/RSV-F virus working pools were free of apparent adventitious mutations except for the rHPIV1 $L^{Y942A}$-F2 virus: for this virus, nine clones were rescued of which only one had the correct genome sequence lacking adventitious mutations. The other eight clones contained adventitious mutations, which were predominantly in the HPIV1 transcriptional signals downstream of the HPIV1 N gene (N gene end-intergenic-P gene start) and preceding the RSV F ORF. Since the insertion sites of the RSV F gene in the second positions of the parallel rHPIV1 $L^{Y942A}$-F2 and rHPIV1 $C^{\Delta 170}$-F2 constructs were identical, this suggests that the problem with the former virus was specific to the $L^{Y942A}$ mutation (e.g., altered polymerase function) rather than the insertion site by itself.

Figure 37D:
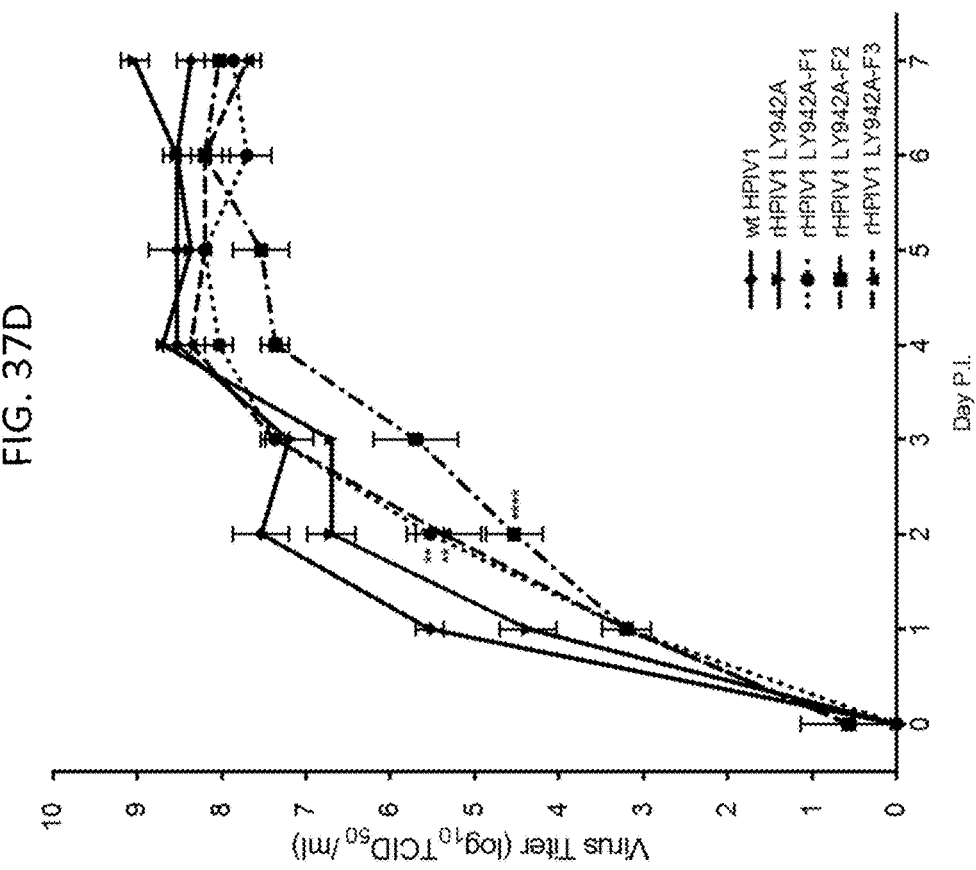
Figure 37C:
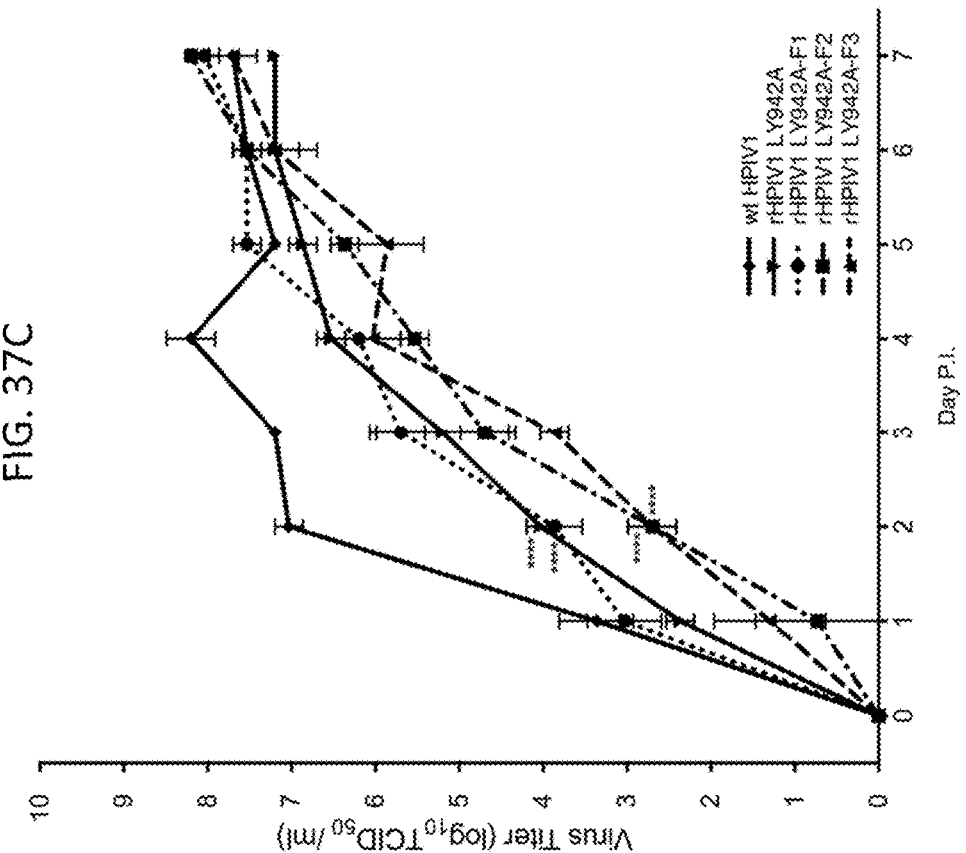

Replication of HPIV1/RSV F viruses in Vero and LLC-MK2 cells. Replication of HPIV1/RSV viruses was evaluated in vitro by determining their multistep growth kinetics in Vero (FIGS. 37A and 37C) and LLC-MK2 (FIGS. 37B and 37D) cells. Cells were infected at an MOI of 0.01 $TCID_{50}$ and incubated at 32° C. Supernatant was harvested at 24 h intervals over 7 days and virus titers were determined by HAD and reported as $TCID_{50}$/ml (FIG. 37). The Student t test was used to determine the statistical significance of difference between the titer of each virus versus wt HPIV1 for day 2 and 7 p.i. On day 7, all viruses replicated to final titers greater than 7.2 $log_{10}$ $TCID_{50}$/ml in Vero cells and 7.4 $log_{10}$ $TCID_{50}$/ml in LLC-MK2 cells, with slight differences among the viruses that were statistically insignificant compared to wt HPIV1 in both cell lines (FIG. 37). However, differences were observed at earlier time points, especially day 2 p.i. In the case of the rHPIV1 $C^{\Delta 170}$ viruses (FIGS. 37A and B), the rHPIV1 $C^{\Delta 170}$ empty vector and rHPIV1 $C^{\Delta 170}$-F3 replicated similar to wt HPIV1 in both cell lines on day 2 post-infection. However, the replication of rHPIV1 $C^{\Delta 170}$-F1 was significantly reduced in Vero ($p<0.001$) and LLC-MK2 ($p<0.05$) cells and that of the rHPIV1$C^{\Delta 170}$-F2 was significantly reduced ($p<0.01$) in Vero cells. For the rHPIV1 $L^{Y942A}$ viruses (FIGS. 37C and 37D), replication of the rHPIV1 $L^{Y942A}$ empty vector was significantly lower than that of the wt rHPIV1 in Vero cells, but both grew to similar titers in LLC-MK2 cells on day 2 post-infection. Highly significant reductions ($p<0.0001$) in replication as compared to wt rHPIV1 were observed for rHPIV1 $L^{Y942A}$-F1, -F2 and -F3 viruses in Vero cells. Likewise, the rHPIV1 $L^{Y942A}$-F1, -F2, and -F3 viruses showed significantly reduced ($p<0.01$, $p<0.0001$, and $p<0.01$, respectively) replication in LLC-MK2 cells. In Vero cells, rHPIV1 $L^{Y942A}$-F1 grew at the same rate as its parent rHPIV1 $L^{Y942A}$ empty vector while the growth of rHPIV1 $L^{Y942A}$-F2 and -F3 viruses (FIG. 37C) was relatively reduced, but these differences among the chimeric viruses were statistically insignificant.

Figure 38B:
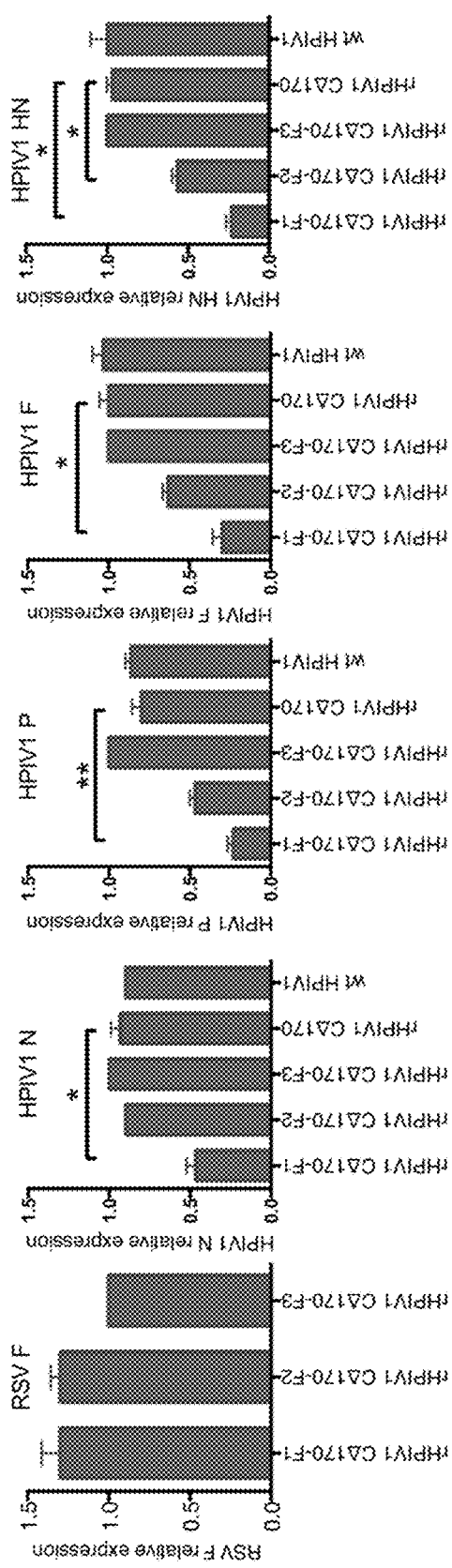

Expression of RSV F and HPIV vector proteins by the chimeric rHPIV1/RSV-F viruses. Expression of the RSV F protein and the HPIV1 vector N, P, F and HN proteins was evaluated for all viruses by Western blot analyses. Vero cells were infected at an MOI of 5 $TCID_{50}$ and incubated for 48 h at 32° C. Denatured and reduced lysates were subjected to SDS-PAGE and Western blot, and were analyzed using antibodies specific to each individual protein. RSV F is initially translated as the F0 precursor that is post-translationally cleaved by furin-like protease into disulfide-linked F1 and F2 subunits. Immunostaining with a monoclonal antibody specific to RSV F detected both F0 (70 kD) and F1 (48 kD). The HPIV1 N, P, F, and HN proteins were detected with corresponding anti-peptide polyclonal antibodies. Representative blots from one of three independent experiments are shown in FIG. 38A, and results from all three experiments are quantified for the rHPIV1 $C^{\Delta 170}$ and rHPIV1 $L^{Y942A}$ constructs in FIGS. 38B and C, respectively, with the values normalized relative to those of the F3 construct in each series as 1.0.

Figure 38C:
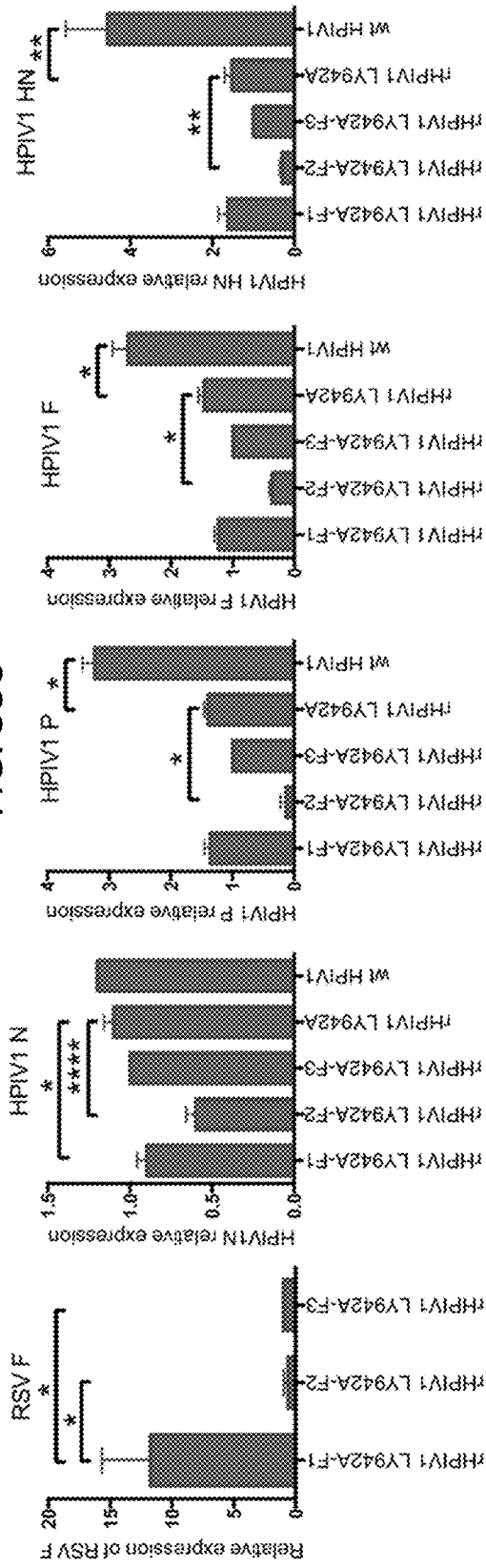

The HPIV1 $C^{\Delta 170}$-F1, -F2, and F3 viruses expressed substantial amounts of RSV F (FIG. 38A, lanes 1-3, and FIG. 38B) that were only slightly higher for F1 and F2 as compared to F3 as indicated by the protein band quantification (FIG. 38B) with the differences being statistically insignificant. Thus, unexpectedly, a 3'-5' polar gradient of expression from F1 to F3 was not observed. In contrast, however, a strong polar gradient of RSV F expression was observed in case of HPIV1 $L^{Y942A}$ viruses, with a significantly higher expression of RSV F by the F1 virus as compared to the F2 (p<0.01) and F3 (p<0.05) viruses (FIG. 38A, lanes 5-6, and FIG. 38C).

The expression of the vector N, P, F, and HN proteins was evaluated for wt HPIV1, the empty vectors, and the F1, F2, and F3 constructs in the $C^{\Delta 170}$ and $L^{Y942A}$ series. In general, the $C^{\Delta 170}$ mutation did not affect vector protein expression, with the result that the rHPIV1 $C^{\Delta 170}$ empty vector had a vector protein expression profile similar to that of wt rHPIV1 (FIG. 38B). In the case of the three versions of rHPIV1$C^{\Delta 170}$ vector expressing RSV F, the F3 virus expressed N, P, F, and HN at levels similar to that of empty rHPIV1$C^{\Delta 170}$ vector. The F2 virus expressed N protein similar to the empty rHPIV1$C^{\Delta 170}$ vector but showed reduced expression of P, F, and HN proteins of which only the HN reduction was statistically significant compared to the empty vector. The F1 virus demonstrated significant reduction in all vector proteins including N (p<0.05), P (p<0.01), F (p<0.05), and HN (p<0.05) compared to the empty vector. Thus, insertion of the RSV F gene into the rHPIV1 $C^{\Delta 170}$ vector reduced the expression of downstream vector genes except in the F3 virus. Both the F1 and F2 viruses exhibited significantly reduced replication early during infection of Vero cells (FIG. 37A), and the reduced synthesis of vector proteins provides a plausible explanation.

In contrast to the $C^{\Delta 170}$ mutation, the $L^{Y942A}$ mutation did affect the expression of vector proteins: specifically, compared with wt HPIV1, the rHPIV1 $L^{Y942A}$ empty vector had significantly reduced expression of the P (p<0.05), F (p<0.05), and HN (P≤0.01) proteins, with no significant difference for the N protein (FIGS. 38A, C). In case of the three versions of rHPIV1 $L^{Y942A}$ expressing RSV F, the F3 virus had modest reductions in the abundance of vector proteins as compared with the empty backbone, but none of the reductions was significant. Interestingly, this lack of significant vector protein reduction was consistent with the rHPIV1 $C^{\Delta 170}$-F3 virus, suggesting that the F3 insert position does not interfere with vector protein expression and provides a site for which interference with the vector is minimal. The F2 virus on the other hand exhibited highly pronounced and significant reduction in N, P, F, and HN proteins as compared to the rHPIV1 $L^{Y942A}$ empty vector. In comparison, the rHPIV1 $C^{\Delta 170}$-F2 virus, also showed reduced expression of the P, F, and HN proteins but not the N protein. This was to be expected because insertion after N at the second F2 position might be expected to reduce the expression of downstream genes due to the 3'-5' polar transcriptional gradient, whereas the upstream N gene might be expected to be unaffected, as was observed. Unexpectedly, however, in case of the rHPIV1 $L^{Y942A}$-F2, although RSV F was inserted downstream of the N gene, the expression of N protein was also negatively affected. The rHPIV1 $L^{Y942A}$-F1 had significantly reduced expression only in the case of the N protein, while expression of the P, F, and HN proteins was comparable to that of the rHPIV1 $L^{Y942A}$ empty vector.

Comparison of syncytium formation by rHPIV1/RSV-F vectors. A hallmark of RSV infection in vitro is the characteristic syncytium formation mediated by the RSV F protein. Infection of LLC-MK2 cell monolayers by wt HPIV3 or the rHPIV1 $C^{\Delta 170}$ or $L^{Y942A}$ empty vectors did not induce evident syncytium formation (FIG. 39, panels I, D, or H, respectively). In sharp contrast, HPIV1 vectors expressing high levels of RSV F protein, namely the rHPIV1 $C^{\Delta 170}$-F1 and -F2 viruses (FIGS. 39A and 39B) and the rHPIV1-$L^{Y942A}$-F1 virus (FIG. 39E), induced high levels of syncytia. Syncytium formation was not evident with the rHPIV1 $C^{\Delta 170}$-F3 virus (FIG. 39C) even though the level of expression of RSV F protein was only modestly less than with the F1 and F2 viruses (FIG. 38). Syncytium formation also was not evident with the rHPIV1-$L^{Y942A}$-F2 and -F3 viruses (FIGS. 39F and 39G), which expressed very low levels of RSV F protein (FIG. 38). This functional assay (syncytium formation) suggested that the RSV F protein expressed from the HPIV1 vectors was folded and processed correctly and accumulated at the cell surface in active form.

In addition, the $C^{\Delta 170}$ mutation was associated with a second cytopathic effect, namely increased apoptosis. This was most evident with the rHPIV1-$C^{\Delta 170}$ empty vector (FIG. 39D), because the enhanced apoptosis was more readily observed in the absence of syncytium formation. Enhanced induction of apoptosis due to the $C^{\Delta 170}$ mutation may explain why the rHPIV1-$L^{Y942A}$-F3 virus was inefficient in inducing syncytium formation (FIG. 39C) despite the expression of a high level of RSV-F (FIG. 38B): it is reasonable to suggest that the cell rounding associated with the $C^{\Delta 170}$-mediated enhanced apoptosis (e.g., FIG. 39D) might reduce the cell-to-cell contact necessary for syncytium formation, but very efficient expression of RSV F with other constructs might allow syncytium formation to begin sufficiently early to overcome the apoptosis effect (e.g., FIG. 39B versus FIG. 39C).

The observations made with LLC-MK2 cells in FIG. 39 also were obtained with Vero cells.

Temperature sensitivity of the rHPIV1/RSV-F viruses. As noted, the $C^{\Delta 170}$ mutation did not confer the ts phenotype in previous studies, whereas the $L^{Y942A}$ mutation did so (McAuliffe, et al. 2004. J virology 78:2029-2036; Newman, et al. 2004. J Virol 78:2017-2028). Insertion of RSV F into an HPIV vector also has been shown to confer the ts phenotype (Liang, et al. 2014. *J virology* 88:4237-4250). The HPIV1/RSV-F constructs were therefore evaluated for the presence and magnitude of the ts phenotype. Specifically, 10-fold serial dilutions were prepared and used to infect LLC-MK2 cells and incubated at 32, 35, 36, 37, 38, 39, and 40° C., in 7 replicates. Virus titers were determined by HAD using guinea pig erythrocytes, and titers were reported as $\log_{10}$ TCID$_{50}$/ml (FIG. 43). The reduction in titer ($\log_{10}$) at each restrictive temperature compared to the titer at the permissive temperature of 32° C. was calculated. The shut-off temperature for a given virus was defined as the lowest restrictive temperature at which the mean $\log_{10}$ reduction in virus titer at that temperature versus 32° C. was ≥2.0 $\log_{10}$ compared to that of wt rHPIV1 at the same two temperatures (Bartlett, et al. 2005. *Vaccine* 23:4631-4646). The ts phenotype was defined as having a shut-off temperature of ≤40° C.

While the $C^{\Delta 170}$ mutation did not confer the ts phenotype in previous studies, in the present study the rHPIV1 $C^{\Delta 170}$ empty vector had a shut-off temperature of 40° C. (FIG. 39) and thus was ts compared to wt HPIV1, but the effect was small. The rHPIV1 $C^{\Delta 170}$-F2 and -F3 constructs also had shut-off temperatures of 40° C. and thus did not differ significantly from the empty vector. However, the rHPIV1 $C^{\Delta 170}$-F1 virus had a lower shut-off temperature of 39° C. (FIG. 43). In the present study the rHPIV1 $L^{Y942A}$ empty vector had a shut-off temperature of 36° C., similar to the values of 35-37° C. associated with this mutation in previous studies (McAuliffe et al JVI 78:2029-2036, 2004; Bartlett et al Virol J 4:67, 2007). The rHPIV1 $L^{Y942A}$-F1 and -F2 constructs were more ts than the empty vector, with shut-off temperatures of 35° C., while the rHPIV1 $L^{Y942A}$-F3 vector had the same 36° C. shut-off temperature as the empty vector (FIG. 43). Thus, insertion of the RSV F gene into the F1 position of either attenuated backbone increased the ts phenotype, insertion into the F3 position of either backbone did not increase the ts phenotype, and insertion into the F2 position increased the phenotype only for the $L^{Y942A}$ backbone.

Percentage of virions in the vaccine inoculum that express RSV-F (vaccine stability in vitro). The working pools of the rHPIV1/RSV-F constructs were evaluated for the frequency of RSV F expression in individual viral plaques using a fluorescent double-staining plaque assay. Vero cells were inoculated with 10-fold serially diluted viruses and allowed to form plaques for 6 days under a methycellulose overlay at the permissive temperature of 32° C. Viral plaques were co-immunstained for RSV F and HPIV1 proteins by using a mix of three RSV F-specific murine monoclonal antibodies and a goat HPIV1-specific polyclonal antiserum (see Materials and Methods). The primary antibodies were detected using anti-mouse-IgG and anti-goat-IgG second antibodies conjugated with red and green infrared dyes, and the percentage of HPIV1 plaques expressing RSV F was determined. A total number of 140, 77, and 59 plaques were counted for rHPIV1 $C^{\Delta 170}$-F1, -F2, and -F3, respectively, and all were found to have 100% of the HPIV1 plaques expressing RSV F protein. F1 made plaques of smaller size than F2 and F3 while F2 and F3 plaque size was similar to each other. A total of 214, 70, and 192 plaques were counted for rHPIV1 $L^{Y942A}$-F1, -F2, and -F3, respectively, that showed 100%, 100%, and 97% of the HPIV1 plaques expressing RSV F antigen. Overall, the rHPIV1 $L^{Y942A}$ viruses formed plaques of much smaller size as compared to the rHPIV1 $C^{\Delta 170}$ viruses. Since the assay was performed at the permissive temperature (32° C.), the smaller plaque phenotype, suggesting a relatively more attenuated phenotype and slower spread, may not be a ts effect. This was also consistent with their relatively slower replication profile (FIG. 37).

Figure 40B:
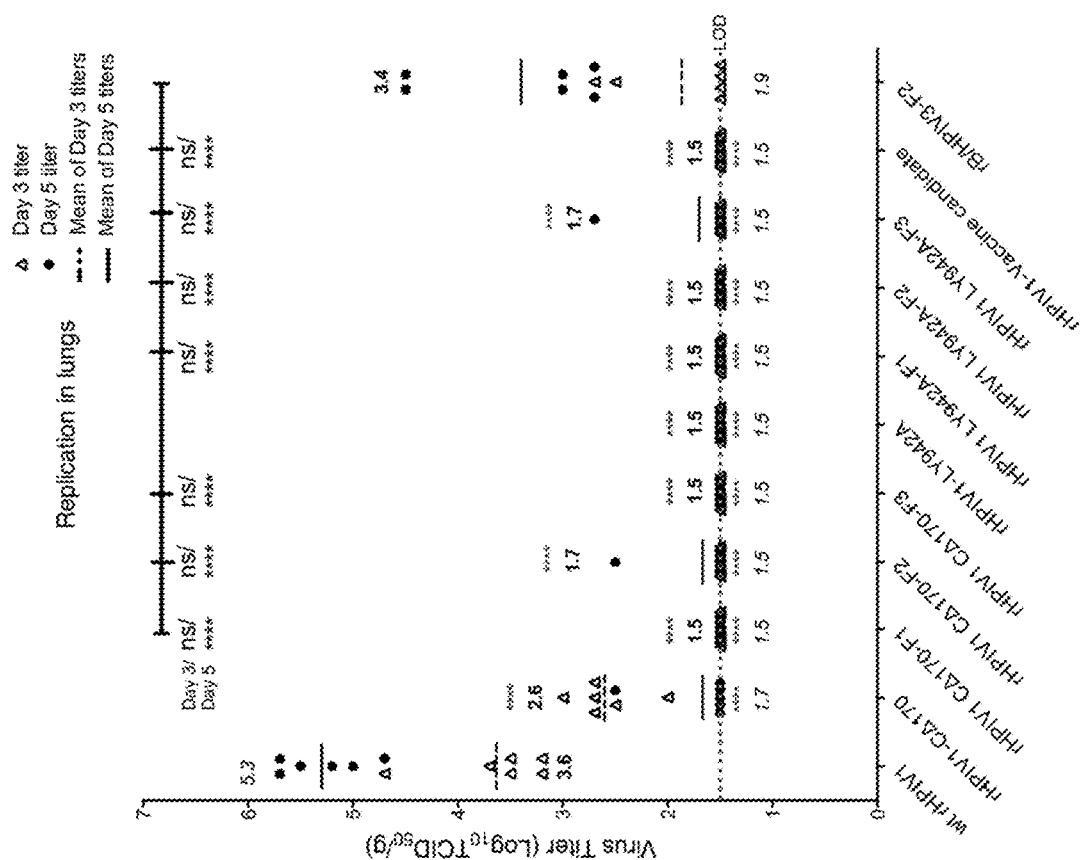
FIGS. 40A and 40B. Replication of RSV F expressing HPIV1 vectors in the nasal turbinates (40A) and lungs (40B) of hamsters. Hamsters were inoculated intra-nasally with $10^5$ $TCID_{50}$ of the wt HPIV1, rHPIV1 $C_{D170}$ or rHPIV1 $L^{Y942A}$ empty vectors, rHPIV1 $C_{D170}$ or rHPIV1 $L^{Y942A}$ expressing RSV F from three genome positions (F1, F2, or F3), rHPIV1-$C^{R84G}_{D170}$ $HN^{553A}L^{Y942A}$ (a previously-described HPIV1 vaccine candidate (Bartlett et al 2007 Virol J 4:6)), or the rB/HPIV3-F2, a chimeric bovine/human PIV3 expressing RSV F from the $2^{nd}$ position (also known as HEK/GA-opt, see FIG. 1). Virus titers were determined in LLC-MK2 cells by hemadsorption assay and reported as $\log_{10} TCID_{50}$/g of tissue. Titers for individual animals (6 per group) are shown for day 3 (Δ) and day 5 (•), each symbol representing an individual animal. The mean values are shown for each group in boldface for day 3 and in italicized type for day 5. The limit of detection (LOD) was 1.5 $\log_{10} TCID_{50}$/ml, indicated with a dotted line across the bottom of each graph. The statistical significance of the difference between each virus versus wt HPIV1 (red asterisks) or versus rB/HPIV3-F2 (bar at the top) was determined by One-way ANOVA at 95% confidence interval using Tukey's multiple comparisons test for day 3 and day 5 p.i . . . *, p≤0.05; *, p≤0.001; **, p≤0.0001; or ns, not significant.

Replication of the rHPIV1/RSV-F viruses in the respiratory tract of hamsters. Viruses were evaluated for their ability to replicate in the upper and lower respiratory tract (URT and LRT, respectively) of hamsters. Hamsters were inoculated intranasally with a dose of $10^5$ $TCID_{50}/0.1$ ml per animal. To assess virus replication, hamsters were euthanized on days 3 and 5 post-infection (6 animals per virus per day) and the nasal turbinates (URT) and lungs (LRT) were collected. Homogenates of individual nasal turbinates and lungs were analyzed for virus replication by titration on LLC-MK2 cells using HAD assay, and the titers were reported as $\log_{10} TCID_{50}/ml$. Virus titers are shown for days 3 and 5 as open triangles and filled circles, respectively, in the URT (FIG. 40A) and the LRT (FIG. 40B). Each symbol represents an individual animal.

Overall, the peak virus titers for all rHPIV1 vectors expressing RSV F were lower than that of the wt HPIV1 suggesting the attenuating effects of the backbone mutations ($C^{\Delta 170}$ or the $L^{Y942A}$) as well as that of the inserted RSV F gene. In the URT, the rHPIV1 $C^{\Delta 170}$ empty vector was significantly attenuated on day 5 and not on day 3 but was significantly restricted on both days in the lungs as compared to the wt HPIV1. In the URT, significantly reduced replication was observed for rHPIV1 $C^{\Delta 170}$-F1 on day 3 (p<0.05) only and for -F2 on both days (p<0.0001); -F3 replicated at levels similar to those of wt rHPIV1 on both days. rHPIV1 $C^{\Delta 170}$-F1, -F2, and -F3 were all significantly (p<0.0001) attenuated in the lungs on day 3 and 5; F1 and F3 were undetectable in all and F2 was undetectable in 5 of 6 animals. The rHPIV1 $L^{Y942A}$ empty vector replication was significantly reduced on day 3 and no virus was detected on day 5 in the URT whereas no virus was detected on both days in the lungs suggesting significant attenuation consistent with the ts phenotype of the $L^{Y942A}$ mutation (McAuliffe, et al. 2004. J virology 78:2029-2036) (FIG. 43). The rHPIV1 $L^{Y942A}$-F1, -F2, and -F3 viruses were also significantly (p<0.0001) attenuated both in the URT and lungs on day 3 and 5 with virus replication undetectable for majority of the animals.

The HPIV1 vaccine candidate (rHPIV1-$C^{R84G/\Delta 170}HN^{553A}L^{Y942A}$) previously demonstrated to be strongly attenuated in AGMs (Bartlett, et al. 2007. Virology J 4:67) and over attenuated in sero-negative children, was included as a control for replication comparison and to assess the level of attenuation of the vaccine candidates being developed. As expected, this virus was significantly attenuated in hamsters with no replication observed in the URT and lungs on day 3 and 5. The observation that most of the constructs developed in the present study had attenuated but detectable replication suggests that they are somewhat less attenuated than the previous vaccine candidate, which was over-attenuated in children, suggesting that the constructs developed in the present study may have suitable attenuation phenotypes. The chimeric bovine/human PIV3 expressing RSV F from the second genome position (rB/HPIV3-F2) is being developed as a live RSV vaccine (Introduction, and Example 1). In clinical trials, this vaccine candidate was found to be safe in 6-24 month old RSV seronegative children with a safe and well-tolerated level of replication (Bernstein, et al. 2012. Pediatric infectious disease journal 31:109-114). The rB/HPIV3-F2 virus was included as a reference virus for the comparative assessment of attenuation and immunogenicity of the rHPIV1 vaccine candidates being tested. The replication level of the rHPIV1 $C^{\Delta 170}$-F1, -F2, or -F3 on both days was either statistically similar to or significantly lower than that of the rB/HPIV3-F2 in both the URT and lungs. Likewise, the rHPIV1 $L^{Y942A}$-F1, -F2, and -F3 viruses also showed significantly reduced replication in both the URT and lungs on day 3 and 5 as compared to rB/HPIV3-F2. These data suggest that the HPIV1 vectors with either the $C^{\Delta 170}$ or the $L^{Y942A}$ backbone mutations are sufficiently attenuated in vivo and show replication phenotype that is similar to or even more attenuated than the rB/HPIV3-F2 virus.

In the URT, the titers for all viruses (except rHPIV1 $L^{Y942A}$-F1 and -F3, which did not replicate) were higher on day 3 (FIG. 40A) than on day 5. In contrast, rB/HPIV3-F2 attained peak titer on day 5. Overall, in the lungs, all vectors expressing RSV F were significantly (p<0.0001) restricted as compared to wt HPIV1 on days 3 and 5 post-infection (FIG. 40B) and were also significantly restricted as compared to rB/HPIV3-F2 on day 5.

Stability of RSV F protein expression by the chimeric rHPIV1 viruses after in vivo replication. Positive selection of viruses that silence the expression of RSV F may happen during replication in vivo that may compromise RSV F immunogenicity (Yang, et al. 2013. Vaccine 31:2822-2827). Mutations may occur in the RSV F ORF or the regulatory transcriptional signals controlling its expression such that the RSV F protein expression is either reduced or ablated. To evaluate the rHPIV1 vectors for in vivo stability, Vero cells were infected with serially diluted homogenates of the nasal turbinates and lungs of the infected hamsters. A fluorescent double immunostaining plaque assay was performed to determine the percentage of virus particles expressing RSV F. Consistent with the lack of replication in the lungs (FIG. 40B), no plaques could be detected for all vectors expressing RSV F in the lung homogenates. Similarly, no plaques were detectable for the rHPIV1 $L^{Y942A}$ viruses expressing RSV F in the URT due to poor replication. The stability results for rHPIV1 $C^{\Delta170}$ viruses, which replicated efficiently in the URT are shown (FIG. 44). These viruses were stable after in vivo replication with an overall >98% plaques expressing RSV F on days 3 and 5 post-infection Of the 30 samples analyzed, 29 had 100% and only one sample had 98% (2% loss) PFUs expressing RSV F. These data suggest that the rHPIV1 $C^{\Delta170}$ vectors expressing RSV F are quite stable in hamster model and did not show evidence of the selection of mutants with silenced RSV F expression after in vivo replication for at least 5 days.

Immunogenicity

Figure 40A:
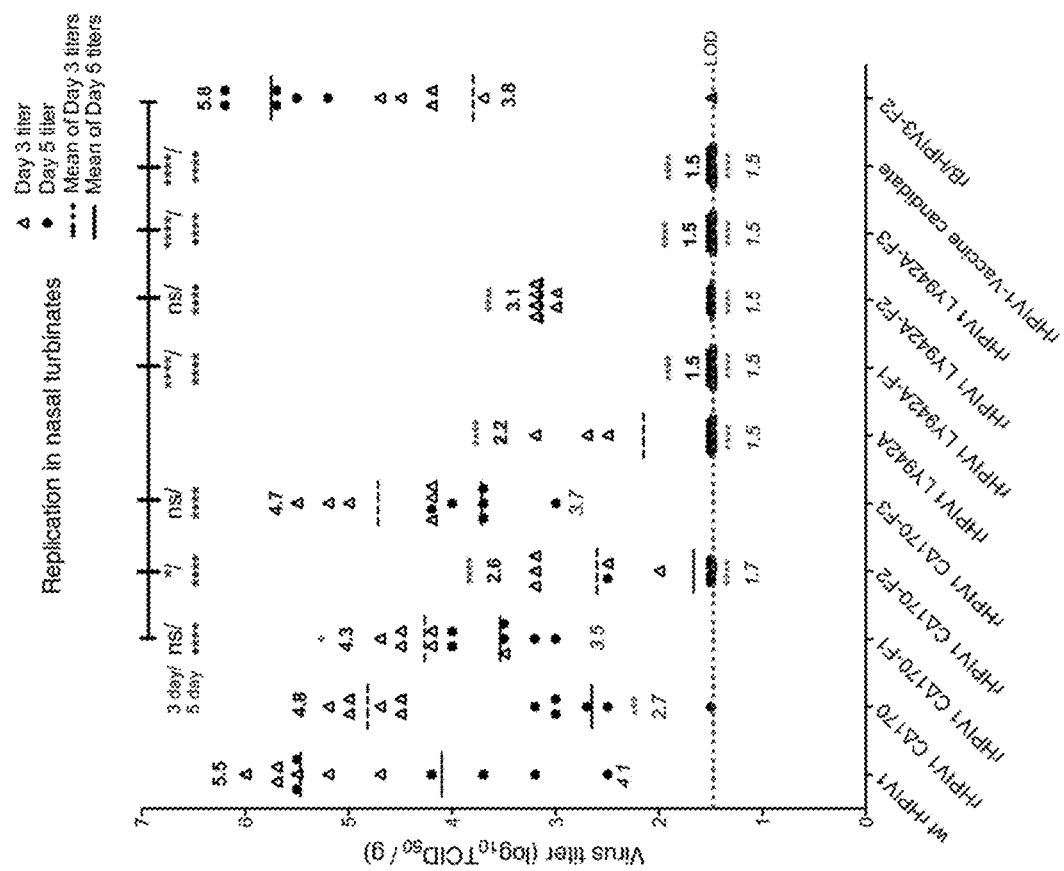

Immunization with the chimeric rHPIV1 viruses expressing RSV F induces serum virus neutralizing antibodies (NAbs) against RSV and HPIV1. To determine the immunogenicity of the rHPIV1 viruses expressing RSV F, groups of six hamsters per virus were inoculated intranasally with $10^5$ $TCID_{50}$ per animal. wt RSV, rHPIV1 $C^{\Delta170}$, rHPIV1 $L^{Y942A}$, and rB/HPIV3-F2 were included as controls. Sera from immunized hamsters were collected at 28 days post-infection and the NAb titers against RSV and HPIV1 were determined by $PRNT_{60}$ assay (FIG. 45). The rHPIV1 $C^{\Delta170}$-F1, -F2, and -F3 induced RSV-specific NAbs at titers that were not statistically different from each other. This was not surprising because all three viruses showed similar level of RSV F protein expression (FIGS. 38A and 38B). The rHPIV1 $C^{\Delta170}$-F1 and -F2 had a slightly higher RSV F expression than the -F3 virus but this difference was not statistically significant (FIG. 38B). Likewise, the -F1 and -F2 viruses also showed relatively higher fusion activity and syncytia formation than the -F3 virus that is presumably correlated with the amount of RSV F synthesized during infection (FIG. 39A-39C) Although statistically insignificant, the NAb titer seems to be slightly higher for F1 and F3 viruses as compared to F2 which is more consistent with their in vivo replication profile (FIG. 40A) rather than the amount of RSV F expressed. The RSV NAb titer induced by rHPIV1 $C^{\Delta170}$-F1, -F2, and -F3 were significantly lower than that induced by rB/HPIV3-F2, a difference that likely stems from the significantly reduced replication of these viruses as compared to rB/HPIV3-F2 (FIGS. 40A and 40B).

The rHPIV1 $L^{Y942A}$-F1, -F2, and -F3 viruses failed to induce NAb response to RSV. This was unexpected because the rHPIV1 $L^{Y942A}$-F1 showed RSV F expression similar to that of rHPIV1 $C^{\Delta170}$-F1, -F2, and -F3 on in vitro infection of Vero cells (FIG. 38A). However, it is important to note that the $L^{Y942A}$ mutation is highly attenuating and confers a ts phenotype with a shut-off temperature of 36° C. (FIG. 43).

The $L^{Y942A}$ mutant viruses were expected to show minimal or no detectable replication in hamsters (body temperature: 36.7 to 38.3° C.; The Merck Manual). Consistent with the backbone phenotype, the rHPIV1 $L^{Y942A}$-F1, -F2, and -F3 were also ts with a shut off temperature of 35° C., 35° C., and 36° C., respectively, indicating that the insertion of RSV F at the F1 and F2 positions reduced the shut off temperature by 1° C. making them even more ts. Therefore, although the rHPIV1 $L^{Y942A}$-F1 was able to express RSV F at levels comparable to those of the rHPIV1 $C^{\Delta170}$-F1, -F2, and -F3 viruses at permissive temperature (FIG. 38A), it failed to induce RSV NAbs likely due to its strong ts phenotype and inability to replicate in vivo. The rHPIV1 $L^{Y942A}$-F2 and -F3 viruses seemingly had two confounding factors: they showed relatively poor RSV F expression (FIGS. 38A and 38C) and in addition were ts and did not replicate in vivo (FIGS. 40A and 40B), resulting in lack of an RSV NAb response. Thus, the rHPIV1 $L^{Y942A}$-F1, -F2, and -F3 viruses were not immunogenic and did not generate vaccine candidates because of their over attenuated ts phenotype and lack of replication and immunogenicity in vivo.

The HPIV1 specific NAb response in hamsters was also evaluated by $PRNT_{60}$ assay (FIG. 45). Overall, the levels of HPIV1 NAb titers were lower as compared to the RSV NAb titers. As indicated in the methods, guinea pig complement was included in the neutralization assay for RSV but was excluded from the HPIV1 neutralization assay as it neutralizes HPIV1. The lack of complement may be the reason for generally reduced HPIV1 NAb titers. The rHPIV1 $C^{\Delta170}$-F2 and -F3 viruses did not induce detectable levels of HPIV1 NAbs. Only the rHPIV1 $C^{\Delta170}$ empty vector and the rHPIV1 $C^{\Delta170}$-F1 induced detectable HPIV1-specific NAb responses, which were at titers that were not statistically different from each other. This was contrary to the expectation because the expression of all vector proteins was significantly reduced for rHPIV1 $C^{\Delta170}$-F1 (FIGS. 38A and 38B). It also had a lower shut off temperature by 1 C as compared to the F2 or F3 viruses and it replicated in vivo at levels similar to those of F3 virus. Thus, the rHPIV1 $C^{\Delta170}$-F1 was expected to induce similar or weaker HPIV1 specific NAb response as compared to the -F3 virus. However, the poor HPIV1 immunogenicity of the $C^{\Delta170}$-F2 was consistent with its reduced expression of F and HN proteins (FIG. 38B) and poor replication in the URT and LRT (FIG. 40). The lack of HPIV1 NAb response was unexpected for the $C^{\Delta170}$-F3 virus. It expressed all HPIV1 proteins at levels similar to those of the empty vector (FIGS. 38A and 38B), replicated similarly, and had the shut off temperature similar to that of the empty vector but showed no detectable NAb response.

All of the rHPIV1 $L^{Y942A}$ viruses, including the empty vector, did not induce detectable levels of HPIV1 specific NAbs. All rHPIV1 $L^{Y942A}$ viruses expressed reduced levels of HPIV1 proteins in vitro (FIGS. 38A and 38C) and showed poor or no replication in vivo. Consistent with this, these viruses also showed lack of immunogenicity against RSV. Their poor immunogenicity is likely a result of their strong ts phenotype (FIG. 43) and lack of in vivo replication (FIG. 40).

Figure 41A:
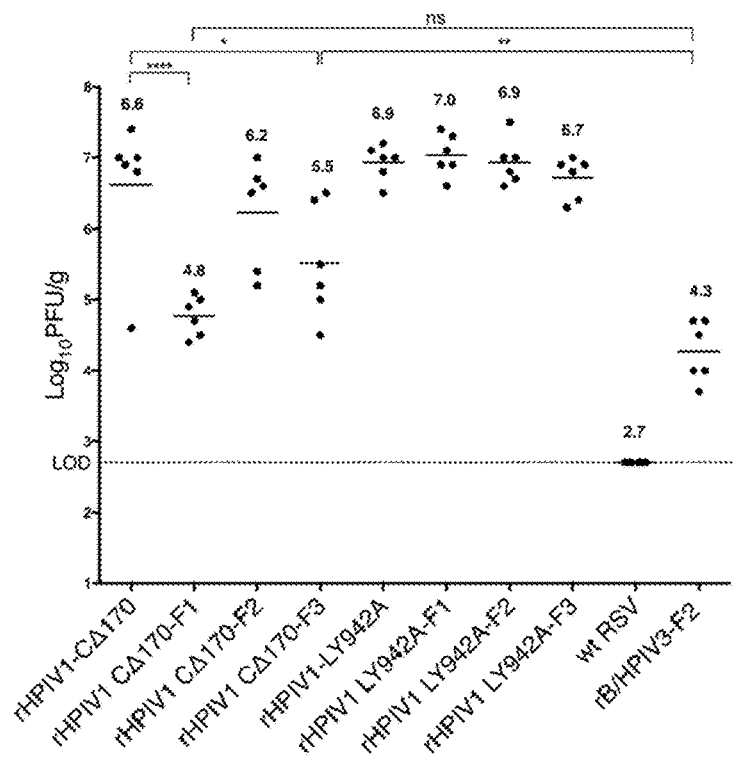
FIGS. 41A and 41B. Protection against wt RSV challenge virus replication in the nasal turbinates (41A) and lungs (41B) of the immunized hamsters. Hamsters (n=6) in each group were challenged intranasally with $10^6$ PFU of wt RSV A2 at 30 days post-immunization. Nasal turbinates and lungs were collected from euthanized animals on day 3 post-challenge, virus titers were determined for each sample by RSV specific plaque assay on Vero cells and reported as $\log_{10}$ PFU/g of tissue. Mean value for each group is shown in bold face number and by a horizontal bar. Statistical significance of difference among viruses was determined by one-way ANOVA at 95% confidence interval using Tukey's multiple comparisons test and is indicated by *, p<0.05; , p<0.01; **p<0.0001; or ns, not significant.
Figure 41B:
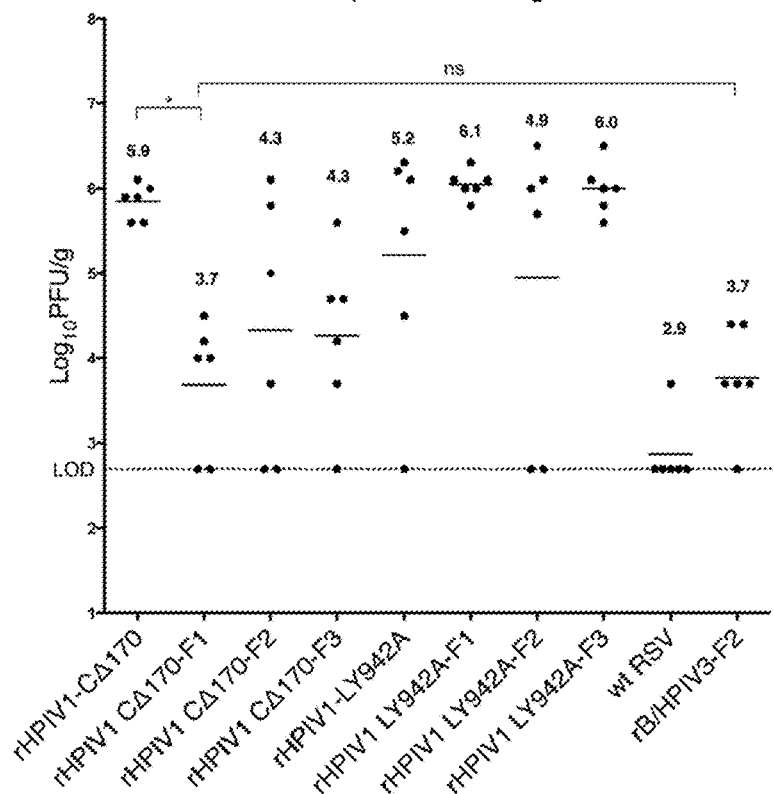

Immunization with rHPIV1 vectors expressing RSV F provides protection against wt RSV challenge. Hamsters were immunized with rHPIV1 expressing RSV F as described above and were challenged on day 30 post-immunization with $10^6$ PFU of wt RSV. Hamsters were euthanized on day 3 post-challenge and RSV titers in the nasal turbinates and lungs were determined by plaque assay on Vero cells to assess the protection against challenge RSV replication (FIGS. 41A and 41B). The protection provided by vaccine candidates against RSV infection and replication correlated with their ability to induce RSV specific serum NAb. The rHPIV1 $C^{\Delta 170}$-F1 and -F3 provided significant protection against RSV replication and showed significantly reduced (p<0.0001 and p<0.05, respectively) RSV titers in the URT as compared with the rHPIV1 $C^{\Delta 170}$ empty vector, with the -F2 virus having no effect. In the lungs, although all three rHPIV1 $C^{\Delta 170}$-F1, -F2, and -F3 viruses reduced the mean RSV titers as compared to the rHPIV1 $C^{\Delta 170}$ empty vector, only the RSV reduction by -F1 virus was statistically significant (p<0.05). As expected, the rB/HPIV3-F2 provided significant protection against RSV challenge in the URT (P≤0.0001) and lungs (p<0.05), which was consistent with a previous report (Liang, et al. 2014. J virology 88:4237-4250, and Example 1).

Statistical comparison of the rHPIV1 vaccine candidates with the rB/HPIV3-F2 virus showed that the protection provided by rHPIV1 $C^{\Delta 170}$-F1 was statistically similar to that of rB/HPIV3-F2 both in the URT and lungs. The rHPIV1 $C^{\Delta 170}$-F1 replicated in hamsters to titers similar to those of rB/HPIV3-F2 on day 3 post-infection but demonstrated significantly reduced replication on day 5 post-infection suggesting that the rHPIV1 $C^{\Delta 170}$-F1 may be sufficiently attenuated in vivo. This along with its ability to protect against RSV challenge similar to that of rB/HPIV3-F2 also indicated that rHPIV1 $C^{\Delta 170}$-F1 has desirable features of attenuation and immunogenicity and should be further developed as a live attenuated RSV vaccine candidate.

The rHPIV1 $L^{Y942A}$-F1, -F2, and -F3 viruses did not provide protection against RSV challenge in the URT and lungs and showed challenge RSV loads similar to that of the rHPIV1 $L^{Y942A}$ empty vector. This was consistent with their lack of in vivo replication and immunogenicity against RSV.

Discussion

Various attenuated versions of rHPIV1 bearing attenuating and/or ts mutations have been previously developed that were immunogenic in rodents and/or non-human primates. Two attenuated rHPIV1 backbones containing either the $C^{\Delta 170}$ or the $L^{Y942A}$ mutation involving a deletion of 6 and substitution of 3 nucleotides, respectively, were assayed. RSV F was inserted at the first, second, or third genome position of each backbone with the aim to identify a construct that is appropriately attenuated and yet sufficiently immunogenic and protects against wt RSV challenge. All rHPIV1 viruses expressing RSV F were successfully rescued by reverse genetics. Growth kinetics in Vero and LLC-MK2 cells indicated that all viruses grew to very similar and statistically indistinguishable final titers determined at 7 days post-infection (FIG. 37). However significant differences in replication were observed on day 2 in both cell lines. The $L^{Y942A}$ mutation seemed to have a stronger attenuating effect than the $C^{\Delta 170}$ mutation at least in Vero cells. Contrary to the expectation, the rHPIV1$C^{\Delta 170}$ viruses were not attenuated in type I interferon (IFN-I) competent LLC-MK2 as compared to IFN-I deficient Vero cells. Among the rHPIV1$C^{\Delta 170}$ viruses expressing RSV F, significant attenuation as compared to the wt HPIV1 was observed for the -F1 and -F2 viruses in Vero (FIG. 37A) and for -F1 in LLC-MK2 cells (FIG. 37B), whereas the -F3 replication was similar to the empty vector and wt HPIV1. These data suggest that insertion of RSV F closer to the 3' proximal positions in -F1 or -F2 viruses may be attenuating but this effect was transient and all viruses grew to similar final titers (FIGS. 37A and 37B). All rHPIV1 $L^{Y942A}$ backbone vectors including -F1, -F2 and -F3 grew to similar final titers on day 7. However, they also demonstrated reduced replication in both Vero and LLC-MK2 cells on days 2, 3, and 4 but were similar to wt HPIV1 between 5-7 days. The RSV F insert induced attenuation was much greater in magnitude for the rHPIV1$L^{Y942A}$ as compared to the rHPIV1$C^{\Delta 170}$ vectors (FIG. 37D) indicating that RSV F insertion has a stronger attenuating effect on a backbone that is already significantly attenuated.

All viruses were examined for their ability to express RSV F protein by Western blot analysis of infected Vero cells incubated at a permissive temperature of 32° C. The expression of the HPIV1 N, P, F, and HN proteins was also evaluated to determine the effect of RSV F insertion at various positions on the vector protein expression. Unexpectedly, a polar gradient of RSV F expression was not observed for the rHPIV1$C^{\Delta 170}$ vectors. The rHPIV1$C^{\Delta 170}$-F1 demonstrated significantly decreased expression of all vector proteins tested. Similarly, with the exception of N protein, the rHPIV1$C^{\Delta 170}$-F2 also showed reduced expression of P, F, and HN proteins (FIGS. 38A and 38B). Consistent with this both the -F1 and -F2 viruses showed reduced replication in Vero cells early during infection (FIG. 37A). These data suggest that for F1 and F2 viruses, the combined effect of reduced vector protein synthesis and the consequent attenuated replication might be responsible for reduced RSV F expression and a lack of its polar gradient. rHPIV1 $C^{\Delta 170}$-F3 showed a modest reduction in RSV F expression as compared to F1 and F2, likely due to its distal genome location. The RSV F expression profile was very different for the rHPIV1 $L^{Y942A}$ vectors that demonstrated a strong polar gradient of expression (FIGS. 38A and 38C) with the F1 virus showing significantly higher RSV F expression as compared to F2 and F3. As anticipated, insertion of RSV F in the first position significantly reduced the N protein expression for the F1 vector while the P, F and HN proteins were unaffected and had expression similar to that of their empty vector counterpart (FIGS. 38A and 38C). The rHPIV1 $L^{Y942A}$-F2 showed very poor expression of RSV F as well as all vector proteins (FIGS. 38A and 38C). As stated above, this virus was the most difficult to rescue due to its highly attenuated phenotype and the accumulation of mutations during rescue. However, the virus finally used in the experiments had no adventitious mutations confirmed by genome sequencing. Therefore, it appears that insertion of RSV F at the F2 location in rHPIV1 $L^{Y942A}$ backbone seems to be quite detrimental with the virus showing drastically significant reduction of all vector proteins tested including RSV F. One non-limiting explanation for this result is that this is a combined effect of insert position and the highly attenuated backbone because such effects were not observed for rHPIV1 $C^{\Delta 170}$-F2. Referring to its growth kinetics (FIGS. 37C-37D), the rHPIV1$L^{Y942A}$-F2 was the most attenuated of all the rHPIV1 $L^{Y942A}$ vectors. Thus, it seems that an overall reduction of vector protein synthesis significantly reduced its replication resulting in reduced RSV F expression. The rHPIV1 $L^{Y942A}$-F3 virus expressed vector proteins at levels similar to the empty vector but showed a >10-fold reduction in RSV F expression as compared to F1 (FIGS. 38A and 38C). This indicates that RSV F insertion at the third genome position did not negatively affect vector protein expression (FIGS. 38A and 38C) but demonstrated poor RSV F expression likely due to its distal location in the polar transcriptional gradient.

Native RSV F causes plasma membrane fusion of the neighboring infected cells resulting in syncytia formation.

The HPIV1 vector F protein does not cause syncytium formation, which therefore could be used as an indicator of RSV F functionality and native form as well as quantity of expression. Formation of syncytia by RSV F expressed from rHPIV1 $C^{\Delta 170}$ or $L^{Y942A}$ vectors was evaluated in Vero and LLC-MK2 cells. Extensive syncytia formation showing fusion of the majority of cells in the monolayer was observed with the rHPIV1 $C^{\Delta 170}$-F1 and -F2 as well as with the rHPIV1 $L^{Y942A}$-F1 (FIG. 39) suggesting that the recombinant RSV F protein is functional and presumably in a native conformation. The rHPIV1 $C^{\Delta 170}$-F3 and $L^{Y942A}$-F2 and -F3 did not show apparently obvious syncytia formation. The extent of syncytia formation was consistent with the level of RSV F expression detected by Western blot (FIGS. 38A-38C).

Since the ts phenotype plays an important role in virus replication in vivo and may determine immunogenicity, the ts phenotype of the vectors expressing RSV F was evaluated. In contrast to the wt HPIV1 that is not ts even at 40° C., the rHPIV1 $C^{\Delta 170}$ and $L^{Y942A}$ backbones were ts at 40° C. and 36° C., respectively (FIG. 43). Important to note is that the insertion of RSV F in the rHPIV1 $C^{\Delta 170}$ at F1 and the rHPIV1 $L^{Y942A}$ at F1 or F2 positions lowered the shut off temperature by 1° C. thus making them slightly more ts. This effect may not be unique to HPIV1 because similar effect was observed on RSV F insertion into the rB/HPIV3 vector in a previous study Liang, et al. 2014. *J virology* 88:4237-4250). The enhancement of ts phenotype was observed for rHPIV1 $L^{Y942A}$-F2 but not for rHPIV1 $C^{\Delta 170}$-F2 indicating that the insertion of foreign gene may enhance the ts phenotype of a virus that is already significantly ts.

The rHPIV1 vectors were evaluated in hamsters to assess their replication and immunogenicity. All of the rHPIV1 $L^{Y942A}$ viruses were over-attenuated and virus replication was undetectable in the URT and lungs of the majority of animals. This is consistent with their highly ts phenotype with a shut off temperature of 35-36 C. Failure to replicate seems not to be due to RSV F insertion but is likely an effect of their ts phenotype because even the empty vector did not replicate in the lungs and had poor replication in the URT. The rHPIV1 $C^{\Delta 170}$-F1, -F2, and -F3 were overall highly restricted and undetectable in the lungs while the empty rHPIV1 $C^{\Delta 170}$ vector did show low level replication, which was significantly lower than that of the wt HPIV1, suggesting that the presence of RSV F insert had an additional attenuating effect on the already attenuated rHPIV1 $C^{\Delta 170}$ backbone in the lungs. In contrast to the lungs, all rHPIV1 $C^{\Delta 170}$ vectors replicated well in the URT of all animals. The F1 and F2 viruses, but not F3, were significantly attenuated as compared to wt HPIV1, with F2 being more attenuated than F1. This was unexpected because in general insertion closer to the 3' end of the genome results in higher attenuation. This was also consistent with the relatively slower early growth of F1 and F2, but not F3, in vitro (FIG. 37) indicating that insertion of RSV F, in the F1 and particularly at F2 position, has an additive attenuating effect. The F1 virus appears to have the desired degree of attenuation, whereas the F2 and F3 viruses are over- and under-attenuated, respectively.

Attaining an optimal balance between attenuation and immunogenicity is a challenge with live attenuated vaccines. To assess if the attenuated rHPIV1 vectors were sufficiently attenuated, their replication was compared with that of the rB/HPIV3-F2, a leading RSV vaccine vector expressing RSV F from the second genome position (Liang, et al. 2014. J virology 88:4237-4250). The replication of rHPIV1 $C^{\Delta 170}$-F1, -F2, or -F3 on day 3 and 5 was either statistically similar to or significantly lower than that of the rB/HPIV3-F2 in both the URT and lungs. This suggests that the $C^{\Delta 170}$ mutation together with the insertion of RSV F appear to have achieved the desired level of attenuation, at least in this animal model, such that all three vectors are highly restricted in the lungs but do demonstrate attenuated replication similar to rB/HPIV3-F2 in the URT that will be needed for immunogenicity.

A difficulty encountered by RNA virus vectored vaccines is the instability of the foreign antigen gene in vivo (Yang, et al. 2013. Vaccine 31:2822-2827). Mutations are generated due to the error prone polymerase, and the lack of a need to maintain the expression of the insert. Any mutations in the foreign antigen acquired due to infidelity of the RNA dependent RNA polymerase could be positively selected as they provide a selective advantage. To determine the stability of RSV F expression in vivo after immunization, viruses recovered from respiratory tissues of hamsters were analyzed by fluorescent double staining plaque assay. This could only be performed for HPIV1 $C^{\Delta 170}$-F1, -F2, and F3 viruses that showed detectable replication in the URT (FIG. 44). For majority of the samples, stable RSV F expression was observed for all three viruses, except one HPIV1 $C^{\Delta 170}$-F1 sample for which RSV F expression was detected for 98% plaques. These data indicated that the rHPIV1 $C^{\Delta 170}$ vectors maintain a stable expression of RSV F during in vivo replication.

Immunogenicity of the rHPIV1 vectors was evaluated by performing the $PRNT_{60}$ assay. The assay for RSV was performed in the presence of guinea pig complement, which was excluded from the HPIV1 neutralization assay because of the direct neutralization of HPIV1 by the complement alone. The rHPIV1 $C^{\Delta 170}$-F1, -F2, and -F3 induced RSV neutralizing antibodies at a $PRNT_{60}$ ($\log_2$) titer of 7.3, 4.7, and 6.7, respectively (FIG. 45). Although F1 demonstrated the highest antibody titer, it was statistically similar to that induced by F2 and F3. These titers were significantly lower than those induced by rB/HPIV3-F2 or wt RSV controls which could be a result of their overall relatively reduced replication both in the URT and lungs. The rHPIV1 $L^{Y942A}$-F1, F2, and F3 viruses did not induce a detectable RSV or HPIV1 neutralizing antibody response, which was consistent with their lack of replication in vivo. Only the rHPIV1 $C^{\Delta 170}$-F1, and not the F2 or F3, induced detectable HPIV1 neutralizing antibodies. This was unexpected because the F2 and F3 did show replication in hamsters (FIG. 40) and induced RSV NAbs. As indicated above guinea pig complement, known to enhance the $PRNT_{60}$ read out, could not be included in the HPIV1 neutralization assay. The overall low HPIV1 antibody titers and lack of a detectable response, even for viruses that replicated in hamsters, could be due to weaker sensitivity of the assay lacking complement.

To determine the protective efficacy of the vectors against RSV infection, all immunized hamsters were intranasally challenged at 30 days post-immunization with a high dose ($10^6$ pfu) of wt RSV per animal. Protection against challenge was assessed by determining RSV replication in the nasal turbinates and lungs (FIGS. 41A and 41B). Protection directly correlated with the immunogenicity (FIG. 45). Highly consistent with the RSV NAb titers, rHPIV1 $C^{\Delta 170}$-F1 was more protective than F3 and no protection was afforded by F2. The protection was statistically significant for F1 in both the URT and lungs and for F3 in the URT only. Importantly, rHPIV1 $C^{\Delta 170}$-F1 afforded protection in the URT and lungs that was statistically indistinguishable from rB/HPIV3-F2. This was somewhat unexpected because the rHPIV1 $C^{\Delta 170}$-F1 induced significantly lower RSV NAb titer than that of the rB/HPIV3-F2 suggesting that the relatively lower NAb titer was sufficient to achieve similar protection. This interpretation is supported by the evidence that RSV replication in the respiratory tract of cotton rats could be reduced if the serum NAb titer was 1:100 or greater (Prince, et al. 1985. *J Virol* 55:517-520). Again, consistent with their lack of sero-conversion, rHPIV1 $L^{Y942A}$-F1, F2, and F3 did not provide any protection against challenge and had RSV loads similar to that of the empty vector. These data clearly show that the rHPIV1 $L^{Y942A}$ vectors were over-attenuated due to their ts phenotype and did not replicate in the hamsters resulting in a lack of immunogenicity both for RSV and HPIV1. In contrast, the rHPIV1 $C^{\Delta 170}$ vectors, although highly restricted in the lungs, did replicate in the URT. Among the vectors tested in this study, the rHPIV1 $C^{\Delta 170}$-F1 appears to be adequately attenuated and yet sufficiently immunogenic against RSV. It is recognized that constructs that appear to be over-attenuated in hamsters may perform more suitably when evaluated in a more permissive primate host.

In summary, this example identifies the rHPIV1 $C^{\Delta 170}$ as a promising attenuated backbone suitable for expressing RSV F antigen from an inserted gene. It was also systematically determined that the F1 (pre-N) genome position of the rHPIV1 $C^{\Delta 170}$ vector was preferred among the positions tested for inserting RSV F. This study also demonstrated that the rHPIV1 $C^{\Delta 170}$-F1 is a promising vaccine candidate and possesses several desirable features: (i) it is based on a backbone well characterized for attenuation in non-human primates (3), (ii) it replicated in Vero cells to final titers similar to that of wt HPIV1, an essential feature for vaccine manufacture, (iii) insertion of RSV F attenuated it slightly more than the empty $C^{\Delta 170}$ backbone to a level similar to rB/HPIV3-F2, (iv) the construct was stable after in vivo replication and maintained RSV F expression, and (v) it was the most immunogenic HPIV1 vector inducing the highest RSV and HPIV1 neutralizing antibody titer and was also the most protective against a wt RSV challenge.

The findings indicate that it is possible to use an HPIV1 vector expressing RSV F as a bivalent vaccine for mucosal immunization against RSV and HPIV1. An HPIV1 vectored RSV vaccine could be used either as a primary RSV vaccine or to boost immunity primarily induced by a live attenuated RSV. The HPIV1 vectored RSV vaccine approach would obviate the inherent problems associated with developing attenuated RSV strains and may facilitate RSV immunization programs even in resource-limited settings.

Example 3

Development of rHPIV1-$C^{\Delta 170}$ Vectors Expressing Optimized Versions of RSV F Protein This example presents assays showing that a gene encoding a modified RSV F ectodomain can be inserted into a HPIV1 vector backbone to produce a recombinant virus that expresses RSV F ectodomain on its envelope, is attenuated, infective, and can induce a protective antibody response. The F2 position also was identified as an effective insertion site. These findings indicate that:
1. The operational boundaries of the HPIV1 F TMCT domains have been identified (FIG. 60).
2. The HPIV1 F TMCT domain can be added to a recombinant RSV F ectodomain, e.g., HEK/GS-opt/DS-Cav1 to achieve a protein that is efficiently expressed at the cell surface and reactive with anti-RSV-F antibodies.
3. RSV F containing the HPIV1 F TMCT (HEK/GS-opt/DS-Cav1/H1TMCT) was efficiently packaged into the HPIV1 vector particle (i.e., at a higher level per μg virion protein than RSV, FIG. 64). This was completely contrary to expectations based on previous studies with Sendai virus (the murine relative of HPIV1, and hence presumably a close predictive model), in which RSV F containing the Sendai virus CT or TMCT was packaged efficiently into the particle only if the endogenous Sendai virus F protein was deleted (Zimmer et al 2005 *J Virol* 79:10467-10477).
3. HEK/GS-opt/DS-Cav1 and HEK/GS-opt/DS-Cav1/H1TMCT forms of the RSV F protein can be inserted into the first or second gene positions to yield vector constructs that stably express RSV F, replicate efficiently in vitro (FIG. 63), and are efficiently incorporated into the vector particle (when HPIV1 F TMCT is present, FIG. 64).
4. Unexpectedly, while either the F1 or F2 positions are efficient in expressing RSV F protein that is fusogenic (e.g., HEK/GA-opt, Example 2), the F2 position was particularly efficient for intracellular expression of RSV F that was non-fusogenic (e.g., HEK/GS-opt/DS-Cav1).
5. The rHPIV1-$C^{\Delta 170}$-F2/HEK/GS-opt/DS-Cav1 and rHPIV1-$C^{\Delta 170}$-F2/HEK/GS-opt/DS-Cav1/H1TMCT constructs were identified as ones that efficiently expressed RSV F protein and, particularly in the latter case, efficiently incorporated RSV F into the vector particle.

HEK/GS-opt/DS-Cav1. In the present Example, the rHPIV1-$C^{\Delta 170}$ vector was used to express further-modified versions of the RSV F protein. All inserts contain RSV F that was codon optimized by Genescript (GS-opt) for human expression and had two HEK amino acid assignments, i.e., Glu and Pro at residues 66 and 101. In addition, the HEK/GS-opt RSV F protein contained the stabilized prefusion mutations DS (S155C and S290C) and Cav1 (S190F, and V207L) to stabilize the RSV F prefusion head and antigenic site 0 that have been shown to be responsible for the preponderance of RSV-neutralizing antibodies (McLellan et al 2013 Science 342:592-598).

HPIV1 TMCT. In addition, a version of the HEK/GS-opt/DS-Cav1 RSV F protein was made in which its TMCT domain was replaced by that of HPIV1 F protein. The composition of the HPIV1 TM and CT domains had not been previously determined. FIG. 60 indicates the TM and CT domains of RSV F protein (top line) and HPIV1 F protein (second line), and shows a chimera in which the predicted ectodomain of RSV F protein was attached to the predicted TMCT domains of HPIV1 F protein. This was done with the goal of increasing the incorporation of the RSV F protein into the HPIV1 vector, on the premise that the HPIV1 F-specific TMCT domain would interact more efficiently with the other vector proteins during viral assembly, and would facilitate incorporation of the chimeric RSV F protein.

rHPIV1-$C^{\Delta 170}$ vector constructs. FIGS. 61 and 62 show constructs in which the rHPIV1-$C^{\Delta 170}$ vector from Example 2 was used to accept either of two inserts, placed in the first gene position (F1): expressed RSV F HEK/GS-opt/DS-Cav1, yielding rHPIV1-$C^{\Delta 170}$-F1/HEK/GS-opt/DS-Cav1 (FIGS. 61 and 62, top construct); or RSV F HEK/GS-opt/DS-Cav1/H1TMCT, yielding rHPIV1-$C^{\Delta 170}$-F1/HEK/GS-opt/DS-Cav1/H1TMCT (bottom construct). Note that these two constructs differ only in that the RSV F in the second construct has TMCT from HPIV1 F protein. FIG. 62 shows two parallel constructs in which either insert was placed in the second gene position (F2) of the rHPIV1-C$^{\Delta 170}$ vector. All viruses were designed to keep the hexameric genome nucleotide length (rule of six) (Kolakofsky et al 1998 J Virol 72:891-899). Each vector gene maintained its wild type hexamer phasing; the F1 and F2 inserts had the hexamer phasing of the N and P genes, respectively Recovery of viruses. The four constructs were rescued by co-transfecting BHK BSR T7/5 cells (baby hamster kidney cells that constitutively express T7 RNA polymerase (Buchholz et al 1999 J Virol 73:251-259)) with each of the full-length anti-genome plasmids and three expression plasmids expressing the HPIV1 N, P, and L proteins. Double staining plaque assays detecting co-expression of HPIV1 and RSV F proteins were performed to determine the stability of RSV F expression. The vast majority of plaques efficiently expressed RSV F protein. These same four preparations were subjected to consensus sequence analysis by automated sequencing (which analyzed each genome in its entirety except for 22 and 26 nucleotides at the 3' and 5' end, respectively, which were obscured by primers). The viruses were found to be free of adventitious mutations detectable by this method.

Multi-cycle replication in vitro. The four recovered viruses (i.e., HEK/GS-opt/DS-Cav1, with or without H1TMCT, in the F1 or F2 position) were evaluated for multi-cycle replication in vitro by infecting Vero cells at an MOI of 0.01 TCID$_{50}$ per cell with each virus in triplicate and collecting culture supernatant every 24 h for 7 days. Virus titers in the collected samples were determined by serial dilution on LLC-MK2 cells and hemadsorption assay. All vectors with RSV F insert were relatively attenuated as compared to wt HPIV1 and rHPIV1-C$^{\Delta 170}$ and grew to final titers around 7.0 TCID$_{50}$/mL (FIG. 63). The F1/DS-Cav1 and F1/DS-Cav1/H1TMCT (note, the "HEK/GS-opt" part of the name may be omitted in the text and figures for the sake of brevity) replicated slower than the F2/DS-Cav1 and F2/DS-Cav1/H1TMCT on day 1 and 2 post-infection (p.i.) (during the exponential phase of replication) but reached high titers by day 7 (harvest day) that were similar to F2/DS-Cav1 and F2/DS-Cav1/H1TMCT. Thus, all constructs grew to high final titers that are amenable to vaccine manufacture in Vero cells.

Incorporation of proteins into vector virions. The set of four constructs along with wt HPIV1, and rHPIV1-C$^{\Delta 170}$ empty vector were grown in LLC-MK2 cells and purified by sucrose gradient centrifugation. wt RSV was propagated in Vero cells followed by sucrose gradient purification and was included as a control. Approximately 1 μg of each sucrose-purified virus was lysed in RIPA buffer, reduced, denatured and subjected to SDS-PAGE and Western blot analysis. RSV F protein and HPIV1 proteins (N, F, and HN) were detected with mouse monoclonal (Abcam) and rabbit polyclonal peptide-specific antibodies (see Example 2), respectively, along with their corresponding infrared dye-conjugated secondary antibodies as previously described (Example 2; Mackow et al 2015 J Virol 89:10319-10332) (FIG. 64). Analysis of the F1/DS-Cav1 and F2/DS-Cav1 purified virions, which expressed full length RSV F from the 1$^{st}$ and 2$^{nd}$ position, respectively, demonstrated no detectable packaging of RSV F in the HPIV1 vector virions (FIG. 64, top panel, lanes 3 and 5). In contrast, both the F1/DS Cav1-H1TMCT and F2/DS Cav1-H1TMCT virions (FIG. 64, lanes 4 and 6) showed considerable incorporation, which was higher for the F1/DS Cav1-H1TMCT than F2/DS Cav1-H1TMCT. Interestingly, both H1TMCT versions show higher amounts of RSV F packaged in the virions as compared to wt RSV (FIG. 64, lane 7), per μg of virion protein.

In the same experiment, the incorporation of the HPIV1 N, HN, and F proteins into the HPIV1 vector virions was also evaluated (FIG. 64). The virion incorporation of HPIV1 N protein was little affected by expression of any of the inserts (FIG. 64, second panel from the top). HN protein was reduced for F1/DS-Cav1/H1TMCT, F2/DS-Cav1, and F2/DS-Cav1/H1TMCT constructs (FIG. 64, third panel from the top, lanes 4, 5, and 6). Virion incorporation of HPIV1 F protein was reduced for F2/DS-Cav1 and F2/DS-Cav1/H1TMCT (FIG. 64, fourth panel from the top, lanes 5 and 6). Note that the antiserum for the HPIV1 F protein had been raised against a peptide containing the last 18 amino acids of the CT domain of the HPIV1 F protein, and thus this antiserum detected, in addition to the HPIV1 F0 and F1 proteins, the forms of RSV F protein containing the HPIV1 F protein TMCT, namely F1/DS-Cav1/H1TMCT and F2/DS-Cav1/TMCT. The identity of the RSV F band was confirmed by co-staining with the anti-RSV F monoclonal antibody; this confirms that RSV F is indeed expressed with HPIV1 F TMCT domain.

Figure 65:
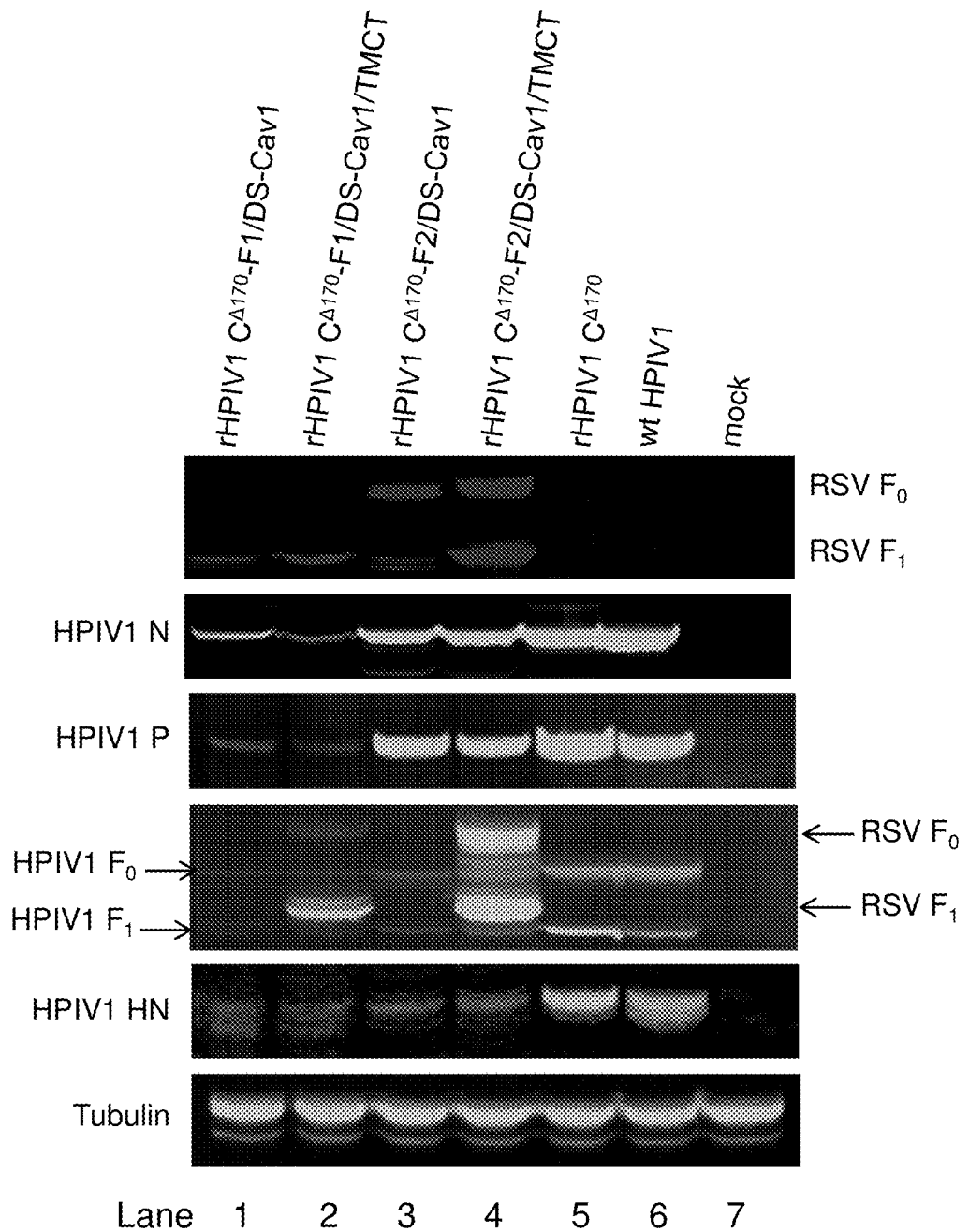
FIG. 65. Expression in infected Vero cells of RSV F protein stabilized in the prefusion conformation (DS-Cav1) without and with TMCT from HPIV1 F protein. Vero cell monolayers in 6-well plates were inoculated with the indicated viruses (the designations HEK/GS-opt were omitted for the sake of brevity) including the wt HPIV1 and rHPIV1-C$^{\Delta170}$ empty vector controls at an MOI of 5 and incubated for 48 h at 32° C. Cell lysates were prepared by lysing the monolayers in 200 µL LDS sample buffer. Protein samples were reduced and denatured, and 45 µL of each sample were electrophoresed followed by protein transfer to PVDF membranes. RSV F and HPIV1 proteins were detected using the same primary and secondary antibodies as described for FIG. 64.

Intracellular protein expression. Next, the intracellular expression of RSV F protein and HPIV1 vector proteins in vector-infected cells was evaluated. Vero cells were infected at an MOI of 10 TCID$_{50}$ per cell with each construct and incubated at 32° C. for 48 h. Cellular proteins were harvested by direct lysis of the monolayer with 1×LDS buffer, reduced, denatured, and subjected to SDS-PAGE and Western blot analysis (FIG. 65). RSV F and HPIV1 proteins were detected by using the same antibodies as described in FIG. 64. All constructs were able to express RSV F protein in infected cells; F2/DS-Cav1/H1TMCT had the highest expression followed by F2/DS-Cav1, F1/DS-Cav1/H1TMCT, and F1/DS-Cav1 (FIG. 65, lanes 4, 3, 2, and 1). Contrary to the expectation that insertion of the RSV F insert into the first gene position would result in the highest levels of expression (due to the transcriptional gradient), the F1/DS-Cav1 and F1/DS-Cav1/H1TMCT viruses (FIG. 64, lanes 1 and 2) had reduced RSV F expression as compared to the F2 viruses (lanes 3 and 4). As already noted, the F1 viruses replicated somewhat more slowly during exponential growth than the F2 viruses (FIG. 63), which likely contributed to the reduced RSV F expression. The low level of intracellular expression of RSV F in cells infected with the F1 viruses is in contrast to the virion incorporation profile (FIG. 64) that shows higher incorporation of RSV F for F1/DS-Cav1/H1TMCT as compared to F2/DS-Cav1/H1TMCT (lane 4 versus 6). In both F1 and F2 positions, DS-Cav1 with TMCT was expressed at somewhat higher level than DS-Cav1 alone, suggesting TMCT may enhance the RSV F expression by making the protein or mRNA transcript more stable. Similar effect was also observed with RSV F with BPIV3 F TMCT in Vero cells infected by B/HPIV3 vectors (FIG. 50A). It also is noteworthy that the intracellular expression of the HPIV1 N, P, F, and HN proteins also was very low for the F1 viruses compared to the F2 viruses (FIG. 65, second, third, and fourth panels, lanes 1 and 2 versus 3 and 4). This reveals very low gene expression for the F1 viruses (FIG. 65, lanes 1 and 2), although the RSV F protein that is made apparently was very efficiently incorporated into the HPIV1 virion in the case of RSV F bearing the HPIV1 TMCT (FIG. 64, lane 4).

Reduced RSV F expression by the F1 viruses in this present experiment is in contrast to the results reported in Example 2 involving expression of an HEK/GA-opt form of the RSV F protein from the first gene position of this same vector. In that case, intracellular expression of the RSV F protein was efficient and was very similar for the F1 versus the F2 construct, whereas the expression of the HPIV1 vector proteins was somewhat reduced for F1 versus F2, but not drastically so (FIG. 38A, first two lanes at the left, and FIG. 38B). The difference may be that the version of RSV F expressed in FIG. 38 was fusogenic, and this may have helped the virus spread more efficiently through the cell monolayer and promote a more efficient infection resulting in greater protein synthesis, whereas the F protein expressed in FIG. 64 was the DS-Cav1 version that was frozen in the prefusion conformation and thus would be non-fusogenic. While the constructs expressing DS-Cav1 may not have spread efficiently, each infected cell might have made more RSV F protein, and this could account for the higher level of virion incorporation. However, since a relatively high MOI of infection was used in each experiment (MOI of 5), and thus the great majority of cells should have been infected and spread may not have been a major factor. Therefore, the reduced intracellular expression of the DS-Cav1 form of the F protein from the F1 position was unexpected and points to the F2 position as likely being the more suitable for vector use.

Example 4

Development of Wt rHPIV3 Strain JS Vectors Expressing Optimized Versions of RSV F Protein As discussed above, the addition of the TMCT of the BPIV3 F protein (B3TMCT) to the RSV F HEK/GA-opt/DS construct resulted in substantial attenuation of the rB/HPIV3 vector in rhesus monkeys (FIG. 29). There also was evidence of attenuation in hamsters due to the B3TMCT (FIG. 51). This raised the possibility that this would render the rB/HPIV3 vector over-attenuated. One solution would be to use a less attenuated virus, such as wt HPIV3, as vector. In addition, if an HPIV3 vector was used (i.e, all of the backbone genes were derived from HPIV3), this would provide a complete complement of HPIV3 proteins as antigens for cellular immunity against HPIV3, and thus an HPIV3-based vector might be more protective against HPIV3 than an rB/HPIV3-based vector. The findings discussed in this example indicate that, unexpectedly, the stability of expression of the RSV F insert F1-HEK/GS-opt/DS-Cav1/H3TMCT appeared to be more stable than its version lacking TMCT, namely F1-HEK/GS-opt/DS-Cav1. This is contrary to expectations, since incorporation into the vector particle might have been expected to place an added selective pressure against maintenance of RSV F expression, but this was not observed.

Wt rHPIV3 JS strain vector. The wild type (wt) recombinant (r) HPIV3 JS strain (which also was the source of the F and HN genes in rB/HPIV3) was selected as vector. The biological version of this virus was previously shown to be naturally attenuated in adults (Clements et al. J Clin Microbiol 29:1175-1182, 1991) compared to a previously-evaluated strain (Kapikian et al 1961 JAMA 178:123-127), presumably due to one or more adventitious attenuating mutations that remain to be identified. The recombinant version of this virus (rHPIV3) has two mutations in HN (A263T and T370P) that were introduced when the HPIV3 reverse-genetic system was established. In the present study, the rHPIV3 vector was modified to contain the 263T and 370P amino acid assignments in the HN protein that had been found to prevent large plaque formation by the rB/HPIV3 vector (the mutations were shown in detail in FIG. 58B). In addition, the rHPIV3 vector was modified by the creation of a unique BlpI site at positions 103-109 (FIG. 67A, top construct), for insertion of RSV F (or potentially any other insert) in the first gene position, or the creation of a unique AscI site at positions 1675-1682 (FIG. 67B, top construct), for insertion of RSV F in the second gene position.

HEK/GS-opt/DS-Cav1+/−H3TMCT. The wt rHPIV3 JS vector was used to express the RSV F HEK/GS-opt/DS-Cav1 protein as is or with the further modification in which the TMCT domains of the RSV F protein was replaced by that of the HPIV3 F protein (called H3TMCT, FIG. 66). The activity of the TM and CT domains of HPIV3 F protein (H3TMCT) in the context of the RSV F protein was not known. FIG. 66 also shows a chimera in which the H3TMCT was introduced into the RSV F protein.

Figure 67A:
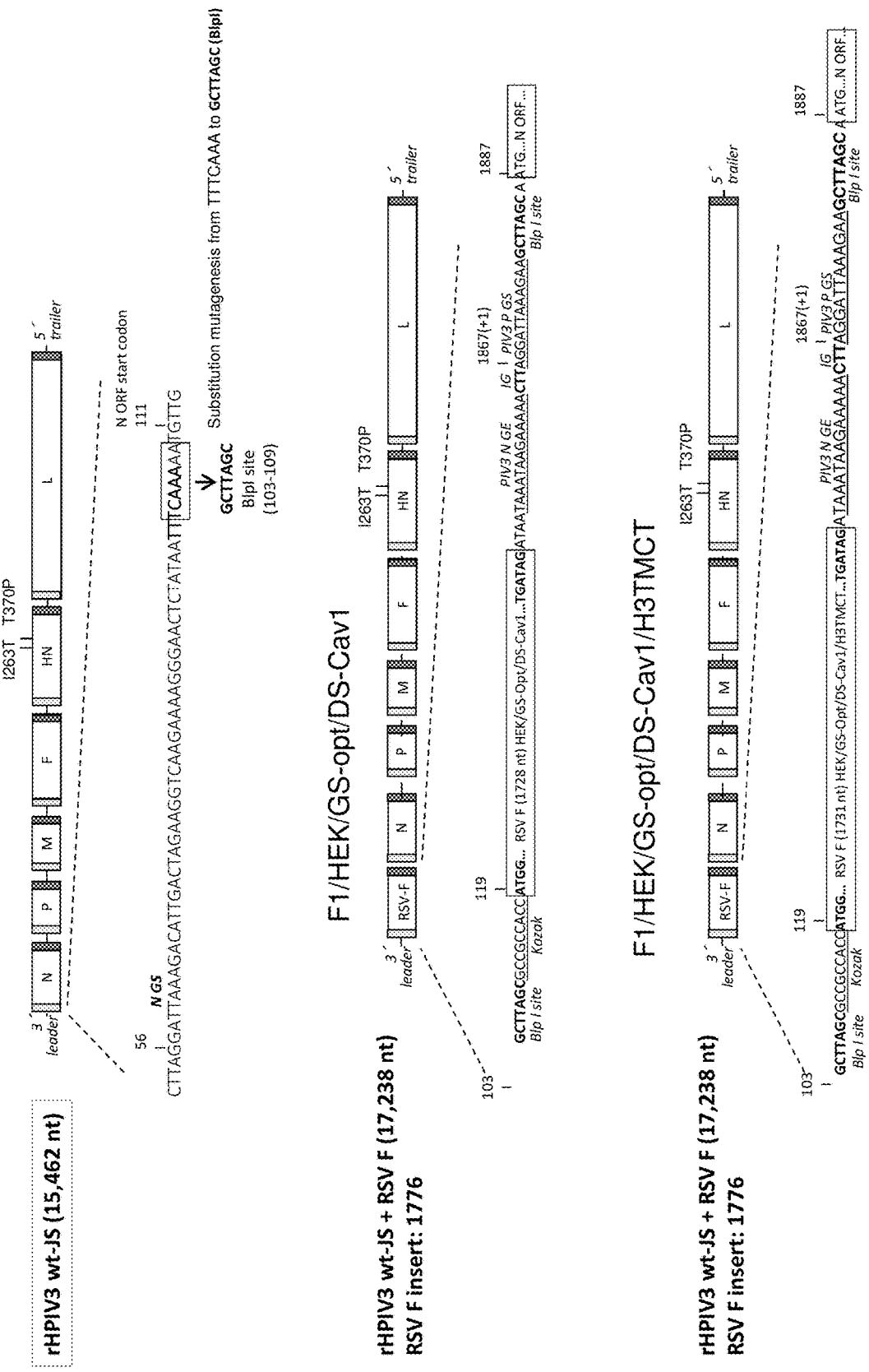

Examples of four rHPIV3-based constructs expressing RSV F are shown in FIG. 67. Specifically, the examples are:
HEK/GS-opt/DS-Cav1 inserted into the first gene position (F1) (FIG. 67A);
HEK/GS-opt/DS-Cav1/H3TMCT inserted into the first gene position (F1) (FIG. 67A);
HEK/GS-opt/DS-Cav1 inserted into the second gene position (F2) (FIG. 67B);
HEK/GS-opt/DS-Cav1/H3TMCT inserted into the second gene position (F2) (FIG. 67B).

Note that these RSV F ORFs are the same as were inserted into the rHPIV1-$C^{\Delta 170}$ vector in FIGS. 61 and 62, except that the TMCT in FIG. 67 is H3TMCT derived from HPIV3 F protein. In addition, each RSV F insert in FIG. 67 was under the control of HPIV3 transcription signals for expression as a separate mRNA. Nucleotide numbering (FIG. 67) is relative to the complete antigenome RNA sequence of each final construct. All viruses were designed to maintain the hexameric genome length and wild type hexamer phasing; the F1 and F2 inserts had the hexamer phasing of the original N and P genes (normally in the first and second gene positions), respectively. All inserts were synthetically derived (Genscript).

Recovery of viruses and double staining analysis. The viruses were rescued by co-transfecting BHK BSR T7/5 cells with each of the full-length anti-genome plasmid and three expression plasmids expressing the HPIV3 N, P, and L proteins. All viruses were successfully rescued, and two P2 (i.e., second passage) viral stocks were prepared for each of the four constructs.

Comments on the Results Shown in Examples 1-4

The following examples show that several different PIV vector systems (including rB/HPIV3, rHPIV1, and rHPIV3 JS) can be used to efficiently express the RSV F protein as an added gene. Panels of mutants were constructed to systematically evaluate a variety of variables with the vectors (e.g., insert position, level of attenuation, etc.) and the RSV F insert (e.g. prefusion stabilization, packaging into the vector particle, etc.), The panels of mutants were subjected to detailed analysis in cell culture, in hamsters, and in non-human primates to identify effective mutants with regard to expression level, stability in vitro and in vivo, attenuation in vivo, immunogenicity, and protective efficacy.

Previous studies had shown that highly fusogenic proteins like RSV F can be unstable in nonsegmented negative strand viral vectors because their high level of syncytium formation interferes with vector replication: for example, the fusion F protein of measles virus was shown to exhibit "extreme instability" when expressed by the prototype virus vesicular stomatitis virus (VSV) (Quinones-Kochs et al 2001 Virology 287; 427-435). Since respiratory syncytial virus is notorious for its high level of syncytium formation, and since high levels of syncytium formation indeed were observed when functional RSV F protein was expressed from PIV vectors (e.g., Example 1), it was very surprising that this did not interfere with vector replication in vitro. Thus, efficiencies of replication of the disclosed constructs allows for efficient vaccine manufacture in Vero cells. Furthermore, modifications that reduced (HEK assignments) or essentially eliminated (DS, DS-Cav1) gross syncytium formation were introduced, which thus would obviate any problems due to high levels of syncytium formation.

Multiple specific strategies were demonstrated to increase the expression of the foreign RSV F gene, including inclusion of HEK assignments, codon optimization, and placement in promoter-proximal positions. However, the results were not necessarily predictable, illustrating the importance of the extensive experimentation provided in this disclosure. In addition, while expression from the first gene position would be expected to yield the highest levels of expression, this was not the case with the HPIV1 vector when it expressed RSV F protein that was non-fusogenic due to the DS-Cav1 mutations (FIG. 65). Thus, the nature of the vector and the nature of the insert contributed to yield novel characteristics.

Multiple means of attenuation were investigated, including the use of the bovine/human chimera rB/HPIV3, the use of the naturally-attenuated HPIV3 JS strain, and the use of stabilized point and deletion mutations exemplified with HPIV1 ($C^{\Delta 170}$ and $L^{Y942A}$). In addition, presence of the foreign insert provided attenuation in some circumstances, and the B3TMCT modification was substantially attenuating. Thus, the reagents and biological characterization provide vectors exhibiting a range of useful attenuation phenotypes. Importantly, the vectors of interest were shown to have retained efficient replication and stability in Vero cells, necessary for vaccine manufacture.

The stability of expression of the RSV F insert was a major problem with a prior construct (Bernstein et al 2012, Pediatr Infect Dis 31:109-114). However, the modified constructs described in the present disclosure were substantially stable. Factors such as reducing or inhibiting syncytium formation likely contributed to stability. In some case, unpredictable factors were identified. For example, the HN gene in the rB/HPIV3 vector was found to exhibit substantial instability that resulted in a large plaque phenotype. However, this problem was eliminated by I263T and T370P substitutions in the HN gene (FIG. 58). Another example of an unexpected finding regarding stability was the increased stability of RSV F expression with the combination of the HEK/GS-opt/DS-Cav1/H3TMCT construct expressed from the F1 position of rHPIV3 JS (FIG. 67A). It might have been expected that expression from the F1 position would be the most unstable, because of the high level of expression, but this was not observed. It also might have been expected that packaging of the RSV F protein into the vector also would place a selective pressure for loss of expression, but this was not observed.

Two modifications were shown to be of primary importance for increasing immunogenicity: namely, mutations DS and Cav1 that stabilize the prefusion conformation of the RSV F protein, and the TMCT modification that serves as a packaging signal to direct efficient incorporation of the foreign glycoprotein into the vector particle. It was not known if RSV F that was stabilized in the prefusion conformation would be expressed efficiently and would be compatible with a virus infection, but this was the case. It also was surprising that the TMCT packaging signals worked with such a high degree of efficiency of packaging, which equaled or exceeded that of RSV particles examined in parallel. It also was surprising that this highly efficient packaging did not disrupt the production of vector particles, such as by displacing the endogenous F and HN surface glycoproteins.

Particularly unexpected was the finding that the DS and DS-Cav1 modifications on the one hand, and the TMCT modification on the other hand, each provided a very substantial increase in the production of high quality RSV-neutralizing antibodies, which are thought to be the most relevant for protection in vivo. These two types of modifications likely achieved this effect through different mechanisms: specifically, the DS and Cav1 modifications presumably have their effect by stabilizing the antigenic site 0, whereas packaging mediated by TMCT likely provides a tightly-packed highly-repetitive array of RSV F antigen produced in a particle form, providing for increased antigen presentation. Importantly, these effects were very evident in non-human primates (FIG. 31), yielding reciprocal titers of >250 from a single primary dose for complement-independent antibodies. In addition, the two effects (DS-Cav1 and TMCT) were additive to some extent.

It will be apparent that the precise details of the methods or compositions described may be varied or modified without departing from the spirit of the described embodiments. We claim all such modifications and variations that fall within the scope and spirit of the claims below.

SEQUENCE LISTING

```
Sequence total quantity: 153
SEQ ID NO: 1            moltype = AA  length = 574
FEATURE                 Location/Qualifiers
REGION                  1..574
                        note = Recombinant RSV F
source                  1..574
                        mol_type = protein
                        organism = synthetic construct
SEQUENCE: 1
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
```

```
KCTASNKNRG IIKTFSNGCD YVSNKGVDTV SVGNTLYYVN KQEGKSLYVK GEPIINFYDP    480
LVFPSDEFDA SISQVNEKIN QSLAFIRKSD ELLHNVNAGK STTNIMITTI IIVIIVILLS    540
LIAVGLLLYC KARSTPVTLS KDQLSGINNI AFSN                                574

SEQ ID NO: 2            moltype = AA  length = 574
FEATURE                 Location/Qualifiers
source                  1..574
                        mol_type = protein
                        organism = Respiratory syncytial virus
SEQUENCE: 2
MELLIHRLSA IFLTLAINAL YLTSSQNITE EFYQSTCSAV SRGYFSALRT GWYTSVITIE     60
LSNIKETKCN GTDTKVKLIK QELDKYKNAV TELQLLMQNT PAANNRARRE APQYMNYTIN    120
TTKNLNVSIS KKRKRRFLGF LLGVGSAIAS GIAVSKVLHL EGEVNKIKNA LLSTNKAVVS    180
LSNGVSVLTS KVLDLKNYIN NQLLPIVNQQ SCRISNIETV IEFQQKNSRL LEINREFSVN    240
AGVTTPLSTY MLTNSELLSL INDMPITNDQ KKLMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNTGK STTNIMITTI IIVIIVVLLS    540
LIAIGLLLYC KAKNTPVTLS KDQLSGINNI AFSK                                574

SEQ ID NO: 3            moltype = RNA  length = 1725
FEATURE                 Location/Qualifiers
source                  1..1725
                        mol_type = genomic RNA
                        organism = Respiratory syncytial virus
SEQUENCE: 3
atggagctgc tgatccacag gttaagtgca atcttcctaa ctcttgctat taatgcattg     60
tacctcacct caagtcagaa cataactgag gagttttacc aatcgacatg tagtgcagtt    120
agcagaggtt attttagtgc tttaagaaca ggttggtata ccagtgtcat aacaatagaa    180
ttaagtaata taaagaaaac caaatgcaat ggaactgaca ctaaagtaaa acttataaaa    240
caagaattag ataagtataa gaatgcagtg acagaattac agctacttat gcaaacacaa    300
ccagctgcca acaaccgggc cagaagagaa gcaccacagt atatgaacta caatcaat     360
accactaaaa acctaaatgt atcaataagc aagaagagga aacgaagatt tctgggcttc    420
ttgttaggtg taggatctgc aatagcaagt ggtatagctg tatccaaagt tctacacctt    480
gaaggagaag tgaacaagat caaaaatgct tgttatcta caaacaaagc tgtagtcagt    540
ctatcaaatg gggtcagtgt tttaaccagc aaagtgttag atctcaagaa ttacataaat    600
aaccaattat tacccatagt aaatcaacag agctgtcgca tctccaacat tgaaacagtt    660
atagaattcc agcagaagaa cagcagattg ttggaaatca acagagaatt cagtgtcaat    720
gcaggtgtaa caacaccttt aagcacttac atgttaacaa acagtgagtt actatcattg    780
atcaatgata tgcctataac aaatgatcag aaaaaattaa tgtcaagcaa tgttcagata    840
gtaaggcaac aaagttattc tatcatgtct ataataaagg aagaagtcct tgcatatgtt    900
gtacagctac ctatctatgg tgtaatagat acaccttgct ggaaattaca cacatccct    960
ctatgcacca ccaacatcaa agaaggatca aatatttgtt taacaaggac tgatagagga   1020
tggtattgtg ataatgcagg atcagtatcc ttctttccac aggctgacac ttgtaaagta   1080
cagtccaatc gagtatttg tgacactatg aacagttga cattaccaag tgaagtcagc   1140
ctttgtaaca ctgacatatt caattccaag tatgactgca aaattatgac atcaaaaaca   1200
gacataagca gctcagtaat tacttctctt ggagcctata gtgtcatgca tggtaaaact   1260
aaatgcactg catccaacaa aaatcgtggg attataaaga cattttctaa tggttgtgac   1320
tatgtgtcaa acaaaggagt agatactgtg tcagtgggca cactttata ctatgtaaac   1380
aagctggaag gcaagaacct ttatgtaaaa ggggaaccta taataaatta ctatgaccct   1440
ctagtgtttc cttctgatga gtttgatgca tcaatatctc aagtcaatga aaaaatcaat   1500
caaagtttag cttttattcg tagatctgat gaattactac ataatgtaaa tactggcaaa   1560
tctactacaa atattatgat aactacaatt attatagtaa tcattgtagt attgttatca   1620
ttaatagcta ttgggttgct gttgtattgc aaagccaaaa acacaccagt tacactaagc   1680
aaaagaccaa caagtggaat caataatatt gcattcagca aatag                   1725

SEQ ID NO: 4            moltype = DNA  length = 1725
FEATURE                 Location/Qualifiers
misc_feature            1..1725
                        note = Recombinant RSV F
source                  1..1725
                        mol_type = other DNA
                        organism = synthetic construct
SEQUENCE: 4
atggaactgc tgatcctgaa ggccaacgcc atcacaacaa tcctgaccgc cgtgaccttc     60
tgcttcgcca gcggcagaa cataccgag gaattctacc agagcacctg tagcgccgtg    120
tccaagggct acctgagcgc cctgagaacc ggctggtaca ccagcgtgat caccatcgag    180
ctgtccaaca tcaaagaaaa caagtgcaac ggcaccgacg ccaaagtgaa gctgatcaag    240
caggaactgg acaagtacaa gaacgccgtg accgagctgc agctgctgat gcagtccacc    300
cccgccacca caaccgggc cagaagagaa ctgcccgt tcatgaacta caccctcaac    360
aacgccaaaa gaccaacgt gaccctgagc aagaagcgga gcggcggtt cctgggcttc    420
ctgctggcg tgggcagcgc cattgcctct ggcgtggccg tgtctaaggt gctgcacctg    480
gaaggcgaag tgaacaagat caagagcgcc ctgctgtcca caaacaaggc tgtgtccctg    540
ctgagcaacg gcgtgtccgt gctgaccccc aaggtgctgg atctgaagaa ctacatcgac    600
aagcagctgc tgcccatcgt gaacaagcag agctgcagca tcagcaacat cgagacagtg    660
atcgagttcc agcagaagaa caccggctg ctggaaatca cccgcgagtt cagcgtgaac    720
gccggcgtga ccaccccgt gtccacctac atgctgacca acagcgagct gctgtccctg    780
atcaatgaca tgcccatcac caacgaccag aaaaagctga tgagcaacaa cgtgcagatc    840
```

-continued gtgcggcagc agagctactc catcatgagc atcatcaaag aagaggtgct ggcctacgtg 900
gtgcagctgc ccctgtacgg cgtgatcgac accccctgct ggaagctgca caccagcccc 960
ctgtgcacca ccaacacaaa agagggcagc aacatctgcc tgacccggac cgaccggggc 1020
tggtactgcg ataatgccgg cagcgtgtca ttctttccac aggccgagac atgcaaggtg 1080
cagagcaacc gggtgttctg cgacaccatg aacagcctga ccctgccctc cgaagtgaac 1140
ctgtgcaacg tggacatctt caaccctaag tacgactgca agatcatgac cagcaagacc 1200
gacgtgtcca gctccgtgat cacctccctg ggcgccatcg tgtcctgcta cggcaagacc 1260
aagtgcaccg ccagcaacaa gaaccggggc atcatcaaga ccttcagcaa cggctgcgac 1320
tacgtgtcca acaaggggt ggacaccgtg tccgtgggca acaccctgta ctacgtgaac 1380
aaacaggaag gcaagagcct gtacgtgaag ggcgagccca tcatcaactt ctacgacccc 1440
ctggtgttcc ccagcgacga gttcgacgcc agcatcagcc aggtcaacga gaagatcaac 1500
cagagcctgg ccttcatcag aaagagcgac gagctgctgc acaatgtgaa tgccggcaag 1560
agcaccacaa acatcatgat caccactatc atcatcgtga tcatcgtcat cctgctgagt 1620
ctgatcgccg tgggcctgct gctgtactgc aaggccagat ccacccctgt gaccctgtcc 1680
aaggatcagc tgtccggcat caacaatatc gccttctcca actga 1725

SEQ ID NO: 5 moltype = DNA length = 1725
FEATURE Location/Qualifiers
misc_feature 1..1725
note = Recombinant RSV F
source 1..1725
mol_type = other DNA
organism = synthetic construct
SEQUENCE: 5
atggaactgc tgatcctgaa agccaacgct attactacta tcctgaccgc cgtgacattt 60
tgcttcgcat ctggacagaa cattactgag gaattctacc agtcaacatg cagcgccgtg 120
tccaaaggat acctgagcgc cctgcggacc ggctggtata catcagtgat tactatcgag 180
ctgtccaaca tcaaggaaaa caaatgtaat gggaccgacg caaaggtgaa actgatcaag 240
caggagctgg ataagtacaa aaatgccgtg acagaactgc agctgctgat gcagtccaca 300
ccagcaacta acaatcgcgc ccggagagag ctgccccggt tcatgaacta taccctgaac 360
aatgctaaga aaaccaatgt gacactgtcc aagaaacgca agaggcgctt cctgggattt 420
ctgctgggcg tggggtctgc catcgctagt ggagtggccg tctctaaagt cctgcacctg 480
gagggcgaag tgaacaagat caaaagcgcc ctgctgtcca ctaacaaggc agtggtcagt 540
ctgtcaaatg gcgtgtccgt cctgacctct aaggtgctgg acctgaaaaa ttatattgat 600
aagcagctgc tgcctatcgt caacaaacag agctgctcca tttctaatat cgagacagtg 660
atcgaattcc agcagaagaa caatagactg ctggagatta ccagagagtt cagcgtgaac 720
gccggcgtca ccacacccgt gtccacctac atgctgacaa atagtgagct gctgtcactg 780
attaacgaca tgcctatcac caatgatcag aagaaactga tgtccaacaa tgtgcagatc 840
gtcagacagc agagttactc aatcatgtct atcattaagg aggaagtcct ggcctacgtg 900
gtccagctgc cactgtatgg cgtgatcgac accccctgct ggaaactgca tacatctcct 960
ctgtgcacta ccaacacaaa ggaaggaagt aatatctgcc tgactcgaac cgaccgggga 1020
tggtactgtg ataacgcagg cagcgtgtcc ttctttccac aggccgagac ctgcaaggtc 1080
cagagcaaca gggtgttctg tgacactatg aatagcctga ccctgccttc cgaagtcaac 1140
ctgtgcaatg tggacatctt taatccaaag tacgattgta agatcatgac tagcaagacc 1200
gatgtcagct cctctgtgat tacttctctg gggccatcg tgagttgcta cggaaagaca 1260
aaatgtactg ccagcaacaa aaatcgcggc atcattaaga ccttctccaa cgggtgcgac 1320
tatgtctcta acaagggcgt ggatacagtg agtgtcggga acactctgta ctatgtcaat 1380
aagcaggagg gaaaaagcct gtacgtgaag ggcgaaccca tcattaactt ctatgacccc 1440
ctggtgttcc cttccgacga gtttgatgca tctattagtc aggtgaacga aaaaatcaat 1500
cagagtctgg cctttattcg gaagtcagat gagctgctgc acaacgtgaa tgctggcaaa 1560
tctacaacta acatcatgat caccacaatc atcatcgtga ttatcgtcat tctgctgtca 1620
ctgatcgctg tggggctgct gctgtactgt aaggcaagaa gcaccccagt cactctgtca 1680
aaagaccagc tgtcagggat taacaacatt gccttcagta actga 1725

SEQ ID NO: 6 moltype = DNA length = 1725
FEATURE Location/Qualifiers
misc_feature 1..1725
note = Recombinant RSV F
source 1..1725
mol_type = other DNA
organism = synthetic construct
SEQUENCE: 6
atggaactgc tgatcctgaa ggccaacgcc atcacaacaa tcctgaccgc cgtgaccttc 60
tgcttcgcca gcggccagaa catcaccgag gaattctacc agagcacctg tagcgccgtg 120
tccaagggct acctgagcgc cctgagaacc ggctggtaca ccagcgtgat caccatcgag 180
ctgtccaaca tcaaagaaaa caagtgcaac ggcaccgacg ccaaagtgaa gctgatcaag 240
caggaactgg acaagtacaa gaacgccgtg accgagctgc agctgctgat gcagtccacc 300
cccgccacca acaaccgggc cagaagagaa ctgccccggt tcatgaacta caccctcaac 360
aacgccaaaa agaccaacgt gaccctgagc aagaagcgga agcggcggtt cctgggcttc 420
ctgctgggcg tgggcagcgc cattgcctct ggcgtggccg tgtctaaggt gctgcacctg 480
gaaggcgaag tgaacaagat caagagcgcc ctgctgtcca caaacaaggc cgtggtgtcc 540
ctgagcaacg gcgtgtccgt gctgacctcc aaggtgctgg atctgaagaa ctacatcgac 600
aagcagctgc tgcccatcgt gaacaagcag agctgcagca tcagcaacat cgagacagtg 660
atcgagttcc agcagaagaa caaccggctg ctggaaatca cccgcgagtt cagcgtgaac 720
gccggcgtga ccacccccgt gtccacctac atgctgacca acagcgagct gctgtccctg 780
atcaatgaca tgcccatcac caacgaccag aaaaagctga tgagcaacaa cgtgcagatc 840
gtgcggcagc agagctactc catcatgagc atcatcaaag aagaggtgct ggcctacgtg 900
gtgcagctgc ccctgtacgg cgtgatcgac accccctgct ggaagctgca caccagcccc 960
ctgtgcacca ccaacacaaa agagggcagc aacatctgcc tgacccggac cgaccggggc 1020

```
tggtactgcg ataatgccgg cagcgtgtca ttctttccac aggccgagac atgcaaggtg  1080
cagagcaacc gggtgttctg cgacaccatg aacagcctga ccctgccctc cgaagtgaac  1140
ctgtgcaacg tggacatctt caaccctaag tacgactgca agatcatgac cagcaagacc  1200
gacgtgtcca gctccgtgat cacctccctg ggcgccatcg tgtcctgcta cggcaagacc  1260
aagtgcaccg ccagcaacaa gaaccggggc atcatcaaga ccttcagcaa cggctgcgac  1320
tacgtgtcca acaaggggg tggacaccgtg tccgtgggca cacccctgta ctacgtgaac  1380
aaacaggaag gcaagagcct gtacgtgaag ggcgagccca tcatcaactt ctacgaccc  1440
ctggtgttcc ccagcgacga gttcgacgcc agcatcagcc aggtcaacga gaagatcaac  1500
cagagcctgg ccttcatcag aaagagcgac gagctgctgc acaatgtgaa tgccggcaag  1560
agcaccacaa acatcatgat caccactatc atcatcgtga tcatcgtcat cctgctgagt  1620
ctgatcgccg tgggcctgct gctgtactgc aaggccagat ccaccctgt gaccctgtcc  1680
aaggatcagc tgtccggcat caacaatatc gccttctcca actga              1725

SEQ ID NO: 7              moltype = DNA  length = 1725
FEATURE                   Location/Qualifiers
misc_feature              1..1725
                          note = Recombinant RSV F
source                    1..1725
                          mol_type = other DNA
                          organism = synthetic construct
SEQUENCE: 7
atggaactgc tgatcctgaa agccaacgct attactacta tcctgaccgc cgtgacattt  60
tgcttcgcat ctggacagaa cattactgag gaattctacc agtcaacatg cagcgccgtg  120
tccaaaggat acctgagcgc cctgcggacc ggctggtata tcagtgat tactatcgag  180
ctgtccaaca tcaaggaaaa caatgtaat gggaccgacg caaaggtgaa actgatcaag  240
caggagctgg ataagtacaa aaatgccgtg acagaactgc agctgctgat gcagtccaca  300
ccagcaacta caatcgcgc ccggagagag ctgccccggt tcatgaacta taccctgaac  360
aatgctaaga aaccaatgt gacactgtcc aagaaacgca gaggcgctt cctgggattt  420
ctgctgggcg tggggtctgc catcgctagt ggagtggccg tctctaaagt cctgcacctg  480
gagggcgaag tgaacaagat caaaagcgcc ctgctgtcca ctaacaaggc agtggtcagt  540
ctgtcaaatg gcgtgtccgt cctgacctct aaggtgctgg acctgaaaa ttatattgat  600
aagcagctgc tgcctatcgt caacaaacag agctgctcca tttctaatat cgagacagtg  660
atcgaattcc agcagaagaa caatagactg ctggagatta ccagagagtt cagcgtgaac  720
gccggcgtca ccacaccgt gtccacctac atgctgacaa atagtgagct gctgtcactg  780
attaacgaca tgcctatcac caatgatcag aagaaactga tgtccaacaa tgtgcagatc  840
gtcagacagc agagttactc aatcatgtct atcattaagg aggaagtcct ggcctacgtg  900
gtccagctgc cactgtatgg cgtgatcgac acccccctgct ggaaactgca tacatctcct  960
ctgtgcacta ccaacacaaa ggaaggaagt aatatctgcc tgactcgaac cgaccgggga  1020
tggtactgtg ataacgcagg cagcgtgtcc ttctttccac aggccgagac ctgcaaggtc  1080
cagagcaaca gggtgttctg tgacactatg aatagcctga ccctgccctt cgaagtcaac  1140
ctgtgcaatg tggacatctt taatccaaag tacgattgta gatcatgac tagcaagacc  1200
gatgtcagct cctctgtgat tacttctctg ggggccatcg tgagttgcta cggaaagaca  1260
aaatgtactg ccagcaacaa aaatcgcggc atcattaaga ccttctccaa cgggtgcgac  1320
tatgtctcta caagggcgt ggatacagtg agtgtcggga cactctgta ctatgtcaat  1380
aagcaggagg gaaaaagcct gtacgtgaag ggcgaaccca tcattaactt ctatgacccc  1440
ctggtgttcc cttccgacga gtttgatgca tctattagtc aggtgaacga aaaaatcaat  1500
cagagtctgg cctttattcg gaagtcagat gagctgctgc acaacgtgaa tgctggcaaa  1560
tctacaacta acatcatgat caccacaatc atcatcgtga ttatcgtcat tctgctgtca  1620
ctgatcgctg tggggctgct gctgtactgt aaggcaagaa gcacccccagt cactctgtca  1680
aaagaccagc tgtcagggat taacaacatt gccttcagta actga              1725

SEQ ID NO: 8              moltype = AA  length = 573
FEATURE                   Location/Qualifiers
REGION                    1..573
                          note = Recombinant RSV F
source                    1..573
                          mol_type = protein
                          organism = synthetic construct
SEQUENCE: 8
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KYYRIQKRNR VDQNDKPYVL TNK                               573

SEQ ID NO: 9              moltype = DNA  length = 1722
FEATURE                   Location/Qualifiers
misc_feature              1..1722
                          note = Recombinant RSV F
source                    1..1722
                          mol_type = other DNA
                          organism = synthetic construct
SEQUENCE: 9
atggaactgc tgatcctgaa agccaacgct attactacta tcctgaccgc cgtgacattt  60
```

```
tgcttcgcat ctggacagaa cattactgag gaattctacc agtcaacatg cagcgccgtg    120
tccaaaggat acctgagcgc cctgcggacc ggctggtata catcagtgat tactatcgag    180
ctgtccaaca tcaaggaaaa caaatgtaat gggaccgacg caaaggtgaa actgatcaag    240
caggagctgg ataagtacaa aaatgccgtg acagaactgc agctgctgat gcagtccaca    300
ccagcaacta acaatcgcgc ccggagagag ctgccccgtt catgaactac taccctgaac    360
aatgctaaga aaaccaatgt gacactgtcc aagaaacgca agaggcgctt cctgggattt    420
ctgctgggcg tggggtctgc catcgctagt ggagtggccg tctgcaaagt cctgcacctg    480
gagggcgaag tgaacaagat caaaagcgcc ctgctgtcca ctaacaaggc agtggtcagt    540
ctgtcaaatg gcgtgtccgt cctgaccttc aaggtgctgg acctgaaaaa ttatattgat    600
aagcagctgc tgcctatcct gaacaaacag agctgctcca tttctaatat cgagacagtg    660
atcgaattcc agcagaagaa caatagactg ctggagatta ccagagagtt cagcgtgaac    720
gccggcgtca ccacaccegt gtccacctac atgctgacaa atagtgagct gctgtcactg    780
attaacgaca tgcctatcac caatgatcag aagaaactga tgtccaacaa tgtgcagatc    840
gtcagacagc agagttactc aatcatgtgc atcattaagg aggaagtcct ggcctacgtg    900
gtccagctgc cactgtatgg cgtgatcgac acccccgct ggaaactgca tacatctcct    960
ctgtgcacta ccaacacaaa ggaaggaagt aatatctgcc tgactcgaac cgaccgggga   1020
tggtactgtg ataacgcagg cagcgtgtcc ttctttccac aggccgagac ctgcaaggtc   1080
cagagcaaca gggtgttctg tgacactatg aatagcctga ccctgcccttc gaagtcaac    1140
ctgtgcaatg tggacatctt taatccaaag tacgattgta gatcatgac tagcaagacc    1200
gatgtcagct cctctgtgat tacttctctg ggggccatcg tgagttgcta cggaaagaca   1260
aaaatgtactg ccagcaacaa aaatcgcggg atcattaaga ccttctccaa cggtgcgac    1320
tatgtctcta caaagggcgt ggatacagtg agtgtcggga acactctgta ctatgtcaat   1380
aagcaggagg gaaaaagcct gtacgtgaag ggcgaaccca tcattaactt ctatgacccc   1440
ctggtgttcc cttccgacga gttttgatgca tctattagtc aggtgaacga aaaaatcaat   1500
cagagtctgg cctttattcg gaagtcagat gagctgctgc acaacgtgaa tgctggcaaa   1560
tctacaacta acatcatgat caccacaatc atcatcgta ttatcgtcat tctgctgtca     1620
ctgatcgctg tggggctgct gctgtactgt aagtactacc gtatccagaa gaggaacaga   1680
gttgaccaga acgataagcc atacgtgctc actaacaagt ga                      1722

SEQ ID NO: 10          moltype = AA   length = 575
FEATURE                Location/Qualifiers
REGION                 1..575
                       note = Recombinant RSV F
source                 1..575
                       mol_type = protein
                       organism = synthetic construct
SE

```
aagcaggagg gaaaaagcct gtacgtgaag ggcgaaccca tcattaactt ctatgacccc   1440
ctggtgttcc cttccgacga gtttgatgca tctattagtc aggtgaacga aaaaatcaat   1500
cagagtctgg cctttattcg gaagtcgatg agctgctgc acaacgtgaa tgctggcaaa    1560
tctacaacta acatcatgat caccacaatc atcatcatct tgatcatgat catcatcctg   1620
ttcatcatca acatcacaat catcaccatc gctatcaagt actaccgtat ccagaagagg   1680
aacagagttg accagaacga taagccatac gtgctcacta caagtga                1728

SEQ ID NO: 12            moltype = AA  length = 576
FEATURE                  Location/Qualifiers
REGION                   1..576
                         note = Recombinant RSV F
source                   1..576
                         mol_type = protein
                         organism = synthetic construct
SEQUENCE: 12
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI TIIIVMIIIL  540
VIINITIIVV IIKFHRIQGK DQNDKNSEPY ILTNRQ                            576

SEQ ID NO: 13            moltype = DNA  length = 1731
FEATURE                  Location/Qualifiers
misc_feature             1..1731
                         note = Recombinant RSV F
source                   1..1731
                         mol_type = other DNA
                         organism = synthetic construct
SEQUENCE: 13
atggaactgc tgatcctgaa ggccaacgcc atcaccacca tcctgaccgc cgtgaccttc    60
tgctttgcca gcggccagaa catcaccgag gaattctacc agagcacctg tagcgccgtg   120
tccaagggct acctgagcgc cctgagaacc ggctggtaca ccagcgtgat caccatcgag   180
ctgagcaaca tcaaagaaaa caagtgcaac ggcaccgacg ccaaagtgaa gctgatcaag   240
caggaactgg acaagtacaa gaatgccgtg accgaactgc agctgctgat gcagagcacc   300
cccgccacca caaccgggc cagaagagaa ctgcccagat tcatgaacta cacccctgaac  360
aacgccaaaa agaccaacgt gaccctgagc aagaagcgga agcggcggtt cctgggcttt   420
ctgctgggag tgggaagcgc cattgctagc ggagtggccg tgtctaaggt gctgcacctg   480
gaaggcgaag tgaacaagat caagtccgcc ctgctgagca ccaacaaggc cgtggtgtct   540
ctgagcaacg gcgtgtccgt gctgaccagc aaggtgctgg atctgaagaa ctacatcgac   600
aaacagctgc tgcccatcgt gaacaagcag agctgcagca tcagcaacat cgagacagtg   660
atcgagttcc agcagaagaa caaccggctg ctggaaatca cccgcgagtt cagcgtgaac   720
gctggcgtga cacccccgt gtccacctac atgctgacca cagcgagct gctgtccctg    780
atcaacgaca tgcccatcac caacgaccag aaaaagctga tgagcaacaa cgtgcagatc   840
gtgcggcagc agagctactc catcatgagc attatcaaag aagaggtgct ggcctacgtg   900
gtgcagctgc ctctgtacgg cgtgatcgac acccctgct ggaagctgca caccagccct   960
ctgtgcacca ccaacaccaa gagggctcc aacatctgcc tgacccggac cgacagacgg   1020
tggtactgcg ataatgccgg ctccgtctca ttctttccac aagccgagac atgcaaggtg   1080
cagagcaacc gggtgttctg cgacaccatg aacagcctga ccctgccctc gaagtgaat    1140
ctgtgcaacg tggacatctt caaccctaag tacgactgca agatcatgac ctccaagacc   1200
gacgtgtcca gctccgtgat cacaagcctg ggcgccatcg tgtcctgctg cggcaagacc   1260
aagtgcaccg ccagcaacaa gaaccggggc atcatcaaga ccttcagcaa cggctgcgac   1320
tacgtgtcca acaaggggt ggacaccgtg tctgtgggca cacccgtga ctacgtgaac    1380
aaacaggaag gcaagagcct gtacgtgaag ggcgagccca tcatcaactt ctacgacccc   1440
ctggtgttcc ccagcgacga gttcgatgcc agcatctccc aagtgaacga agatcaac    1500
cagagcctgg ccttcatcag aaagtccgat gagctgctgc acaatgtgaa cgccggcaag   1560
tccaccacca atatcatgat caccacaatc accatcatca ttgtgatgat tatcatcctc   1620
gtgatcatca acatcacaat catcgtcgtg attattaagt tccaccggat ccagggcaag   1680
gaccagaacg acaagaactc cgagccctac atcctgacaa accggcagtg a            1731

SEQ ID NO: 14            moltype = AA  length = 576
FEATURE                  Location/Qualifiers
REGION                   1..576
                         note = Recombinant RSV F
source                   1..576
                         mol_type = protein
                         organism = synthetic construct
SEQUENCE: 14
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
```

```
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC IIKFHRIQGK DQNDKNSEPY ILTNRQ                             576

SEQ ID NO: 15           moltype = DNA   length = 1731
FEATURE                 Location/Qualifiers
misc_feature            1..1731
                        note = Recombinant RSV F
source                  1..1731
                        mol_type = other DNA
                        organism = synthetic construct
SEQUENCE: 15
atggaactgc tgatcctgaa ggccaacgcc atcaccacca tcctgaccgc cgtgaccttc    60
tgctttgcca gcggccagaa catcaccgag gaattctacc agagcacctg tagcgccgtg   120
tccaagggct acctgagcgc cctgagaacc ggctggtaca ccagcgtgat caccatcgag   180
ctgagcaaca tcaagaaaaa caagtgcaac ggcaccgacg ccaaagtgaa gctgatcaag   240
caggaactgg acaagtacaa gaatgccgtg accgaactgc agctgctgat gcagagcacc   300
cccgccacca caaccgggc cagaagagaa ctgcccagat tcatgaacta ccccctgaac   360
aacgccaaaa agaccaacgt gaccctgagc aagaagcgga agcggcggtt cctgggcttt   420
ctgctgggag tgggaagcgc cattgctagc ggagtggccg tgtgcaaggt gctgcacctg   480
gaaggcgaag tgaacaagat caagtccgcc ctgctgagca ccaacaaggc cgtggtgtct   540
ctgagcaacg gcgtgtccgt gctgaccagc aaggtgctgg atctgaagaa ctacatcgat   600
aaacagctgc tgcccatcgt gaacaagcag agctgcagca tcagcaacat cgagacagtg   660
atcgagttcc agcagaagaa caccggctg tggaaatca cccgcgagtt cagcgtgaac   720
gctggcgtga ccaccccccgt gtccacctac atgctgacca cagcgagct gctgtccctg   780
atcaacgaca tgcccatcac caacgaccag aaaaagctga tgagcaacaa cgtgcagatc   840
gtgcggcagc agagctactc catcatgtgc atcatcaaag aagaggtgct ggcctacgtg   900
gtgcagctgc ctctgtacgg cgtgatcgac acccccctgct ggaagctgca caccagccct   960
ctgtgcacca ccaacaccaa agagggctcc aacatctgcc tgacccggac cgacagaggc  1020
tggtactgcg ataatgccgg ctccgtctca ttctttccac aagccgagac atgcaaggtg  1080
cagagcaacc gggtgttctg cgacaccatg aacagcctga ccctgccctc cgaagtgaat  1140
ctgtgcaacg tggacatctt caaccctaag tacgactgca agatcatgac ctccaagacc  1200
gacgtgtcca gctccgtgat cacaagcctg ggcgccatcg tgtcctgcta cggcaagacc  1260
aagtgcacca gcaacaacaa gagacggggc atcatcaaga ccttcagcaa cggctgcgac  1320
tacgtgtcca acaaggggt ggacaccgtg tctgtgggca cacccctgta ctacgtgaac  1380
aaacaggaag caagagcct gtacgtgaag ggcgagccca tcatcaactt ctacgacccc  1440
ctggtgttcc ccagcgacga gttcgatgcc agcatctccc aagtgaacga gaagatcaac  1500
cagagcctgg ccttcatcag aaagtccgat gagctgctgc acaatgtgaa cgccggcaag  1560
tccaccacca atatcatgat caccacaatc ttatcgtgat cctgctgagc  1620
ctgatcgccg tgggcctgct gctgtactgt atcatcaagt tccaccggat ccagggcaag  1680
gaccagaacg acaagaactc cgagccctac atcctgacaa accggcagtg a           1731

SEQ ID NO: 16           moltype = AA   length = 576
FEATURE                 Location/Qualifiers
REGION                  1..576
                        note = Recombinant RSV F
source                  1..576
                        mol_type = protein
                        organism = synthetic construct
SEQUENCE: 16
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC IIKFHRIQGK DQNDKNSEPY ILTNRQ                             576

SEQ ID NO: 17           moltype = DNA   length = 1731
FEATURE                 Location/Qualifiers
misc_feature            1..1731
                        note = Recombinant RSV F
source                  1..1731
                        mol_type = other DNA
                        organism = synthetic construct
SEQUENCE: 17
atggaactgc tgatcctgaa ggccaacgcc atcaccacca tcctgaccgc cgtgaccttc    60
tgctttgcca gcggccagaa catcaccgag gaattctacc agagcacctg tagcgccgtg   120
tccaagggct acctgagcgc cctgagaacc ggctggtaca ccagcgtgat caccatcgag   180
ctgagcaaca tcaagaaaaa caagtgcaac ggcaccgacg ccaaagtgaa gctgatcaag   240
caggaactgg acaagtacaa gaatgccgtg accgaactgc agctgctgat gcagagcacc   300
cccgccacca caaccgggc cagaagagaa ctgcccagat tcatgaacta cccctgaac   360
aacgccaaaa agaccaacgt gaccctgagc aagaagcgga agcggcggtt cctgggcttt   420
ctgctgggag tgggaagcgc cattgctagc ggagtggccg tgtgcaaggt gctgcacctg   480
gaaggcgaag tgaacaagat caagtccgcc ctgctgagca ccaacaaggc cgtggtgtct   540
ctgagcaacg gcgtgtccgt gctgaccttc aaggtgctgg atctgaagaa ctacatcgac   600
```

-continued

```
aaacagctgc tgcccatctt gaacaagcag agctgcagca tcagcaacat cgagacagtg  660
atcgagttcc agcagaagaa caaccggctg ctggaaatca cccgcgagtt cagcgtgaac  720
gctggcgtga ccaccccgt gtccacctac atgctgacca acagcgagct gctgtccctg  780
atcaacgaca tgcccatcac caacgaccag aaaaagctga tgagcaacaa cgtgcagatc  840
gtgcggcagc agagctactc catcatgtgc atcatcaaag aagaggtgct ggcctacgtg  900
gtgcagctgc ctctgtacgg cgtgatcgac acccctgct ggaagctgca caccagccct  960
ctgtgcacca ccaacaccaa agagggctcc aacatctgcc tgacccggac cgacagaggc  1020
tggtactgcg ataatgccgg ctccgtctca ttctttccac aagccgagac atgcaaggtg  1080
cagagcaacc gggtgttctg cgacaccatg aacagcctga ccctgccctc cgaagtgaat  1140
ctgtgcaacg tggacatctt caaccctaag tacgactgca agatcatgac ctccaagacc  1200
gacgtgtcca gctccgtgat cacaagcctg ggcgccatcg tgtcctgcta cggcaagacc  1260
aagtgcaccg ccagcaacaa gaaccggggc atcatcaaga ccttcagcaa cggctgcgac  1320
tacgtgtcca acaaggggt ggacaccgtg tctgtgggca acaccctgta ctacgtgaac  1380
aaacaggaag gcaagagcct gtacgtgaag ggcgagccca tcatcaactt ctacgacccc  1440
ctggtgttcc ccagcgacga gttcgatgcc agcatctccc aagtgaacga gaagatcaac  1500
cagagcctgg ccttcatcag aaagtccgat gagctgctgc acaatgtgaa cgccggcaag  1560
tccaccacca atatcatgat caccacaatc atcatcgtga ttatcgtgat cctgctgagc  1620
ctgatcgccg tgggcctgct gctgtactgt atcatcaagt tccaccggat ccagggcaag  1680
gaccagaacg acaagaactc cgagccctac atcctgacaa accggcagtg a  1731

SEQ ID NO: 18          moltype = DNA  length = 1728
FEATURE                Location/Qualifiers
misc_feature           1..1728
                       note = Recombinant RSV F
source                 1..1728
                       mol_type = other DNA
                       organism = synthetic construct
SEQUENCE: 18
atggaactgc tgatcctgaa agccaacgct attactacta tcctgaccgc cgtgacattt  60
tgcttcgcat ctggacagaa cattactgag gaattctacc agtcaacatg cagcgccgtg  120
tccaaaggat acctgagcgc cctgcggacc ggctggtata catcagtgat tactatcgag  180
ctgtccaaca tcaaggaaaa caaatgtaat gggaccgacg caaaggtgaa actgatcaag  240
caggagctgg ataagtacaa aaatgccgtg acagaactgc agctgctgat gcagtccaca  300
ccagcaacta acaatcgcgc ccggagagag ctgccccggt tcatgaacta taccctgaac  360
aatgctaaga aaaccaatgt gacactgtcc aagaaacgca agaggcgctt cctgggattt  420
ctgctgggcg tggggtctgc catcgctagt ggagtggccg tctgcaaagt cctgcacctg  480
gagggcgaag tgaacaagat caaaagcgcc ctgctgtcca ctaacaaggc agtggtcagt  540
ctgtcaaatg gcgtgtccgt cctgaccttc aaggtgctgg acctgaaaaa ttatattgat  600
aagcagctgc tgcctatcct gaacaaacag agctgctcca tttctaatat cgagacagtg  660
atcgaattcc agcagaagaa caatagactg ctggagatta ccagagagtt cagcgtgaac  720
gccggcgtca ccacacccgt gtccacctac atgctgacaa atagtgagct gctgtcactg  780
attaacgaca tgcctatcac caatgatcag aagaaactga tgtccaacaa tgtgcagatc  840
gtcagacagc agagttactc aatcatgtgc atcattaagg aggaagtcct ggcctacgtg  900
gtccagctgc cactgtatgg cgtgatcgac acccctgct ggaaactgca tacatctcct  960
ctgtgcacta ccaacacaaa ggaaggaagt aatatctgcc tgactcgaac cgaccgggga  1020
tggtactgtg ataacgcagg cagcgtgtcc ttctttccac aggccgagac ctgcaaggtc  1080
cagagcaaca gggtgttctg tgacactatg aatagcctga ccctgccttc cgaagtcaac  1140
ctgtgcaatg tggacatctt taatccaaag tacgattgta agatcatgac tagcaagacc  1200
gatgtcagct cctctgtgat tacttctctg gggccatcg tgagttgcta cggaaagaca  1260
aaatgtactg ccagcaacaa aaatcgcggc atcattaaga ccttctccaa cgggtgcgac  1320
tatgtctcta acaagggcgt ggatacagtg agtgtcggga acactctgta ctatgtcaat  1380
aagcaggagg gaaaaagcct gtacgtgaag ggcgaaccca tcattaactt ctatgacccc  1440
ctggtgttcc cttccgacga gtttgatgca tctattagtc aggtgaacga aaaaatcaat  1500
cagagtctgg cctttattcg gaagtcagat gagctgctgc acaacgtgaa tgctggcaaa  1560
tctacaacta acatcatgat caccacaatc atcatcgtga ttatcgtcat tctgctgtca  1620
ctgatcgctg tggggctgct gctgtactgt atcattaagt tccaccggat ccagggcaag  1680
gaccagaacg ataaaaatag cgagccctac attctgacca acagacag  1728

SEQ ID NO: 19          moltype = AA  length = 576
FEATURE                Location/Qualifiers
REGION                 1..576
                       note = Recombinant RSV F
source                 1..576
                       mol_type = protein
                       organism = synthetic construct
SEQUENCE: 19
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI TIIVMIIIL  540
VIINITIIVV IIKFHRIQGK DQNDKNSEPY ILTNRQ  576

SEQ ID NO: 20          moltype = DNA  length = 1731
FEATURE                Location/Qualifiers
```

```
misc_feature            1..1731
                        note = Recombinant RSV F
source                  1..1731
                        mol_type = other DNA
                        organism = synthetic construct
SEQUENCE: 20
atggaactgc tgatcctgaa ggccaacgcc atcaccacca tcctgaccgc cgtgaccttc  60
tgctttgcca gcggccagaa catcaccgag gaattctacc agagcacctg tagcgccgtg  120
tccaagggct acctgagcgc cctgagaacc ggctggtaca ccagcgtgat caccatcgag  180
ctgagcaaca tcaaagaaaa caagtgcaac ggcaccgacg ccaaagtgaa gctgatcaag  240
caggaactgg acaagtacaa gaatgccgtg accgaactgc agctgctgat gcagagcacc  300
cccgccacca acaaccgggc cagaagagaa ctgcccagat tcatgaacta caccctgaac  360
aacgccaaaa agaccaacgt gaccctgagc aagaagcgga agcggcggtt cctgggcttt  420
ctgctgggag tgggaagcgc cattgctagc ggagtggccg tgtgcaaggt gctgcacctg  480
gaaggcgaag tgaacaagat caagtccgcc ctgctgagca ccaacaaggc cgtggtgtct  540
ctgagcaacg gcgtgtccgt gctgaccagc aaggtgctgg atctgaagaa ctacatcgac  600
aaacagctgc tgcccatcgt gaacaagcag agctgcagca tcagcaacat cgagacagtg  660
atcgagttcc agcagaagaa caaccggctg ctggaaatca cccgcgagtt cagcgtgaac  720
gctggcgtga ccaccccgt gtccacctac atgctgacca acagcgagct gctgtccctg  780
atcaacgaca tgcccatcac caacgaccag aaaaagctga tgagcaacaa cgtgcagatc  840
gtgcggcagc agagctactc catcatgtgc atcatcaaag aagaggtgct ggcctacgtg  900
gtgcagctgc ctctgtacgg cgtgatcgac accccctgct ggaagctgca caccagccct  960
ctgtgcacca ccaacaccaa agagggctcc aacatctgcc tgacccggac cgacagaggc  1020
tggtactgcg ataatgccgg ctccgtctca ttctttccac aagccgagac atgcaaggtg  1080
cagagcaacc gggtgttctg cgacaccatg aacagcctga ccctgccctc cgaagtgaat  1140
ctgtgcaacg tggacatctt caaccctaag tacgactgca agatcatgac ctccaagacc  1200
gacgtgtcca gctccgtgat cacaagcctg ggcgccatcg tgtcctgcta cggcaagacc  1260
aagtgcaccg ccagcaacaa gaaccggggc atcatcaaga ccttcagcaa cggctgcgac  1320
tacgtgtcca acaaggggt ggacaccgtg tctgtgggca acaccctgta ctacgtgaac  1380
aaacaggaag gcaagagcct gtacgtgaag ggcgagccca tcatcaactt ctacgacccc  1440
ctggtgttcc ccagcgacga gttcgatgcc agcatctccc aagtgaacga gaagatcaac  1500
cagagcctgg ccttcatcag aaagtccgat gagctgctgc acaatgtgaa cgccggcaag  1560
tccaccacca atatcatgat caccacaatc accatcatca ttgtgatgat tatcatcctc  1620
gtgatcatca acatcacaat catcgtcgtg attattaagt tccaccggat ccagggcaag  1680
gaccagaacg acaagaactc cgagccctac atcctgacaa accggcagtg a           1731

SEQ ID NO: 21           moltype = AA  length = 576
FEATURE                 Location/Qualifiers
REGION                  1..576
                        note = Recombinant RSV F
source                  1..576
                        mol_type = protein
                        organism = synthetic construct
SEQUENCE: 21
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI TIIIVMIIIL  540
VIINITIIVV IIKFHRIQGK DQNDKNSEPY ILTNRQ                            576

SEQ ID NO: 22           moltype = DNA  length = 1731
FEATURE                 Location/Qualifiers
misc_feature            1..1731
                        note = Recombinant RSV F
source                  1..1731
                        mol_type = other DNA
                        organism = synthetic construct
SEQUENCE: 22
atggaactgc tgatcctgaa ggccaacgcc atcaccacca tcctgaccgc cgtgaccttc  60
tgctttgcca gcggccagaa catcaccgag gaattctacc agagcacctg tagcgccgtg  120
tccaagggct acctgagcgc cctgagaacc ggctggtaca ccagcgtgat caccatcgag  180
ctgagcaaca tcaaagaaaa caagtgcaac ggcaccgacg ccaaagtgaa gctgatcaag  240
caggaactgg acaagtacaa gaatgccgtg accgaactgc agctgctgat gcagagcacc  300
cccgccacca acaaccgggc cagaagagaa ctgcccagat tcatgaacta caccctgaac  360
aacgccaaaa agaccaacgt gaccctgagc aagaagcgga agcggcggtt cctgggcttt  420
ctgctgggag tgggaagcgc cattgctagc ggagtggccg tgtgcaaggt gctgcacctg  480
gaaggcgaag tgaacaagat caagtccgcc ctgctgagca ccaacaaggc cgtggtgtct  540
ctgagcaacg gcgtgtccgt gctgaccttc aaggtgctgg atctgaagaa ctacatcgac  600
aaacagctgc tgcccatctt gaacaagcag agctgcagca tcagcaacat cgagacagtg  660
atcgagttcc agcagaagaa caaccggctg ctggaaatca cccgcgagtt cagcgtgaac  720
gctggcgtga ccaccccgt gtccacctac atgctgacca acagcgagct gctgtccctg  780
atcaacgaca tgcccatcac caacgaccag aaaaagctga tgagcaacaa cgtgcagatc  840
gtgcggcagc agagctactc catcatgtgc atcatcaaag aagaggtgct ggcctacgtg  900
gtgcagctgc ctctgtacgg cgtgatcgac accccctgct ggaagctgca caccagccct  960
```

```
ctgtgcacca ccaacaccaa agagggctcc aacatctgcc tgacccggac cgacagaggc  1020
tggtactgcg ataatgccgg ctccgtctca ttctttccac aagccgagac atgcaaggtg  1080
cagagcaacc gggtgttctg cgacaccatg aacagcctga ccctgccctc cgaagtgaat  1140
ctgtgcaacg tggacatctt caaccctaag tacgactgca agatcatgac ctccaagacc  1200
gacgtgtcca gctccgtgat cacaagcctg ggcgccatcg tgtcctgcta cggcaagacc  1260
aagtgcaccg ccagcaacaa gaaccggggc atcatcaaga ccttcagcaa cggctgcgac  1320
tacgtgtcca acaagggggt ggacaccgtg tctgtgggca acaccctgta ctacgtgaac  1380
aaacaggaag gcaagagcct gtacgtgaag ggcgagccca tcatcaactt ctacgacccc  1440
ctggtgttcc ccagcgacga gttcgatgcc agcatctccc aagtgaacga gaagatcaac  1500
cagagcctgg ccttcatcag aaagtccgat gagctgctgc acaatgtgaa cgccggcaag  1560
tccaccacca atatcatgat caccacaatc accatcatca ttgtgatgat tatcatcctc  1620
gtgatcatca acatcacaat catcgtcgtg attattaagt tccaccggat ccagggcaag  1680
gaccagaacg acaagaactc cgagccctac atcctgacaa accggcagtg a           1731
```

```
SEQ ID NO: 23           moltype = DNA  length = 1731
FEATURE                 Location/Qualifiers
misc_feature            1..1731
                        note = Recombinant RSV F
source                  1..1731
                        mol_type = other DNA
                        organism = synthetic construct
SEQUENCE: 23
atggaactgc tgatcctgaa agccaacgct attactacta tcctgaccgc cgtgacattt  60
tgcttcgcat ctggacagaa cattactgag gaattctacc agtcaacatg cagcgccgtg  120
tccaaaggat acctgagcgc cctgcggacc ggctggtata catcagtgat tactatcgag  180
ctgtccaaca tcaaggaaaa caaatgtaat gggaccgacg caaaggtgaa actgatcaag  240
caggagctgg ataagtacaa aaatgccgtg acagaactgc agctgctgat gcagtccaca  300
ccagcaacta acaatcgcgc ccggagagag ctgccccggt tcatgaacta taccctgaac  360
aatgctaaga aaaccaatgt gacactgtcc aagaaacgca agaggcgctt cctgggattt  420
ctgctgggcg tggggtctgc catcgctagt ggagtggccg tctgcaaagt cctgcacctg  480
gagggcgaag tgaacaagat caaaagcgcc ctgctgtcca ctaacaaggc agtggtcagt  540
ctgtcaaatg gcgtgtccgt cctgaccttc aaggtgctgg acctgaaaaa ttatattgat  600
aagcagctgc tgcctatcct gaacaaacag agctgctcca tttctaatat cgagacagtg  660
atcgaattcc agcagaagaa caatagactg ctggagatta ccagagagtt cagcgtgaac  720
gccggcgtca ccacacccgt gtccacctac atgctgacaa atagtgagct gctgtcactg  780
attaacgaca tgcctatcac caatgatcag aagaaactga tgtccaacaa tgtgcagatc  840
gtcagacagc agagttactc aatcatgtgc atcattaagg aggaagtcct ggcctacgtg  900
gtccagctgc cactgtatgg cgtgatcgac acccccctgct ggaaactgca tacatctcct  960
ctgtgcacta ccaacacaaa ggaaggaagt aatatctgcc tgactcgaac cgaccgggga  1020
tggtactgtg ataacgcagg cagcgtgtcc ttctttccac aggccgagac ctgcaaggtc  1080
cagagcaaca gggtgttctg tgacactatg aatagcctga ccctgccttc cgaagtcaac  1140
ctgtgcaatg tggacatctt taatccaaag tacgattgta agatcatgac tagcaagacc  1200
gatgtcagct cctctgtgat tacttctctg gggccatcg tgagttgcta cggaaagaca  1260
aaatgtactg ccagcaacaa aaatcgcggc atcattaaga ccttctccaa cgggtgcgac  1320
tatgtctcta acaagggcgt ggatacagtg agtgtcggga acactctgta ctatgtcaat  1380
aagcaggagg gaaaaagcct gtacgtgaag ggcgaaccca tcattaactt ctatgacccc  1440
ctggtgttcc cttccgacga gtttgatgca tctattagtc aggtgaacga aaaaatcaat  1500
cagagtctgg cctttattcg gaagtcagat gagctgctgc acaacgtgaa tgctggcaaa  1560
tctacaacta acatcatgat caccacaatc accatcatta tcgtgatgat tatcattctg  1620
gtcatcatta acatcacaat cattgtggtc atcattaagt tccaccggat tcagggcaag  1680
gaccagaacg ataaaaatag cgagccctac atcctgacca atagacagtg a           1731
```

```
SEQ ID NO: 24           moltype = AA  length = 524
FEATURE                 Location/Qualifiers
source                  1..524
                        mol_type = protein
                        organism = Human parainfluenza virus 1
SEQUENCE: 24
MAGLLSTFDT FSSRRSESIN KSGGGAIIPG QRSTVSVFTL GPSVTDDADK LLIATTFLAH  60
SLDTDKQHSQ RGGFLVSLLA MAYSSPELYL TTNGVNADVK YVIYNIERDP KRTKTDGFIV  120
KTRDMEYERT TEWLFGPMIN KNPLFQGQRE NADLEALLQT YGYPACLGAI IVQVWIVLVK  180
AITSSAGLRK GFFNRLEAFR QDGTVKSALV FTGDTVEGIG AVMRSQQSLV SLMVETLVTM  240
NTSRSDLTTL EKNIQIVGNY IRDAGLASFM NTIKYGVETK MAALTLSNLR PDINKLRSLV  300
DIYLSKGARA PFICILRDPV HGDFAPGNYP ALWSYAMGVA VVQNKAMQQY VTGRTYLDME  360
MFLLGQAVAK DADSKISSAL EEELGVTDTA KERLRHHLTN LSGGDGAYHK PTGGGAIEVA  420
IDHTDITFGV EDTADRDNKN WTNDSNERWM NHSISNHTIT IRGAEELEEE TNDEDITDIE  480
NKIARRLADR KQRLSQANNK RDTSSDADYE NDDDATAAAG IGGI                   524
```

```
SEQ ID NO: 25           moltype = AA  length = 568
FEATURE                 Location/Qualifiers
source                  1..568
                        mol_type = protein
                        organism = Human parainfluenza virus 1
SEQUENCE: 25
MDQDAFFFER DPEAEGEAPR KQESLSDVIG LLDVVLSYKP TEIGEDRSWL HGIIDNPKEN  60
KPSCKADDNN KDRAISTSTQ DHRSSEESGI SRRTSESKTE THARILDQQG IHRASRRGTS  120
PNPLPENMGN ERNTRIDEDS PNERRHQRSV LTDEDRKMAE NSNKREEDQV EGFPEEVRRS  180
TPLSDDGEGR TNNNGRSMET SSTHSTRITD VITNPSPELE DAVLQRNKRR PTTIKRNQTR  240
SERTQSSELH KSTSENSSNL EDHNTKTSPK VPPSKNEESA ATPKNNHNHR KTRYTTNNAN  300
```

```
NNTKSPPTPE HDATANEEET SNTSVDEMAK LLVSLGVMKS QHEFELSRSA SHVFAKRMLK  360
SANYKEMTFN LCGMLISVEK SLENKVEENR TLLKQIQEEI NSSRDLHKRF SEYQKEQNSL  420
MMANLSTLHI ITDRGGKTGN PSDTTRSPSV FTKGKDNKVK KTRFDPSMEA LGGQEFKPDL  480
IREDELRDDI KNPVLEENNN EPQASNASRL IPSTEKHTLH SLKLVIENSP LSRVEKKAYI  540
KSLYKCRTNQ EVKNVMELFE EDIDSLTN                                    568

SEQ ID NO: 26            moltype = AA  length = 204
FEATURE                  Location/Qualifiers
source                   1..204
                         mol_type = protein
                         organism = Human parainfluenza virus 1
SEQUENCE: 26
MPSFLRGILK PKERHHENKN HSQMSSDSLT SSYPTSPQKL EKTEAGSMVS STTQKKTSHH   60
AKPTITTKTE QSQRRPKIID QVRRVESLGE QVSQKQRHML ESLINKVYTG PLGEELVQTL  120
YLRIWAMKET PESTKILQMR EDIRDQYLRM KTERWLRTLI RGKKTKLRDF QKRYEEVHPY  180
LMMERVEQII MEEAWKLAAH IVQE                                        204

SEQ ID NO: 27            moltype = AA  length = 348
FEATURE                  Location/Qualifiers
source                   1..348
                         mol_type = protein
                         organism = Human parainfluenza virus 1
SEQUENCE: 27
MAETYRFPRF SHEENGTVEP LPLKTGPDKK AIPHIRIVKV GDPPKHGVRY LDVLLLGFFE   60
TPKQGPLSGS ISDLTESTSY SICGSGSLPI GIAKYYGTDQ ELLKACIDLK ITVRRTVRSG  120
EMIVYMVDSI HAPLLPWSSR LRQGMIYNAN KVALAPQCLP VDKDIRFRVV FVNGTSLGTI  180
TIAKVPKTLA DLALPNSISV NLLVTLRAGV STEQKGILPV LDDDGEKKLN FMVHLGIIRR  240
KVGKIYSVEY CKNKIEKMKL IFSLGLVGGI SFHVHATGTL SKTLMSQLAW KKAVCYPLMD  300
VNPHMNLVIW AASVEITSVD AVFQPAIPKE FRYYPNVVAK SIGKIRRI               348

SEQ ID NO: 28            moltype = AA  length = 555
FEATURE                  Location/Qualifiers
source                   1..555
                         mol_type = protein
                         organism = Human parainfluenza virus 1
SEQUENCE: 28
MQKSEILFLV YSSLLLSSSL CQIPVEKLSN VGVIINEGKL LKIAGSYESR YIVLSLVPSI   60
DLQDGCGTTQ IIQYKNLLNR LLIPLKDALD LQESLITITN DTTVTNDNPQ TRFFGAVIGT  120
IALGVATAAQ ITAGIALAEA REARKDIALI KDSIVKTHNS VELIQRGIGE QIIALKTLQD  180
FVNDEIRPAI GELRCETTAL KLGIKLTQHY SELATAFSSN LGTIGEKSLT LQALSSLYSA  240
NITEILSTTK KDKSDIYDII YTEQVKGTVI DVDLEKYMVT LLVKIPILSE IPGVLIYRAS  300
SISYNIEGEE WHVAIPNYII NKASSLGGAD VTNCIESKLA YICPRDPTQL IPDNQQKCIL  360
GDVSKCPVTK VINNLVPKFA FINGGVVANC IASTCTCGTN RIPVNQDRSR GVTFLTYTNC  420
GLIGINGIEL YANKRGRDTT WGNQIIKVGP AVSIRPVDIS LNLASATNFL EESKTELMKA  480
RAIISAVGGW HNTESTQIIM IIIVCILIII ICGILYYLYR VRRLLVMINS THNSPVNAYT  540
LESRMRNPYM GNNSN                                                  555

SEQ ID NO: 29            moltype = AA  length = 575
FEATURE                  Location/Qualifiers
source                   1..575
                         mol_type = protein
                         organism = Human parainfluenza virus 1
SEQUENCE: 29
MAEKGKTNSS YWSTTRNDNS TVNTHINTPA GRTHIWLLIA TTMHTVLSFI IMILCIDLII   60
KQDTCMKTNI MTVSSMNESA KIIKETITEL IRQEVISRTI NIQSSVQSGI PILLNKQSRD  120
LTQLIEKSCN RQELAQICEN TIAIHHADGI SPLDPHDFWR CPVGEPLLSN NPNISLLPGP  180
SLLSGSTTIS GCVRLPSLSI GDAIYAYSSN LITQGCADIG KSYQVLQLGY ISLNSDMYPD  240
LNPVISHTYD INDNRKSCSV IAAGTRGYQL CSLPTVNETT DYSSEGIEDL VFDILDLKGK  300
TKSHRYKNED ITFDHPFSAM YPSVGSGIKI ENTLIFLGYG GLTTPLQGDT KCVINRCTNV  360
NQSVCNDALK ITWLKKRQVV NVLIRINNYL SDRPKIVVET IPITQNYLGA EGRLLKLGKK  420
IYIYTRSSGW HSNLQIGSLD INNPMTIKWA PHEVLSRPGN QDCNWYNRCP RECISGVYTD  480
AYPLSPDAVN VATTTLYANT SRVNPTIMYS NTSEIINMLR LKNVQLEAAY TTTSCITHFG  540
KGYCFHIVEI NQTSLNTLQP MLFKTSIPKI CKITS                            575

SEQ ID NO: 30            moltype = AA  length = 2223
FEATURE                  Location/Qualifiers
source                   1..2223
                         mol_type = protein
                         organism = Human parainfluenza virus 1
SEQUENCE: 30
MDKQESTQNS SDILYPECHL NSPIVKSKIA QLHVLLDINQ PYDLKDNSII NITKYKIRNG   60
GLSPRQIKIR SLGKILKQEI KDIDRYTFEP YPIFSLELLR LDIPEICDKI RSIFSVSDRL  120
IRELSSGFQE LWLNILRQLG CVEGKEGFDS LKDVDIIPDI TDKYNKNTWY RPFLTWFSIK  180
YDMRWMQKNK SGNHLDVSNS HNFLDCKSYI LIIYRDLVII INKLKLTGYV LTPELVLMYC  240
DVVEGRWNMS SAGRLDKRSS KITCKGEELW ELIDSLFPNL GEDVYNIISL LEPLSLALIQ  300
LDDPVTNLKG AFMRHVLTEL HTILIKDNIY TDSEADSIME SLIKIFRETS IDEKAEIFSF  360
FRTFGHPSLE AITAADKVRT HMYSSKKIIL KTLYECHAIF CAIIINGYRE RHGGQWPPCE  420
FPNHVCLELK NAQGSNSAIS YECAVDNYSS FIGFKFLKPI EPQLDEDLTI YMKDKALSPR  480
KAAWDSVYPD SNLYYKVPES EETRRLIEVF INDNNFPNAD IINYVESGEW LNDDSFNISY  540
```

```
SLKEKEIKQE GRLFAKMTYK MRAVQVLAET LLAKGVGELF SENGMVKGEI DLLKRLTTLS    600
VSGVPRSNSV YNNPILHEKL IKNMNKCNSN GYWDERKKSK NEFKAADSST EGYETLSCFL    660
TTDLKKYCLN WRFESTALFG QRCNEIFGFK TFFNWMHPIL EKSTIYVGDP YCPVPDRMHK    720
ELQDHDDTGI FIHNPRGGIE GYCQKLWTLI SISAIHLAAV KVGVRVSAMV QGDNQAIAVT    780
SRVPVTQTYK QKKTHVYEEI TRYFGALREV MFDIGHELKN NETIISSKMF VYSKRIYYDG    840
KILPQCLKAL TRCVFWSETL VDENRSACSN IATSIAKAIE NGYSPILGYC IALFKTCQQV    900
CISLGMTINP TITSTIKDQY FKGKNWLRCA ILIPANIGGF NYMSTARCFV RNIGDPAVAA    960
LADLKRFIKA GLLDKQVLYR VMNQEPGDSS FLDWASDPYS CNLPHSQSIT TIIKNVTARS   1020
VLQESPNPLL SGLFSESSSE EDLNLASFLM DRKAILPRVA HEILDNSLTG VREAIAGMLD   1080
TTKSLVRASV RRGGLSYSIL RRLINYDLLQ YETLTRTLRK PVKDNIEYEY MCSVELAIGL   1140
RQKMWFHLTY GRPIHGLETP DPLELLRGSF IEGSEICKFC RSEGNNPMYT WFYLPDNIDL   1200
DTLSNGSPAI RIPYFGSATD ERSEAQLGYV KNLSKPAKAA IRIAMVYTWA YGTDEISWME   1260
AALIAQTRAN LSLENLKLLT PVSTSTNLSH RLRDTATQMK FSSATLVRAS RFITISNDNM   1320
ALKEAGESKD TNLVYQQIML TGLSLFEFNM RYKQGSLSKP MILHLHLNNK CCIIESPQEL   1380
NIPPRSTLDL EITQENNKLI YDPDPLKDID LELFSKVRDV VHTIDMNYWS DDEIIRATSI   1440
CTAMTIADTM SQLDRDNLKE MIALINDDDI NSLITEFMVI DIPLFCSTFG GILINQFAYS   1500
LYGLNVRGRD EIWGYVIRII KDTSHAVLKV LSNALSHKPI FKRFWDAGVV EPVYGPNLSN   1560
QDKILLAISV CEYSVDLFMR DWQEGIPLEI FICDNDPNIA EMRKLSFLAR HLAYLCSLAE   1620
IAKEGPKLES MTSLERLESL KEYLELTFLD DPILRYSQLT GLVIKIFPST LTYIRKSSIK   1680
VLRVRGIGIP EVLEDWDPDA DSMLLDNITA EVQHNIPLKK NERTPFWGLR VSKSQVLRLR   1740
GYEEIKREER GRSGVGLTLP FDGRYLSHQL RLFGINSTSC LKALELTYLL NPLVNKDKDR   1800
LYLGEGAGAM LSCYDATLGP CMNYYNSGVN SCDLNGQREL NIYPSEVALV GKKLNNVTSL   1860
CQRVKVLFNG NPGSTWIGND ECETLIWNEL QNNSIGFIHC DMEGGEHKCD QVVLHEHYSV   1920
IRIAYLVGDK DVILVSKIAP RLGTDWTKQL SLYLRYWRDV SLIVLKTSNP ASTEMYLISK   1980
DPKSDIIEDS NTVLANLLPL SKEDSIKIEK WILVEKAKVH DWIVRELKEG SASSGMLRPY   2040
HQALQIFGFE PNLNKLCRDF LSTLNIVDTK NCIITFDRVL RDTIFEWTRI KDADKKLRLT   2100
GKYDLYPLRD SGKLKVISRR LVISWIALSM STRLVTGSFP DIKFESRLQL GIVSISSREI   2160
KNLRVISKIV IDKFEDIIHS VTYRFLTKEI KILMKILGAV KLFGARQSTS ADITNIDTSD   2220
SIQ                                                                2223

SEQ ID NO: 31            moltype = AA  length = 59
FEATURE                  Location/Qualifiers
source                   1..59
                         mol_type = protein
                         organism = Human parainfluenza virus 1
SEQUENCE: 31
QIIMIIVCI LIIIICGILY YLYRVRRLLV MINSTHNSPV NAYTLESRMR NPYMGNNSN      59

SEQ ID NO: 32            moltype = AA  length = 543
FEATURE                  Location/Qualifiers
source                   1..543
                         mol_type = protein
                         organism = Human parainfluenza virus 2
SEQUENCE: 32
MSSVLKTFER FTIQQELQEQ SEDTPIPLET IRPTIRVFVI NNNDPIVRSR LLFFNLRIIM    60
SNTAREGHRA GALLSLLSLP SAAMSNHIKL AMHSPEASID RVEITGFENN SFRVIPDARS   120
TMSRGEVLAF EALAEDIPDT LNHQTPFVNN DVEDDIFDET EKFLDVCYSV LMQAWIVTCK   180
CMTAPDQPPV SVAKRMAKYQ QQGRINARYV LQPEAQRLIQ NAIRKSMVVR HFMTYELQLS   240
QSRSLLANRY YAMVGDIGKY IEHSMGGFF LTLKYGLGTR WPTLALAAFS GELQKLKALM    300
LHYQSLGPMA KYMALLESPK LMDFVPSEYP LVYSYAMGIG TVLDTNMRNY AYGRSYLNPQ   360
YFQLGVETAR KQQGAVDNRT AEDLGMTAAD KADLTATISK LSLSQLPRGR QPISDPFAGA   420
NDRETGGQAT DTPVYNFNPI NNRRYDNYDS DSEDRIDNDQ DQAIRENRGE PGQPNNQTSE   480
NQQRLNLPVP QRTSGMSSEE FQHSMNQYIR AMHEQYRGSQ DDDANDATDG NDISLELVGD   540
FDS                                                                543

SEQ ID NO: 33            moltype = AA  length = 395
FEATURE                  Location/Qualifiers
source                   1..395
                         mol_type = protein
                         organism = Human parainfluenza virus 2
SEQUENCE: 33
MAEEPTYTTE QVDELIHAGL GTVDFFLSRP IDAQSSLGKG SIPPGVTAVL TNAAEAKSKP    60
VAAGPVKPRR KKVISNTTPY TIADNIPPEK LPINTPIPNP LLPLARPHGK MTDIDIVTGN   120
ITEGSYKGVE LAKLGKQTLL TRFTSNEPVS SAGSAQDPNF KRGGELIEKE QEATIGENGV   180
LHGSEIRSKS SSGVIPGVPQ SRLQLASSPA HVDPAPASAE NVKEIIELLK GLDLRLQTVE   240
GKVDKILATS ATIINLKNEM TSLKASVATV EGMITTIKIM DPSTPTNVPV EEIRKSLHNV   300
PVVIAGPTSG GFTAEGSDMI SMDELARPTL SSTKKITRKP ESKKDLTGIK LTLMQLANDC   360
ISRPDTKTEF VTKIQAATTE SQLNEIKRSI IRSAI                              395

SEQ ID NO: 34            moltype = AA  length = 225
FEATURE                  Location/Qualifiers
source                   1..225
                         mol_type = protein
                         organism = Human parainfluenza virus 2
SEQUENCE: 34
MAEEPTYTTE QVDELIHAGL GTVDFFLSRP IDAQSSLGKG SIPPGVTAVL TNAAEAKSKP    60
VAAGPVKPRR KKVISNTTPY TIADNIPPEK LPINTPIPNP LLPLARPHGK MTDIDIVTGN   120
ITEGSYKGVE LAKLGKQTLL TRFTSNEPVS SAGSAQDPNF KRGGANRERA RGNHRREWSI   180
AWVGDQVKVF EWCNPRCAPV TASARKFTCT CGSCPSICGE CEGDH                   225
```

```
SEQ ID NO: 35            moltype = AA  length = 377
FEATURE                  Location/Qualifiers
source                   1..377
                         mol_type = protein
                         organism = Human parainfluenza virus 2
SEQUENCE: 35
MPIISLPADP TSPSQSLTPF PIQLDTKDGK AGKLLKQIRI RYLNEPNSRH TPITFINTYG   60
FVYARDTSGG IHSEISSDLA AGSITACMMT LGPGPNIQNA NLVLRSLNEF YVKVKKTSSQ  120
REEAVFELVN IPTLLREHAL CKRKTLVCSA EKFLKNPSKL QAGFEYVYIP TFVSITYSPR  180
NLNYQVARPI LKFRSRFVYS IHLELILRLL CKSDSPLMKS YNADRTGRGC LASVWIHVCN  240
ILKNKSIKQQ GRESYFIAKC MSMQLQVSIA DLWGPTIIIK SLGHIPKTAL PFFSKDGIAC  300
HPLQDVSPTL TKSLWSVGCE IESAKLILQE SDINELMGHQ DLITDKIAIR SGQRTFERSK  360
FSPFKKYASI PNLEAIN                                                377

SEQ ID NO: 36            moltype = AA  length = 551
FEATURE                  Location/Qualifiers
source                   1..551
                         mol_type = protein
                         organism = Human parainfluenza virus 2
SEQUENCE: 36
MHHLHPMIVC IFVMYTGIVG SDAIAGDQLL NVGVIQSKIR SLMYYTDGGA SFIVVKLLPN   60
LPPSNGTCNI TSLDAYNVTL FKLLTPLIEN LSKISAVTDT KPRRERFAGV VIGLAALGVA  120
TAAQITAAVA IVKANANAAA INNLASSIQS TNKAVSDVIT ASRTIATAVQ AIQDHINGAI  180
VNGITSASCR AHDALIGSIL NLYLTELTTI FHNQITNPAL TPLSIQALRI LLGSTLPIVI  240
ESKLNTKLNT AELLSSGLLT GQIISISPMY MQMLIQINVP TFIMQPGAKV IDLIAISANH  300
KLQEVVVQVP NRILEYANEL QNYPANDCVV TPNSVFCRYN EGSPIPESQY QCLRGNLNSC  360
TFTPIIGNFL KRFAFANGVL YANCKSLLCK CADPPHVVSQ DDNQGISIID IKRCSEMMLD  420
TFSFRITSTF NATYVTDFSM INANIVHLSP LDLSNQINSI NKSLKSAEDW IADSNFFANQ  480
ARTAKTLYSL SAIALILSVI TLVVVGLLIA YIIKLVSQIH QFRALAATTM FHRENPAVFS  540
KNNHGNIYGI S                                                      551

SEQ ID NO: 37            moltype = AA  length = 571
FEATURE                  Location/Qualifiers
source                   1..571
                         mol_type = protein
                         organism = Human parainfluenza virus 2
SEQUENCE: 37
MEDYSNLSLK SIPKRTCRII FRTATILGIC TLIVLCSSIL HEIIHLDVSS GLMNSDESQQ   60
GIIQPIIESL KSLIALANQI LYNVAIVIPL KIDSIETVIL SALKDMHTGS MSNANCTPGN  120
LLLHDAAYIN GINKFLVLES YNGTPKYGPL LNIPSFIPSA TSPHGCTRIP SFSLIKTHWC  180
YTHNVMLGDC LDFTASNQYL SMGIIQQSAA GFPIFRTMKT IYLSDGINRK SCSVTAIPGG  240
CVLYCYVATR SEKEDYATTD LAELRLAFYY YNDTFIERVI SLPNTTGQWA TINPAVGSGI  300
YHLGFILFPV YGGLINGTTS YNEQSSRYFI PKHPNITCAG NSSKQAAIAR SSYVIRYHSN  360
RLIQSAVLIC PLSDMHTEEC NLVMFNNSQV MMGAEGRLYV IGNNLYYQR SSSWWSASLF   420
YRINTDFSKG IPPIIEAQWV PSYQVPRPGV MPCNATSFCP ANCITGVYAD VWPLNDPELM  480
SRNALNPNYR FAGAFLKNES NRTNPTFYTA SANSLLNTTG FNNTNHKAAY TSSTCFKNTG  540
TQKIYCLIII EMGSSLLGEF QIIPFLRELM L                                571

SEQ ID NO: 38            moltype = AA  length = 2263
FEATURE                  Location/Qualifiers
source                   1..2263
                         mol_type = protein
                         organism = Human parainfluenza virus 2
SEQUENCE: 38
MAASSEILLP EVHLNSPIVK HKLIYYLLLG HFPHDLDISE ISPLHNNDWD QIAREESNLA   60
ERLGVAKSEL IKRVPAFRAT RWRSHAAVLI WPSCIPFLVK FLPHSKLQPI EQWYKLINAS  120
CNTISDSIDR CMENISIKLT GKNNLFSRSR GTAGAGKNSK ITLNDIQSIW ESNKWQPNVS  180
LWLTIKYQMR QLIMHQSSRQ PTDLVHIVDT RSGLIVITPE LVICFDRLNN VLMYFTFEMT  240
LMVSDMFEGR MNVAALCTIS HYLSPLGPRI DRLFSIVDEL AQLLGDTVYK IIASLESLVY  300
GCLQLKDPVV ELTGSFHSFI TQEIIDILIG SKALDKDESI TVTTQLLDIF SNLSPDLIAE  360
MLCLMRLWGH PTLTAAQAAG KVRESMCAGK LLDFPTIMKT LAFFHTILIN GYRRKKNGMW  420
PPLILPKNAS KSLIEFQHDN AEISYEYTLK HWKEISLIEF RKCFDFDPGE ELSIFMKDKA  480
ISAPKSDWMS VFRRSLIKQR HQRHHIPMPN PFNRRLLLNF LEDDSFDPVA ELQYVTSGEY  540
LRDDTFCASY SLKEKEIKPD GRIFAKLTNR MRSCQVIAEA ILANHAGTLM KENGVVLNQL  600
SLTKSLLTMS QIGIISEKAK RYTRDNISSQ GFHTIKTDSK NKKKSKIASS YLTDPDDTFE  660
LSACFITTDL AKYCLQWRYQ TIIHFARTLN RMYGVPHLFE WIHLRLIRST LYVGDPFNPP  720
ATTDAFDLDK VLNGDIFIVS PKGGIEGLCQ KMWTMISISV IILSSAESKT RVMSMVQGDN  780
QAIAVTTRVP RSLPSVQKKE LAYAASKLFF ERLRANNYGL GHQLKAQETI ISSTFFIYSK  840
RVFYQGRILT QALKNASKLC LTADVLGECT QASCSNSATT IMRLTENGVE KDTCYKLNIY  900
QSIRQLTYDL IFPQYSIPGE TISEIFLQHP RLISRIVLLP SQLGGLNYLA CSRLFNRNIG  960
DPLGTAVADL KRLIKCGALE SWILYNLLAR KPGKGSWATL AADPYSLNQE YLYPPTTILK 1020
RHTQNTLMEI CRNPMLKGVF TDNAKEEENL LAKFLLDRDI VLPRVAHIII DQSSIGRKKQ 1080
IQGFFDTTRT IMRRSFEIKP LSTKKTLSVI EYNTNYLSYN YPVILNLPLI PGYLNYITDQ 1140
TCSIDISRSL RKLSWSSLLN GRTLEGLETP DPIEVVNGSL IVGTGDCDFC MQGDDKFTWF 1200
FLPMGIIIDG NPETNPPIRV PYIGSRTEER RVASMAYIKG ATHSLKAALR GAGVYIWAFG 1260
DTVVNWNDAL DIANTRVKIS LEQLQTLTPL PTSANITHRL DDGATTLKFT PASSYAFSSY 1320
THISNDQQYL EIDQRVVDSN IIYQQLMITG LGIIETYHNP PIRTSTQEIT LHLHTSSSCC 1380
VRSVDGCLIC ESNGEVPQIT VPYTNSFVYD PDPLADYEIA HLDYLSYQAK IGSTDYYSLT 1440
```

```
DKIDLLAHLT AKQMINSIIG LDETVSIVND AVILSDYTNN WISECSYTKI DLVFKLMAWN    1500
FLLELAFQMY YLRISSWTNI FDYTYMTLRR IPGTALNNIA ATISHPKLLR RAMNLDIITP    1560
IHAPYLASLD YVKLSIDAIQ WGVKQVLADL SNGIDLEILI LSEDSMEISD RAMNLIARKL    1620
TLLALVKGEN YTFPKIKGMP PEEKCLVLTE YLAMCYQNTH HLDPDLQKYL YNLTNPKLTA    1680
FPSNNFYLTR KILNQIRESD EGQYIITSYY ESFEQLETDI ILHSTLTAPY DNSETLTKFD    1740
LSLDIFPHPE SLEKYPLPVD HDSQSAISTL IPGPPSHHVL RPLGVSSTAW YKGISYCRYL    1800
ETQKIQTGDH LYLAEGSGAS MSLLELLFPG DTVYYNSLFS SGENPPQRNY APLPTQFVQS    1860
VPYKLWQADL ADDSNLIKDF VPLWNGNGAV TDLSTKDAVA FIIHKVGAEK ASLVHIDLES    1920
TANINQQTLS RSQIHSLIIA TTVLKRGGIL VYKTSWLPFS RFSQLASLLW CFFDRIHLIR    1980
SSYSDPHSHE VYLVCRLAAD FRTIGFSAAL VTATTLHNDG FTTIHPDVVC SYWQHHLENV    2040
GRVEKVIDEI LDGLATNFFA GDNGLILRCG GTPSSRKWLE IDQLASFDSV QDALVTLITI    2100
HLKEIIEVQS SHTEDYTSLL FTPYNIGAAG KVRTIIKLIL ERSLMYTVRN WLVLPSSIRD    2160
SVRQDLELGS FRLMSILSEQ TFLKKTPTKK YLLDQLTRTY ISTFFNSHSV LPLHRPYQKQ    2220
IWKALGSVIY CSETVDIPLI RDIQIEDIND FEDIERGIDG EEL                     2263

SEQ ID NO: 39           moltype = AA  length = 66
FEATURE                 Location/Qualifiers
source                  1..66
                        mol_type = protein
                        organism = Human parainfluenza virus 2
SEQUENCE: 39
TLYSLSAIAL ILSVITLVVV GLLIAYIIKL VSQIHQFRAL AATTMFHREN PAVFSKNNHG    60
NIYGIS                                                               66

SEQ ID NO: 40           moltype = AA  length = 515
FEATURE                 Location/Qualifiers
source                  1..515
                        mol_type = protein
                        organism = Human parainfluenza virus 3
SEQUENCE: 40
MLSLFDTFNA RRQENITKSA GGAIIPGQKN TVSIFALGPT ITDDNEKMTL ALLFLSHSLD    60
NEKQHAQRAG FLVSLLSMAY ANPELYLTTN GSNADVKYVI YMIEKDLKRQ KYGGFVVKTR   120
EMIYEKTTDW IFGSDLDYDQ ETMLQNGRNN STIEDLVHTF GYPSCLGALI IQIWIVLVKA   180
ITSISGLRKG FFTRLEAFRQ DGTVQAGLVL SGDTVDQIGS IMRSQQSLVT LMVETLITMN   240
TSRNDLTTIE KNIQIVGNYI RDAGLASFFN TIRYGIETRM AALTLSTLRP DINRLKALME   300
LYLSKGPRAP FICILRDPIH GEFAPGNYPA IWSYAMGVAV VQNRAMQQYV TGRSYLDIDM   360
FQLGQAVARD AEAQMSSTLE DELGVTHESK ESLKRHIRNI NSSETSFHKP TGGSAIEMAI   420
DEEPEQFEHR ADQEQNGEPQ SSIIQYAWAE GNRSDDQTEQ ATESDNIKTE QQNIRDRLNK   480
RLNDKKKQSS QPPTNPTNRT NQDEIDDLFN AFGSN                              515

SEQ ID NO: 41           moltype = AA  length = 603
FEATURE                 Location/Qualifiers
source                  1..603
                        mol_type = protein
                        organism = Human parainfluenza virus 3
SEQUENCE: 41
MESDAKNYQI MDSWEEESRD KSTNISSALN IIEFILSTDP QEDLSENDTI NTRTQQLSAT    60
ICQPEIKPTE TSEKDSGSTD KNRQSGSSHE CTTEAKDRNI DQETVQRGPG RRSSSDSRAE   120
TVVSGGIPRS ITDSKNGTQN TEDIDLNEIR KMDKDSIEGK MRQSANVPSE ISGSDDIFTT   180
EQSRNSDHGR SLESISTPDT RSISVVTAAT PDDEEEILMK NSRTKKSSST HQEDDKRIKK   240
GGKGKDWFKK SKDTDNQIPT SDYRSTSKGQ KKISKTTTTN TDTKGQTEIQ TESSETQSSS   300
WNLIIDNNTD RNEQTSTTPP TTTSRSTYTK ESIRTNSESK PKTQKTNGKE RKDTEESNRF   360
TERAITLLQN LGVIQSTSKL DLYQDKRVVC VANVLNNVDT ASKIDFLAGL VIGVSMDNDT   420
KLTQIQNEML NLKADLKKMD ESHRRLIENQ REQLSLITSL ISNLKIMTER GGKKDQNESN   480
ERVSMIKTKL KEEKIKKTRF DPLMEAQGID KNIPDLYRHA GDTLENDVQV KSEILSSYNE   540
SNATRLIPKK VSSTMRSLVA VINNSNLSQS TKQSYINELK RCKNDEEVSE LMDMFNEDVN   600
NCQ                                                                 603

SEQ ID NO: 42           moltype = AA  length = 353
FEATURE                 Location/Qualifiers
source                  1..353
                        mol_type = protein
                        organism = Human parainfluenza virus 3
SEQUENCE: 42
MSITNSAIYT FPESSFSENG HIEPLPLKVN EQRKAVPHIR VAKIGNPPKH GSRYLDVFLL    60
GFFEMERIKD KYGSVNDLDS DPSYKVCGSG SLPIGLAKYT GNDQELLQAA TKLDIEVRRT   120
VKAKEMVVYT VQNIKPELYP WSNRLRKGML FDANKVALAP QCLPLDRSIK FRVIFVNCTA   180
IGSITLFKIP KSMASLSLPN TISINLQVHI KTGVQTDSKG IVQILDEKGE KSLNFMVHLG   240
LIKRKVGRMY SVEYCKQKIE KMRLIFSLGL VGGISLHVNA TGSISKTLAS QLVFKREICY   300
PLMDLNPHLN LVIWASSVEI TRVDAIFQPS LPGEFRYYPN IIAKGVGKIK QWN           353

SEQ ID NO: 43           moltype = AA  length = 539
FEATURE                 Location/Qualifiers
source                  1..539
                        mol_type = protein
                        organism = Human parainfluenza virus 3
SEQUENCE: 43
MPTSILLIIT TMIMASFCQI DITKLQHVGV LVNSPKGMKI SQNFETRYLI LSLIPKIEDS    60
NSCGDQQIKQ YKKLLDRLII PLYDGLRLQK DVIVTNQESN ENTDPRTKRF FGGVIGTIAL   120
```

```
GVATSAQITA AVALVEAKQA RSDIEKLKEA IRDTNKAVQS VQSSIGNLIV AIKSVQDYVN     180
KEIVPSIARL GCEAAGLQLG IALTQHYSEL TNIFGDNIGS LQEKGIKLQG IASLYRTNIT     240
EIFTTSTVDK YDIYDLLFTE SIKVRVIDVD LNDYSITLQV RLPLLTRLLN TQIYKVDSIS     300
YNIQNREWYI PLPSHIMTKG AFLGGADVKE CIEAFSSYIC PSDPGFVLNH EIESCLSGNI     360
SQCPRTTVTS DIVPRYAFVN GGVVANCITT TCTCNGIGNR INQPPDQGVK IITHKECSTI     420
GINGMLFNTN KEGTLAFYTP NDITLNNSVA LDPIDISIEL NKAKSDLEES KEWIRRSNQK     480
LDSIGNWHQS STTIIIILIM IIILFIINIT ITIIAIKYYR IQKRNRVDQN DKPYVLTNK      539

SEQ ID NO: 44              moltype = AA  length = 572
FEATURE                    Location/Qualifiers
source                     1..572
                           mol_type = protein
                           organism = Human parainfluenza virus 3
SEQUENCE: 44
MEYWKHTNHG KDAGNELETS MATHGNKLTN KIIYILWTII LVLLSIVFII VLINSIKSEK     60
AHESLLQDIN NEFMEITEKI QMASDNTNDL IQSGVNTRLL TIQSHVQNYI PISLTQQMSD     120
LRKFISEITI RNDNQEVLPQ RITHDVGIKP LNPDDFWRCT SGLPSLMKTP KIRLMPGPGL    180
LAMPTTVDGC VRTPSLVIND LIYAYTSNLI TRGCQDIGKS YQVLQIGIIT VNSDLVPDLN     240
PRISHTFNIN DNRKSCSLAL LNTDVYQLCS TPKVDERSDY ASSGIEDIVL DIVNYDGSIS     300
TTRFKNNNIS FDQPYAALYP SVGPGIYYKG KIIFLGYGGL EHPINENVIC NTTGCPGKTQ    360
RDCNQASHSP WFSDRRMVNS IIVVDKGLNS IPKLKVWTIS MRQNYWGSEG RLLLLGNKIY    420
IYTRSTSWHS KLQLGIIDIT DYSDIRIKWT WHNVLSRPGN NECPWGHSCP DGCITGVYTD    480
AYPLNPTGSI VSSVILDSQK SRVNPVITYS TATERVNELA ILNRTLSAGY TTTSCITHYN    540
KGYCFHIVEI NHKSLNTFQP MLFKTEIPKS CS                                  572

SEQ ID NO: 45              moltype = AA  length = 2233
FEATURE                    Location/Qualifiers
source                     1..2233
                           mol_type = protein
                           organism = Human parainfluenza virus 3
SEQUENCE: 45
MDTESNNGTV SDILYPECHL NSPIVKGKIA QLHTIMSLPQ PYDMDDDSIL VITRQKIKLN     60
KLDKRQRSIR RLKLILTEKV NDLGKYTFIR YPEMSKEMFK LYIPGINSKV TELLLKADRT    120
YSQMTDGLRD LWINVLSKLA SKNDGSNYDL NEEINNISKV HTTYKSDKWY NPFKTWFTIK    180
YDMRRLQKAR NEITFNVGKD YNLLEDQKNF LLIHPELVLI LDKQNYNGYL ITPELVLMYC    240
DVVEGRWNIS ACAKLDPKLQ SMYQKGNNLW EVIDKLFPIM GEKTFDVISL LEPLALSLIQ    300
THDPVKQLRG AFLNHVLSEM ELIFESRESI KEFLSVDYID KILDIFNKST IDEIAEIFSF    360
FRTFGHPPLE ASIAAEKVRK YMYIGKQLKF DTINKCHAIF CTIIINGYRE RHGGQWPPVT    420
LPDHAHEFII NAYGSNSAIS YENAVDYYQS FIGIKFNKFI EPQLDEDLTI YMKDKALSPK    480
KSNWDTVYPA SNLLYRTNAS NESRRLVEVF IADSKFDPHQ ILDYVESGDW LDDPEFNISY    540
SLKEKEIKQE GRLFAKMTYK MRATQVLSET LLANNIGKFF QENGMVKGEI ELLKRLTTIS    600
ISGVPRYNEV YNNSKSHTDD LKTYNKISNL NLSSNQKSKK FEFKSTDIYN DGYETVSCFL    660
TTDLKKYCLN WRYESTALFG ETCNQIFGLN KLFNWLHPRL EGSTIYVGDP YCPPSDKEHI    720
SLEDHPDSGF YVHNPRGGIE GFCQKLWTLI SISAIHLAAV RIGVRVTAMV QGDNQAIAVT    780
TRVPNNYDYR VKKEIVYKDV VRFFDSLREV MDDLGHELKL NETIISSKMF IYSKRIYYDG    840
RILPQALKAL SRCVFWSETV IDETRSASSN LATSFAKAIE NGYSPVLGYA CSIFKNIQQL    900
YIALGMNINP TITQNIRDQY FRNPNWMQYA SLIPASVGGF NYMAMSRCFV RNIGDPSVAA    960
LADIKRFIKA NLLDRSVLYR IMNQEPGESS FLDWASDPYS CNLPQSQNIT TMIKNITARN   1020
VLQDSPNPLL SGLFTNTMIE EDEELAEFLM DRKVILPRVA HDILDNSLTG IRNAIAGMLD   1080
TTKSLIRVGI NRGGLTYSLL RKISNYDLVQ YETLSRTLRL IVSDKIKYED MCSVDLAIAL   1140
RQKMWIHLSG GRMISGLETP DPLELLSGVV ITGSEHCKIC YSSDGTNPYT WMYLPGNHLG   1200
GSAETGISSL RVPYFGSVTD ERSEAQLGYI KNLSKPAKAA IRIAMIYTWA FGNDEISWME   1260
ASQIAQTRAN FTLDSLKILT PVATSTNLSH RLKDTATQMK FSSTSLIRVS RFITMSNDNM   1320
SIKEANETKD TNLIYQQIML TGLSVFEYLF RLKETTGHNP IVMHLHIEDE CCIKESFNDE   1380
HINPESTLEL IRYPESNEFI YDKDPLKDVD LSKLMVIDYT STIDMNYWD DTDIIHAISI   1440
CTAITIADTM SQLDRDNLKE IIVIANDDDI NSLITEFLTL DILVFLKTFG GLLVNQFAYT   1500
LYSLKIEGRD LIWDYIMRTL RDTSHSILKV LSNALSHPKV FKRFWDCGVL NPIYGPNTAS   1560
QDQIKLALSI CEYSLDLFMR EWLNGVSLEI YICDSDMEVA NDRKQAFISR HLSFVCCLAE   1620
IASFGPNLLN LTYLERLDLL KQYLELNIKE DPTLKYVQIS GLLIKSFPST VTYVRKTAIK   1680
YLRIRGISPP EVIDDWDPVE DENMLDNIVK TINDNCNKDN KGNKINNFWG LALKNYQVLK   1740
IRSITSDSDD NDRLDANTSG LTLPQGGNYL SHQLRLFGIN STSCLKALEL SQILMKEVNK   1800
DKDRLFLGEG AGAMLACYDA TLGPAVNYYN SGLNITDVIG QRELKIFPSE VSLVGKKLGN   1860
VTQILNRVKV LFNGNPNSTW IGNMECESLI WSELNDKSIG LVHCDMEGAI GKSEETVLHE   1920
HYSVIRITYL IGDDDVVLVS KIIPTITPNW SRILYLYKLY WKDVSIISLK TSNPASTELY   1980
LISKDAYCTI MEPSEIVLSK LKRLSLLEEN NLLKWIILSK KRNNEWLHHE IKEGERDYGI   2040
MRPYHMALQI FGFQINLNHL AKEFLSTPDL TNINNIIQSF QRTIKDVLFE WINITHDDKR   2100
HKLGGRYNIF PLKNKGKLRL LSRRLVLSWI SLSLSTRLLT GRFPDEKFEH RAQTGYVSLA   2160
DTDLESLKLL SKNIIKNYRE CIGSISYWFL TKEVKILMKL IGGAKLLGIP RQYKEPEDQL   2220
LENYNQHDEF DID                                                      2233

SEQ ID NO: 46              moltype = AA  length = 46
FEATURE                    Location/Qualifiers
source                     1..46
                           mol_type = protein
                           organism = Human parainfluenza virus 3
SEQUENCE: 46
IIIILIMIII LFIINITIIT IAIKYYRIQK RNRVDQNDKP YVLTNK                    46

SEQ ID NO: 47              moltype = AA  length = 515
```

```
FEATURE                 Location/Qualifiers
source                  1..515
                        mol_type = protein
                        organism = Bovine parainfluenza virus 3
SEQUENCE: 47
MLSLFDTFSA RRQENITKSA GGAVIPGQKN TVSIFALGPS ITDDDKMTL ALLFLSHSLD     60
NEKQHAQRAG FLVSLLSMAY ANPELYLTSN GSNADVKYVI YMIEKDPGRQ KYGGFVVKTR   120
EMVYEKTTDW MFGSDLEYDQ DNMLQNGRST STIEDLVHTF GYPSCLGALI IQVWIILVKA   180
ITSISGLRKG FFTRLEAFRQ DGTVKSSLVL SGDAVEQIGS IMRSQQSLVT LMVETLITMN   240
TGRNDLTTIE KNIQIVGNYI RDAGLASFFN TIRYGIETRM AALTLSTLRP DINRLKALIE   300
LYLSKGPRAP FICILRDPVH GEFAPGNYPA LWSYAMGVAV VQNKAMQQYV TGRSYLDIEM   360
FQLGQAVARD AESQMSSILE DELGVTQEAK QSLKKHMKNI SSSDTTFHKP TGGSAIEMAI   420
DEEAGQPESR GDQDQGDEPR SSIVPYAWAD ETGNDNQTES TTEIDSIKTE QRNIRDRLNK   480
RLNEKRKQSD PRSTDITNNT NQTEIDDLFS AFGSN                              515

SEQ ID NO: 48           moltype = AA  length = 596
FEATURE                 Location/Qualifiers
source                  1..596
                        mol_type = protein
                        organism = Bovine parainfluenza virus 3
SEQUENCE: 48
MEDNVQNNQI MDSWEEGSGD KSSDISSALD IIEFILSTDS QENTADSNEI NTGTTRLSTT    60
IYQPESKTTE TSKENSGPAN KNRQFGASHE RATETKDRNV NQEETVQGGYR RGSSPDSRTE  120
TMVTRRISRS SPDPNNGTQI QEDIDYNEVG EMDKDSTKRE MRQFKDVPVK VSGSDAIPPT   180
KQDGDGDDGR GLESISTFDS GYTSIVTAAT LDDEEELLMK NNRPRKYQST PQNSDKGIKK   240
GVGRPKDTDK QSSILDYELN FKGSKKSQKI LKASTNTGEP TRPQNGSGQK RITSWNILNS   300
ESGNRTESTN QTHQTSTSGQ NHTMGPSRTT SEPRIKTQKT DGKEREDTEE STRFTERAIT   360
LLQNLGVIQS AAKLDLYQDK RVVCVANVLN NADTASKIDF LAGLMIGVSM DHDTKLNQIQ   420
NEILSLKTDL KKMDESHRRL IENQKEQLSL ITSLISNLKI MTERGGKKDQ PEPSGRTSMI   480
KTKAKEEKIK KVRFDPLMET QGIEKNIPDL YRSIEKTPEN DTQIKSEINR LNDESNATRL   540
VPRRISSTMR SLIIIINNSN LSSKAKQSYI NELKLCKSDE EVSSELMDMFN EDVSSQ       596

SEQ ID NO: 49           moltype = AA  length = 351
FEATURE                 Location/Qualifiers
source                  1..351
                        mol_type = protein
                        organism = Bovine parainfluenza virus 3
SEQUENCE: 49
MSITNSTIYT FPESSFSENG NIEPLPLKVN EQRKAIPHIR VVKIGDPPKH GSRYLDVFLL    60
GFFEMERSKD RYGSISDLDD DPSYKVCGSG SLPLGLARYT GNDQELLQAA TKLDIEVRRT   120
VKATEMIVYT VQNIKPELYP WSSRLRKGML FDANKVALAP QCLPLDRGIK FRVIFVNCTA   180
IGSITLFKIP KSMALLSLPN TISINLQVHI KTGVQTDSKG VVQILDEKGE KSLNFMVHLG   240
LIKRKMGRMY SVEYCKQKIE KMRLLFSLGL VGGISFHVNA TGSISKTLAS QLAFKREICY   300
PLMDLNPHLN SVIWASSVEI TRVDAVLQPS LPGEFRYYPN IIAKGVGKIR Q            351

SEQ ID NO: 50           moltype = AA  length = 540
FEATURE                 Location/Qualifiers
source                  1..540
                        mol_type = protein
                        organism = Bovine parainfluenza virus 3
SEQUENCE: 50
MTITTTIIAI LLIPPSFCQI DITKLQRVGV LVNNPKGMKI SQNFETRYLI LSLIPKIENS    60
HSCGDQQINQ YKKLLDRLII PLYDGLKLQK DVIVVSHETH NNTNLRTKRF FGEIIGTIAI   120
GIATSAQITA AVALVEAKQA KSDIEKLKEA IRDTNKAVQS IQSSVGNLIV AVKSVQDYVN   180
NEIIPSITRL GCEAAGLQLG IALTQHYSEL TNIFGDNIT LKEKGIKLQG IASLYHTNIT   240
EIFTTSTVDQ YDIYDLLFTE SIKMRVIDVD LSDYSITLQV RLPLLTKLSN TQIYKVDSIS   300
YNIQGKEWYI PLPNHIMTKG AFLGGADIKE CIEAFSSYIC PSDPGYILNH EIENCLSGNI   360
TQCPKTVVTS DVVPRYAFVN GGLIANCITT TCTCNGIDNR INQSPDQGIK IITHKECQVI   420
GINGMLFNTN REGTLATYTF DDIILNNSVA LNPIDISMEL NKAKLELEES KEWIKKSNQK   480
LDSVGSWYQS SATITIIIVM IIILVIINIT IIVVIIKFHR IQGKDQNDKN SEPYILTNRQ   540

SEQ ID NO: 51           moltype = AA  length = 572
FEATURE                 Location/Qualifiers
source                  1..572
                        mol_type = protein
                        organism = Bovine parainfluenza virus 3
SEQUENCE: 51
MEYWKHTNSI NNTNNETETA RGKHSSKVTN IIMYTFWTIT LTILSVIFIM ILTNLIQENN    60
HNKLMLQEIR KEFAAIDTKI QRTSDDIGTS IQSGINTRLL TIQSHVQNYI PLSLTQQMSD   120
LRKFINDLTN KREHQEVPIQ RMTHDRGIEP LNPNKFWRCT SGNPSLTSSP KIRLIPGPGL   180
LATSTTVNGC IRIPSLVINH LIYAYTSNLI TQGCQDIGKS YQVLQIGIIT INSDLVPDLN   240
PRVTHTFNID DNRRSCSLAL LNTDVYQLCS TPKVDERSDY ASTGIEDIVL DIVTNNGLII   300
TTRFTNNNIT FDKPYAALYP SVGPGIYYKD KVIFLGYGGL EHEENGDVIC NTTGCGPKTQ   360
RDCNQASYSP WFSNRRMVNS IIVVDKGIDA TFSLRVWTIP MSQNYWGSEG RLLLLGDRIY   420
IYTRSTSWHS KLQLGVIDIS DYTNIRINWT WHNVLSRPGN DECPWGHSCP DGCITGVYTD   480
AYPLNPSGSV VSSVILDSQK SRENPIITYS TATNRINELA IYNRTLPAAY TTTNCITHYD   540
KGYCFHIVEI NHRSLNTFQP MLFKTEVPKN CS                                 572

SEQ ID NO: 52           moltype = AA  length = 2233
```

| FEATURE | Location/Qualifiers |
|---|---|
| source | 1..2233 |
| | mol_type = protein |
| | organism = Bovine parainfluenza virus 3 |

SEQUENCE: 52

```
MDTESHSGTT SDILYPECHL NSPIVKGKIA QLHTIMSLPQ PYDMDDDSIL IITRQKIKLN   60
KLDKRQRSIR KLRSVLMERV SDLGKYTFIR YPEMSSEMPQ LCIPGINNKI NELLSKASKT  120
YNQMTDGLRD LWVTILSKLA SKNDGSNYDI NEDISNISNV HMTYQSDKWY NPFKTWFTIK  180
YDMRRLQKAK NEITFNRHKD YNLLEDQKNI LLIHPELVLI LDKQNYNGYI MTPELVLMYC  240
DVVEGRWNIS SCAKLDPKLQ SMYYKGNNLW EIIDGLFSTL GERTFDIISL LEPLALSLIQ  300
TYDPVKQLRG AFLNHVLSEM ELIFAAECTT EEIPNVDYID KILDVFKEST IDEIAEIFSF  360
FRTFGHPPLE ASIAAEKVRK YMYTEKCLKF DTINKCHAIF CTIIINGYRE RHGGQWPPVT  420
LPVHAHEFII NAYGSNSAIS YENAVDYYKS FIGIKFDKFI EPQLDEDLTI YMKDKALSPK  480
KSNWDTVYPA SNLLYRTNVS HDSRRLVEVF IADSKFDPHQ VLDYVESGYW LDDPEFNISY  540
SLKEKEIKQE GRLFAKMTYK MRATQVLSET LLANNIGKFF QENGMVKGEI ELLKRLTTIS  600
MSGVPRYNEV YNNSKSHTEE LQAYNAISSS NLSSNQKSKK FEFKSTDIYN DGYETVSCFL  660
TTDLKKYCLN WRYESTALFG DTCNQIFGLK ELFNWLHPRL EKSTIYVGDP YCPPSDIEHL  720
PLDDHPDSGF YVHNPKGGIE GFCQKLWTLI SISAIHLAAV KIGVRVTAMV QGDNQAIAVT  780
TRVPNNYDYK VKKEIVYKDV VRFFDSLREV MDDLGHELKL NETIISSKMF IYSKRIYYDG  840
RILPQALKAL SRCVFWSETI IDETRSASSN LATSFAKAIE NGYSPVLGYV CSIFKNIQQL  900
YIALGMNINP TITQNIKDQY FRNIHWMQYA SLIPASVGGF NYMAMSRCFV RNIGDPTVAA  960
LADIKRFIKA NLLDRGVLYR IMNQEPGESS FLDWASDPYS CNLPQSQNIT TMIKNITARN 1020
VLQDSPNPLL SGLFTSTMIE EDEELAEFLM DRRIILPRVA HDILDNSLTG IRNAIAGMLD 1080
TTKSLIRVGI SRGGLTYNLL RKISNYDLVQ YETLSKTLRL IVSDKIKYED MCSVDLAISL 1140
RQKMWMHLSG GRMINGLETP DPLELLSGVI ITGSEHCRIC YSTEGESPYT WMYLPGNLNI 1200
GSAETGIASL RVPYFGSVTD ERSEAQLGYI KNLSKPAKAA IRIAMIYTWA FGNDEISWME 1260
ASQIAQTRAN FTLDSLKILT PVTTSTNLSH RLKDTATQMK FSSTSLIRVS RFITISNDNM 1320
SIKEANETKD TNLIYQQVML TGLSVFEYLF RLEESTGHNP MVMHLHIEDG CCIKESYNDE 1380
HINPESTLEL IKYPESNEFI YDKDPLKDID LSKLMVIRDH SYTIDMNYWD DTDIVHAISI 1440
CTAVTIADTM SQLDRDNLKE LVVIANDDDI NSLITEFLTL DILVFLKTFG GLLVNQFAYT 1500
LYGLKIEGRD PIWDYIMRTL KDTSHSVLKV LSNALSHPKV FKRFWDCGVL NPIYGPNTAS 1560
QDQVKLALSI CEYSLDLFMR EWLNGASLEI YICDSDMEIA NDRRQAFLSR HLAFVCCLAE 1620
IASFGPNLLN LTYLERLDEL KQYLDLNIKE DPTLKYVQVS GLLIKSFPST VTYVRKTAIK 1680
YLRIRGINPP ETIEDWDPIE DENILDNIVK TVNDNCSDNQ KRNKSSYFWG LALKNYQVVK 1740
IRSITSDSEV NEASNVTTHG MTLPQGGSYL SHQLRLFGVN STSCLKALEL SQILMREVKK 1800
DKDRLFLGEG AGAMLACYDA TLGPAINYYN SGLNITDVIG QRELKIFPSE VSLVGKKLGN 1860
VTQILNRVRV LFNGNPNSTW IGNMECESLI WSELNDKSIG LVHCDMEGAI GKSEETVLHE 1920
HYSIIRITYL IGDDDVVLVS KIIPTITPNW SKILYLYKLY WKDVSVVSLK TSNPASTELY 1980
LISKDAYCTV MEPSNLVSK LKRISSIEEN NLLKWIILSK RKNNEWLQHE IKEGERDYGI 2040
MRPYHTALQI FGFQINLNHL AREFLSTPDL TNINNIIQSF TRTIKDVMFE WVNITHDNKR 2100
HKLGGRYNLF PLKNKGKLRL LSRRLVLSWI SLSLSTRLLT GRFPDEKFEN RAQTGYVSLA 2160
DIDLESLKLL SRNIVKNYKE HIGLISYWFL TKEVKILMKL IGGVKLLGIP KQYKELEDRS 2220
SQGYEYDNEF DID                                                   2233
```

| SEQ ID NO: 53 | moltype = AA  length = 47 |
|---|---|
| FEATURE | Location/Qualifiers |
| source | 1..47 |
| | mol_type = protein |
| | organism = Bovine parainfluenza virus 3 |

SEQUENCE: 53

```
ITIIIVMIII LVIINITIIV VIIKFHRIQG KDQNDKNSEP YILTNRQ          47
```

| SEQ ID NO: 54 | moltype = DNA  length = 10 |
|---|---|
| FEATURE | Location/Qualifiers |
| source | 1..10 |
| | mol_type = genomic DNA |
| | organism = Human parainfluenza virus 1 |

SEQUENCE: 54

```
agggttaaag                                                  10
```

| SEQ ID NO: 55 | moltype = DNA  length = 12 |
|---|---|
| FEATURE | Location/Qualifiers |
| source | 1..12 |
| | mol_type = genomic DNA |
| | organism = Human parainfluenza virus 1 |

SEQUENCE: 55

```
aagtaagaaa aa                                               12
```

| SEQ ID NO: 56 | moltype = DNA  length = 10 |
|---|---|
| FEATURE | Location/Qualifiers |
| source | 1..10 |
| | mol_type = genomic DNA |
| | organism = Human parainfluenza virus 1 |

SEQUENCE: 56

```
agggtgaatg                                                  10
```

| SEQ ID NO: 57 | moltype = DNA  length = 12 |
|---|---|
| FEATURE | Location/Qualifiers |
| source | 1..12 |

```
                              mol_type = genomic DNA
                              organism = Human parainfluenza virus 1
SEQUENCE: 57
aattaagaaa aa                                                            12

SEQ ID NO: 58                 moltype = DNA   length = 10
FEATURE                       Location/Qualifiers
source                        1..10
                              mol_type = genomic DNA
                              organism = Human parainfluenza virus 1
SEQUENCE: 58
agggtcaaag                                                               10

SEQ ID NO: 59                 moltype = DNA   length = 12
FEATURE                       Location/Qualifiers
source                        1..12
                              mol_type = genomic DNA
                              organism = Human parainfluenza virus 1
SEQUENCE: 59
aaataagaaa aa                                                            12

SEQ ID NO: 60                 moltype = DNA   length = 10
FEATURE                       Location/Qualifiers
source                        1..10
                              mol_type = genomic DNA
                              organism = Human parainfluenza virus 1
SEQUENCE: 60
agggacaaag                                                               10

SEQ ID NO: 61                 moltype = DNA   length = 10
FEATURE                       Location/Qualifiers
source                        1..10
                              mol_type = genomic DNA
                              organism = Human parainfluenza virus 1
SEQUENCE: 61
agggttaaag                                                               10

SEQ ID NO: 62                 moltype = DNA   length = 12
FEATURE                       Location/Qualifiers
source                        1..12
                              mol_type = genomic DNA
                              organism = Human parainfluenza virus 1
SEQUENCE: 62
gaataagaaa aa                                                            12

SEQ ID NO: 63                 moltype = DNA   length = 10
FEATURE                       Location/Qualifiers
source                        1..10
                              mol_type = genomic DNA
                              organism = Human parainfluenza virus 1
SEQUENCE: 63
agggttaatg                                                               10

SEQ ID NO: 64                 moltype = DNA   length = 12
FEATURE                       Location/Qualifiers
source                        1..12
                              mol_type = genomic DNA
                              organism = Human parainfluenza virus 1
SEQUENCE: 64
tagtaagaaa aa                                                            12

SEQ ID NO: 65                 moltype = DNA   length = 14
FEATURE                       Location/Qualifiers
source                        1..14
                              mol_type = genomic DNA
                              organism = Human parainfluenza virus 2
SEQUENCE: 65
agattccggt gccg                                                          14

SEQ ID NO: 66                 moltype = DNA   length = 14
FEATURE                       Location/Qualifiers
source                        1..14
                              mol_type = genomic DNA
                              organism = Human parainfluenza virus 2
SEQUENCE: 66
aatttaagaa aaaa                                                          14

SEQ ID NO: 67                 moltype = DNA   length = 17
FEATURE                       Location/Qualifiers
```

```
source                         1..17
                               mol_type = genomic DNA
                               organism = Human parainfluenza virus 2
SEQUENCE: 67
aggcccggac gggttag                                                              17

SEQ ID NO: 68                  moltype = DNA  length = 14
FEATURE                        Location/Qualifiers
source                         1..14
                               mol_type = genomic DNA
                               organism = Human parainfluenza virus 2
SEQUENCE: 68
aatttaataa aaaa                                                                 14

SEQ ID NO: 69                  moltype = DNA  length = 12
FEATURE                        Location/Qualifiers
source                         1..12
                               mol_type = genomic DNA
                               organism = Human parainfluenza virus 2
SEQUENCE: 69
aggtccgaaa gc                                                                   12

SEQ ID NO: 70                  moltype = DNA  length = 15
FEATURE                        Location/Qualifiers
source                         1..15
                               mol_type = genomic DNA
                               organism = Human parainfluenza virus 2
SEQUENCE: 70
aatctaacaa aaaaa                                                                15

SEQ ID NO: 71                  moltype = DNA  length = 12
FEATURE                        Location/Qualifiers
source                         1..12
                               mol_type = genomic DNA
                               organism = Human parainfluenza virus 2
SEQUENCE: 71
aggccaaatt at                                                                   12

SEQ ID NO: 72                  moltype = DNA  length = 14
FEATURE                        Location/Qualifiers
source                         1..14
                               mol_type = genomic DNA
                               organism = Human parainfluenza virus 2
SEQUENCE: 72
aatttaagaa aaaa                                                                 14

SEQ ID NO: 73                  moltype = DNA  length = 12
FEATURE                        Location/Qualifiers
source                         1..12
                               mol_type = genomic DNA
                               organism = Human parainfluenza virus 2
SEQUENCE: 73
aagcacgaac cc                                                                   12

SEQ ID NO: 74                  moltype = DNA  length = 14
FEATURE                        Location/Qualifiers
source                         1..14
                               mol_type = genomic DNA
                               organism = Human parainfluenza virus 2
SEQUENCE: 74
tatttaagaa aaaa                                                                 14

SEQ ID NO: 75                  moltype =      length =
SEQUENCE: 75
000

SEQ ID NO: 76                  moltype = DNA  length = 13
FEATURE                        Location/Qualifiers
source                         1..13
                               mol_type = genomic DNA
                               organism = Human parainfluenza virus 2
SEQUENCE: 76
tatttaagaa aaa                                                                  13

SEQ ID NO: 77                  moltype = DNA  length = 12
FEATURE                        Location/Qualifiers
source                         1..12
                               mol_type = genomic DNA
                               organism = Human parainfluenza virus 3
```

-continued

| | | |
|---|---|---|
| SEQUENCE: 77 aggattaaag ac | | 12 |
| SEQ ID NO: 78 FEATURE source | moltype = DNA  length = 12 Location/Qualifiers 1..12 mol_type = genomic DNA organism = Human parainfluenza virus 3 | |
| SEQUENCE: 78 aaataagaaa aa | | 12 |
| SEQ ID NO: 79 FEATURE source | moltype = DNA  length = 10 Location/Qualifiers 1..10 mol_type = genomic DNA organism = Human parainfluenza virus 3 | |
| SEQUENCE: 79 aggattaaag | | 10 |
| SEQ ID NO: 80 FEATURE source | moltype = DNA  length = 12 Location/Qualifiers 1..12 mol_type = genomic DNA organism = Human parainfluenza virus 3 | |
| SEQUENCE: 80 aaataagaaa aa | | 12 |
| SEQ ID NO: 81 FEATURE source | moltype = DNA  length = 10 Location/Qualifiers 1..10 mol_type = genomic DNA organism = Human parainfluenza virus 3 | |
| SEQUENCE: 81 aggattaaag | | 10 |
| SEQ ID NO: 82 FEATURE source | moltype = DNA  length = 20 Location/Qualifiers 1..20 mol_type = genomic DNA organism = Human parainfluenza virus 3 | |
| SEQUENCE: 82 aaataaagga taatcaaaaa | | 20 |
| SEQ ID NO: 83 FEATURE source | moltype = DNA  length = 10 Location/Qualifiers 1..10 mol_type = genomic DNA organism = Human parainfluenza virus 3 | |
| SEQUENCE: 83 aggacaaaag | | 10 |
| SEQ ID NO: 84 FEATURE source | moltype = DNA  length = 12 Location/Qualifiers 1..12 mol_type = genomic DNA organism = Human parainfluenza virus 3 | |
| SEQUENCE: 84 aattataaaa aa | | 12 |
| SEQ ID NO: 85 FEATURE source | moltype = DNA  length = 10 Location/Qualifiers 1..10 mol_type = genomic DNA organism = Human parainfluenza virus 3 | |
| SEQUENCE: 85 aggagtaaag | | 10 |
| SEQ ID NO: 86 FEATURE source | moltype = DNA  length = 12 Location/Qualifiers 1..12 mol_type = genomic DNA organism = Human parainfluenza virus 3 | |
| SEQUENCE: 86 aaatataaaa aa | | 12 |
| SEQ ID NO: 87 FEATURE source | moltype = DNA  length = 10 Location/Qualifiers 1..10 mol_type = genomic DNA | |

-continued

```
                        organism = Human parainfluenza virus 3
SEQUENCE: 87
aggagcaaag                                                              10

SEQ ID NO: 88           moltype = DNA   length = 13
FEATURE                 Location/Qualifiers
source                  1..13
                        mol_type = genomic DNA
                        organism = Human parainfluenza virus 3
SEQUENCE: 88
aaagtaagaa aaa                                                          13

SEQ ID NO: 89           moltype = DNA   length = 12
FEATURE                 Location/Qualifiers
source                  1..12
                        mol_type = genomic DNA
                        organism = Bovine parainfluenza virus 3
SEQUENCE: 89
aggattaaag aa                                                           12

SEQ ID NO: 90           moltype = DNA   length = 13
FEATURE                 Location/Qualifiers
source                  1..13
                        mol_type = genomic DNA
                        organism = Bovine parainfluenza virus 3
SEQUENCE: 90
caagtaagaa aaa                                                          13

SEQ ID NO: 91           moltype = DNA   length = 12
FEATURE                 Location/Qualifiers
source                  1..12
                        mol_type = genomic DNA
                        organism = Bovine parainfluenza virus 3
SEQUENCE: 91
aggattaatg ga                                                           12

SEQ ID NO: 92           moltype = DNA   length = 13
FEATURE                 Location/Qualifiers
source                  1..13
                        mol_type = genomic DNA
                        organism = Bovine parainfluenza virus 3
SEQUENCE: 92
tgattaagaa aaa                                                          13

SEQ ID NO: 93           moltype = DNA   length = 12
FEATURE                 Location/Qualifiers
source                  1..12
                        mol_type = genomic DNA
                        organism = Bovine parainfluenza virus 3
SEQUENCE: 93
aggatgaaag ga                                                           12

SEQ ID NO: 94           moltype = DNA   length = 13
FEATURE                 Location/Qualifiers
source                  1..13
                        mol_type = genomic DNA
                        organism = Bovine parainfluenza virus 3
SEQUENCE: 94
gaaaaatcaa aaa                                                          13

SEQ ID NO: 95           moltype = DNA   length = 12
FEATURE                 Location/Qualifiers
source                  1..12
                        mol_type = genomic DNA
                        organism = Bovine parainfluenza virus 3
SEQUENCE: 95
aggatcaaag gg                                                           12

SEQ ID NO: 96           moltype = DNA   length = 14
FEATURE                 Location/Qualifiers
source                  1..14
                        mol_type = genomic DNA
                        organism = Bovine parainfluenza virus 3
SEQUENCE: 96
aaaagtacaa aaaa                                                         14

SEQ ID NO: 97           moltype = DNA   length = 12
FEATURE                 Location/Qualifiers
source                  1..12
```

```
                        mol_type = genomic DNA
                        organism = Bovine parainfluenza virus 3
SEQUENCE: 97
aggaacaaag tt                                                              12

SEQ ID NO: 98           moltype = DNA   length = 14
FEATURE                 Location/Qualifiers
source                  1..14
                        mol_type = genomic DNA
                        organism = Bovine parainfluenza virus 3
SEQUENCE: 98
gaaataataa aaaa                                                            14

SEQ ID NO: 99           moltype = DNA   length = 12
FEATURE                 Location/Qualifiers
source                  1..12
                        mol_type = genomic DNA
                        organism = Bovine parainfluenza virus 3
SEQUENCE: 99
aggagaaaag tg                                                              12

SEQ ID NO: 100          moltype = DNA   length = 13
FEATURE                 Location/Qualifiers
source                  1..13
                        mol_type = genomic DNA
                        organism = Bovine parainfluenza virus 3
SEQUENCE: 100
aaagtaagaa aaa                                                             13

SEQ ID NO: 101          moltype = AA   length = 572
FEATURE                 Location/Qualifiers
source                  1..572
                        mol_type = protein
                        organism = Human parainfluenza virus 3
SEQUENCE: 101
MEYWKHTNHG KDAGNELETS MATHGNKLTN KIIYILWTII LVLLSIVFII VLINSIKSEK           60
AHESLLQDIN NEFMEITEKI QMASDNTNDL IQSGVNTRLL TIQSHVQNYI PISLTQQMSD          120
LRKFISEITI RNDNQEVLPQ RITHDVGIKP LNPDDFWRCT SGLPSLMKTP KIRLMPGPGL          180
LAMPTTVDGC VRTPSLVIND LIYAYTSNLI TRGCQDIGKS YQVLQIGIIT VNSDLVPDLN          240
PRISHTFNIN DNRKSCSLAL LNIDVYQLCS TPKVDERSDY ASSGIEDIVL DIVNYDGSIS          300
TTRFKNNNIS FDQPYAALYP SVGPGIYYKG KIIFLGYGGL EHPINENVIC NTTGCPGKTQ          360
RDCNQASHST WFSDRRMVNS IIVVDKGLNS IPKLKVWTIS MRQNYWGSEG RLLLLGNKIY          420
IYTRSTSWHS KLQLGIIDIT DYSDIRIKWT WHNVLSRPGN NECPWGHSCP DGCITGVYTD          480
AYPLNPTGSI VSSVILDSQK SRVNPVITYS TATERVNELA ILNRTLSAGY TTTSCITHYN          540
KGYCFHIVEI NHKSLNTFQP MLFKTEIPKS CS                                        572

SEQ ID NO: 102          moltype = AA   length = 1719
FEATURE                 Location/Qualifiers
source                  1..1719
                        mol_type = protein
                        organism = Human parainfluenza virus 3
SEQUENCE: 102
ATGGAATACT GGAAGCATAC CAATCACGGA AGGATGCTG GTAATGAGCT GGAGACGTCT           60
ATGGCTACTC ATGGCAACAA GCTCACTAAT AAGATAATAT ACATATTATG GACAATAATC         120
CTGGTGTTAT TATCAATAGT CTTCATCATA GTGCTAATTA ATTCCATCAA AAGTGAAAAG         180
GCCCACGAAT CATTGCTGCA AGACATAAAT AATGAGTTTA TGGAAATTAC AGAAAAGATC         240
CAAATGGCAT CGGATAATAC CAATGATCTA ATACAGTCAG GAGTGAATAC AAGGCTTCTT         300
ACAATTCAGA GTCATGTCCA GAATTACATA CCAATATCAT TGACACAACA GATGTCAGAT         360
CTTAGGAAAT TCATTAGTGA AATTACAATT AGAAATGATA ATCAAGAAGT GCTGCCACAA         420
AGAATAACAC ATGATGTAGG TATAAAACCT TTAAATCCAG ATGATTTTTG GAGATGCACG         480
TCTGGTCTTC CATCTTTAAT GAAAACTCCA AAAATAAGGT TAATGCCAGG GCCGGGATTA         540
TTAGCTATGC CAACGACTGT TGATGGCTGT GTTAGAACTC CGTCTTTAGT TATAAATGAT         600
CTGATTTATG CTTATACCTC AAATCTAATT ACTCGAGGTT GTCAGGATAT AGGAAAATCA         660
TATCAAGTCT TACAGATAGG GATAATAACT GTAAACTCAG ACTTGGTACC TGACTTAAAT         720
CCTAGGATCT CTCATACCTT TAACATAAAT GACAATAGGA AGTCATGTTC TCTAGCACTC         780
CTAAATATAG ATGTATATCA ACTGTGTTCA ACTCCCAAAG TTGATGAAAG ATCAGATTAT         840
GCATCATCAG GCATAGAAGA TATTGTACTT GATATTGTCA ATTATGATGG TTCAATCTCA         900
ACAACAAGAT TTAAGAATAA TAACATAAGC TTTGATCAAC CATATGCAGC ATACCTACCC         960
TCTGTTGGAC CAGGGATATA CTACAAAGGC AAAATAATAT TTCTCGGGTA TGGAGGTCTT        1020
GAACATCCAA TAAATGAGAA TGTAATCTGC AACACAACTG GGTGCCCCGG AAAACACAG         1080
AGAGACTGTA ATCAAGCATC TCATAGTACT TGGTTTTCAG ATAGGAGGAT GGTCAACTCC        1140
ATCATTGTTT TGACAAAGG CTTAAACTCA ATTCCAAAAT TGAAAGTATG GACGATATCT         1200
ATGCGACAAA ATTACTGGGG GTCAGAAGGA AGGTTACTTC TACTAGGTAA CAAGATCTAT        1260
ATATATACAA GATCTACAAG TTGGCATAGC AAGTTACAAT TAGGAATAAT TGATATTACT        1320
GATTACAGTG ATATAAGGAT AAAATGGACA TGGCATAATG TGCTATCAAG ACCAGGAAAC        1380
AATGAATGTC CATGGGGACA TTCATGTCCA GATGGATGTA TAACAGGAGT ATATACTGAT        1440
GCATATCCAC TCAATCCCAC AGGGAGCATT GTGTCATCTG TCATATTAGA CTCACAAAAA        1500
TCGAGAGTGA ACCCAGTCAT AACTTACTCA ACAGCAACCG AAAGAGTAAA CGAGCTGGCC        1560
ATCCTAAACA GAACACTCTC AGCTGGATAT ACAACAACAA GCTGCATTAC ACACTATAAC        1620
```

```
AAAGGATATT GTTTTCATAT AGTAGAAATA AATCATAAAA GCTTAAACAC ATTTCAACCC    1680
ATGTTGTTCA AAACAGAGAT TCCAAAAAGC TGCAGTTAA                           1719

SEQ ID NO: 103         moltype = AA  length = 65
FEATURE                Location/Qualifiers
source                 1..65
                       mol_type = protein
                       organism = Sendai virus
SEQUENCE: 103
VITIIVVMVV ILVVIIVIII VLYRLRRSML MGNPDDRIPR DTYTLEPKIR HMYTNGGFDA    60
MAEKR                                                                65

SEQ ID NO: 104         moltype = AA  length = 49
FEATURE                Location/Qualifiers
source                 1..49
                       mol_type = protein
                       organism = Newcastle disease virus
SEQUENCE: 104
IVLTIISLVF GILSLILACY LMYKQKAQQK TLLWLGNNTL DQMRATTKM                49

SEQ ID NO: 105         moltype = AA  length = 594
FEATURE                Location/Qualifiers
REGION                 1..594
                       note = Recombinant RSV F
source                 1..594
                       mol_type

```
REGION                    1..594
                          note = Recombinant RSV F
source                    1..594
                          mol_type = protein
                          organism = synthetic construct
SEQUENCE: 108
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTV ITIIVVMVVI   540
LVVIIVIIIV LYRLRRSMLM GNPDDRIPRD TYTLEPKIRH MYTNGGFDAM AEKR         594

SEQ ID NO: 109            moltype = AA  length = 578
FEATURE                   Location/Qualifiers
REGION                    1..578
                          note = Recombinant RSV F
source                    1..578
                          mol_type = protein
                          organism = synthetic construct
SEQUENCE: 109
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC MYKQKAQQKT LLWLGNNTLD QMRATTKM                           578

SEQ ID NO: 110            moltype = AA  length = 578
FEATURE                   Location/Qualifiers
REGION                    1..578
                          note = Recombinant RSV F
source                    1..578
                          mol_type = protein
                          organism = synthetic construct
SEQUENCE: 110
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI VLTIISLVFG   540
ILSLILACYL MYKQKAQQKT LLWLGNNTLD QMRATTKM                           578

SEQ ID NO: 111            moltype = DNA  length = 49
FEATURE                   Location/Qualifiers
misc_feature              1..49
                          note = Oligonucleotide primer
source                    1..49
                          mol_type = other DNA
                          organism = synthetic construct
SEQUENCE: 111
gcggccgccg tacgctatca gttggagaag gcgatattgt tgatgccgg              49

SEQ ID NO: 112            moltype = AA  length = 578
FEATURE                   Location/Qualifiers
REGION                    1..578
                          note = Recombinant RSV F
source                    1..578
                          mol_type = protein
                          organism = synthetic construct
SEQUENCE: 112
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
```

```
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC MYKQKAQQKT LLWLGNNTLD QMRATTKM                          578

SEQ ID NO: 113            moltype = AA   length = 594
FEATURE                   Location/Qualifiers
REGION                    1..594
                          note = Recombinant RSV F
source                    1..594
                          mol_type = protein
                          organism = synthetic construct
SEQUENCE: 113
MELLIL

```
SEQ ID NO: 120            moltype = DNA   length = 42
FEATURE                   Location/Qualifiers
source                    1..42
                          mol_type = genomic DNA
                          organism = human parainfluenza virus 2
SEQUENCE: 120
taatctttat ataatgtaac aatactacta agattataat at                          42

SEQ ID NO: 121            moltype = DNA   length = 34
FEATURE                   Location/Qualifiers
misc_feature              1..34
                          note = Oligonucleotide primer
source                    1..34
                          mol_type = other DNA
                          organism = synthetic construct
SEQUENCE: 121
aagaagacca agttgagcca gaagaggtac gaag                                   34

SEQ ID NO: 122            moltype = DNA   length = 34
FEATURE                   Location/Qualifiers
misc_feature              1..34
                          note = Oligonucleotide primer
source                    1..34
                          mol_type = other DNA
                          organism = synthetic construct
SEQUENCE: 122
cttcgtacct cttctggctc aacttggtct tctt                                   34

SEQ ID NO: 123            moltype = DNA   length = 51
FEATURE                   Location/Qualifiers
misc_feature              1..51
                          note = Oligonucleotide primer
source                    1..51
                          mol_type = other DNA
                          organism = synthetic construct
SEQUENCE: 123
ccagctaaca taggagggtt caacgcgatg tctacagcta gatgttttgt c                51

SEQ ID NO: 124            moltype = DNA   length = 51
FEATURE                   Location/Qualifiers
misc_feature              1..51
                          note = Oligonucleotide primer
source                    1..51
                          mol_type = other DNA
                          organism = synthetic construct
SEQUENCE: 124
gacaaaacat ctagctgtag acatcgcgtt gaaccctcct atgttagctg g                51

SEQ ID NO: 125            moltype = DNA   length = 12
FEATURE                   Location/Qualifiers
source                    1..12
                          mol_type = genomic DNA
                          organism = Human parainfluenza virus 1
SEQUENCE: 125
aagtaagaaa aa                                                           12

SEQ ID NO: 126            moltype = DNA   length = 10
FEATURE                   Location/Qualifiers
source                    1..10
                          mol_type = genomic DNA
                          organism = Human parainfluenza virus 1
SEQUENCE: 126
agggtgaatg                                                              10

SEQ ID NO: 127            moltype = DNA   length = 46
FEATURE                   Location/Qualifiers
misc_feature              1..46
                          note = Oligonucleotide primer
source                    1..46
                          mol_type = other DNA
                          organism = synthetic construct
SEQUENCE: 127
acgcgtcccg ggaacaatgg aactgctgat cctgaaggcc aacgcc                      46

SEQ ID NO: 128            moltype = DNA   length = 73
FEATURE                   Location/Qualifiers
misc_feature              1..73
                          note = Oligonucleotide primer
```

```
source                    1..73
                          mol_type = other DNA
                          organism = synthetic construct
SEQUENCE: 128
acgcgtcgta cgcattcacc ctaagttttt cttactttct atcagttgga gaaggcgata    60
ttgttgatgc cgg                                                       73

SEQ ID NO: 129            moltype = DNA  length = 48
FEATURE                   Location/Qualifiers
misc_feature              1..48
                          note = Oligonucleotide primer
source                    1..48
                          mol_type = other DNA
                          organism = synthetic construct
SEQUENCE: 129
ggcgcgcccc cgggaacaat ggaactgctg atcctgaagg ccaacgcc                 48

SEQ ID NO: 130            moltype = DNA  length = 79
FEATURE                   Location/Qualifiers
misc_feature              1..79
                          note = Oligonucleotide primer
source                    1..79
                          mol_type = other DNA
                          organism = synthetic construct
SEQUENCE: 130
ggcgcgcccg tacgccattc accctaagtt tttcttactt gattctatca gttggagaag    60
gcgatattgt tgatgccgg                                                 79

SEQ ID NO: 131            moltype = DNA  length = 72
FEATURE                   Location/Qualifiers
misc_feature              1..72
                          note = Oligonucleotide primer
source                    1..72
                          mol_type = other DNA
                          organism = synthetic construct
SEQUENCE: 131
gcggccgccc gggaagtaag aaaaacttag ggtgaatgaa caatggaact gctgatcctg    60
aaggccaacg cc                                                        72

SEQ ID NO: 132            moltype = AA  length = 31
FEATURE                   Location/Qualifiers
REGION                    1..31
                          note = linker and foldon domain
source                    1..31
                          mol_type = protein
                          organism = synthetic construct
SEQUENCE: 132
SAIGGYIPEA PRDGQAYVRK DGEWVLLSTF L                                   31

SEQ ID NO: 133            moltype = AA  length = 586
FEATURE                   Location/Qualifiers
REGION                    1..586
                          note = Recombinant RSV F
source                    1..586
                          mol_type = protein
                          organism = synthetic construct
SEQUENCE: 133
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSDEFDA SISQVNEKIN QSLAFIRKSD ELLHNVNAGK STTNIMITTI IIVIIVILLS    540
LIAVGLLLYC RVRRLLVMIN STHNSPVNAY TLESRMRNPY MGNNSN                   586

SEQ ID NO: 134            moltype = DNA  length = 1764
FEATURE                   Location/Qualifiers
misc_feature              1..1764
                          note = recombinant RSV F
source                    1..1764
                          mol_type = other DNA
                          organism = synthetic construct
SEQUENCE: 134
atggaactgc tgatcctgaa agccaacgct attactacta tcctgaccgc cgtgacattt    60
tgcttcgcat ctggacagaa cattactgag gaattctacc agtcaacatg cagcgccgtg   120
tccaaaggat acctgagcgc cctgcggacc ggctggtata tcagtgat actatcgag     180
```

-continued

```
ctgtccaaca tcaaggaaaa caaatgtaat gggaccgacg caaaggtgaa actgatcaag  240
caggagctgg ataagtacaa aaatgccgtg acagaactgc agctgctgat gcagtccaca  300
ccagcaacta acaatcgcgc ccggagagag ctgccccggt tcatgaacta taccctgaac  360
aatgctaaga aaaccaatgt gacactgtcc aagaaacgca agaggcgctt cctgggattt  420
ctgctgggcg tggggtctgc catcgctagt ggagtggccg tctgcaaagt cctgcacctg  480
gagggcgaag tgaacaagat caaaagcgcc ctgctgtcca ctaacaaggc agtggtcagt  540
ctgtcaaatg gcgtgtccgt cctgaccttc aaggtgctgg acctgaaaaa ttatattgat  600
aagcagctgc tgcctatcct gaacaaacag agctgctcca tttctaatat cgagacagtg  660
atcgaattcc agcagaagaa caatagactg ctggagatta ccagagagtt cagcgtgaac  720
gccggcgtca ccacacccgt gtccacctac atgctgacaa atagtgagct gctgtcactg  780
attaacgaca tgcctatcac caatgatcag aagaaactga tgtccaacaa tgtgcagatc  840
gtcagacagc agagttactc aatcatgtgc atcattaagg aggaagtcct ggcctacgtg  900
gtccagctgc cactgtatgg cgtgatcgac accccctgct ggaaactgca tacatctcct  960
ctgtgcacta ccaacacaaa ggaaggaagt aatatctgcc tgactcgaac cgaccgggga  1020
tggtactgtg ataacgcagg cagcgtgtcc ttctttccac aggccgagac ctgcaaggtc  1080
cagagcaaca gggtgttctg tgacactatg aatagcctga ccctgccttc cgaagtcaac  1140
ctgtgcaatg tggacatctt taatccaaag tacgattgta agatcatgac tagcaagacc  1200
gatgtcagct cctctgtgat tacttctctg gggccatcg tgagttgcta cggaaagaca  1260
aaatgtactg ccagcaacaa aaatcgcggc atcattaaga ccttctccaa cgggtgcgac  1320
tatgtctcta acaagggcgt ggatacagtg agtgtcggga acactctgta ctatgtcaat  1380
aagcaggagg gaaaaagcct gtacgtgaag ggcgaaccca tcattaactt ctatgacccc  1440
ctggtgttcc cttccgacga gtttgatgca tctattagtc aggtgaacga aaaaatcaat  1500
cagagtctgg cctttattcg gaagtcagat gagctgctgc acaacgtgaa tgctggcaaa  1560
tctacaacta acatcatgat caccacaatc atcatcgtga ttatcgtcat tctgctgtca  1620
ctgatcgctg tggggctgct gctgtactgt cgagtgcgga gactgctggt catgattaac  1680
agcacccaca attcccccgt caacgcctac acactggagt ctaggatgcg caatccttat  1740
atggggaaca atagcaactg atag                                        1764
```

```
SEQ ID NO: 135         moltype = AA  length = 588
FEATURE                Location/Qualifiers
REGION                 1..588
                       note = recombinant RSV F
source                 1..588
                       mol_type = protein
                       organism = synthetic construct
SEQUENCE: 135
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTQ IIMIIIVCIL  540
IIIICGILYY LYRVRRLLVM INSTHNSPVN AYTLESRMRN PYMGNNSN              588
```

```
SEQ ID NO: 136         moltype = DNA  length = 1770
FEATURE                Location/Qualifiers
misc_feature           1..1770
                       note = recombinant RSV F
source                 1..1770
                       mol_type = other DNA
                       organism = synthetic construct
SEQUENCE: 136
atggaactgc tgatcctgaa agccaacgct attactacta tcctgaccgc cgtgacattt  60
tgcttcgcat ctggacagaa cattactgag gaattctacc agtcaacatg cagcgccgtg  120
tccaaaggat acctgagcgc cctgcggacc ggctggtata catcagtgat tactatcgag  180
ctgtccaaca tcaaggaaaa caaatgtaat gggaccgacg caaaggtgaa actgatcaag  240
caggagctgg ataagtacaa aaatgccgtg acagaactgc agctgctgat gcagtccaca  300
ccagcaacta acaatcgcgc ccggagagag ctgccccggt tcatgaacta taccctgaac  360
aatgctaaga aaaccaatgt gacactgtcc aagaaacgca agaggcgctt cctgggattt  420
ctgctgggcg tggggtctgc catcgctagt ggagtggccg tctgcaaagt cctgcacctg  480
gagggcgaag tgaacaagat caaaagcgcc ctgctgtcca ctaacaaggc agtggtcagt  540
ctgtcaaatg gcgtgtccgt cctgaccttc aaggtgctgg acctgaaaaa ttatattgat  600
aagcagctgc tgcctatcct gaacaaacag agctgctcca tttctaatat cgagacagtg  660
atcgaattcc agcagaagaa caatagactg ctggagatta ccagagagtt cagcgtgaac  720
gccggcgtca ccacacccgt gtccacctac atgctgacaa atagtgagct gctgtcactg  780
attaacgaca tgcctatcac caatgatcag aagaaactga tgtccaacaa tgtgcagatc  840
gtcagacagc agagttactc aatcatgtgc atcattaagg aggaagtcct ggcctacgtg  900
gtccagctgc cactgtatgg cgtgatcgac accccctgct ggaaactgca tacatctcct  960
ctgtgcacta ccaacacaaa ggaaggaagt aatatctgcc tgactcgaac cgaccgggga  1020
tggtactgtg ataacgcagg cagcgtgtcc ttctttccac aggccgagac ctgcaaggtc  1080
cagagcaaca gggtgttctg tgacactatg aatagcctga ccctgccttc cgaagtcaac  1140
ctgtgcaatg tggacatctt taatccaaag tacgattgta agatcatgac tagcaagacc  1200
gatgtcagct cctctgtgat tacttctctg gggccatcg tgagttgcta cggaaagaca  1260
aaatgtactg ccagcaacaa aaatcgcggc atcattaaga ccttctccaa cgggtgcgac  1320
tatgtctcta acaagggcgt ggatacagtg agtgtcggga acactctgta ctatgtcaat  1380
aagcaggagg gaaaaagcct gtacgtgaag ggcgaaccca tcattaactt ctatgacccc  1440
```

```
ctggtgttcc cttccgacga gtttgatgca tctattagtc aggtgaacga aaaaatcaat   1500
cagagtctgg cctttattcg gaagtcagat gagctgctgc acaacgtgaa tgctggcaaa   1560
tctacaacta acatcatgat caccacacag atcattatga tcattatcgt gtgcattctg   1620
attatcatta tctgtggcat cctgtactat ctgtaccgag tgcggagact gctggtcatg   1680
attaacagca cccacaattc ccccgtcaac gcctacacac tggagtctag gatgcgcaat   1740
ccttatatgg ggaacaatag caactgatag                                     1770

SEQ ID NO: 137          moltype = DNA   length = 1731
FEATURE                 Location/Qualifiers
misc_feature            1..1731
                        note = recombinant RSV F
source                  1..1731
                        mol_type = other DNA
                        organism = syn

```
                             -continued source              1..21
                    mol_type = genomic DNA
                    organism = Human parainfluenza virus 1
SEQUENCE: 142
cagggcgcgc ccccgggaac a                                           21

SEQ ID NO: 143      moltype = DNA   length = 44
FEATURE             Location/Qualifiers
source              1..44
                    mol_type = genomic DNA
                    organism = Human parainfluenza virus 1
SEQUENCE: 143
aatcaagtaa gaaaaactta gggtgaatgg cgtacgggcg cgcc                  44

SEQ ID NO: 144      moltype = DNA   length = 42
FEATURE             Location/Qualifiers
source              1..42
                    mol_type = genomic DNA
                    organism = Human parainfluenza virus 1
SEQUENCE: 144
gcggccgccc gggaagtaag aaaaacttag ggtgaatgaa ca                    42

SEQ ID NO: 145      moltype = DNA   length = 31
FEATURE             Location/Qualifiers
source              1..31
                    mol_type = genomic DNA
                    organism = Human parainfluenza virus 1
SEQUENCE: 145
cgtacggcgg ccgcaaaaca attaagaaaa a                                31

SEQ ID NO: 146      moltype = DNA   length = 15
FEATURE             Location/Qualifiers
source              1..15
                    mol_type = genomic DNA
                    organism = Human parainfluenza virus 1
SEQUENCE: 146
acgcgtgccg ccacc                                                  15

SEQ ID NO: 147      moltype = DNA   length = 37
FEATURE             Location/Qualifiers
source              1..37
                    mol_type = genomic DNA
                    organism = Human parainfluenza virus 1
SEQUENCE: 147
aaaagtaaga aaacttaggg gtgaatgacg cgtaatg                          37

SEQ ID NO: 148      moltype = DNA   length = 64
FEATURE             Location/Qualifiers
source              1..64
                    mol_type = genomic DNA
                    organism = Human parainfluenza virus 3
SEQUENCE: 148
cttaggatta aagacattga ctagaaggtc aagaaaaggg aactctataa tttcaaaaat  60
gttg                                                              64

SEQ ID NO: 149      moltype = DNA   length = 20
FEATURE             Location/Qualifiers
source              1..20
                    mol_type = genomic DNA
                    organism = Human parainfluenza virus 3
SEQUENCE: 149
gcttagcgcc gccaccatgg                                             20

SEQ ID NO: 150      moltype = DNA   length = 49
FEATURE             Location/Qualifiers
source              1..49
                    mol_type = genomic DNA
                    organism = Human parainfluenza virus 3
SEQUENCE: 150
tgatagataa taaataagaa aaacttagga ttaaagaagc ttagcaatg             49

SEQ ID NO: 151      moltype = AA    length = 63
FEATURE             Location/Qualifiers
source              1..63
                    mol_type = protein
                    organism = Bovine parainfluenza virus 3
SEQUENCE: 151
NQKLDSVGSW YQSSATITII IVMIIILVII NITIIVVIIK FHRIQGKDQN DKNSEPYILT  60
NRQ                                                               63
```

```
SEQ ID NO: 152       moltype = AA  length = 79
FEATURE              Location/Qualifiers
source               1..79
                     mol_type = protein
                     organism = Human parainfluenza virus 1
SEQUENCE: 152
LMKARAIISA VGGWHNTEST QIIMIIIVCI LIIIICGILY YLYRVRRLLV MINSTHNSPV  60
NAYTLESRMR NPYMGNNSN                                              79

SEQ ID NO: 153       moltype = AA  length = 66
FEATURE              Location/Qualifiers
source               1..66
                     mol_type = protein
                     organism = Human parainfluenza virus 3
SEQUENCE: 153
IRRSNQKLDS IGNWHQSSTT IIILIMIII LFIINITIIT IAIKYYRIQK RNRVDQNDKP   60
YVLTNK                                                            66
```

The invention claimed is:

1. A recombinant human parainfluenza virus 1 (HPIV1), comprising:
a viral genome comprising genes encoding HPIV1 N, P, M, F, HN, and L proteins, and further comprising a heterologous gene encoding a type I membrane protein comprising a recombinant respiratory syncytial virus (RSV) F ectodomain linked to a transmembrane domain (TM) and cytoplasmic tail (CT) of a human parainfluenza virus 1 (HPIV1) F protein; and
wherein the recombinant HPIV1 is infectious, attenuated, and self-replicating.

2. The recombinant HPIV1 of claim 1, wherein the RSV F ectodomain is stabilized in a RSV F prefusion-conformation by S155C and S290C substitutions to introduce a non-native disulfide bond and S190F and V207L substitutions, wherein the amino acid numbering corresponds to the reference RSV F protein sequence set forth as SEQ ID NO: 1.

3. The recombinant HPIV1 of claim 1, wherein the RSV F ectodomain comprises K66E and Q101P substitutions, wherein the amino acid numbering corresponds to the reference RSV F protein sequence set forth as SEQ ID NO: 1.

4. The recombinant HPIV1 of claim 1, wherein the RSV F ectodomain comprises K66E, Q101P, S155C, S290C, S190F, and V207L substitutions, wherein the amino acid numbering corresponds to the reference RSV F protein sequence set forth as SEQ ID NO: 1.

5. The recombinant HPIV1 of claim 1, wherein the TM and CT comprise the amino acid sequence set forth as SEQ ID NO: 31, or an amino acid sequence at least 90% identical thereto.

6. The recombinant HPIV1 of claim 1, wherein the RSV F ectodomain linked to the TM and CT comprises an amino acid sequence at least 90% identical to SEQ ID NO: 135.

7. The recombinant HPIV1 of claim 1, wherein the RSV F ectodomain linked to the TM and CT comprises the amino acid sequence set forth as SEQ ID NO: 135.

8. The recombinant HPIV1 of claim 1, wherein the heterologous gene encoding the recombinant RSV F ectodomain is the first, second, or third gene downstream of a genomic promoter of the viral genome.

9. The recombinant HPIV1 of claim 1, wherein the HPIV1 comprises a $C^{\Delta 170}$ or a $LY^{942A}$ attenuating mutation.

10. The recombinant HPIV1 of claim 1, wherein the viral genome comprises, from upstream to downstream, a HPIV1 genomic promoter followed by the genes encoding the HPIV1 N, P, M, F, HN, and L proteins, and wherein the heterologous gene encoding the recombinant RSV F ectodomain is located between the genomic promoter and the gene encoding the N protein, between the genes encoding the N and the P proteins, or between genes encoding the P and M proteins.

11. The recombinant HPIV1 of claim 10, wherein the RSV F ectodomain comprises K66E, Q101P, S155C, S290C, S190F, and V207L substitutions, wherein the amino acid numbering corresponds to the reference RSV F protein sequence set forth as SEQ ID NO: 1.

12. The recombinant HPIV1 of claim 11, wherein the HPIV1 comprises a $C^{\Delta 170}$ or a $LY^{942A}$ attenuating mutation.

13. The recombinant HPIV1 of claim 1, wherein at least 90% of viral particles produced by a host cell infected with the recombinant HPIV1 or viral vector comprise a viral envelope comprising the ectodomain encoded by the heterologous gene.

14. The recombinant HPIV1 of claim 1, wherein the RSV F ectodomain is present on the viral envelope of the HPIV1.

15. An immunogenic composition comprising the recombinant HPIV1 of claim 1 and a pharmaceutically acceptable carrier.

16. A method of eliciting an immune response to RSV and/or PIV in a subject comprising administering a therapeutically effective amount of the immunogenic composition of claim 15 to the subject.

17. The method of claim 16, wherein the immune response protects against RSV and/or HPIV1 infection.

18. The method of claim 16, comprising intranasal administration of the immunogenic composition.

19. The method of claim 16, wherein the subject is less than one year old.

20. A nucleic acid molecule comprising the genome of the recombinant HPIV1 of claim 1.

* * * * *